(12) United States Patent
Xu et al.

(10) Patent No.: US 9,920,074 B2
(45) Date of Patent: Mar. 20, 2018

(54) HETEROCYCLIC COMPOUNDS AND USES THEREOF

(71) Applicant: ACEA BIOSCIENCES INC., San Diego, CA (US)

(72) Inventors: Xiao Xu, San Diego, CA (US); Xiaobo Wang, San Diego, CA (US); Long Mao, San Diego, CA (US); Li Zhao, San Diego, CA (US); Biao Xi, San Diego, CA (US)

(73) Assignee: ACEA BIOSCIENCES INC., San Diego, CA (US)

( * ) Notice: Subject to any disclaimer, the term of this patent is extended or adjusted under 35 U.S.C. 154(b) by 0 days.

(21) Appl. No.: 15/271,124

(22) Filed: Sep. 20, 2016

(65) Prior Publication Data
US 2017/0029442 A1  Feb. 2, 2017

Related U.S. Application Data

(62) Division of application No. 14/329,890, filed on Jul. 11, 2014, now Pat. No. 9,464,089.

(60) Provisional application No. 61/845,342, filed on Jul. 11, 2013, provisional application No. 61/923,179, filed on Jan. 2, 2014.

(51) Int. Cl.
| C07D 519/00 | (2006.01) |
| C07D 487/04 | (2006.01) |
| C07D 239/49 | (2006.01) |
| C07D 239/52 | (2006.01) |
| C07D 403/12 | (2006.01) |
| C07D 401/12 | (2006.01) |
| C07D 473/18 | (2006.01) |
| C07D 417/12 | (2006.01) |
| C07D 239/47 | (2006.01) |
| C07D 239/48 | (2006.01) |

(52) U.S. Cl.
CPC ......... *C07D 519/00* (2013.01); *C07D 239/47* (2013.01); *C07D 239/48* (2013.01); *C07D 239/49* (2013.01); *C07D 239/52* (2013.01); *C07D 401/12* (2013.01); *C07D 403/12* (2013.01); *C07D 417/12* (2013.01); *C07D 473/18* (2013.01); *C07D 487/04* (2013.01)

(58) Field of Classification Search
CPC .... A61K 31/52; A61K 31/506; A61K 31/519; A61K 45/06
See application file for complete search history.

(56) References Cited

U.S. PATENT DOCUMENTS

| 7,192,752 | B2 | 3/2007 | Xu et al. |
| 7,459,303 | B2 | 12/2008 | Wang et al. |
| 7,468,255 | B2 | 12/2008 | Xu et al. |
| 7,470,533 | B2 | 12/2008 | Xu et al. |
| 7,560,269 | B2 | 7/2009 | Wang et al. |
| 7,732,127 | B2 | 6/2010 | Wang et al. |
| 8,685,988 | B2 | 4/2014 | Xu et al. |
| 8,975,249 | B2 | 3/2015 | Lee et al. |
| 9,034,885 | B2 | 5/2015 | Xu et al. |
| 2004/0116422 | A1 | 6/2004 | Kitano et al. |
| 2008/0318950 | A1 | 12/2008 | Ahn et al. |
| 2009/0076037 | A1 | 3/2009 | Connolly et al. |
| 2010/0016296 | A1 | 1/2010 | Singh et al. |
| 2010/0029610 | A1 | 2/2010 | Singh et al. |
| 2010/0239631 | A1 | 9/2010 | Bourke et al. |
| 2010/0249092 | A1 | 9/2010 | Singh et al. |
| 2011/0207736 | A1 | 8/2011 | Gray et al. |
| 2012/0094999 | A1 | 4/2012 | Gray et al. |
| 2013/0190320 | A1* | 7/2013 | Xu ................. C07D 239/42 514/252.16 |
| 2015/0133457 | A1 | 5/2015 | Xu et al. |

FOREIGN PATENT DOCUMENTS

| CN | 102083800 | 6/2011 |
| CN | 103748096 | 4/2014 |
| CN | 104306348 | 1/2015 |
| WO | WO-01/32632 | 5/2001 |
| WO | WO-02/083653 | 10/2002 |
| WO | WO-03/026664 | 4/2003 |
| WO | WO-2004/021979 | 3/2004 |
| WO | WO-2004/045624 | 6/2004 |
| WO | WO-2005/062795 | 7/2005 |
| WO | WO-2005/066156 | 7/2005 |
| WO | WO-2005/084401 | 9/2005 |
| WO | WO-2006/009755 | 1/2006 |
| WO | WO-2006/014325 | 2/2006 |

(Continued)

OTHER PUBLICATIONS

Abbot et al., "Synthesis of heteroaryl-fused pyrazoles as P38 kinase inhibitors," Heterocycles (2009) 78(11):2811-2826.
Andries et al., "TMC125, a novel next-generation nonnucleoside reverse transcriptase inhibitor active against nonnucleoside reverse transcriptase inhibitor-resistant human immunodeficiency virus type 1," Antimicrobial Agents and Chemotherapy (2004) 48(12):4680-4686.
Avizienyte et al., "Comparison of the EGFR resistance mutation profiles generated by EGFR-targeted tyrosine kinase inhibitors and the impact of drug combinations," Biochem. J. (2008) 415:197-206.
Bagshawe, "Antibody-directed enzyme prodrug therapy: A review," Drug Dev. Res. (1995) 34(2):220-230.
Bean et al., "Acquired Resistance to Epidermal Growth Factor Receptor Kinase Inhibitors Associated with a Novel T854A Mutation in a Patient with EGFR-Mutant Lung Adenocarcinoma," Clin. Cancer Res. (2008) 14(22):7519-7525.
Berge et al., "Pharmaceutical Salts," J. Pharm. Sci. (1977) 66:1-19.
Bertolini et al., "A new rational hypothesis for the pharmacophore of the active metabolite of leflunomide, a potent immunosuppressive drug," J. Med. Chem. (1997) 40(13):2011-2016.

(Continued)

*Primary Examiner* — Erich A Leeser
(74) *Attorney, Agent, or Firm* — Morrison & Foerster LLP

(57) ABSTRACT

The present invention relates to pharmaceutical compounds, compositions and methods, especially as they are related to compositions and methods for the treatment and/or prevention of a proliferation disorder, a cancer, a tumor, an inflammatory disease, an autoimmune disease, psoriasis, dry eye or an immunologically related disease, and in some embodiments diseases or disorders related to the dysregulation of kinase such as, but not limited to, EGFR (including HER), Alk, PDGFR, BLK, BMX/ETK, FLT3(D835Y), ITK, TEC, TXK, BTK, or JAK, and the respective pathways.

21 Claims, 17 Drawing Sheets

(56) References Cited

FOREIGN PATENT DOCUMENTS

| WO | WO-2007/039404 | | 4/2007 | | |
|---|---|---|---|---|---|
| WO | WO-2007/042298 | | 4/2007 | | |
| WO | WO-2007/055514 | | 5/2007 | | |
| WO | WO-2007/071393 | | 6/2007 | | |
| WO | WO-2007/103233 | | 9/2007 | | |
| WO | WO-2007/126841 | | 11/2007 | | |
| WO | WO-2008/073687 | | 6/2008 | | |
| WO | WO-2008/094737 | | 8/2008 | | |
| WO | WO-2008/150118 | | 12/2008 | | |
| WO | WO-2009/017838 | | 2/2009 | | |
| WO | WO-2009/020990 | | 2/2009 | | |
| WO | WO-2009/032694 | | 3/2009 | | |
| WO | WO-2009/032703 | | 3/2009 | | |
| WO | WO-2009/051822 | | 4/2009 | | |
| WO | WO-2009/131687 | | 10/2009 | | |
| WO | WO-2009/143389 | | 11/2009 | | |
| WO | WO-2009/158571 | | 12/2009 | | |
| WO | WO-2010/045451 | | 4/2010 | | |
| WO | WO-2010/090764 | | 8/2010 | | |
| WO | WO-2010/129053 | | 11/2010 | | |
| WO | WO-2011/079231 | | 6/2011 | | |
| WO | WO 2011/090760 | * | 7/2011 | ............ | A61K 31/33 |
| WO | WO-2011/090760 | | 7/2011 | | |
| WO | WO-2011/140338 | | 11/2011 | | |
| WO | WO-2011/162515 | | 12/2011 | | |
| WO | WO-2012/061299 | | 5/2012 | | |
| WO | WO-2012/061303 | | 5/2012 | | |
| WO | WO-2012/064706 | | 5/2012 | | |
| WO | WO-2012/120048 | | 9/2012 | | |
| WO | WO-2012/135801 | | 10/2012 | | |
| WO | WO-2012/156437 | | 11/2012 | | |
| WO | WO-2013/106792 | | 7/2013 | | |
| WO | WO-2015/006754 | | 1/2015 | | |

OTHER PUBLICATIONS

Blair et al., "Structure-guided development of affinity probes for tyrosine kinases using chemical agents," Nature Chemical Biology (2007) 3(4):229-238.

Bodor, "Novel approaches to the design of safer drugs: soft drugs and site-specific chemical delivery systems," Adv. Drug. Res. (1984) 13:255-331.

Carter et al., "Inhibition of drug-resistant mutants of ABL, KIT, and EGF receptor kinases," *Proc. Natl. Acad. Sci.* 2005, 102(31), 11011-11016.

Chamberlain et al., "Discovery of 4,6-bis-anilino-1H-pyrrolo[2,3-d]pyrimidines: Potent inhibitors of the IGF-1R receptor tyrosine kinase," Bioorganic & Medicinal Chemistry Letters (2009) 19:469-473.

Chamberlain et al., "Optimization of a series of 4,6-bis-anilino-1H-pyrrolo[2,3-d]pyrimidine inhibitors of IGF-1R: Elimination of an acid-mediated decomposition pathway," Bioorganic & Medicinal Chemistry Letters (2009) 19:373-377.

Chamberlain et al., "Optimization of 4,6-bis-anilino-1H-pyrrolo[2,3-d]pyrimidine IGF-1R tyrosine kinase inhibitors. towards JNK selectivity," Bioorganic & Medicinal Chemistry Letters (2009) 19:360-364.

CI-1033 (Canertinib, PD183805), Selleck Chemicals, retrieved from the Internet Aug. 15, 2013, 5 pages.

Frenkel et al., "Concentration and pH Dependent Aggregation of Hydrophobic Drug Molecules and Relevance to Oral Bioavailability," J. Med. Chem. (2005) 48:1974-1983.

Fry et al., "Specific, irreversible inactivation of the epidermal growth factor receptor and erbB2, by a new class of tyrosine kinase inhibitor," PNAS USA (1998) 95:12022-12027.

Ghosh et al., "2,4-bis(aryloxy)pyrimidines as antimicrobial agents," J. Med. Chem. (1968) 11(6):1237-1238.

Gura et al., "Systems for identifying new drugs are often faulty," Science 1997, 278, 1041-1042.

Han et al., "Novel Hybrids of (Phenylsulfonyl)furoxan and Anilinopyrimidine as Potent and Selective Epidermal Growth Factor Receptor Inhibitors for Intervention of Non-Small-Cell Lung Cancer," Journal of Medicinal Chemistry (2013) 56:4738-4748.

International Search Report and Written Opinion for PCT/US2013/021338, dated Jun. 12, 2013, 25 pages.

International Search Report and Written Opinion for PCT Appln. No. PCT/US2013/050163, dated Sep. 4, 2013, 10 pages.

Johnson et al., "Relationships between drug activity in NCI preclinical in vitro and in vivo models and early clinical trials," British Journal of Cancer, 2001, 84, 1424-1431.

Kato et al., "Ketene and its derivatives. XVII. Reaction of diketene with imidates," Chemical and Pharmaceutical Bulletin (1967) 15(9):1334-1338.

Kumar et al., "Structure and Clinical Relevance of the Epidermal Growth Factor Receptor in Human Cancer," *J. Clin. Oncol.* 2008, 26(10), 1742-1751 (Apr. 2008).

Li et al., "BIBW2992, an irreversible EGFR/HER2 inhibitor highly effective in preclinical lung cancer models," Oncogene (2008) 27(34):4702-4711.

Ludovici et al., "Evolution of Anti-HIV Drug Candidates. Part 3: Diarylpyrimidine (DAPY) Analogues," Bioorganic & Medicinal Chemistry Letters (2001) 11:2235-2239.

Patani et al., "Bioisosterism: A Rational Approach in Drug Design," Chem. Rev. (1996) 96:3147-3176.

Petter et al., A novel small-molecule drug platform to silence cancer targets—Application to the pan-ErbB kinases, Poster from AACR 2009, Denver, CO—Abstr. 3746 (presented on Apr. 18-22, 2009).

Profft et al., "Uber in 2- and 6-Stellung substituierte 4-Methylpyrimidine," Archiv der Pharmazie (1962) 295(9):649-662.

Raymond et al., "Epidermal growth factor receptor tyrosine kinase as a target for anticancer therapy," Drugs (2000) 60(Suppl 1):15-23.

Rotili et al., "Diarylpyrimidine-Dihydrobenzyloxopyrimidine Hybrids: New, Wide-Spectrum Anti-HIV-1 Agents Active at (Sub)-Nanomolar Level," J. Med. Chem. (2011) 54(8):3091-3096.

Shan et al., "Prodrug strategies based on intramolecular cyclization reactions," J. Pharm. Sci. (1997) 86(7):765-767.

Slichenmeyer et al., "CI-1033, a pan-erbB tyrosine kinase inhibitor," Semin. Oncol. (2001) 28(5 Suppl. 16):80-85.

Smaill et al., "Tyrosine Kinase Inhibitors. 17. Irreversible Inhibitors of the Epidermal Growth Factor Receptor: 4-(Phenylamino)quinazoline- and 4-(Phenylamino)pyrido[3,2-d]pyrimidine-6-acrylamides Bearing Additional Solubilizing Functions," J. Med. Chem. (2000) 43:1380-1397.

U.S. Provisional U.S. Appl. No. 61/076,450, filed Jun. 27, 2008.

Zhou et al., "Discovery of selective irreversible inhibitors for EGFR-T790M," Bioorganic & Medicinal Chemistry Letters (2011) 21:638-643.

Zhou et al., "Novel mutant-selective EGFR kinase inhibitors against EGFR T790M," Nature (2009) 462(24/31):1070-1074.

Restriction Requirement for U.S. Appl. No. 13/917,514, dated Sep. 10, 2013, 8 pages.

Response to Restriction Requirement for U.S. Appl. No. 13/917,514, filed Oct. 9, 2013, 13 pages.

Notice of Allowance for U.S. Appl. No. 13/917,514, dated Nov. 14, 2013, 10 pages.

Restriction Requirement for U.S. Appl. No. 13/740,182, dated Apr. 11, 2014, 13 pages.

International Preliminary Report on Patentability for PCT/US2013/021338, dated Jul. 15, 2014, 15 pages.

Response to Office Action for U.S. Appl. No. 13/740,182, filed Aug. 15, 2014, 16 pages.

Invitation to Pay Additional Fees for PCT/US2014/046442, dated Oct. 7, 2014, 6 pages.

Office Action for U.S. Appl. No. 13/740,182, dated Dec. 12, 2014, 17 pages.

International Search Report and Written Opinion for PCT/US2014/046442, dated Jan. 5, 2015, 22 pages.

International Preliminary Report on Patentability for PCT/US2013/050163, dated Feb. 10, 2015, 5 pages.

Response to Communication pursuant to Rules 161(1) and 162 EPC for EP 13 701 326.4, filed Feb. 26, 2015, 11 pages.

Communication pursuant to Rules 161(1) and 162 EPC for EP 13745491.4, dated Mar. 17, 2015, 2 pages.

(56) References Cited

OTHER PUBLICATIONS

The First Office Action (translation) for CN 201380013279.0, dated Apr. 29, 2015, 3 pages.
Response to Written Opinion with Chapter II Demand and Article 34 Amendments for PCT/US2014/046442, filed May 11, 2015, 62 pages.
Restriction Requirement for U.S. Appl. No. 14/329,890, dated Jun. 3, 2015, 9 pages.
Final Office Action for U.S. Appl. No. 13/740,182, dated Jun. 30, 2015, 28 pages.
International Preliminary Report on Patentability for PCT/US14/46442, dated Jul. 28, 2015, 5 pages.
Response to Restriction Requirement for U.S. Appl. No. 14/329,890, filed Aug. 3, 2015, 12 pages.
Communication pursuant to Article 94(3) EPC for EP 13701326.4, dated Aug. 10, 2015, 5 pages.
First Examination Report for NZ 629807, dated Aug. 26, 2015, 2 pages.
Response to the First Office Action for CN 201380013279.0, filed Sep. 14, 2015, 30 pages.
Office Action for U.S. Appl. No. 14/329,890, dated Sep. 23, 2015, 16 pages.
Response to Communication pursuant to Rules 161(1) and 162 EPC for EP 13 745 491.4, dated Sep. 25, 2015, 4 pages.
Second Office Action for CN 201380013279.0, dated Dec. 3, 2015, 10 pages.
Response to Final Office Action for U.S. Appl. No. 13/740,182, dated Dec. 17, 2015, 19 pages.
Response to Office Action for U.S. Appl. No. 14/329,890, filed Dec. 21, 2015, 14 pages.
Written Opinion and Search Report for SG 11201500872S dated Dec. 22, 2015, 9 pages.
First Office Action (translation) for CN201380001359.4 dated Jan. 13, 2016, 7 pages.
Response to the Second Office Action for CN 201380013279.0, filed Feb. 22, 2016, 26 pages.
Response to Communication pursuant to Article 94(3) EPC for EP 13701326.4, dated Feb. 22, 2016, 66 pages.
Restriction Requirement for U.S. Appl. No. 14/420,341, dated Feb. 22, 2016, 8 pages.
Final Office Action for U.S. Appl. No. 14/329,890, dated Mar. 3, 2016, 5 pages.
Office Action for U.S. Appl. No. 14/712,794, dated Mar. 8, 2016, 20 pages.
Response to Restriction Requirement for U.S. Appl. No. 14/420,341, filed Apr. 22, 2016, 12 pages.
Communication pursuant to Article 94(3) EPC for EP 13 745 491.4, dated Jan. 25, 2016, 3 pages.
Response to Communication pursuant to Article 94(3) EPC for EP 13 745 491.4, filed May 16, 2016, 27 pages.
The Third Office Action (translation) for CN 201380013279.0, dated May 17, 2016, 3 pages.
Communication pursuant to Article 94(3) EPC for EP 13 701 326.4, dated May 24, 2016, 5 pages.
Communication under Rule 71(3) EPC for EP 13 745 491.4, dated Jun. 20, 2016, 7 pages.
Response to the Third Office Action for CN 201380013279.0, filed Aug. 1, 2016, 24 pages.
Invitation to Respond to Written Opinion for SG 11201500872S, dated Aug. 1, 2016, 7 pages.
Amendment after Notice of Allowance for U.S. Appl. No. 14/329,890, dated Aug. 8, 2016, 3 pages.
Baselga et al., "Critical Update and Emerging Trends in Epidermal Growth Factor Receptor Targeting in Cancer," Journal of Clinical Oncology (2005) 23(11):2445-2459.
Mellinghoff, "Why Do Cancer Cells Become "Addicted" to Oncogenic Epidermal Growth Factor Receptor?" PLoS Medicine (2007) 4(10):e321:1620-1622.
Modjtahedi et al., "Epidermal growth factor receptor inhibitors in cancer treatment: advances, challenges and opportunities," Anti-Cancer Drugs (2009) 220(10):851-855. (Abstract).
Xu et al., "AC0010, an irreversible EGFR inhibitor selectively targeting mutated EGFR and overcoming T790M-induced resistance in animal models and lung cancer patients," Molecular Cancer Therapeutics, Published Online Aug. 29, 2016, DOI: 10.1158/1535-7163.MCT-16-0281, 32 pages.
Request for Continued Examination for U.S. Appl. No. 14/329,890, filed May 3, 2016, 17 pages.
Response to Written Opinion for SG 112015008725, filed May 12, 2016, 22 pages.
Notice of Allowance for U.S. Appl. No. 14/329,890, dated May 27, 2016, 7 pages.
Response to Office Action for CN 201380001359.4, filed May 30, 2016, 31 pages.
Office Action for U.S. Appl. No. 14/420,341, dated Jun. 3, 2016, 7 pages.
Corrected Notice of Allowance for U.S. Appl. No. 14/329,890, dated Jun. 20, 2016, 4 pages.
Response to Office Action for U.S. Appl. No. 14/712,794, filed Jul. 8, 2016, 34 pages.
Second Office Action for CN 201380001359.4, dated Jul. 11, 2016, 11 pages.
Final Office Action for U.S. Appl. No. 14/712,794, dated Jul. 22, 2016, 6 pages.
Response to Office Action for U.S. Appl. No. 14/420,341, filed Sep. 1, 2016, 12 pages.
Patent Examination Report No. 1 for AU 2013207712, dated Sep. 19, 2016, 4 pages.
Final Office Action for U.S. Appl. No. 14/420,341, dated Sep. 22, 2016, 8 pages.
Request for Continued Examination for U.S. Appl. No. 14/712,794, filed Oct. 6, 2016, 27 pages.
Notice of Allowance for U.S. Appl. No. 14/420,341, dated Oct. 18, 2016, 16 pages.
Request for Continued Examination for U.S. Appl. No. 13/740,182, dated Dec. 17, 2015,14 pages.
Supplemental response for U.S. Appl. No. 13/740,182, dated Feb. 9, 2016, 16 pages.
Non-final Rejection for U.S. Appl. No. 13/740,182, dated Sep. 1, 2016, 20 pages.
Response to Non-final Rejection for U.S. Appl. No. 13/740,182, dated Dec. 1, 2016, 17 pages.
Final Rejection for U.S. Appl. No. 13/740,182, dated Mar. 23, 2017, 26 pages.
Response to Examination Report No. 1 for AU 2013207712, filed Mar. 23, 2017, 35 pages.
Examination Report No. 2 for AU 2013207712, dated Apr. 3, 2017, 6 pages.
Decision of Rejection for CN 201380013279.0, dated Dec. 2, 2016, 9 pages.
Request for re-examination for CN 201380013279.0, dated Mar. 15, 2017, 256 pages.
Response to Communication pursuant to Art 94(3) for EP 13 701 326.4, dated Dec. 2, 2016, 25 pages.
Communication pursuant to Art 94(3) for EP 13 701 326.4, dated Feb. 1, 2017, 5 pages.
Notice of grounds of rejection for JP 2014-552357, dated Nov. 4, 2016, 13 pages.
Response to Notice of grounds of rejection for JP 2014-552357, dated Feb. 3, 2017, 20 pages.
Notice of Allowance for U.S. Appl. No. 14/712,794, dated Dec. 2, 2016, 7 pages.
Response to Second Office Action for CN 201380001359.4, dated Nov. 25, 2016.
Third Office Action for CN 201380001359.4, dated Jan. 25, 2017, 15 pages.
Patent Examination Report No. 1 for AU 2013300106, dated Nov. 23, 2016, 3 pages.
Notification of Defects in IL 237023, dated Jan. 4, 2017, 2 pages.
Notice of Reason for Rejection for JP 2015-526540, dated Oct. 17, 2016, 10 pages.

(56) References Cited

OTHER PUBLICATIONS

Response to Notice of Reason for Rejection for JP 2015-526540, dated Jan. 17, 2017, 35 pages.
Response to Examination Report for NZ 629807, dated Nov. 24, 2016, 163 pages.
Further Examination Report for NZ 629807, dated Dec. 13, 2016, 2 pages.
Response to Further Examination Report for NZ 629807, dated Mar. 8, 2017, 168 pages.
Further Examination Report Acceptance for NZ 629807, dated Apr. 4, 2017, 1 page.
Response to Written Opinion for SG 11201500872s, dated Dec. 23, 2016, 25 pages.
Notice of Eligibility to Grant for SG 11201500872s, dated Feb. 1, 2017, 6 pages.
Extended European Search Report for EP 16202341.0, dated Feb. 22, 2017, 7 pages.
Office Action for RU 2015107831, dated Apr. 5, 2017, 14 pages.
Communication pursuant to Article 94(3) EPC for EP 14 748 351.5, dated Apr. 3, 2017, 3 pages.
Official Action (translation) for RU 2015107831, dated Apr. 5, 2017, 5 pages.
Response to Third Office Action for CN 201380001359.4, filed Apr. 10, 2017, 24 pages.
Notice of Allowance for U.S. Appl. No. 14/712,794, dated Apr. 24, 2017, 4 pages.
Request for Continued Examination for U.S. Appl. No. 13/740,182, filed May 23, 2017, 38 pages.
Response to the communication pursuant to Article 94(3) EPC for EP 14 748 351.5, filed Jun. 13, 2017, 13 pages.
Examination Report No. 3 for AU 2013207712, dated Jun. 19, 2017, 11 pages.
Response to Official Action for RU 2015107831, filed Jun. 30, 2017, 6 pages.
Office Action for U.S. Appl. No. 15/435,722, dated Jul. 3, 2017, 48 pages.
Communication pursuant to Article 94(3) EPC for EP 14 748 351.5, dated Jul. 13, 2017, 6 pages.
Notice of Grounds for Rejection (translation) for JP 2014-552357, dated Aug. 1, 2017, 6 pages.
Office Action for JP 2017-005935, dated Aug. 3, 2017, 2 pages.
Official Action (translation) for RU 2015107831, dated Aug. 11, 2017, 3 pages.
Response to examination report for AU 2013207712, filed Aug. 15, 2017, 28 pages.
Notice of acceptance for AU 2013207712, dated Aug. 22, 2017, 3 pages.
Notice of Allowance for JP 2015-526540, dated Sep. 4, 2017, 3 pages.
Notification of Reexamination (translation) for CN 201380013279.0, dated Sep. 8, 2017, 1 page.
Decision to Grant for EP 13745491.4, dated Nov. 10, 2016, 2 pages.
Notice of Reasons for Rejection for JP 2015-526540, dated Apr. 25, 2017, 5 pages.
First Office Action (translation) for CN 201380001359.4, dated Jan. 13, 2016, 9 pages.
Response to Office Action for CN 201380013279.0, filed Feb. 16, 2016, 26 pages.
Response to Non-Final Office Action for U.S. Appl. No. 13/843,554, filed Dec. 19, 2014, 19 pages.
Notice of Allowance for U.S. Appl. No. 13/843,554, dated Jan. 13, 2015, 8 pages.
Restriction Requirement for U.S. Appl. No. 13/843,554, dated Jun. 30, 2014, 8 pages.
Response to Restriction Requirement for U.S. Appl. No. 13/843,554, filed Aug. 5, 2014, 3 pages.
Office Action for U.S. Appl. No. 13/843,554, dated Aug. 19, 2014, 7 pages.
Response to Notification of Reexamination (translation) for CN 201380013279.0, dated Oct. 20, 2017, 12 pages.
Response to Communication pursuant to Art 94(3) for EP 13 701 326.4, dated Jun. 29, 2017, 21 pages.
Response to Notice of Grounds for Rejection for JP 2014-552357, dated Oct. 26, 2017, 14 pages.
Response to Examination Report for AU 2013300106, dated Oct. 26, 2017, 38 pages.
Examination Report for AU 2013300106, dated Oct. 27, 2017, 3 pages.
Response to Examination Report for AU 2013300106, dated Nov. 10, 2017, 34 pages.
Notice of Acceptance for AU 2013300106, dated Nov. 21, 2017, 3 pages.
Response to Official Action for RU 2015107831, filed Nov. 13, 2017, 28 pages.
Decision on grant of patent for invention for RU 2015107831, dated Nov. 24, 2017, 37 pages. (Including English translation).
Notification of Defects in Patent Application IL No. 237023, dated Nov. 14, 2017, 2 pages (English translation).
Response to Communication pursuant to Article 94(3) EPC for EP 14 748 351.5, dated Nov. 14, 2017, 15 pages.
Communication pursuant to Article 94(3) EPC for EP 13 701 326.4, dated Oct. 27, 2017, 5 pages.
Examination Report No. 1 for AU 2014287016, dated Nov. 15, 2017, 6 pages.
International Search Report and Written Opinion for PCT/CN2016/087857, dated Sep. 29, 2016, 10 pages.
Response to Non-Final Rejection for U.S. Appl. No. 15/435,722, dated Oct. 26, 2017, 33 pages.
Non-final Rejection for U.S. Appl. No. 13/740,182, dated Oct. 18, 2017, 17 pages.
First Office Action for CN 2017121302212480, dated Dec. 18, 2017, 10 pages.
Communication pursuant to Article 94(3) EPC for EP 14 748 351.5, dated Dec. 20, 2017, 4 pages.
Notice of Grant for Patent for AU 20132077120, dated Dec. 18, 2017, 144 pages.
Voluntary amendment for CN 201380013279.0, dated Jan. 11, 2018, 14 pages.
Response to Non-Final Rejection for U.S. Appl. No. 13/740,182, dated Jan. 18, 2018, 14 pages.

\* cited by examiner

HETEROCYCLIC COMPOUNDS AND USES THEREOF

CROSS-REFERENCE TO RELATED APPLICATION

This application is a divisional of U.S. patent application Ser. No. 14/329,890, filed Jul. 11, 2014, entitled "HETEROCYCLIC COMPOUNDS AND USES THEREOF," now allowed, which claims the priority benefit of U.S. Provisional Patent Application No. 61/845,342, filed Jul. 11, 2013, entitled "HETEROCYCLIC COMPOUNDS AND USES THEREOF," and U.S. Provisional Patent Application No. 61/923,179, filed Jan. 2, 2014, entitled "HETEROCYCLIC COMPOUNDS AND USES THEREOF," the contents of which applications are incorporated by reference in their entireties. This application, in certain aspects, also relates to U.S. Provisional Patent Application No. 61/586,718, filed Jan. 13, 2012, entitled "Heterocyclic Compounds and Uses as Anticancer Agents," U.S. patent application Ser. No. 13/740,182, filed Jan. 12, 2013, entitled "HETEROCYCLIC COMPOUNDS AND USES AS ANTICANCER AGENTS," U.S. Provisional Application No. 61/680,231, filed Aug. 6, 2012, entitled "NOVEL EGFR MODULATORS AND USES THEREOF," U.S. Provisional Application No. 61/814,147, filed Apr. 19, 2013, entitled "NOVEL PYRROLOPYRIMIDINE COMPOUNDS AS INHIBITORS OF PROTEIN KINASES," U.S. patent application Ser. No. 13/843,554, filed Mar. 15, 2013, entitled "NOVEL EGFR MODULATORS AND USES THEREOF," and U.S. patent application Ser. No. 13/917,514, filed Jun. 13, 2013, entitled "NOVEL EGFR MODULATORS AND USES THEREOF." The contents of the above referenced applications are herein incorporated by reference in their entireties.

FIELD OF THE INVENTION

The field of this invention is compounds, pharmaceutical compositions and methods, especially as they are related to compositions and methods for the treatment of a proliferation disorder, a cancer, a tumor, an inflammatory disease, an autoimmune disease, psoriasis, dry eye or an immunologically related disease, and in some embodiments diseases or disorders related to the dysregulation of kinase such as, but not limited to, EGFR (including HER), Alk, PDGFR, BLK, BMX/ETK, BTK, FLT3 (D835Y), ITK, JAK such as JAK1, JAK2, JAK3, TEC and TXK, and the respective pathways.

BACKGROUND OF THE INVENTION

Protein kinases are a group of enzymes that regulate diverse, important biological processes including cell growth, proliferation, survival, invasion and differentiation, organ formation, tissue repair and regeneration, etc. Protein kinases exert their physiological functions through catalyzing the phsophorylation of protein and thereby modulating the cellular activities. Because protein kinases have profound effects on cells, their activities are highly regulated. Kinases are turned on or off by phosphorylation (sometimes by autophosphorylation), by binding of activator proteins or inhibitor proteins, or small molecules, or by controlling their location in the cell relative to their substrates. Dysfunctions in the activities of kinases, arising from genetic abnormalities or environmental factors, are known to be associated with many diseases. Several severe pathological states, including cancer and chronic inflammation, are associated with stimulation of intra-cellular signaling, and since kinases positively relay signaling events, their inhibition offers a powerful way to inhibit or control signal transduction cascades.

The epidermal growth factor receptor (EGFR; ErbB-1; HER1 in humans) is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4). EGFR is the cell-surface receptor for members of the epidermal growth factor family (EGF-family) of extracellular protein ligands. Mutations affecting EGFR expression or activity could result in cancer. EGFR is reported deregulated in most solid tumor types, i.e., lung cancer, breast cancer and brain tumor. It is estimated that mutations, amplifications or misregulations of EGFR or family members are implicated in about 30% of all epithelial cancers. Therapeutic approaches have been developed based on the inhibition of EGFR by either antibody drug or small molecular inhibitor drug, such as gefitinib and erlotinib. In the case of non small cell lung cancer, gefitinib and erlotinib have shown benefit for 10~40% of the patients. However, acquired resistant to gefitinib or erlotinib after a period of treatment become a major clinical problem. Research has confirmed that one main reason resistance developed is due to the present of the new mutation of T790M, which is the gatekeeper of EGFR. Subsequently, inhibitors can overcome this T790M have been developed and showed advantage in the clinical trial, such as BIBW2992. However, these T790M targeted EGFR inhibitor still has relative inhibitory activity towards wild type EGFR which limit the clinical application. It is needed to further develop more efficient type of EGFR inhibitor which will target mutation only but not the wild type protein.

Other protein kinases that are useful targets for small molecule pharmaceuticals include B lymphoid tyrosine kinase (BLK), bone marrow kinase on the X chromosome (BMX/ETK), Bruton's tyrosine kinase (BTK), janus kinase 1 (JAK1), janus kinase 2 (JAK2), janus kinase 3 (JAK3), tyrosine kinase expressed in hepatocellular carcinoma (TEC), resting lymphocyte kinase (TXK, also known as RLK), FMS-like tyrosine kinase 3 (FLT3), and FLT3 (D835Y).

DISCLOSURE OF THE INVENTION

In one aspect, the present disclosure provides for a heterocyclic compound having a structure according to Formula I:

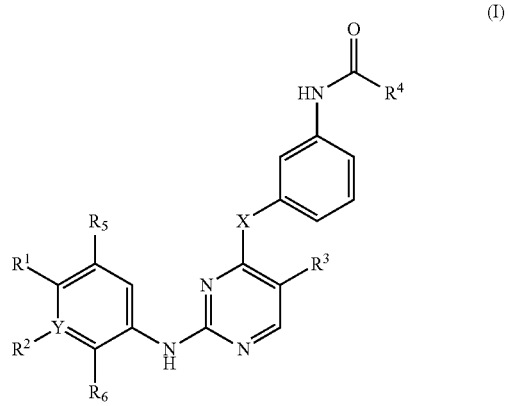

(I)

wherein
R¹ is H, or
NR^c R^d wherein R^c is H, $C_{1-4}$ alkyl or 3-7 member cyclic ring, and R^d is H, $C_{1-4}$ alkyl, optionally substituted with OZ, wherein Z is H or $C_{1-4}$ alkyl; or
3-7 member cyclic ring substituted with R^a wherein R^a is $C_{1-8}$ alkyl optionally substituted with halo;
R² is H, halo, $C_{1-4}$ alkyl, or $C_{1-4}$alkoxy;
R³ is H, halo, $C_{1-4}$ alkyl, or $C_{1-4}$alkoxy;
R⁵ is H, halo, $C_{1-4}$ alkyl, or $C_{1-4}$alkoxy;
R⁶ is H, halo, $C_{1-4}$ alkyl, or $C_{1-4}$alkoxy; or
R¹ and R⁵ are part of 3-7 member cyclic ring, optionally substituted with $C_{1-4}$ alkyl substituted with OZ, wherein Z is H or $C_{1-4}$alkyl; or
R¹ and R² are part of 3-7 member cyclic ring, optionally substituted with $C_{1-4}$ alkyl substituted with OZ, wherein Z is H or $C_{1-4}$ alkyl; or
R² and R⁶ are part of 3-7 member cyclic ring, optionally substituted with $C_{1-4}$ alkyl substituted with OZ, wherein Z is H or $C_{1-4}$ alkyl; or
R⁴ is $C_2$ alkenyl optionally substituted with $C_{1-4}$ alkyl, —CH₂OCH₃, or —CH₂N(CH₃)₂; and
X is O, $C_{1-4}$ alkyl optionally substituted with halo, or NR^b, wherein R^b is H, or $C_{1-8}$ alkyl optionally substituted with halo,
Y is CH optionally substituted with halo, or N,
wherein at least one of R², R³, R⁵ and R⁶ is not H;
or a pharmaceutically acceptable salt thereof.
In another aspect, the present disclosure provides for a heterocyclic compound having a structure according to Formula II:

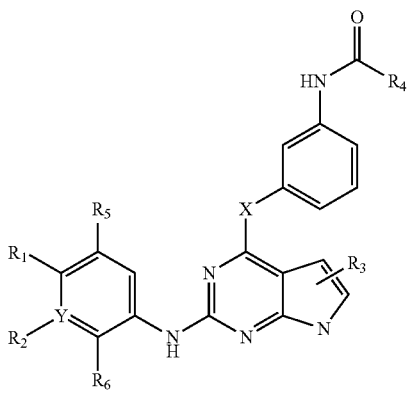
(II)

wherein
R¹ is H, or
NR^c R^d wherein R^c is H, $C_{1-4}$ alkyl or 3-7 member cyclic ring, and R^d is H, $C_{1-4}$ alkyl, optionally substituted with OZ, wherein Z is H or $C_{1-4}$ alkyl; or
NR^e R^f wherein R^e is $C_{1-4}$ alkyl, and R^f is 3-7 member cyclic ring optionally substituted with $C_{1-4}$ alkyl optionally substituted with halo; or
OR^g wherein R^g is $C_{1-4}$ alkyl substituted with CH₃O—, CH₃CH₂O—, CH₃(O)₂S—, CF₃O—,

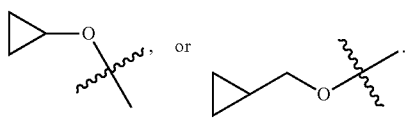 [SMILES: *OC1CC1 ; *OCC1CC1]

R² is H, halo, $C_{1-4}$ alkyl, or $C_{1-4}$alkoxy;
R³ is H, halo, $C_{1-4}$ alkyl, or $C_{1-4}$alkoxy;
R⁵ is H, halo, $C_{1-4}$ alkyl, or $C_{1-4}$alkoxy;
R⁶ is H, halo, $C_{1-4}$ alkyl, or $C_{1-4}$alkoxy; or
R¹ and R⁵ are part of 3-7 member cyclic ring, optionally substituted with $C_{1-4}$ alkyl substituted with OZ, wherein Z is H or $C_{1-4}$ alkyl; or
R¹ and R² are part of 3-7 member cyclic ring, optionally substituted with $C_{1-4}$ alkyl substituted with OZ, wherein Z is H or $C_{1-4}$ alkyl; or
R² and R⁶ are part of 3-7 member cyclic ring, optionally substituted with $C_{1-4}$ alkyl substituted with OZ, wherein Z is H or $C_{1-4}$ alkyl; or
R⁴ is $C_2$ alkenyl optionally substituted with $C_{1-4}$ alkyl, —CH₂OCH₃, or —CH₂N(CH₃)₂; and
X is O, $C_{1-4}$ alkyl optionally substituted with halo, or NR^b, wherein R^b is H, or $C_{1-8}$ alkyl optionally substituted with halo,
Y is CH optionally substituted with halo, or N,
or a pharmaceutically acceptable salt thereof.
In still another aspect, the present disclosure provides for a heterocyclic compound having a structure according to Formula Ia:

(Ia)

wherein
R¹ is H, or
NR^c R^d wherein
R^c is H, $C_{1-4}$ alkyl, $C_{1-4}$alkenyl, or 3-7 member cyclic ring, said $C_{1-4}$ alkyl, $C_{1-4}$ alkenyl, or 3-7 member cyclic ring being optionally substituted with OZ or NR₁₁R₁₂, wherein Z, R₁₁, R₁₂ are independently H or $C_{1-4}$ alkyl, or said 3-7 member cyclic ring being optionally substituted with $C_{1-4}$ alkyl that is further optionally substituted with OZ or NR₁₁R₁₂, wherein Z, R₁₁, R₁₂ are independently H or $C_{1-4}$ alkyl, or said 3-7 member cyclic ring being optionally substituted with SO₂(CH₂)_q H, wherein q is 1-4, or said 3-7 member cyclic ring being optionally substituted with $C_{1-4}$ alkyl that is further optionally substituted with SO₂(CH₂)_q H, wherein q is 1-4, or said 3-7 member cyclic ring being optionally substituted with R₈CO, wherein R₈ is $C_{1-4}$ alkyl, and
R^d is H, $C_{1-4}$ alkyl, $C_{1-4}$alkenyl, or 3-7 member cyclic ring, said $C_{1-4}$ alkyl, $C_{1-4}$ alkenyl or 3-7 member cyclic ring being optionally substituted with OZ or NR₁₁R₁₂, wherein Z, R₁₁, R₁₂ are independently H or $C_{1-4}$ alkyl; or
3-7 member cyclic ring substituted with R^a wherein R^a is $C_{1-8}$ alkyl optionally substituted with halo, $C_{1-4}$ alkoxy or SO₂(CH₂)_q H, wherein q is 1-4; or O(CH$_2$)$_m$SO$_2$(CH$_2$)$_n$H, wherein m is 1-4 and n is 1-4;
R$^2$ is absent, H, halo, C$_{1-4}$ alkyl, C$_{1-4}$ alkoxy, or alkylamine (NR$_{11}$R$_{12}$), wherein R$_{11}$ and R$_{12}$ are independently H or C$_{1-4}$ alkyl;
R$^3$ is H, hydroxyl, halo, C$_{1-4}$ alkyl, C$_{1-4}$ alkoxy, or alkylamine (NR$_{11}$R$_{12}$), wherein R$_{11}$ and R$_{12}$ are independently H or C$_{1-4}$ alkyl;
R$^5$ is absent, H, halo, C$_{1-4}$ alkyl, C$_{1-4}$ alkoxy, or alkylamine (NR$_{11}$R$_{12}$), wherein R$_{11}$ and R$_{12}$ are independently H or C$_{1-4}$ alkyl;
R$^6$ is H, halo, C$_{1-4}$ alkyl, C$_{1-4}$ alkoxy; or alkylamine (NR$_{11}$R$_{12}$), wherein R$_{11}$ and R$_{12}$ are independently H or C$_{1-4}$ alkyl;
R$^7$ is H, halo, C$_{1-4}$ alkyl, C$_{1-4}$ alkoxy, or alkylamine (NR$_{11}$R$_{12}$), wherein R$_{11}$ and R$_{12}$ are independently H or C$_{1-4}$ alkyl;
R$^9$ is H, hydroxyl, halo, C$_{1-4}$ alkyl, C$_{1-4}$ alkoxy, or alkylamine (NR$_{11}$R$_{12}$), wherein R$_{11}$ and R$_{12}$ are independently H or C$_{1-4}$ alkyl;
R$^{10}$ is H, hydroxyl, halo, C$_{1-4}$ alkyl, C$_{1-4}$ alkoxy, or alkylamine (NR$_{11}$R$_{12}$), wherein R$_{11}$ and R$_{12}$ are independently H or C$_{1-4}$ alkyl; or
R$^1$ and R$^5$ are part of 3-7 member cyclic ring, said 3-7 member cyclic being optionally substituted with C$_{1-4}$ alkyl optionally substituted with OZ or NR$_{11}$R$_{12}$ wherein Z, R$_{11}$ and R$_{12}$ are independently H or C$_{1-4}$ alkyl, or said 3-7 member cyclic being optionally substituted with R$_8$CO, wherein R$_8$ is C$_{1-4}$ alkyl, or said 3-7 member cyclic being optionally substituted with SO$_2$(CH$_2$)$_q$H, wherein q is 1-4; or
R$^1$ and R$^2$ are part of 3-7 member cyclic ring, optionally substituted with C$_{1-4}$ alkyl, said C$_{1-4}$ alkyl further optionally substituted with halo, OZ, or NR$_{11}$R$_{12}$ wherein Z, R$_{11}$ and R$_{12}$ are independently H or C$_{1-4}$ alkyl, or one or more members of said 3-7 member cyclic ring is optionally part of a carbonyl group or a sulfonyl group; or
R$^2$ and R$^6$ are part of 3-7 member cyclic ring, optionally substituted with C$_{1-4}$ alkyl optionally substituted with OZ or NR$_{11}$R$_{12}$ wherein Z, R$_{11}$ and R$_{12}$ are independently H or C$_{1-4}$ alkyl;
R$^4$ is C$_2$ alkenyl optionally substituted with C$_{1-4}$ alkyl, —CH$_2$OCH$_3$, or —CH$_2$N(CH$_3$)$_2$;
X is O, C$_{1-4}$ alkyl optionally substituted with halo, or NR$^b$, wherein R$^b$ is H, or C$_{1-8}$ alkyl optionally substituted with halo;
Y is C, CH optionally substituted with halo, or N;
A is C, CH optionally substituted with halo or N; and wherein at least one of R$^2$, R$^3$, R$^5$ and R$^6$ is not H;
or a pharmaceutically acceptable salt thereof.

In yet another aspect, the present disclosure provides for a heterocyclic compound having a structure according to Formula IIa:

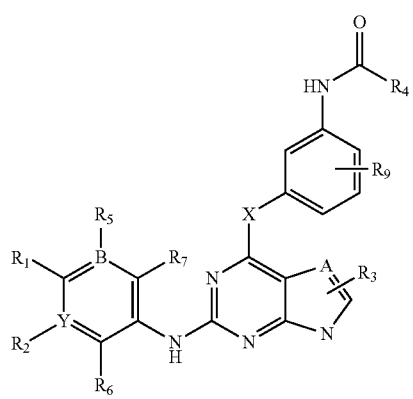

(IIa)

wherein
R$^1$ is H, or
NR$^c$R$^d$ wherein R$^c$ is H, C$_{1-4}$ alkyl or 3-7 member cyclic ring, said 3-7 member cyclic ring optionally substituted with C$_{1-4}$ alkyl optionally substituted with OZ or NR$_{10}$R$_{11}$ wherein Z, R$_{10}$ and R$_{11}$ are independently H or C$_{1-4}$ alkyl, or said 3-7 member cyclic ring being optionally substituted with R$_8$CO, wherein R$_8$ is C$_{1-4}$ alkyl, or said 3-7 member cyclic ring being optionally substituted with SO$_2$(CH$_2$)$_q$H, wherein q is 1-4, and R$^d$ is H, C$_{1-4}$ alkyl, optionally substituted with OZ or NR$_{10}$R$_{11}$ wherein Z, R$_{10}$ and R$_{11}$ are H or C$_{1-4}$ alkyl; or
NR$^e$R$^f$ wherein R$^e$ is C$_{1-4}$ alkyl, and R$^f$ is 3-7 member cyclic ring optionally substituted with C$_{1-4}$ alkyl optionally substituted with halo; or
OR$^g$ wherein R$^g$ is C$_{1-4}$ alkyl substituted with CH$_3$O—, CH$_3$CH$_2$O—, CH$_3$(O)$_2$S—, CF$_3$O—,

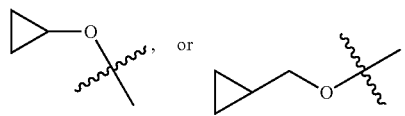 [SMILES: *OC1CC1 ; *OCC1CC1]

or
3-7 member cyclic ring substituted with R$^a$ wherein R$^a$ is C$_{1-8}$ alkyl optionally substituted with halo, C$_{1-4}$alkoxy or SO$_2$(CH$_2$)$_q$H, wherein q is 1-4, or said 3-7 member cyclic ring being optionally substituted with R$_8$CO, wherein R$_8$ is C$_{1-4}$ alkyl;
R$^2$ is absent, H, halo, C$_{1-4}$ alkyl, C$_{1-4}$alkoxy, or alkylamine (NR$_{10}$R$_{11}$), wherein R$_{10}$ and R$_{11}$ are independently H or C$_{1-4}$ alkyl;
R$^3$ is absent, H, halo, C$_{1-4}$ alkyl, or C$_{1-4}$alkoxy, or alkylamine (NR$_{10}$R$_{11}$), wherein R$_{10}$ and R$_{11}$ are independently H or C$_{1-4}$ alkyl;
R$^5$ is absent, H, halo, C$_{1-4}$ alkyl, or C$_{1-4}$alkoxy, or alkylamine (NR$_{10}$R$_{11}$), wherein R$_{10}$ and R$_{11}$ are independently H or C$_{1-4}$ alkyl;
R$^6$ is H, halo, C$_{1-4}$ alkyl, or C$_{1-4}$alkoxy, or alkylamine (NR$_{10}$R$_{11}$), wherein R$_{10}$ and R$_{11}$ are independently H or C$_{1-4}$ alkyl;
R$^7$ is H, halo, C$_{1-4}$ alkyl, C$_{1-4}$ alkoxy, or alkylamine (NR$_{10}$R$_{11}$), wherein R$_{10}$ and R$_{11}$ are independently H or C$_{1-4}$ alkyl;
R$^9$ is H, halo, C$_{1-4}$ alkyl, or C$_{1-4}$alkoxy, or alkylamine (NR$_{10}$R$_{11}$), wherein R$_{10}$ and R$_{11}$ are independently H or C$_{1-4}$ alkyl; or
R$^1$ and R$^5$ are part of 3-7 member cyclic ring, optionally substituted with C$_{1-4}$ alkyl optionally substituted with OZ or NR$_{10}$R$_{11}$ wherein Z, R$_{10}$ and R$_{11}$ are independently H or C$_{1-4}$ alkyl; or
R$^1$ and R$^2$ are part of 3-7 member cyclic ring, optionally substituted with C$_{1-4}$ alkyl optionally substituted with OZ or R$_{10}$ and R$_{11}$ wherein Z, R$_{10}$ and R$_{11}$ are independently are H or C$_{1-4}$alkyl; or
R$^2$ and R$^6$ are part of 3-7 member cyclic ring, optionally substituted with C$_{1-4}$ alkyl optionally substituted with OZ or R$_{10}$ and R$_{11}$ wherein Z, R$_{10}$ and R$_{11}$ are independently H or C$_{1-4}$ alkyl;
R$^4$ is C$_2$ alkenyl optionally substituted with C$_{1-4}$ alkyl, —CH$_2$OCH$_3$, or —CH$_2$N(CH$_3$)$_2$;
X is O, C$_{1-4}$ alkyl optionally substituted with halo, or NR$^b$, wherein R$^b$ is H, or C$_{1-8}$ alkyl optionally substituted with halo;
Y is C, CH optionally substituted with halo, or N;

A is C, CH optionally substituted with halo, or N; and
B is C, CH optionally substituted with halo, or N,
or a pharmaceutically acceptable salt thereof.

The compound described above can be used for any suitable purpose. In some embodiments, the compound described above can be used in therapy.

In still another aspect, the present disclosure provides for a pharmaceutical composition comprising a compound described above admixed with at least one pharmaceutically acceptable carrier or excipient.

In yet another aspect, the present disclosure provides for a method for treating and/or preventing a proliferation disorder, a cancer, a tumor, an inflammatory disease, an autoimmune disease, psoriasis, dry eye or an immunologically related disease, or lupus, which comprises administering to a subject in need thereof an effective amount of a compound described above or a pharmaceutical composition described above.

In yet another aspect, the present disclosure provides for a use of a compound described above for the manufacture of a medicament.

In yet another aspect, the present disclosure provides for a combination for treating and/or preventing a proliferation disorder, a cancer, a tumor, an inflammatory disease, an autoimmune disease, psoriasis, dry eye or an immunologically related disease or lupus in a subject, which combination comprises an effective amount of a compound described above, or a pharmaceutically acceptable salt thereof, and an effective amount of a second prophylactic or therapeutic agent for treating and/or preventing a proliferation disorder, a cancer, a tumor, an inflammatory disease, a n autoimmune disease, psoriasis, dry eye or an immunologically related disease or lupus in a subject.

In yet another aspect, the present disclosure provides for a method for treating and/or preventing a proliferation disorder, a cancer, a tumor, an inflammatory disease, an autoimmune disease, psoriasis, dry eye or an immunologically related disease or lupus in a subject, which methods comprises administering to a subject in need thereof an effective amount of the combination described above.

In yet another aspect, the present disclosure provides for a method for inhibiting an activity of a Bruton's tyrosine kinase (Btk or BTK) or a Janus kinase (JAK), EGFR (including HER), Alk, PDGFR, BLK, BMX/ETK, FLT3 (D835Y), ITK, TEC, TXK, and the respective pathways, in a cell or subject, which methods comprises administering to a cell or subject in need thereof an effective amount of a compound described above, or a pharmaceutical composition described above, or a combination described above.

BRIEF DESCRIPTION OF THE DRAWINGS

FIG. 1A shows reduction of the Btk Tyr223 phosphorylation in Ramos cells by PCI-32765 (Ibrutinib). FIG. 1B shows reduction of the Btk Tyr223 phosphorylation in Ramos cells by Compound No. I-1. FIG. 1C shows reduction of the Btk Tyr223 phosphorylation in Ramos cells by Compound No. I-2.

DESCRIPTION OF SELECTED EMBODIMENTS

General Definitions

Figure 1A:
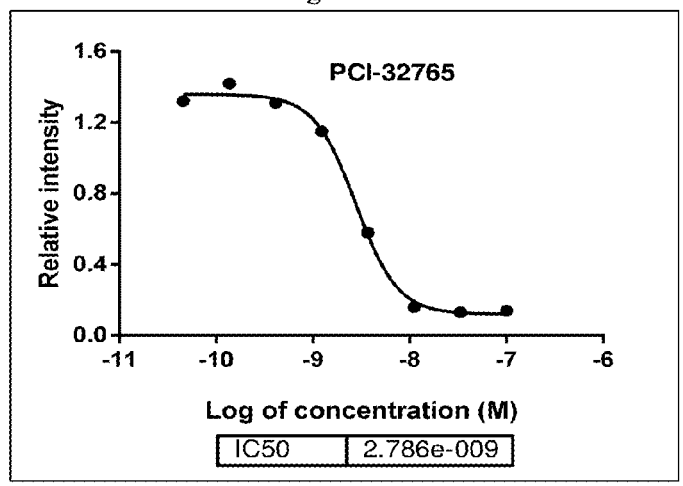
FIGS. 1A-1C show reduction of the Btk Tyr223 phosphorylation in Ramos cells by exemplary compounds.
Figure 1B:
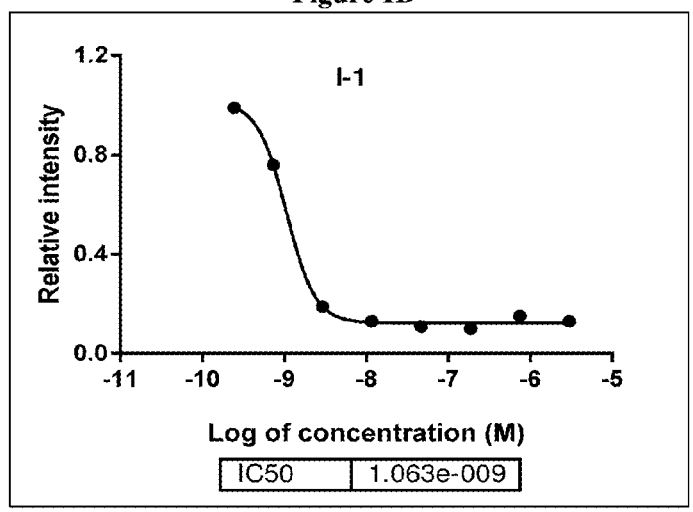
Figure 1C:
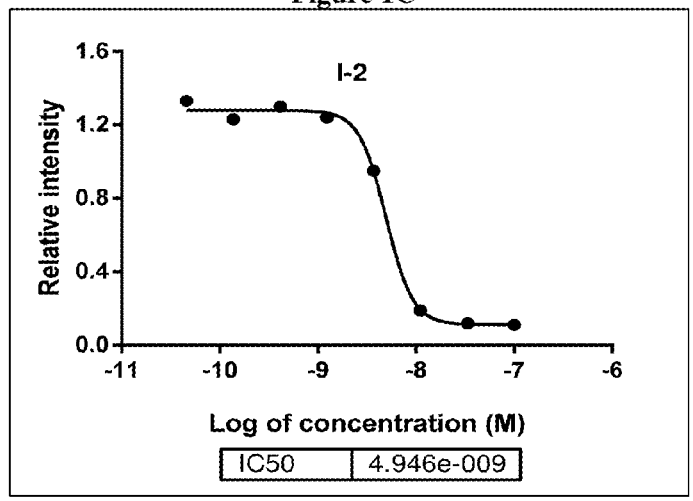
Figure 2A:
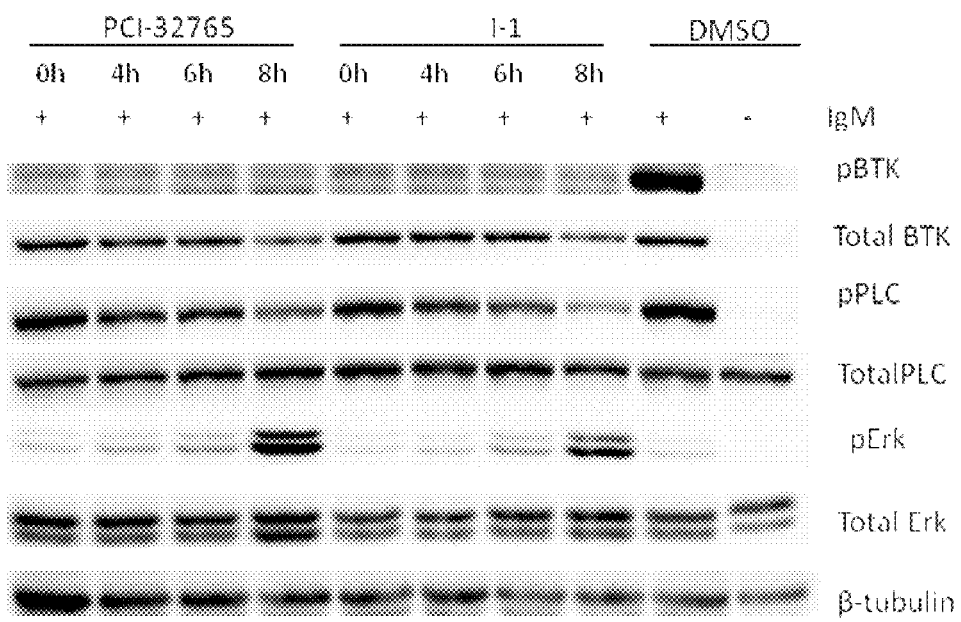
FIGS. 2A and 2B show that compounds I-1 and I-2 irreversibly inhibited the BTK phosphorylation in Ramos cells.
Figure 2B:
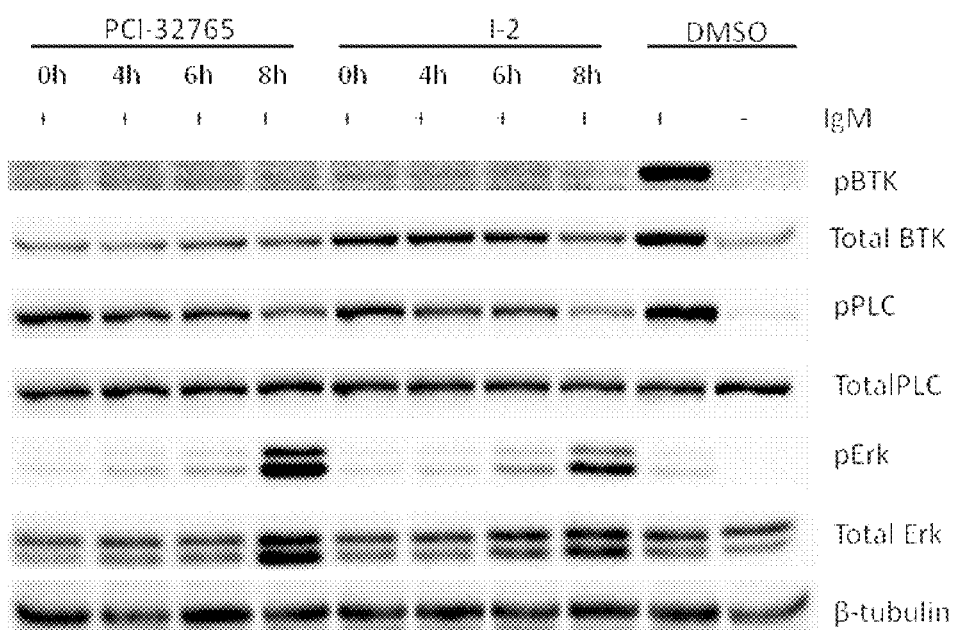

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein, "a" or "an" means "at least one" or "one or more".

The term "alkyl" as used herein refers to saturated hydrocarbon groups in a straight, branched, or cyclic configuration or any combination thereof, and particularly contemplated alkyl groups include those having ten or less carbon atoms, especially 1-6 carbon atoms and lower alkyl groups having 1-4 carbon atoms. Exemplary alkyl groups are methyl, ethyl, propyl, isopropyl, butyl, sec-butyl, tertiary butyl, pentyl, isopentyl, hexyl, cyclopropylmethyl, etc.

Alkyl groups can be unsubstituted, or they can be substituted to the extent that such substitution makes sense chemically. Typical substituents include, but are not limited to, halo, =O, =N—CN, =N—$OR^a$, =$NR^a$, —$OR^a$, —$NR^a_2$, —$SR^a$, —$SO_2R^a$, —$SO_2NR^a_2$, —$NR^aSO_2R^a$, —$NR^a$-$CONR^a_2$, —$NR^aCOOR^a$, —$NR^aCOR^a$, —CN, —$COOR^a$, —$CONR^a_2$, —$OOCR^a$, —$COR^a$, and —$NO_2$, wherein each $R^a$ is independently H, C1-C8 alkyl, C2-C8 heteroalkyl, C3-C8 heterocyclyl, C4-C10 heterocyclylalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each $R^a$ is optionally substituted with halo, =O, =N—CN, =N—$OR^b$, =$NR^b$, $OR^b$, $NR^b_2$, $SR^b$, $SO_2R^b$, $SO_2NR^b_2$, $NR^bSO_2R^b$, $NR^bCONR^b_2$, $NR^bCO$-$OR^b$, $NR^bCOR^b$, CN, $COOR^b$, $CONR^b_2$, $OOCR^b$, $COR^b$, and $NO_2$, wherein each $R^b$ is independently H, C1-C8 alkyl, C2-C8 heteroalkyl, C3-C8 heterocyclyl, C4-C10 heterocyclylalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two $R^a$ or $R^b$ groups on the same or adjacent atoms (e.g., —$NR^b2$, or —$NR^b$—$C(O)R^b$), the two $R^a$ or $R^b$ groups can optionally be taken together with the atoms in the substituent group to which are attached to form a ring having 5-8 ring members, which can be substituted as allowed for the $R^a$ or $R^b$ itself, and can contain an additional heteroatom (N, O or S) as a ring member.

The term "alkenyl" as used herein refers to an alkyl as defined above having at least two carbon atoms and at least one carbon-carbon double bond. Thus, particularly contemplated alkenyl groups include straight, branched, or cyclic alkenyl groups having two to ten carbon atoms (e.g., ethenyl, propenyl, butenyl, pentenyl, etc.) or 5-10 atoms for cyclic alkenyl groups. Alkenyl groups are optionally substituted by groups suitable for alkyl groups as set forth herein.

Similarly, the term "alkynyl" as used herein refers to an alkyl or alkenyl as defined above and having at least two (preferably three) carbon atoms and at least one carbon-carbon triple bond. Especially contemplated alkynyls include straight, branched, or cyclic alkynes having two to ten total carbon atoms (e.g., ethynyl, propynyl, butynyl, cyclopropylethynyl, etc.). Alkynyl groups are optionally substituted by groups suitable for alkyl groups as set forth herein.

The term "cycloalkyl" as used herein refers to a cyclic alkane (i.e., in which a chain of carbon atoms of a hydrocarbon forms a ring), preferably including three to eight carbon atoms. Thus, exemplary cycloalkanes include cyclopropyl, cyclobutyl, cyclopentyl, cyclohexyl, cycloheptyl, and cyclooctyl. Cycloalkyls also include one or two double bonds, which form the "cycloalkenyl" groups. Cycloalkyl groups are optionally substituted by groups suitable for alkyl groups as set forth herein.

The term "aryl" or "aromatic moiety" as used herein refers to an aromatic ring system, which may further include one or more non-carbon atoms. These are typically 5-6 membered isolated rings, or 8-10 membered bicyclic groups, and can be substituted. Thus, contemplated aryl groups include (e.g., phenyl, naphthyl, etc.) and pyridyl. Further contemplated aryl groups may be fused (i.e., covalently bound with 2 atoms on the first aromatic ring) with one or two 5- or 6-membered aryl or heterocyclic group, and are thus termed "fused aryl" or "fused aromatic".

Aromatic groups containing one or more heteroatoms (typically N, O or S) as ring members can be referred to as heteroaryl or heteroaromatic groups. Typical heteroaromatic groups include monocyclic C5-C6 aromatic groups such as pyridyl, pyrimidyl, pyrazinyl, thienyl, furanyl, pyrrolyl, pyrazolyl, thiazolyl, oxazolyl, isothiazolyl, isoxazolyl, and imidazolyl and the fused bicyclic moieties formed by fusing one of these monocyclic groups with a phenyl ring or with any of the heteroaromatic monocyclic groups to form a C8-C10 bicyclic group such as indolyl, benzimidazolyl, indazolyl, benzotriazolyl, isoquinolyl, quinolyl, benzothiazolyl, benzofuranyl, pyrazolopyridyl, pyrazolopyrimidyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. Typically, the ring systems contain 5-12 ring member atoms.

As also used herein, the terms "heterocycle", "cycloheteroalkyl", and "heterocyclic moieties" are used interchangeably herein and refer to any compound in which a plurality of atoms form a ring via a plurality of covalent bonds, wherein the ring includes at least one atom other than a carbon atom as a ring member. Particularly contemplated heterocyclic rings include 5- and 6-membered rings with nitrogen, sulfur, or oxygen as the non-carbon atom (e.g., imidazole, pyrrole, triazole, dihydropyrimidine, indole, pyridine, thiazole, tetrazole etc.). Typically these rings contain 0-1 oxygen or sulfur atoms, at least one and typically 2-3 carbon atoms, and up to four nitrogen atoms as ring members. Further contemplated heterocycles may be fused (i.e., covalently bound with two atoms on the first heterocyclic ring) to one or two carbocyclic rings or heterocycles, and are thus termed "fused heterocycle" or "fused heterocyclic ring" or "fused heterocyclic moieties" as used herein. Where the ring is aromatic, these can be referred to herein as 'heteroaryl' or heteroaromatic groups.

Heterocyclic groups that are not aromatic can be substituted with groups suitable for alkyl group substituents, as set forth above.

Aryl and heteroaryl groups can be substituted where permitted. Suitable substituents include, but are not limited to, halo, —$OR^a$, —$NR^a_2$, —$SR^a$, —$SO_2R^a$, —$SO_2NR^a_2$, —$NR^aSO_2R^a$, —$NR^aCONR^a_2$, —$NR^aCOOR^a$, —$NR^aCOR^a$, —CN, —$COOR^a$, —$CONR^a_2$, —$OOCR^a$, —$COR^a$, and —$NO_2$, wherein each $R^a$ is independently H, C1-C8 alkyl, C2-C8 heteroalkyl, C3-C8 heterocyclyl, C4-C10 heterocyclylalkyl, C1-C8 acyl, C2-C8 heteroacyl, C2-C8 alkenyl, C2-C8 heteroalkenyl, C2-C8 alkynyl, C2-C8 heteroalkynyl, C6-C10 aryl, or C5-C10 heteroaryl, and each $R^a$ is optionally substituted with halo, =O, =N—CN, =N—$OR^b$, =$NR^b$, $OR^b$, $NR^b_2$, $SR^b$, $SO_2R^b$, $SO_2NR^b_2$, $NR^bSO_2R^b_2$, $NR^bCONR^b_2$, $NR^bCOOR^b$, $NR^bCOR^b$, CN, $COOR^b$, $CONR^b_2$, $OOCR^b$, $COR^b$, and $NO_2$, wherein each $R^b$ is independently H, C1-C8 alkyl, C2-C8 heteroalkyl, C3-C8 heterocyclyl, C4-C10 heterocyclylalkyl, C1-C8 acyl, C2-C8 heteroacyl, C6-C10 aryl or C5-C10 heteroaryl. Alkyl, alkenyl and alkynyl groups can also be substituted by C1-C8 acyl, C2-C8 heteroacyl, C6-C10 aryl or C5-C10 heteroaryl, each of which can be substituted by the substituents that are appropriate for the particular group. Where a substituent group contains two $R^a$ or $R^b$ groups on the same or adjacent atoms (e.g., —$NR^b2$, or $NR^b$—$C(O)R^b$), the two $R^a$ or $R^b$ groups can optionally be taken together with the atoms in the substituent group to which are attached to form a ring having 5-8 ring members, which can be substituted as allowed for the $R^a$ or $R^b$ itself, and can contain an additional heteroatom (N, O or S) as a ring member.

As also used herein, the terms "imidazopyridine" or "imidazopyrimidine" or "thiazopyridine" or "thiazopyrimidine" herein refer to any compound in which the two designated heterocyclic rings are fused by any two adjacent atoms on the two heterocyclic rings.

The term "alkoxy" as used herein refers to a hydrocarbon group connected through an oxygen atom, e.g., —O-Hc, wherein the hydrocarbon portion Hc may have any number of carbon atoms, typically 1-10 carbon atoms, may further include a double or triple bond and may include one or two oxygen, sulfur or nitrogen atoms in the alkyl chains, and can be substituted with aryl, heteroaryl, cycloalkyl, and/or heterocyclyl groups. For example, suitable alkoxy groups include methoxy, ethoxy, propyloxy, isopropoxy, methoxyethoxy, benzyloxy, allyloxy, and the like. Similarly, the term "alkylthio" refers to alkylsulfides of the general formula —S-Hc, wherein the hydrocarbon portion Hc is as described for alkoxy groups. For example, contemplated alkylthio groups include methylthio, ethylthio, isopropylthio, methoxyethylthio, benzylthio, allylthio, and the like.

The term 'amino' as used herein refers to the group $NH_2$. The term "alkylamino" refers to amino groups where one or both hydrogen atoms are replaced by a hydrocarbon group Hc as described above, wherein the amino nitrogen "N" can be substituted by one or two Hc groups as set forth for alkoxy groups described above. Exemplary alkylamino groups include methylamino, dimethylamino, ethylamino, diethylamino, etc. Also, the term "substituted amino" refers to amino groups where one or both hydrogen atoms are replaced by a hydrocarbon group Hc as described above, wherein the amino nitrogen "N" can be substituted by one or two Hc groups as set forth for alkoxy groups described above.

The term 'acyl' as used herein refers to a group of the formula —C(=O)-D, where D represents an alkyl, alkenyl, alkynyl, cycloalkyl, aryl, heteroaryl, or heterocycle as described above. Typical examples are groups wherein D is a C1-C10 alkyl, C2-C10 alkenyl or alkynyl, or phenyl, each of which is optionally substituted. In some embodiments, D can be H, Me, Et, isopropyl, propyl, butyl, C1-C4 alkyl substituted with —OH, —OMe, or NH$_2$, phenyl, halophenyl, alkylphenyl, and the like.

The term "aryloxy" as used herein refers to an aryl group connecting to an oxygen atom, wherein the aryl group may be further substituted. For example suitable aryloxy groups include phenyloxy, etc. Similarly, the term "arylthio" as used herein refers to an aryl group connecting to a sulfur atom, wherein the aryl group may be further substituted. For example suitable arylthio groups include phenylthio, etc.

The hydrocarbon portion of each alkoxy, alkylthio, alkylamino, and aryloxy, etc. can be substituted as appropriate for the relevant hydrocarbon moiety.

The term "halogen" as used herein refers to fluorine, chlorine, bromine and iodine. Where present as a substituent group, halogen or halo typically refers to F or Cl or Br, more typically F or Cl.

The term "haloalkyl" refers to an alkyl group as described above, wherein one or more hydrogen atoms on the alkyl group have been substituted with a halo group. Examples of such groups include, without limitation, fluoroalkyl groups, such as fluoroethyl, trifluoromethyl, difluoromethyl, trifluoroethyl and the like.

The term "haloalkoxy" refers to the group alkyl-O— wherein one or more hydrogen atoms on the alkyl group have been substituted with a halo group and include, by way of examples, groups such as trifluoromethoxy, and the like.

The term "sulfonyl" refers to the group $SO_2$-alkyl, $SO_2$-substituted alkyl, $SO_2$-alkenyl, $SO_2$-substituted alkenyl, $SO_2$-cycloalkyl, $SO_2$-substituted cycloalkyl, $SO_2$-cycloalkenyl, $SO_2$-substituted cycloalkenyl, $SO_2$-aryl, $SO_2$-substituted aryl, $SO_2$-heteroaryl, $SO_2$-substituted heteroaryl, $SO_2$-heterocyclic, and $SO_2$-substituted heterocyclic, wherein each alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-$SO_2$—, phenyl-$SO_2$—, and 4-methylphenyl-$SO_2$—.

The term "sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein The term "aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

The term "acylamino" refers to the groups —NR$^{20}$C(O) alkyl, —NR$^{20}$C(O)substituted alkyl, —NR$^{20}$C(O)cycloalkyl, —NR$^{20}$C(O)substituted cycloalkyl, —NR$^{20}$C(O) cycloalkenyl, —NR$^{20}$C(O)substituted cycloalkenyl, —NR$^{20}$C(O)alkenyl, —NR$^{20}$C(O)substituted alkenyl, —NR$^{20}$C(O)alkynyl, —NR$^{20}$C(O)substituted alkynyl, —NR$^{20}$C(O)aryl, —NR$^{20}$C(O)substituted aryl, —NR$^{20}$C (O)heteroaryl, —NR$^{20}$C(O)substituted heteroaryl, —NR$^{20}$C (O)heterocyclic, and —NR$^{20}$C(O)substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "aminocarbonylamino" refers to the group —NR$^{20}$C(O)NR$^{21}$R$^{22}$, wherein R$^{20}$ is hydrogen or alkyl and R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

It should further be recognized that all of the above-defined groups may further be substituted with one or more substituents, which may in turn be substituted with hydroxy, amino, cyano, C1-C4 alkyl, halo, or C1-C4 haloalkyl. For example, a hydrogen atom in an alkyl or aryl can be replaced by an amino, halo or C1-4 haloalkyl or alkyl group.

The term "substituted" as used herein refers to a replacement of a hydrogen atom of the unsubstituted group with a functional group, and particularly contemplated functional groups include nucleophilic groups (e.g., —NH$_2$, —OH, —SH, —CN, etc.), electrophilic groups (e.g., C(O)OR, C(X)OH, etc.), polar groups (e.g., —OH), non-polar groups (e.g., heterocycle, aryl, alkyl, alkenyl, alkynyl, etc.), ionic groups (e.g., —NH$_3^+$), and halogens (e.g., —F, —Cl), NHCOR, NHCONH$_2$, OCH$_2$COOH, OCH$_2$CONH$_2$, OCH$_2$CONHR, NHCH$_2$COOH, NHCH$_2$CONH$_2$, NHSO$_2$R, OCH$_2$-heterocycles, PO$_3$H, SO$_3$H, amino acids, and all chemically reasonable combinations thereof. Moreover, the term "substituted" also includes multiple degrees of substitution, and where multiple substituents are disclosed or claimed, the substituted compound can be independently substituted by one or more of the disclosed or claimed substituent moieties.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, compounds arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal, such as human (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

The compounds and compositions described herein can be administered to a subject in need of treatment for a cell proliferation disorder such as cancer, particularly cancers selected from leukemia, lymphoma, lung cancer, colon cancer, CNS cancer, melanoma, ovarian cancer, renal cancer, prostate cancer, breast cancer, head and neck cancers, and pancreatic cancer. The subject is typically a mammal diagnosed as being in need of treatment for one or more of such proliferative disorders, and frequently the subject is a human. The methods comprise administering an effective amount of at least one compound of the invention; optionally the compound may be administered in combination with one or more additional therapeutic agents, particularly therapeutic agents known to be useful for treating the cancer or proliferative disorder afflicting the particular subject.

Exemplary Compounds

Formula I

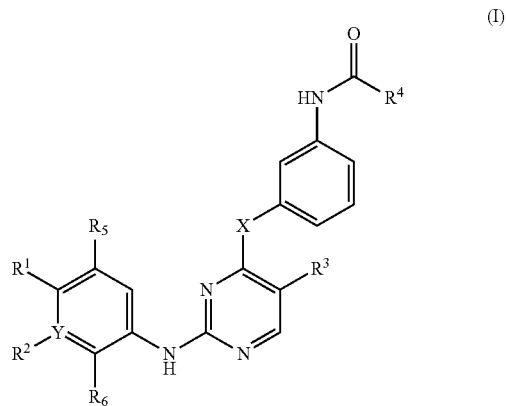

(I)

In one aspect, the present disclosure provides for a compound of Formula (I):
wherein
$R^1$ is H, or
$NR^cR^d$ wherein $R^c$ is H, $C_{1-4}$ alkyl or 3-7 member cyclic ring, and $R^d$ is H, $C_{1-4}$ alkyl, optionally substituted with OZ, wherein Z is H or $C_{1-4}$ alkyl; or
3-7 member cyclic ring substituted with $R^a$ wherein $R^a$ is $C_{1-8}$ alkyl optionally substituted with halo;
$R^2$ is H, halo, $C_{1-4}$ alkyl, or $C_{1-4}$ alkoxy;
$R^3$ is H, halo, $C_{1-4}$ alkyl, or $C_{1-4}$ alkoxy;
$R^5$ is H, halo, $C_{1-4}$ alkyl, or $C_{1-4}$ alkoxy;
$R^6$ is H, halo, $C_{1-4}$ alkyl, or $C_{1-4}$ alkoxy; or
$R^1$ and $R^5$ are part of 3-7 member cyclic ring, optionally substituted with $C_{1-4}$ alkyl substituted with OZ, wherein Z is H or $C_{1-4}$ alkyl; or
$R^1$ and $R^2$ are part of 3-7 member cyclic ring, optionally substituted with $C_{1-4}$ alkyl substituted with OZ, wherein Z is H or $C_{1-4}$ alkyl; or
$R^2$ and $R^6$ are part of 3-7 member cyclic ring, optionally substituted with $C_{1-4}$ alkyl substituted with OZ, wherein Z is H or $C_{1-4}$ alkyl; or
$R^4$ is $C_2$ alkenyl optionally substituted with $C_{1-4}$ alkyl, —$CH_2OCH_3$, or —$CH_2N(CH_3)_2$; and
X is O, $C_{1-4}$ alkyl optionally substituted with halo, or $NR^b$, wherein $R^b$ is H, or $C_{1-8}$ alkyl optionally substituted with halo,
Y is CH optionally substituted with halo, or N,
wherein at least one of $R^2$, $R^3$, $R^5$ and $R^6$ is not H;
or a pharmaceutically acceptable salt thereof.

In some embodiments, $R^1$ is H, and $R^2$ and $R^6$ are part of 3-7 member cyclic ring, optionally substituted with OZ, wherein Z is H or $C_{1-4}$ alkyl, e.g., methyl. The 3-7 member cyclic ring can be a 3, 4, 5, 6, or 7 member cyclic ring. It can be carbon cyclic ring or hetero cyclic ring.

In some embodiments, $R^1$ is $NR^cR^d$ and $R^c$ is methyl. In other embodiments, $R^1$ is $NR^cR^d$ and $R^c$ is 3-7 member cyclic ring. The 3-7 member cyclic ring can be a 3, 4, 5, 6, or 7 member cyclic ring. It can be carbon cyclic ring or hetero cyclic ring. For example, the 3-7 member cyclic ring can be a $C_3$ cyclic ring. $R^d$ can be $C_2$ alkyl substituted with OZ, and Z is H or $C_{1-4}$ alkyl, e.g., methyl.

In some embodiments, $R^1$ is 3-7 member cyclic ring substituted with $R^a$. The 3-7 member cyclic ring can be a 3, 4, 5, 6, or 7 member cyclic ring. It can be carbon cyclic ring or hetero cyclic ring. For example, $R^1$ can be

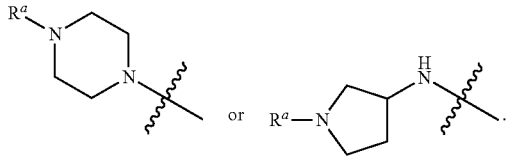

In some embodiments, $R^1$ is

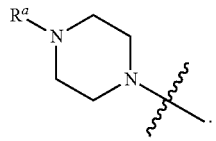

$R^a$ can be $C_{1-4}$ alkyl optionally substituted with halo or $C_{1-4}$ alkoxy. For example, $R^a$ can be $C_{1-4}$ alkyl substituted with fluoro or $C_{1-8}$ alkyl substituted with fluoro. In other embodiments, $R^1$ is

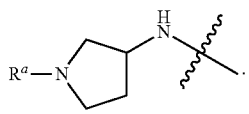

$R^a$ can be $C_{1-4}$ alkyl optionally substituted with halo or $C_{1-4}$ alkoxy. For example, $R^a$ can be $C_{1-4}$ alkyl substituted with fluoro or $C_{1-8}$ alkyl substituted with fluoro.

In some embodiments, $R^2$ can be H. In other embodiments, $R^2$ can be halo, e.g., fluoro. In still other embodiments, $R^2$ can be $C_{1-4}$ alkyl, e.g., methyl, or $C_{1-4}$ alkoxy, e.g., methoxy.

In some embodiments, $R^5$ can be H. In other embodiments, $R^5$ can be halo, e.g., fluoro. In still other embodiments, $R^5$ can be $C_{1-4}$ alkyl, e.g., methyl, or $C_{1-4}$ alkoxy, e.g., methoxy.

In some embodiments, $R^6$ can be H. In other embodiments, $R^6$ can be halo, e.g., fluoro. In still other embodiments, $R^6$ can be $C_{1-4}$ alkyl, e.g., methyl, or $C_{1-4}$ alkoxy, e.g., methoxy.

In some embodiments, $R^1$ and $R^5$ can be part of 3-7 member cyclic ring, optionally substituted with $C_{1-4}$ alkyl substituted with OZ, wherein Z is H or $C_{1-4}$ alkyl, e.g., methyl. In other embodiments, $R^1$ and $R^2$ can be part of 3-7 member cyclic ring, optionally substituted with $C_{1-4}$ alkyl substituted with OZ, wherein Z is H or $C_{1-4}$ alkyl, e.g., methyl. In still other embodiments, $R^2$ and $R^6$ can be part of 3-7 member cyclic ring, optionally substituted with $C_{1-4}$ alkyl substituted with OZ, wherein Z is H or $C_{1-4}$ alkyl, e.g., methyl. The 3-7 member cyclic ring can be a 3, 4, 5, 6, or 7 member cyclic ring. It can be carbon cyclic ring or hetero cyclic ring. For example, the 3-7 member cyclic ring can be a 5 member cyclic ring. The 5 member cyclic ring can be heterocyclic ring, e.g., a 5 member heterocyclic ring that comprises a N atom. The $C_{1-4}$ alkyl can be $C_1$, $C_2$, $C_3$, or $C_4$ alkyl. For example, Z can be methyl.

In some embodiments, $R^3$ can be H. In other embodiments, $R^3$ can be halo, e.g., fluoro. In still other embodiments, $R^3$ can be $C_{1-4}$ alkyl, e.g., methyl, or $C_{1-4}$ alkoxy, e.g., methoxy.

In some embodiments, $R^2$, $R^5$, or $R^6$ is H or halo and $R^3$ is halo, $C_{1-4}$ alkyl, e.g., methyl, or $C_{1-4}$ alkoxy.

In some embodiments, $R^4$ can be unsubstituted $C_2$ alkenyl. In other embodiments, $R^4$ can be $C_2$ alkenyl substituted with $C_{1-4}$ alkyl, —$CH_2OCH_3$, or —$CH_2N(CH_3)_2$.

In some embodiments, X can be O. In other embodiments, X can be $C_{1-4}$ alkyl optionally substituted with halo. For example, X can be unsubstituted $C_{1-4}$ alkyl, e.g., $CH_2$. In another example, X can be $C_{1-4}$ alkyl substituted with halo, e.g., $CF_2$. In still other embodiments, X can be $NR^b$, and $R^b$ can be H, or $C_{1-8}$ alkyl optionally substituted with halo. For example, le can be H. In another example, $R^b$ can be $C_{1-8}$ alkyl. In still another example, $R^b$ is $C_{1-4}$ alkyl, e.g., $C_1$, $C_2$, $C_3$, or $C_4$ alkyl. The $C_{1-4}$ alkyl or $C_{1-8}$ alkyl can be substituted with halo, e.g., fluoro.

In some embodiments, Y can be CH. In other embodiments, Y can be CF or N.

In some embodiments, the present disclosure provides for a compound selected from the group consisting of compound I-1, I-2, I-3, I-4, I-5, I-6, I-7, I-8, I-9, I-12, I-13, I-14, I-15, I-16, I-17, I-18, I-19, I-20, I-21, I-22, I-23, I-24, I-25 and I-41 having the Formula below.

I-1

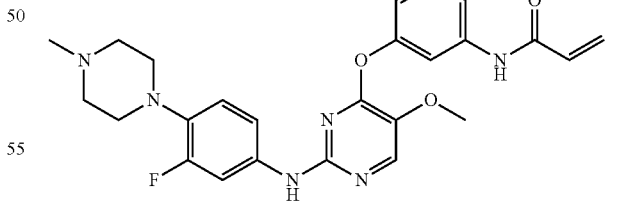

I-2

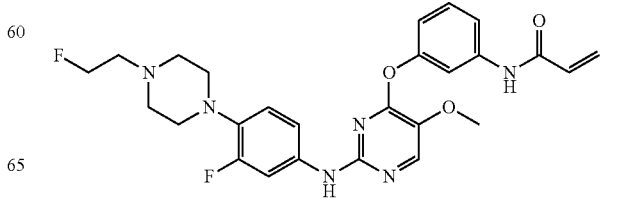

I-3

I-4
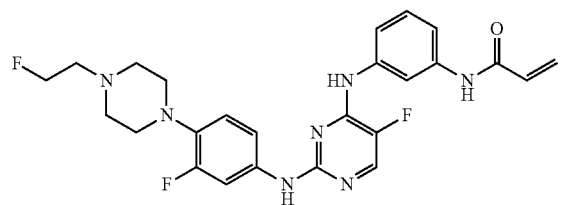
I-5
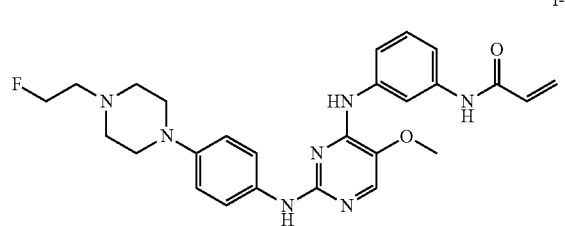
I-6
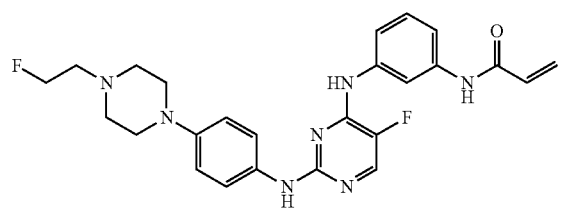
I-7
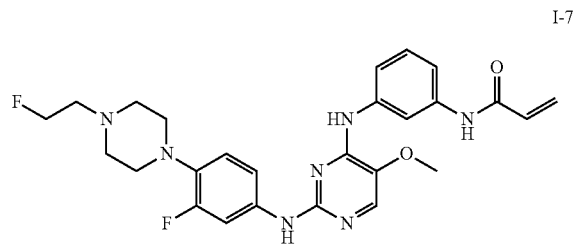
I-8
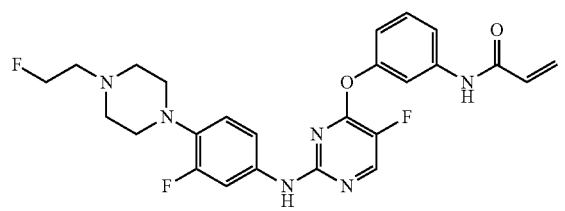
I-9
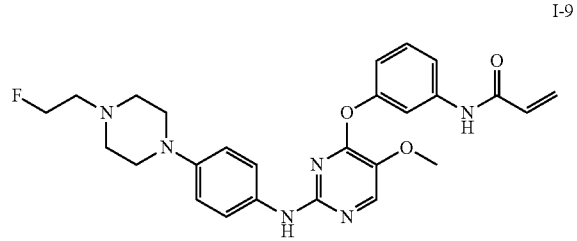
I-12
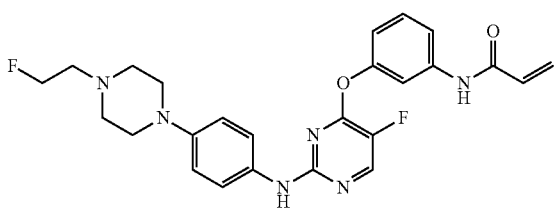
I-13
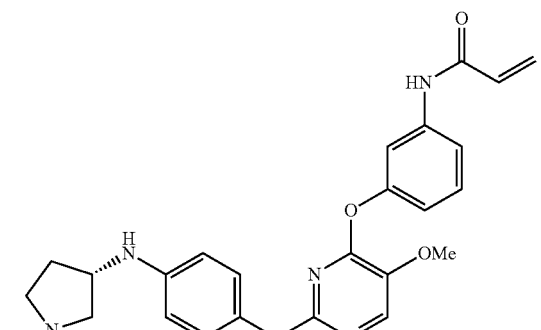
I-14
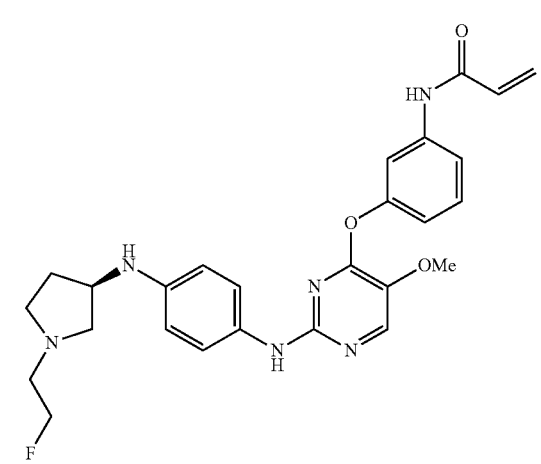
I-15
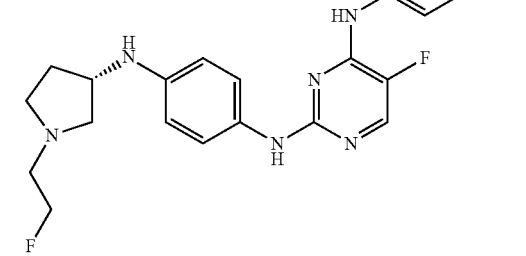

-continued
I-16
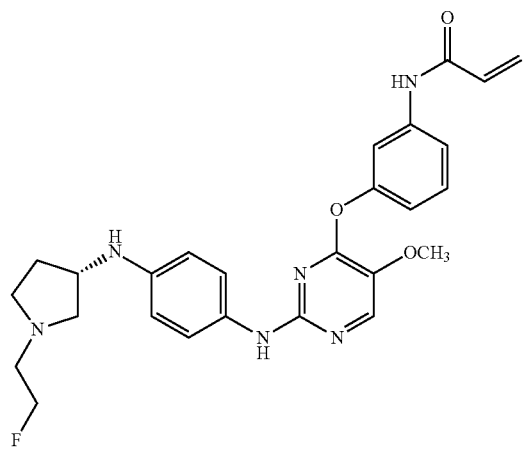
I-17
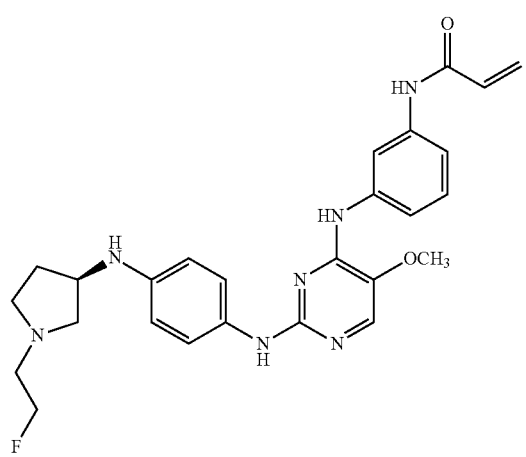
I-18
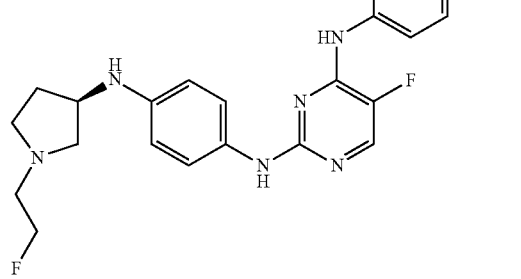
-continued
I-19
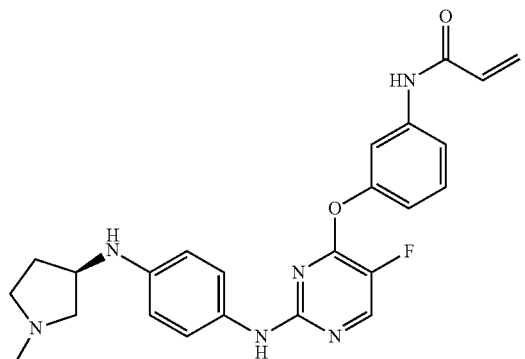
I-20
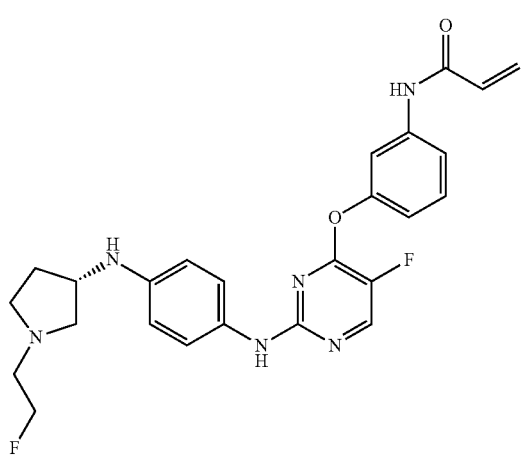
I-21
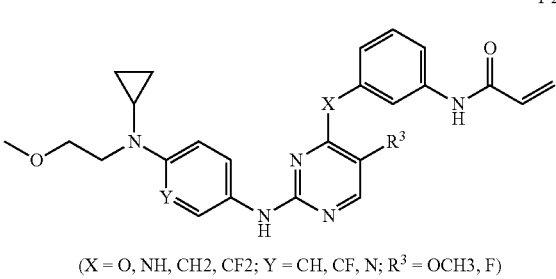
(X = O, NH, CH2, CF2; Y = CH, CF, N; R³ = OCH3, F)
I-22
(X = O, NH, CH2, CF2; Y = CH, CF, N; R³ = OCH3, F)

-continued

I-23
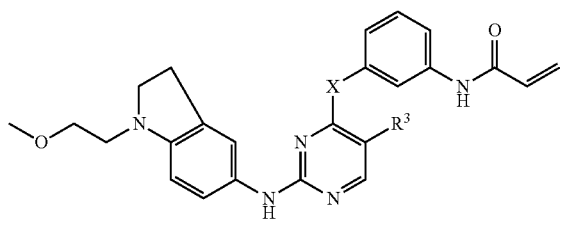
(X = O, NH, CH2, CF2; R³ = OCH3, F)

I-24
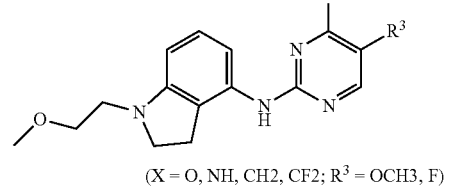
(X = O, NH, CH2, CF2; R³ = OCH3, F)

I-25
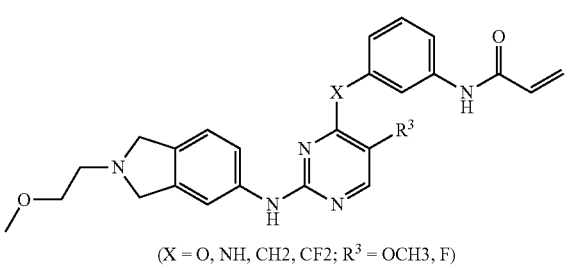
(X = O, NH, CH2, CF2; R³ = OCH3, F)

I-41
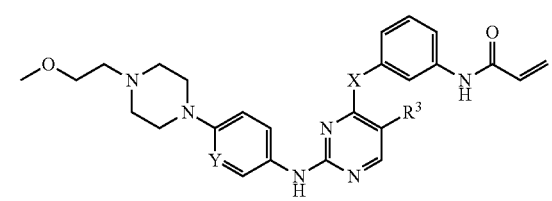
(X = O, NH, CH2, CF2; Y = CH, CF, N; R³ = OCH3, F)

In another aspect, the present disclosure provides for a compound of Formula (II):

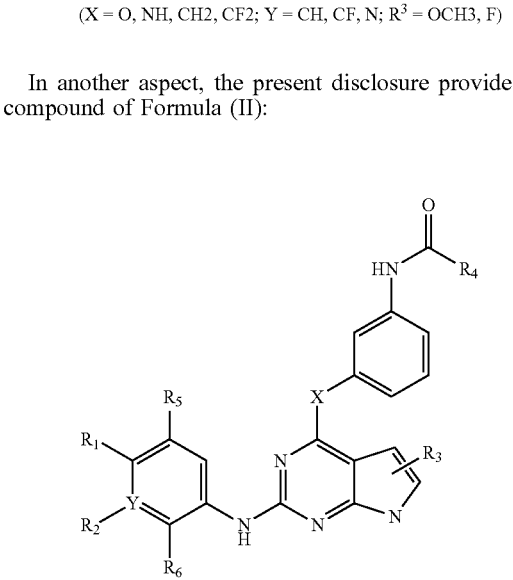

wherein
$R^1$ is H, or
  $NR^cR^d$ wherein $R^c$ is H, $C_{1-4}$ alkyl or 3-7 member cyclic ring, and $R^d$ is H, $C_{1-4}$ alkyl, optionally substituted with OZ, wherein Z is H or $C_{1-4}$ alkyl; or
  $NR^eR^f$ wherein $R^e$ is $C_{1-4}$ alkyl, and $R^f$ is 3-7 member cyclic ring optionally substituted with $C_{1-4}$ alkyl optionally substituted with halo; or
  $OR^g$ wherein $R^g$ is $C_{1-4}$ alkyl substituted with $CH_3O$—, $CH_3CH_2O$—, $CH_3(O)_2S$—, $CF_3O$—,

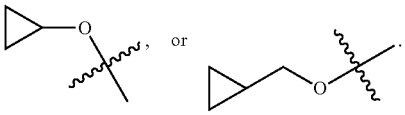 [SMILES: *OC1CC1 ; *OCC1CC1]

$R^2$ is H, halo, $C_{1-4}$ alkyl, or $C_{1-4}$ alkoxy;
$R^3$ is H, halo, $C_{1-4}$ alkyl, or $C_{1-4}$ alkoxy;
$R^5$ is H, halo, $C_{1-4}$ alkyl, or $C_{1-4}$ alkoxy;
$R^6$ is H, halo, $C_{1-4}$ alkyl, or $C_{1-4}$ alkoxy; or
$R^1$ and $R^5$ are part of 3-7 member cyclic ring, optionally substituted with $C_{1-4}$ alkyl substituted with OZ, wherein Z is H or $C_{1-4}$ alkyl; or
$R^1$ and $R^2$ are part of 3-7 member cyclic ring, optionally substituted with $C_{1-4}$ alkyl substituted with OZ, wherein Z is H or $C_{1-4}$ alkyl; or
$R^2$ and $R^6$ are part of 3-7 member cyclic ring, optionally substituted with $C_{1-4}$ alkyl substituted with OZ, wherein Z is H or $C_{1-4}$ alkyl; or
$R^4$ is $C_2$ alkenyl optionally substituted with $C_{1-4}$ alkyl, —$CH_2OCH_3$, or —$CH_2N(CH_3)_2$; and
X is O, $C_{1-4}$ alkyl optionally substituted with halo, or $NR^b$, wherein $R^b$ is H, or $C_{1-8}$ alkyl optionally substituted with halo,
Y is CH optionally substituted with halo, or N,
or a pharmaceutically acceptable salt thereof.

In some embodiments, $R^1$ can be H, and $R^2$ and $R^6$ can be part of 3-7 member cyclic ring, optionally substituted with $C_{1-4}$ alkyl substituted with OZ, wherein Z is H or $C_{1-4}$ alkyl, e.g., methyl. The 3-7 member cyclic ring can be a 3, 4, 5, 6, or 7 member cyclic ring. It can be carbon cyclic ring or hetero cyclic ring.

In some embodiments, $R^1$ can be $NR^cR^d$ and $R^c$ can be $C_{1-4}$ alkyl, e.g., methyl. In other embodiments, $R^1$ can be $NR^cR^d$ and $R^c$ can be 3-7 member cyclic ring. The 3-7 member cyclic ring can be a 3, 4, 5, 6, or 7 member cyclic ring. It can be carbon cyclic ring or hetero cyclic ring. For example, the 3-7 member cyclic ring can be $C_3$ cyclic ring. $R^d$ can be $C_2$ alkyl substituted with OZ, and Z can be $C_{1-4}$ alkyl, e.g., methyl.

In some embodiments, $R^1$ can be $NR^eR^f$, $R^e$ can be $C_{1-4}$ alkyl, and $R^f$ can be 3-7 member cyclic ring optionally substituted with $C_{1-4}$ alkyl optionally substituted with halo. The 3-7 member cyclic ring can be a 3, 4, 5, 6, or 7 member cyclic ring. It can be carbon cyclic ring or hetero cyclic ring. For example, the 3-7 member cyclic ring can be 5 member cyclic ring. In another example, the 5 member cyclic ring can be heterocyclic ring, e.g., the 5 member heterocyclic ring that comprises a N atom. The 3-7 member cyclic ring can be substituted with $FCH_2CH_2$—. The $C_{1-4}$ alkyl can be $C_1$, $C_2$, $C_3$, or $C_4$ alkyl.

In some embodiments, $R^1$ is $OR^g$ and $R^g$ is $C_{1-4}$ alkyl substituted with $CH_3O—$, $CH_3CH_2O—$, $CH_3(O)_2S—$, $CF_3O—$,

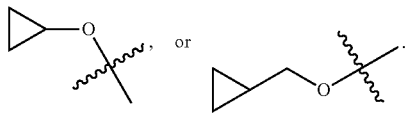

The $C_{1-4}$ alkyl can be $C_1$, $C_2$, $C_3$, or $C_4$ alkyl, e.g., $C_2$ alkyl.

In some embodiments, $R^2$ can be H. In other embodiments, $R^2$ can be halo, e.g., fluoro. In still other embodiments, $R^2$ can be $C_{1-4}$ alkyl, e.g., methyl, or $C_{1-4}$ alkoxy, e.g., methoxy.

In some embodiments, $R^5$ can be H. In other embodiments, $R^5$ can be halo, e.g., fluoro. In still other embodiments, $R^5$ can be $C_{1-4}$ alkyl, e.g., methyl, or $C_{1-4}$ alkoxy, e.g., methoxy.

In some embodiments, $R^6$ can be H. In other embodiments, $R^6$ can be halo, e.g., fluoro. In still other embodiments, $R^6$ can be $C_{1-4}$ alkyl, e.g., methyl, or $C_{1-4}$ alkoxy, e.g., methoxy.

In some embodiments, $R^1$ and $R^5$ can be part of 3-7 member cyclic ring, optionally substituted with $C_{1-4}$ alkyl substituted with OZ, wherein Z is H or $C_{1-4}$ alkyl, e.g., methyl. In other embodiments, $R^1$ and $R^2$ can be part of 3-7 member cyclic ring, optionally substituted with $C_{1-4}$ alkyl substituted with OZ, wherein Z is H or $C_{1-4}$ alkyl, e.g., methyl. In still other embodiments, $R^2$ and $R^6$ can be part of 3-7 member cyclic ring, optionally substituted with $C_{1-4}$ alkyl substituted with OZ, wherein Z is H or $C_{1-4}$ alkyl, e.g., methyl. The 3-7 member cyclic ring can be a 3, 4, 5, 6, or 7 member cyclic ring. It can be carbon cyclic ring or hetero cyclic ring. For example, the 3-7 member cyclic ring can be a 5 member cyclic ring. The 5 member cyclic ring can be heterocyclic ring, e.g., a 5 member heterocyclic ring that comprises a N atom. The $C_{1-4}$ alkyl can be $C_1$, $C_2$, $C_3$, or $C_4$ alkyl. For example, Z can be methyl.

In some embodiments, $R^3$ can be H. In other embodiments, $R^3$ can be halo, e.g., fluoro. In still other embodiments, $R^3$ can be $C_{1-4}$ alkyl, e.g., methyl, or $C_{1-4}$ alkoxy, e.g., methoxy.

In some embodiments, $R^2$, $R^5$, or $R^6$ is H or halo and $R^3$ is halo, $C_{1-4}$ alkyl, e.g., methyl, or $C_{1-4}$ alkoxy.

In some embodiments, $R^4$ can be unsubstituted $C_2$ alkenyl. In other embodiments, $R^4$ can be $C_2$ alkenyl substituted with $C_{1-4}$ alkyl, $—CH_2OCH_3$, or $—CH_2N(CH_3)_2$.

In some embodiments, X can be O. In other embodiments, X can be $C_{1-4}$ alkyl optionally substituted with halo. For example, X can be unsubstituted $C_{1-4}$ alkyl, e.g., $CH_2$. In another example, X can be $C_{1-4}$ alkyl substituted with halo, e.g., $CF_2$. In still other embodiments, X can be $NR^b$, and $R^b$ can be H, or $C_{1-8}$ alkyl optionally substituted with halo. For example, $R^b$ can be H. In another example, $R^b$ can be $C_{1-8}$ alkyl. In still another example, $R^b$ is $C_{1-4}$ alkyl, e.g., $C_1$, $C_2$, $C_3$, or $C_4$ alkyl. The $C_{1-4}$ alkyl or $C_{1-8}$ alkyl can be substituted with halo, e.g., fluoro.

In some embodiments, Y can be CH. In other embodiments, Y can be CF or N.

In some embodiments, $R^1$ is $OR^g$ wherein $R^g$ is $C_{1-4}$ alkyl substituted with $CH_3O—$, $CH_3CH_2O—$, $CH_3(O)_2S—$, $CF_3O—$,

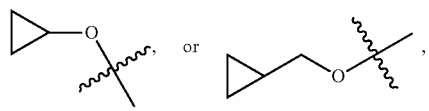

and $R^2$, $R^3$, $R^5$ and $R^6$ are H. In one example, $R^g$ can be $C_2$ alkyl substituted with $CH_3O—$.

In some embodiments, at least one of $R^1$, $R^2$, $R^3$, $R^5$ and $R^6$ is not H. For example, one, two, three, four or five of $R^1$, $R^2$, $R^3$, $R^5$ and $R^6$ is or are not H.

In some embodiments, the present disclosure provides for a compound selected from the group consisting of compound I-10, I-11, I-26, I-27, I-28, I-29, I-30, I-31, I-32, I-33, I-34, I-35, I-36, I-37, I-38, I-39, and I-40 having the Formula below.

I-10

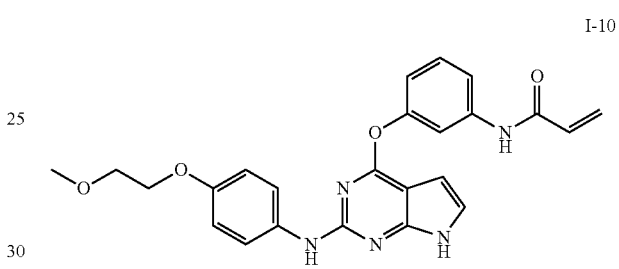

I-11

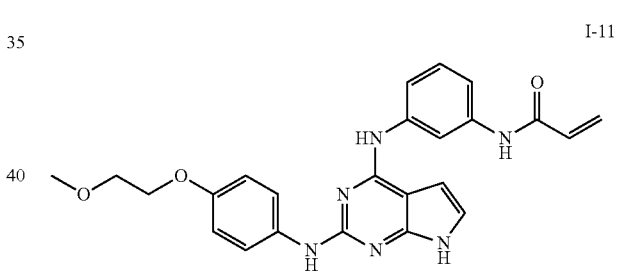

I-26

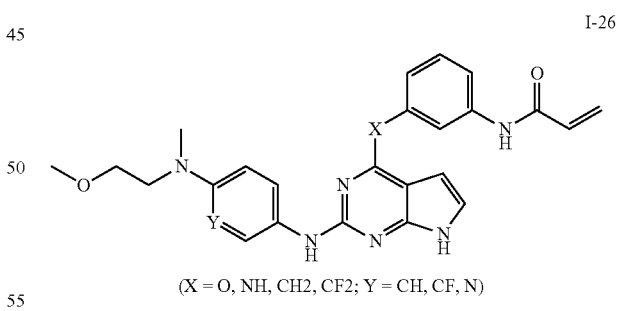

(X = O, NH, CH2, CF2; Y = CH, CF, N)

I-27

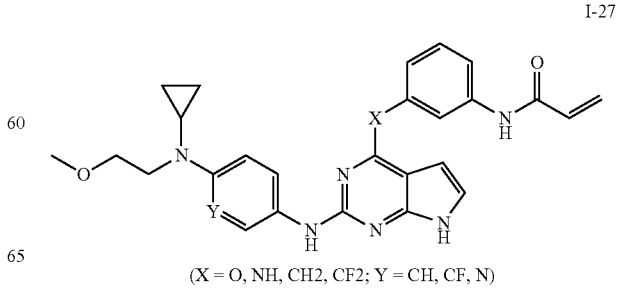

(X = O, NH, CH2, CF2; Y = CH, CF, N)

I-28
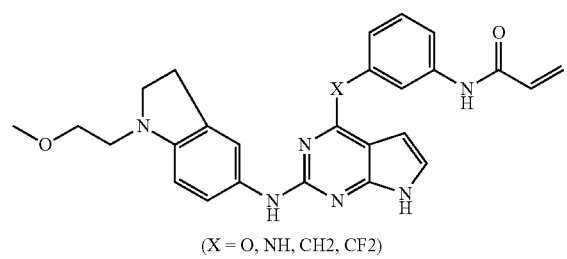
(X = O, NH, CH2, CF2)
I-29
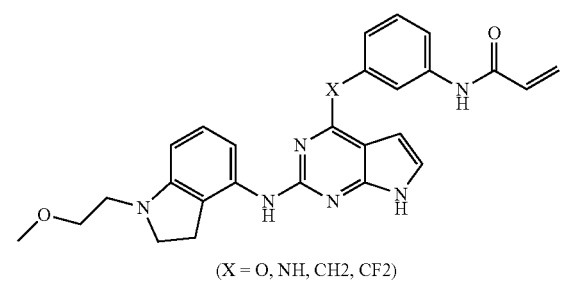
(X = O, NH, CH2, CF2)
I-30
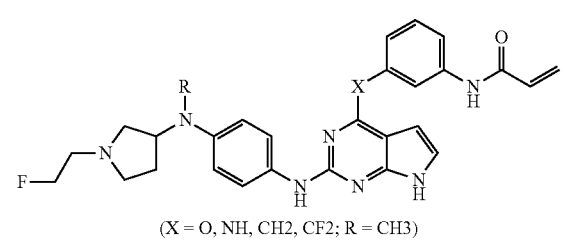
(X = O, NH, CH2, CF2; R = CH3)
I-31
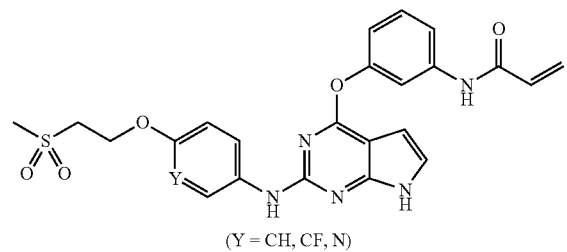
(Y = CH, CF, N)
I-32
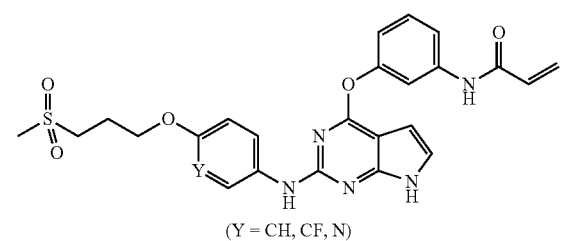
(Y = CH, CF, N)
I-33
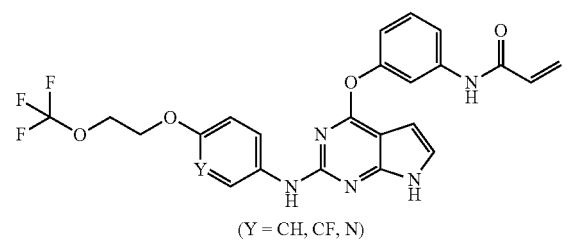
(Y = CH, CF, N)
I-34
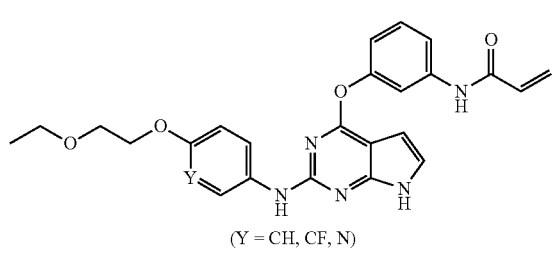
(Y = CH, CF, N)
I-35
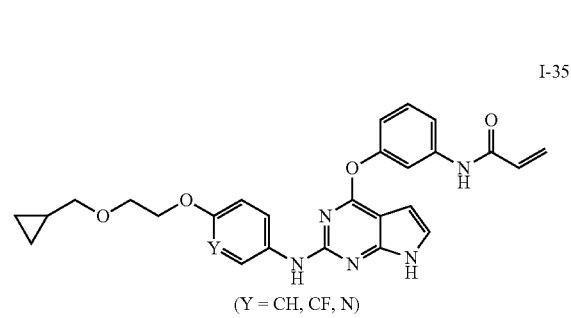
(Y = CH, CF, N)
I-36
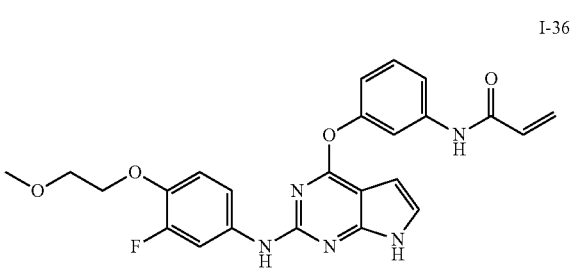
I-37
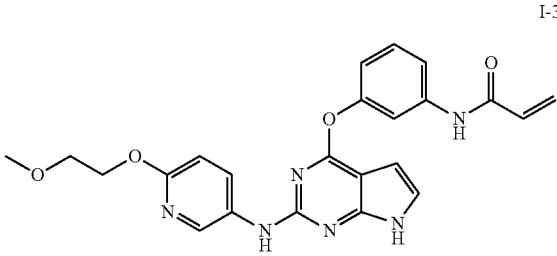
I-38
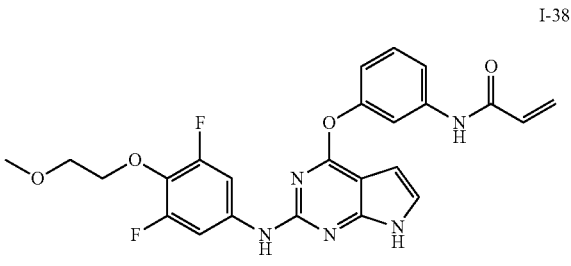
I-39
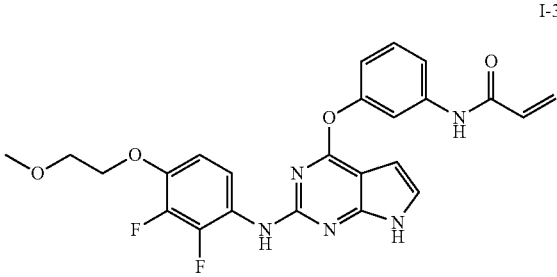

27

-continued

I-40

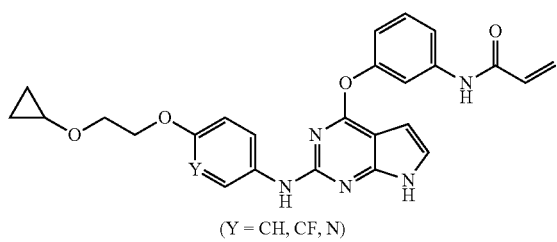

(Y = CH, CF, N)

In another aspect, the present disclosure provides for a compound of Formula (III):

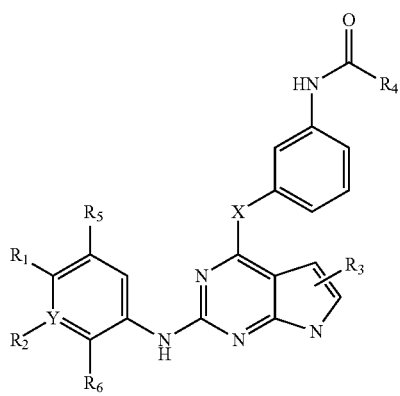

wherein
$R^1$ is

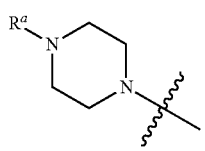

wherein $R^a$ is CO—$C_{1-4}$ alkyl-CONH—($C_{1-4}$ alkyl-O)$_m$—$C_{1-4}$ alkyl-NH-(Detectable Label), m being an integer 1-4;

$R^2$ is H, halo, $C_{1-4}$ alkyl, or $C_{1-4}$ alkoxy;

$R^3$ is H, halo, $C_{1-4}$ alkyl, or $C_{1-4}$ alkoxy;

$R^5$ is H, halo, $C_{1-4}$ alkyl, or $C_{1-4}$ alkoxy;

$R^6$ is H, halo, $C_{1-4}$ alkyl, or $C_{1-4}$ alkoxy; or $R^1$ and $R^5$ are part of 3-7 member cyclic ring, optionally substituted with $C_{1-4}$ alkyl substituted with OZ, wherein Z is H or $C_{1-4}$ alkyl; or $R^1$ and $R^2$ are part of 3-7 member cyclic ring, optionally substituted with $C_{1-4}$ alkyl substituted with OZ, wherein Z is H or $C_{1-4}$ alkyl; or $R^2$ and $R^6$ are part of 3-7 member cyclic ring, optionally substituted with $C_{1-4}$ alkyl substituted with OZ, wherein Z is H or $C_{1-4}$ alkyl; or

28

$R^4$ is $C_2$ alkenyl optionally substituted with $C_{1-4}$ alkyl, —$CH_2OCH_3$, or —$CH_2N(CH_3)_2$; and X is O, $C_{1-4}$ alkyl optionally substituted with halo, or $NR^b$, wherein $R^b$ is H, or $C_{1-8}$ alkyl optionally substituted with halo, Y is CH optionally substituted with halo, or N, or a pharmaceutically acceptable salt thereof.

In some embodiments, in $R^a$ $C_{1-4}$ alkyl can be $C_1$, $C_2$, $C_3$, or $C_4$ alkyl.

In some embodiments, m can be 1, 2, 3 or 4.

Any suitable Detectable Label can be used. In some embodiments, the Detectable Label is biotin.

In some embodiments, $R^2$ can be H. In other embodiments, $R^2$ can be halo, e.g., fluoro. In still other embodiments, $R^2$ can be $C_{1-4}$ alkyl, e.g., methyl, or $C_{1-4}$ alkoxy, e.g., methoxy.

In some embodiments, $R^5$ can be H. In other embodiments, $R^5$ can be halo, e.g., fluoro. In still other embodiments, $R^5$ can be $C_{1-4}$ alkyl, e.g., methyl, or $C_{1-4}$ alkoxy, e.g., methoxy.

In some embodiments, $R^6$ can be H. In other embodiments, $R^6$ can be halo, e.g., fluoro. In still other embodiments, $R^6$ can be $C_{1-4}$ alkyl, e.g., methyl, or $C_{1-4}$ alkoxy, e.g., methoxy.

In some embodiments, $R^1$ and $R^5$ can be part of 3-7 member cyclic ring, optionally substituted with $C_{1-4}$ alkyl substituted with OZ, wherein Z is H or $C_{1-4}$ alkyl, e.g., methyl. In other embodiments, $R^1$ and $R^2$ can be part of 3-7 member cyclic ring, optionally substituted with $C_{1-4}$ alkyl substituted with OZ, wherein Z is H or $C_{1-4}$ alkyl, e.g., methyl. In still other embodiments, $R^2$ and $R^6$ can be part of 3-7 member cyclic ring, optionally substituted with $C_{1-4}$ alkyl substituted with OZ, wherein Z is H or $C_{1-4}$ alkyl, e.g., methyl. The 3-7 member cyclic ring can be a 3, 4, 5, 6, or 7 member cyclic ring. It can be carbon cyclic ring or hetero cyclic ring. For example, the 3-7 member cyclic ring can be a 5 member cyclic ring. The 5 member cyclic ring can be heterocyclic ring, e.g., a 5 member heterocyclic ring that comprises a N atom. The $C_{1-4}$ alkyl can be $C_1$, $C_2$, $C_3$, or $C_4$ alkyl. For example, Z can be methyl.

In some embodiments, $R^3$ can be H. In other embodiments, $R^3$ can be halo, e.g., fluoro. In still other embodiments, $R^3$ can be $C_{1-4}$ alkyl, e.g., methyl, or $C_{1-4}$ alkoxy, e.g., methoxy.

In some embodiments, $R^2$, $R^5$, or $R^6$ is H or halo and $R^3$ is halo, $C_{1-4}$ alkyl, e.g., methyl, or $C_{1-4}$ alkoxy.

In some embodiments, $R^4$ can be unsubstituted $C_2$ alkenyl. In other embodiments, $R^4$ can be $C_2$ alkenyl substituted with $C_{1-4}$ alkyl, —$CH_2OCH_3$, or —$CH_2N(CH_3)_2$.

In some embodiments, X can be O. In other embodiments, X can be $C_{1-4}$ alkyl optionally substituted with halo. For example, X can be unsubstituted $C_{1-4}$ alkyl, e.g., $CH_2$. In another example, X can be $C_{1-4}$ alkyl substituted with halo, e.g., $CF_2$. In still other embodiments, X can be $NR^b$, and $R^b$ can be H, or $C_{1-8}$ alkyl optionally substituted with halo. For example, le can be H. In another example, $R^b$ can be $C_{1-8}$ alkyl. In still another example, $R^b$ is $C_{1-4}$ alkyl, e.g., $C_1$, $C_2$, $C_3$, or $C_4$ alkyl. The $C_{1-4}$ alkyl or $C_{1-8}$ alkyl can be substituted with halo, e.g., fluoro.

In some embodiments, Y can be CH. In other embodiments, Y can be CF or N.

In some embodiments, the present disclosure provides for a compound I-42 having the Formula below.

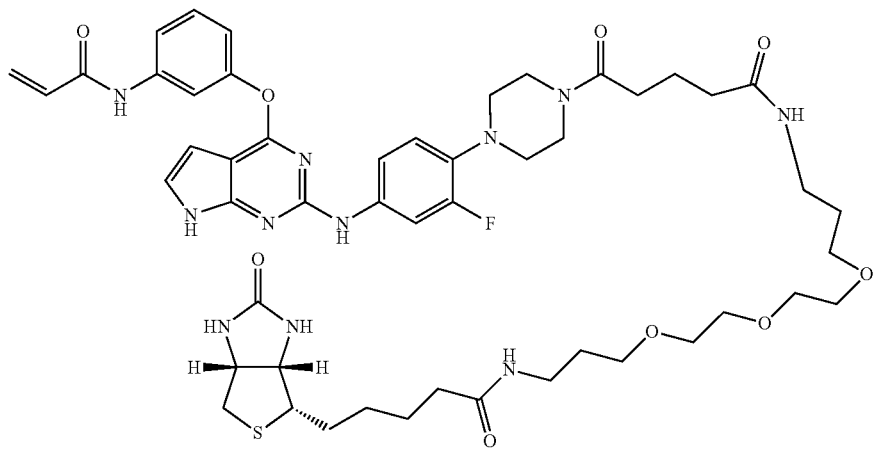 [SMILES: C=CC(=O)Nc1cccc(Oc2nc(Nc3ccc(N4CCN(C(=O)CCCC(=O)NCCCOCCOCCOCCCNC(=O)CCCC[C@@H]5SC[C@@H]6NC(=O)N[C@@H]65)CC4)c(F)c3)nc3[nH]ccc23)c1]

In still another aspect, the present disclosure provides for a compound of Formula (Ia):

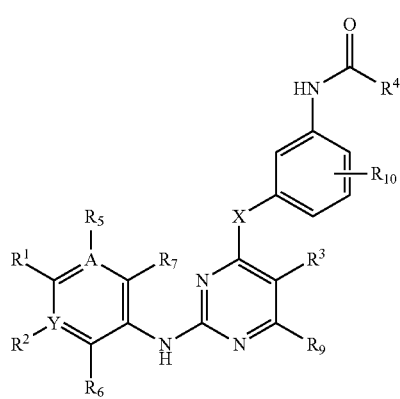

(Ia)

wherein $R^1$ is H, or

NR$^c$R$^d$ wherein

R$^c$ is H, $C_{1-4}$ alkyl, $C_{1-4}$alkenyl, or 3-7 member cyclic ring, said $C_{1-4}$ alkyl, $C_{1-4}$alkenyl, or 3-7 member cyclic ring being optionally substituted with OZ or $NR_{11}R_{12}$, wherein Z, $R_{11}$, $R_{12}$ are independently H or $C_{1-4}$ alkyl, or said 3-7 member cyclic ring being optionally substituted with $C_{1-4}$ alkyl that is further optionally substituted with OZ or $NR_{11}R_{12}$, wherein Z, $R_{11}$, $R_{12}$ are independently H or $C_{1-4}$ alkyl, or said 3-7 member cyclic ring being optionally substituted with $SO_2(CH_2)_qH$, wherein q is 1-4, or said 3-7 member cyclic ring being optionally substituted with $C_{1-4}$ alkyl that is further optionally substituted with $SO_2(CH_2)_qH$, wherein q is 1-4, or said 3-7 member cyclic ring being optionally substituted with $R_8CO$, wherein $R_8$ is $C_{1-4}$ alkyl, and R$^d$ is H, $C_{1-4}$ alkyl, $C_{1-4}$alkenyl, or 3-7 member cyclic ring, said $C_{1-4}$ alkyl, $C_{1-4}$ alkenyl or 3-7 member cyclic ring being optionally substituted with OZ or $NR_{11}R_{12}$, wherein Z, $R_{11}$, $R_{12}$ are independently H or $C_{1-4}$ alkyl; or 3-7 member cyclic ring substituted with R$^a$ wherein R$^a$ is $C_{1-8}$ alkyl optionally substituted with halo, $C_{1-4}$alkoxy or $SO_2(CH_2)_qH$, wherein q is 1-4; or $O(CH_2)_mSO_2(CH_2)_nH$, wherein m is 1-4 and n is 1-4;

$R^2$ is absent, H, halo, $C_{1-4}$ alkyl, $C_{1-4}$alkoxy, or alkylamine ($NR_{11}R_{12}$), wherein $R_{11}$ and $R_{12}$ are independently H or $C_{1-4}$ alkyl;

$R^3$ is H, hydroxyl, halo, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl;

$R^5$ is absent, H, halo, $C_{1-4}$ alkyl, $C_{1-4}$alkoxy, or alkylamine ($NR_{11}R_{12}$), wherein $R_{11}$ and $R_{12}$ are independently H or $C_{1-4}$ alkyl;

$R^6$ is H, halo, $C_{1-4}$ alkyl, $C_{1-4}$ alkoxy; or alkylamine ($NR_{11}R_{12}$), wherein $R_{11}$ and $R_{12}$ are independently H or $C_{1-4}$ alkyl;

$R^7$ is H, halo, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl;

$R^9$ is H, hydroxyl, halo, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl;

$R^{10}$ is H, hydroxyl, halo, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl; or $R^1$ and $R^5$ are part of 3-7 member cyclic ring, said 3-7 member cyclic being optionally substituted with $C_{1-4}$ alkyl optionally substituted with OZ or $NR_{11}R_{12}$ wherein Z, $R_{11}$ and $R_{12}$ are independently H or $C_{1-4}$ alkyl, or said 3-7 member cyclic being optionally substituted with $R_8CO$, wherein $R_8$ is $C_{1-4}$ alkyl, or said 3-7 member cyclic being optionally substituted with $SO_2(CH_2)_qH$, wherein q is 1-4; or $R^1$ and $R^2$ are part of 3-7 member cyclic ring, optionally substituted with $C_{1-4}$ alkyl, said $C_{1-4}$ alkyl further optionally substituted with halo, OZ, or $NR_{11}R_{12}$ wherein Z, $R_{11}$ and $R_{12}$ are independently H or $C_{1-4}$ alkyl, or one or more members of said 3-7 member cyclic ring is optionally part of a carbonyl group or a sulfonyl group; or $R^2$ and $R^6$ are part of 3-7 member cyclic ring, optionally substituted with $C_{1-4}$ alkyl optionally substituted with OZ or $NR_{11}R_{12}$ wherein Z, $R_{11}$ and $R_{12}$ are independently H or $C_{1-4}$ alkyl;

$R^4$ is $C_2$ alkenyl optionally substituted with $C_{1-4}$ alkyl, —$CH_2OCH_3$, or —$CH_2N(CH_3)_2$;

X is O, $C_{1-4}$ alkyl optionally substituted with halo, or $NR^b$, wherein $R^b$ is H, or $C_{1-8}$ alkyl optionally substituted with halo;

Y is C, CH optionally substituted with halo, or N;

A is C, CH optionally substituted with halo or N; and wherein at least one of $R^2$, $R^3$, $R^5$ and $R^6$ is not H;

or a pharmaceutically acceptable salt thereof.

In some embodiments, $R^1$ is H, and $R^2$ and $R^6$ are part of 3-7 member cyclic ring, optionally substituted with $C_{1-4}$ alkyl substituted with OZ or $NR_{11}R_{12}$ wherein Z, $R_{11}$ and $R_{12}$ are independently H or $C_{1-4}$ alkyl.

In some embodiments, $R^1$ is $NR^cR^d$ and $R^c$ is H.

In some embodiments, $R^1$ is $NR^cR^d$ and $R^c$ is $C_{1-4}$ alkyl, e.g., methyl, optionally substituted with OZ or $NR_{11}R_{12}$, wherein Z, $R_{11}$, $R_{12}$ are independently H or $C_{1-4}$ alkyl.

In some embodiments, $R^1$ is $NR^cR^d$ and $R^c$ is $C_{1-4}$alkenyl, optionally substituted with OZ or $NR_{11}R_{12}$, wherein Z, $R_{11}$, $R_{12}$ are independently H or $C_{1-4}$ alkyl.

In some embodiments, $R^1$ is $NR^cR^d$ and $R^c$ is 3-7 member cyclic ring, optionally substituted with OZ or $NR_{11}R_{12}$, wherein Z, $R_{11}$, $R_{12}$ are independently H or $C_{1-4}$ alkyl.

In some embodiments, $R^1$ is $NR^cR^d$ and $R^c$ is 3-7 member cyclic ring being optionally substituted with $C_{1-4}$ alkyl that is further optionally substituted with OZ or $NR_{11}R_{12}$, wherein Z, $R_{11}$, $R_{12}$ are independently H or $C_{1-4}$ alkyl.

In some embodiments, $R^1$ is $NR^cR^d$ and $R^c$ is 3-7 member cyclic ring being optionally substituted with $SO_2(CH_2)_qH$, wherein q is 1-4.

In some embodiments, the 3-7 member cyclic ring is a 5 member cyclic ring that comprises a N atom, the H linked to the N atom is substituted with $SO_2(CH_2)_qH$, wherein q is 1-4, e.g., q is 1.

In some embodiments, $R^1$ is $NR^cR^d$ and $R^c$ is 3-7 member cyclic ring being optionally substituted with $C_{1-4}$ alkyl that is further substituted with $SO_2(CH_2)_qH$, wherein q is 1-4. The 3-7 member cyclic ring can be a 5 member cyclic ring that comprises a N atom, the H linked to the N atom is substituted with $C_{1-4}$ alkyl that is further substituted with $SO_2(CH_2)_qH$, wherein q is 1-4. The H linked to the N atom is substituted with $C_2$ alkyl that is further substituted with $SO_2CH_3$.

In some embodiments, $R^1$ is $NR^cR^d$ and $R^c$ is 3-7 member cyclic ring being optionally substituted with $R_8CO$, wherein $R_8$ is $C_{1-4}$ alkyl. $R^1$ can be $NR^cR^d$ and $R^c$ is a 5 member cyclic ring that comprises a N atom, the H linked to the N atom is substituted with $R_8CO$, wherein $R_8$ is $C_{1-4}$ alkyl. The H linked to the N atom can be substituted with $CH_3CO$.

In some embodiments, $R^d$ is H. In other embodiments, $R^d$ is $C_{1-4}$ alkyl, optionally substituted with OZ or $NR_{11}R_{12}$, wherein Z, $R_{11}$, $R_{12}$ are independently H or $C_{1-4}$ alkyl. In still other embodiments, $R^d$ is $C_{1-4}$ alkenyl, optionally substituted with OZ or $NR_{11}R_{12}$, wherein Z, $R_{11}$, $R_{12}$ are independently H or $C_{1-4}$ alkyl. In yet other embodiments, $R^d$ is 3-7 member cyclic ring, optionally substituted with OZ or $NR_{11}R_{12}$, wherein Z, $R_{11}$, $R_{12}$ are independently H or $C_{1-4}$ alkyl.

In some embodiments, $R^c$ is a 5 member cyclic ring that comprises a N atom, the H linked to the N atom is substituted with $C_{1-4}$ alkyl that is further substituted with OZ, wherein Z is independently $C_{1-4}$ alkyl, and $R^d$ is 3-7 member cyclic ring, e.g., $C_3$ cyclic ring.

In some embodiments, $R^1$ is 3-7 member cyclic ring substituted with $R^a$ wherein $R^a$ is $C_{1-8}$ alkyl optionally substituted with halo, $C_{1-4}$ alkoxy or $SO_2(CH_2)_qH$, wherein q is 1-4. The 3-7 member cyclic ring can comprise a N atom.

The H linked to the N atom can be substituted with halo, $C_{1-4}$ alkoxy or $SO_2(CH_2)_qH$, wherein q is 1-4.

$R^1$ can be any suitable 3-7 member cyclic ring. In some embodiments, $R^1$ is selected from the group consisting of

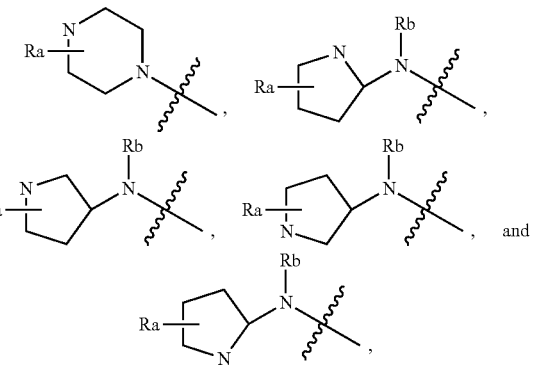

$R^a$ is $C_{1-8}$ alkyl optionally substituted with halo, $C_{1-4}$ alkoxy or $SO_2(CH_2)_qH$, wherein q is 1-4, and $R^b$ is H or $C_{1-8}$ alkyl optionally substituted with halo, $C_{1-4}$alkoxy or $SO_2(CH_2)_qH$, wherein q is 1-4. In other embodiments, $R^1$ is selected from the group consisting of

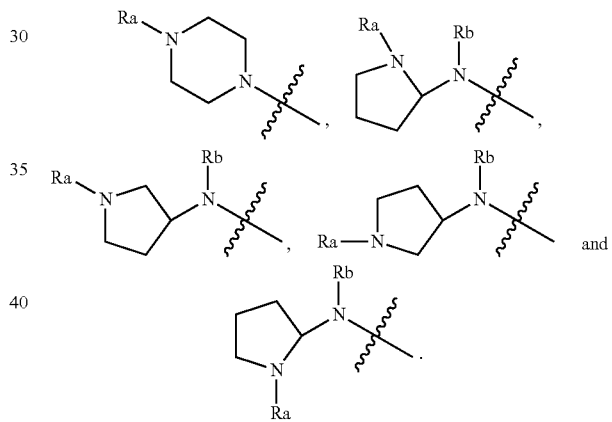

In still other embodiments, $R^1$ is

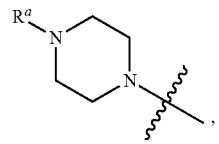

and $R^a$ is $C_2$ alkyl further substituted with methoxy. In yet other embodiments, $R^1$ is

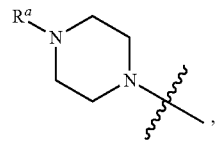

and $R^a$ is $C_2$ alkyl further substituted with $SO_2CH_3$.

In some embodiments, $R^1$ is $O(CH_2)_m SO_2(CH_2)_n H$, wherein m is 1-4 and n is 1-4. For example, $R^1$ can be $O(CH_2)_2 SO_2 CH_3$.

In some embodiments, $R^2$ is absent, H or halo. In other embodiments, $R^2$ is $C_{1-4}$ alkyl or $C_{1-4}$ alkoxy. In still other embodiments, $R^2$ is alkylamine ($NR_{11}R_{12}$), and $R_{11}$ and $R_{12}$ are independently H or $C_{1-4}$ alkyl.

In some embodiments, $R^3$ is H. In other embodiments, $R^3$ is hydroxyl. In still other embodiments, $R^3$ is halo, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl. In yet other embodiments, $R^1$ is

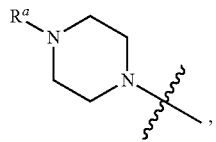

and $R^a$ is $C_{1-8}$ alkyl optionally substituted with halo, $C_{1-4}$ alkoxy or $SO_2(CH_2)_q H$, wherein q is 1-4.

In some embodiments, $R^5$ is absent or H. In other embodiments, $R^5$ is halo. In still other embodiments, $R^5$ is $C_{1-4}$ alkyl. In yet other embodiments, $R^5$ is $C_{1-4}$ alkoxy. In yet other embodiments, $R^5$ is alkylamine ($NR_{11}R_{12}$), wherein $R_{11}$ and $R_{12}$ are independently H or $C_{1-4}$ alkyl.

In some embodiments, $R^6$ is H. In other embodiments, $R^6$ is halo. In still other embodiments, $R^6$ is $C_{1-4}$ alkyl. In yet other embodiments, $R^6$ is $C_{1-4}$ alkoxy. In yet other embodiments, $R^6$ is alkylamine ($NR_{11}R_{12}$), wherein $R_{11}$ and $R_{12}$ are independently H or $C_{1-4}$ alkyl.

In some embodiments, $R^7$ is H. In other embodiments, $R^7$ is halo. In still other embodiments, $R^7$ is $C_{1-4}$ alkyl. In yet other embodiments, $R^7$ is $C_{1-4}$ alkoxy, e.g., methoxy. In yet other embodiments, $R^7$ is alkylamine ($NR_{11}R_{12}$), wherein $R_{11}$ and $R_{12}$ are independently H or $C_{1-4}$ alkyl.

In some embodiments, $R^9$ is H. In other embodiments, $R^9$ is halo. In still other embodiments, $R^9$ is $C_{1-4}$ alkyl. In yet other embodiments, $R^9$ is $C_{1-4}$ alkoxy. In yet other embodiments, $R^9$ is alkylamine ($NR_{11}R_{12}$), wherein $R_{11}$ and $R_{12}$ are independently H or $C_{1-4}$ alkyl.

In some embodiments, $R^{10}$ is H. In other embodiments, $R^{10}$ is halo. In still other embodiments, $R^{10}$ is $C_{1-4}$ alkyl. In yet other embodiments, $R^{10}$ is $C_{1-4}$ alkoxy. In yet other embodiments, $R^{10}$ is alkylamine ($NR_{11}R_{12}$), wherein $R_{11}$ and $R_{12}$ are independently H or $C_{1-4}$ alkyl.

In some embodiments, $R^1$ and $R^5$ are part of 3-7 member cyclic ring, said 3-7 member cyclic being optionally substituted with $C_{1-4}$ alkyl optionally substituted with OZ or $NR_{11}R_{12}$ wherein Z, $R_{11}$ and $R_{12}$ are independently H or $C_{1-4}$ alkyl. In other embodiments, $R^1$ and $R^5$ are part of 3-7 member cyclic ring, said 3-7 member cyclic being optionally substituted with $R_8 CO$, wherein $R_8$ is $C_{1-4}$ alkyl. For example, the 3-7 member cyclic ring is substituted with $CH_3 CO$. In still other embodiments, $R^1$ and $R^5$ are part of 3-7 member cyclic ring, said 3-7 member cyclic being optionally substituted with $SO_2(CH_2)_q H$, wherein q is 1-4. For example, the 3-7 member cyclic is substituted with $SO_2 CH_3$.

In some embodiments, $R^1$ and $R^2$ are part of 3-7 member cyclic ring, optionally substituted with $C_{1-4}$ alkyl, said $C_{1-4}$ alkyl further optionally substituted with halo, OZ, or $NR_{11}R_{12}$ wherein Z, $R_{11}$ and $R_{12}$ are independently H or $C_{1-4}$ alkyl. In other embodiments, $R^1$ and $R^2$ are part of 3-7 member cyclic ring, and one or more members of said 3-7 member cyclic ring is optionally part of a carbonyl group or a sulfonyl group. The carbonyl group can be an amide or an ester group.

In some embodiments, $R^2$ and $R^6$ are part of 3-7 member cyclic ring, optionally substituted with $C_{1-4}$ alkyl substituted optionally with OZ or $NR_{11}R_{12}$ wherein Z, $R_{11}$ and $R_{12}$ are independently H or $C_{1-4}$ alkyl.

In some embodiments, $R^4$ is unsubstituted $C_2$ alkenyl. In other embodiments, $R^4$ is $C_2$ alkenyl substituted with $C_{1-4}$ alkyl. For example, $R^4$ can be $C_2$ alkenyl substituted with $-CH_2 OCH_3$, or $-CH_2 N(CH_3)_2$.

In some embodiments, X is O. In other embodiments, X is unsubstituted $C_{1-4}$ alkyl, e.g., $CH_2$, or $C_{1-4}$ alkyl substituted with halo, e.g., $CF_2$. In still other embodiments, X is $NR^b$, and $R^b$ is H, or $C_{1-8}$ alkyl optionally substituted with halo.

In some embodiments, Y is C. In other embodiments, Y is CH or CH substituted with halo, e.g., $CF_2$. In still other embodiments, Y is N.

In some embodiments, A is C. In other embodiments, A is CH or CH substituted with halo, e.g., $CF_2$. In still other embodiments, A is N.

In some embodiments, the 3-7 member cyclic ring is a 3 member cyclic ring. In other embodiments, the 3-7 member cyclic ring is a 4 member cyclic ring. In still other embodiments, the 3-7 member cyclic ring is a 5 member cyclic ring. In yet embodiments, the 3-7 member cyclic ring is a 6 member cyclic ring. In yet embodiments, the 3-7 member cyclic ring is a 7 member cyclic ring.

In some embodiments, the 3-7 member cyclic ring is hydrocarbon 3-7 member cyclic ring. In other embodiments, the 3-7 member cyclic ring is a heterocyclic ring. For example, the heterocyclic ring can comprise one or more N atom.

In some embodiments, the present disclosure provides for a compound selected from the group consisting of compound I-1, I-2, I-3, I-4, I-5, I-6, I-7, I-8, I-9, I-12, I-13, I-14, I-15, I-16, I-17, I-18, I-19, I-20, I-21, I-22, I-23, I-24, I-25, I-41, I-23a, I-25a, I-28a, I-29a, I-30a, I-31a, I-32a, I-33a, I-34a, I-35a, I-38a, I-39a, I-42a, I-43a, I-44a, I-45a, I-50a, I-51a, I-52a, I-53a, I-54a, I-55a, I-56a, I-57a, I-58a, I-59a, I-60a, I-66a, I-70a, and I-72a.

In still another aspect, the present disclosure provides for a compound of Formula (IIa):

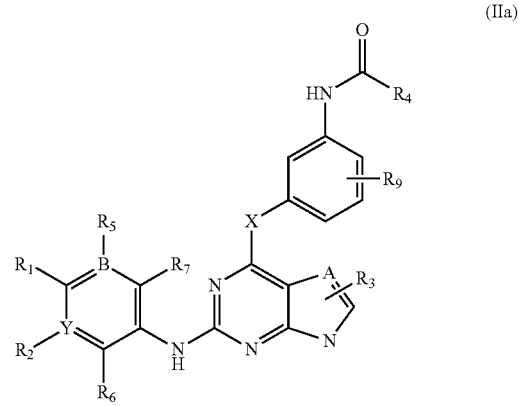

wherein
$R^1$ is H, or
$NR^c R^d$ wherein $R^c$ is H, $C_{1-4}$ alkyl or 3-7 member cyclic ring, said 3-7 member cyclic ring optionally substituted with $C_{1-4}$ alkyl optionally substituted with OZ or $NR_{10}R_{11}$ wherein Z, $R_{10}$ and $R_{11}$ are independently H or $C_{1-4}$ alkyl, or said 3-7 member cyclic ring being optionally substituted with $R_8CO$, wherein $R_8$ is $C_{1-4}$ alkyl, or said 3-7 member cyclic ring being optionally substituted with $SO_2(CH_2)_qH$, wherein q is 1-4, and $R^d$ is H, $C_{1-4}$ alkyl, optionally substituted with OZ or $NR_{10}R_{11}$ wherein Z, $R_{10}$ and $R_{11}$ are H or $C_{1-4}$ alkyl; or $NR^eR^f$ wherein $R^e$ is $C_{1-4}$ alkyl, and $R^f$ is 3-7 member cyclic ring optionally substituted with $C_{1-4}$ alkyl optionally substituted with halo; or $OR^g$ wherein $R^g$ is $C_{1-4}$ alkyl substituted with $CH_3O-$, $CH_3CH_2O-$, $CH_3(O)_2S-$, $CF_3O-$,

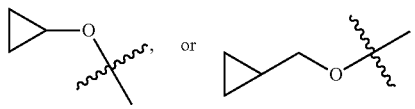 [SMILES: *OC1CC1 ; *OCC1CC1]

or
3-7 member cyclic ring substituted with $R^a$ wherein $R^a$ is $C_{1-8}$ alkyl optionally substituted with halo, $C_{1-4}$ alkoxy or $SO_2(CH_2)_qH$, wherein q is 1-4, or said 3-7 member cyclic ring being optionally substituted with $R_8CO$, wherein $R_8$ is $C_{1-4}$ alkyl;

$R^2$ is absent, H, halo, $C_{1-4}$ alkyl, $C_{1-4}$alkoxy, or alkylamine ($NR_{10}R_{11}$), wherein $R_{10}$ and $R_{11}$ are independently H or $C_{1-4}$ alkyl;

$R^3$ is absent, H, halo, $C_{1-4}$ alkyl, or $C_{1-4}$alkoxy, or alkylamine ($NR_{10}R_{11}$), wherein $R_{10}$ and $R_{11}$ are independently H or $C_{1-4}$ alkyl;

$R^5$ is absent, H, halo, $C_{1-4}$ alkyl, or $C_{1-4}$alkoxy, or alkylamine ($NR_{10}R_{11}$), wherein $R_{10}$ and $R_{11}$ are independently H or $C_{1-4}$ alkyl;

$R^6$ is H, halo, $C_{1-4}$ alkyl, or $C_{1-4}$alkoxy, or alkylamine ($NR_{10}R_{11}$), wherein $R_{10}$ and $R_{11}$ are independently H or $C_{1-4}$ alkyl;

$R^7$ is H, halo, $C_{1-4}$ alkyl, $C_{1-4}$ alkoxy, or alkylamine ($NR_{10}R_{11}$), wherein $R_{10}$ and $R_{11}$ are independently H or $C_{1-4}$ alkyl;

$R^9$ is H, halo, $C_{1-4}$ alkyl, or $C_{1-4}$alkoxy, or alkylamine ($NR_{10}R_{11}$), wherein $R_{10}$ and $R_{11}$ are independently H or $C_{1-4}$ alkyl; or $R^1$ and $R^5$ are part of 3-7 member cyclic ring, optionally substituted with $C_{1-4}$ alkyl optionally substituted with OZ or $NR_{10}R_{11}$ wherein Z, $R_{10}$ and $R_{11}$ are independently H or $C_{1-4}$ alkyl; or $R^1$ and $R^2$ are part of 3-7 member cyclic ring, optionally substituted with $C_{1-4}$ alkyl optionally substituted with OZ or $R_{10}$ and $R_{11}$ wherein Z, $R_{10}$ and $R_{11}$ are independently are H or $C_{1-4}$alkyl; or $R^2$ and $R^6$ are part of 3-7 member cyclic ring, optionally substituted with $C_{1-4}$ alkyl optionally substituted with OZ or $R_{10}$ and $R_{11}$ wherein Z, $R_{10}$ and $R_{11}$ are independently H or $C_{1-4}$ alkyl;

$R^4$ is $C_2$ alkenyl optionally substituted with $C_{1-4}$ alkyl, $-CH_2OCH_3$, or $-CH_2N(CH_3)_2$;

X is O, $C_{1-4}$ alkyl optionally substituted with halo, or $NR^b$, wherein $R^b$ is H, or $C_{1-8}$ alkyl optionally substituted with halo;

Y is C, CH optionally substituted with halo, or N;

A is C, CH optionally substituted with halo, or N; and

B is C, CH optionally substituted with halo, or N, or a pharmaceutically acceptable salt thereof.

In some embodiments, $R^1$ is H, and $R^2$ and $R^6$ are part of 3-7 member cyclic ring, optionally substituted with $C_{1-4}$ alkyl optionally substituted with OZ or $R_{10}$ and $R_{11}$ wherein Z, $R_{10}$ and $R_{11}$ are independently H or $C_{1-4}$ alkyl.

In some embodiments, $R^1$ is $NR^cR^d$ and $R^c$ is H. In other embodiments, $R^1$ is $NR^cR^d$ and $R^c$ is $C_{1-4}$ alkyl.

In some embodiments, $R^1$ is $NR^cR^d$ and $R^c$ is 3-7 member cyclic ring, said 3-7 member cyclic ring optionally substituted with $C_{1-4}$ alkyl optionally substituted with OZ or $NR_{10}R_{11}$ wherein Z, $R_{10}$ and $R_{11}$ are independently H or $C_{1-4}$ alkyl. Said 3-7 member cyclic ring can be substituted with $C_2$ alkyl substituted with methoxy.

In some embodiments, $R^1$ is $NR^cR^d$ and $R^c$ is 3-7 member cyclic ring, said 3-7 member cyclic ring being optionally substituted with $R_8CO$, wherein $R_8$ is $C_{1-4}$ alkyl. Said 3-7 member cyclic ring can be substituted with $CH_3CO$.

In some embodiments, $R^1$ is $NR^cR^d$ and $R^c$ is 3-7 member cyclic ring, said 3-7 member cyclic ring being optionally substituted with $SO_2(CH_2)_qH$, wherein q is 1-4. For example, said 3-7 member cyclic ring can be substituted with $CH_3SO_2$.

In some embodiments, $R^d$ is H. In other embodiments, $R^d$ is $C_{1-4}$ alkyl, optionally substituted with OZ or $NR_{10}R_{11}$ wherein Z, $R_{10}$ and $R_{11}$ are H or $C_{1-4}$ alkyl.

In some embodiments, $R^1$ is $NR^eR^f$ and $R^e$ is $C_{1-4}$ alkyl. In other embodiments, $R^1$ is $NR^eR^f$ and $R^f$ is 3-7 member cyclic ring optionally substituted with $C_{1-4}$ alkyl optionally substituted with halo.

In some embodiments, $R^1$ is $OR^g$ wherein $R^g$ is $C_{1-4}$ alkyl substituted with $CH_3O-$, $CH_3CH_2O-$, $CH_3(O)_2S-$, $CF_3O-$,

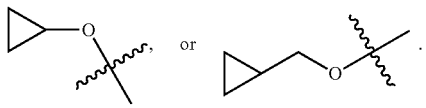 [SMILES: *OC1CC1 ; *OCC1CC1]

In some embodiments, $R^1$ is 3-7 member cyclic ring substituted with $R^a$ wherein $R^a$ is $C_{1-8}$ alkyl optionally substituted with halo, $C_{1-4}$ alkoxy or $SO_2(CH_2)_qH$, wherein q is 1-4. For example, $R^a$ can be $C_2$ alkyl substituted with methoxy. In another example, $R^a$ is $CH_3SO_2CH_2CH_2$.

In some embodiments, $R^1$ is 3-7 member cyclic ring, said 3-7 member cyclic ring being optionally substituted with $R_8CO$, wherein $R_8$ is $C_{1-4}$ alkyl. For example, said 3-7 member cyclic ring can be substituted with $CH_3CO$.

$R^1$ can be any suitable 3-7 member cyclic ring. In some embodiments, $R^1$ is selected from the group consisting of

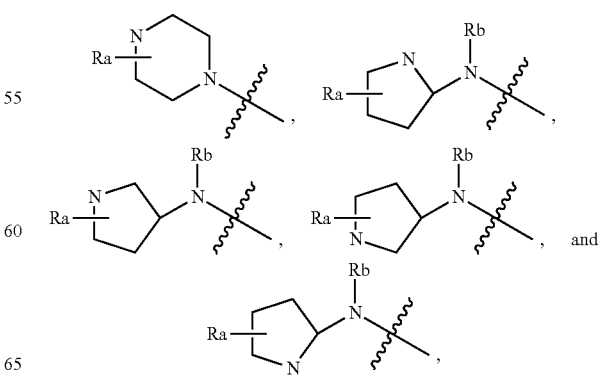

$R^a$ is $C_{1-8}$ alkyl optionally substituted with halo, $C_{1-4}$ alkoxy or $SO_2(CH_2)_qH$, wherein q is 1-4, and $R^b$ is H or $C_{1-8}$ alkyl optionally substituted with halo, $C_{1-4}$ alkoxy or $SO_2(CH_2)_qH$, wherein q is 1-4. In other embodiments, $R^1$ is selected from the group consisting of

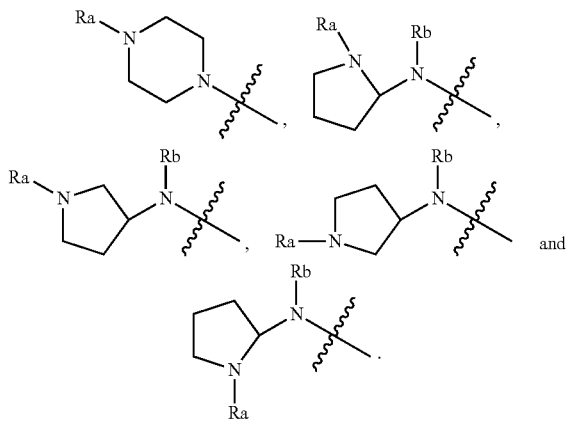

In still other embodiments, $R^1$ is

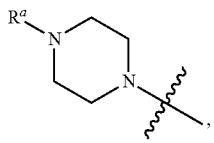

and $R^a$ is $C_2$ alkyl further substituted with methoxy. In yet other embodiments, $R^1$ is

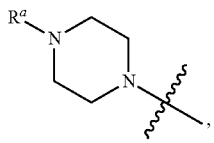

and $R^a$ is $C_2$ alkyl further substituted with $SO_2CH_3$.

In some embodiments, $R^2$ is absent or H. In other embodiments, $R^2$ is halo. In still other embodiments, $R^2$ is $C_{1-4}$ alkyl or $C_{1-4}$ alkoxy. In yet embodiments, $R^2$ is alkylamine ($NR_{10}R_{11}$), wherein $R_{10}$ and $R_{11}$ are independently H or $C_{1-4}$ alkyl.

In some embodiments, $R^3$ is absent. In other embodiments, $R^3$ is H. In still other embodiments, $R^3$ is halo. In yet embodiments, $R^3$ is $C_{1-4}$ alkyl. In yet embodiments, $R^3$ is $C_{1-4}$ alkoxy. In yet embodiments, $R^3$ is alkylamine ($NR_{10}R_{11}$), wherein $R_{10}$ and $R_{11}$ are independently H or $C_{1-4}$ alkyl.

In some embodiments, $R^5$ is absent. In other embodiments, $R^5$ is H. In still other embodiments, $R^5$ is halo. In yet embodiments, $R^5$ is $C_{1-4}$ alkyl. In yet embodiments, $R^5$ is $C_{1-4}$ alkoxy. In yet embodiments, $R^5$ is alkylamine ($NR_{10}R_{11}$), wherein $R_{10}$ and $R_{11}$ are independently H or $C_{1-4}$ alkyl.

In some embodiments, $R^6$ is H. In other embodiments, $R^6$ is halo. In still other embodiments, $R^6$ is $C_{1-4}$ alkyl. In yet embodiments, $R^6$ is $C_{1-4}$ alkoxy. In yet embodiments, $R^6$ is alkylamine ($NR_{10}R_{11}$), wherein $R_{10}$ and $R_{11}$ are independently H or $C_{1-4}$ alkyl.

In some embodiments, $R^7$ is H. In other embodiments, $R^7$ is halo. In still other embodiments, $R^7$ is $C_{1-4}$ alkyl. In yet embodiments, $R^7$ is $C_{1-4}$ alkoxy. In yet embodiments, $R^7$ is alkylamine ($NR_{10}R_{11}$), wherein $R_{10}$ and $R_{11}$ are independently H or $C_{1-4}$ alkyl.

In some embodiments, $R^9$ is H. In other embodiments, $R^9$ is halo. In still other embodiments, $R^9$ is $C_{1-4}$ alkyl. In yet embodiments, $R^9$ is $C_{1-4}$ alkoxy. In yet embodiments, $R^9$ is alkylamine ($NR_{10}R_{11}$), wherein $R_{10}$ and $R_{11}$ are independently H or $C_{1-4}$ alkyl.

In some embodiments, $R^1$ and $R^5$ are part of 3-7 member cyclic ring, optionally substituted with $C_{1-4}$ alkyl optionally substituted with OZ or $NR_{10}R_{11}$ wherein Z, $R_{10}$ and $R_{11}$ are independently H or $C_{1-4}$ alkyl.

In some embodiments, $R^1$ and $R^2$ are part of 3-7 member cyclic ring, optionally substituted with $C_{1-4}$ alkyl optionally substituted with OZ or $R_{10}$ and $R_{11}$ wherein Z, $R_{10}$ and $R_{11}$ are independently are H or $C_{1-4}$ alkyl.

In some embodiments, $R^2$ and $R^6$ are part of 3-7 member cyclic ring, optionally substituted with $C_{1-4}$ alkyl optionally substituted with OZ or $R_{10}$ and $R_{11}$ wherein Z, $R_{10}$ and $R_{11}$ are independently H or $C_{1-4}$ alkyl.

In some embodiments, X is O. In other embodiments, X is unsubstituted $C_{1-4}$ alkyl, e.g., $CH_2$, or $C_{1-4}$ alkyl substituted with halo, e.g., $CF_2$. In still other embodiments, X is $NR^b$, and $R^b$ is H, or $C_{1-8}$ alkyl optionally substituted with halo.

In some embodiments, Y is C. In other embodiments, Y is CH or CH substituted with halo, e.g., CF. In still other embodiments, Y is N.

In some embodiments, A is C. In other embodiments, A is CH or CH substituted with halo, e.g., CF. In still other embodiments, A is N.

In some embodiments, B is C. In other embodiments, B is CH or CH substituted with halo, e.g., CF. In still other embodiments, B is N.

In some embodiments, the 3-7 member cyclic ring is a 3 member cyclic ring. In other embodiments, the 3-7 member cyclic ring is a 4 member cyclic ring. In still other embodiments, the 3-7 member cyclic ring is a 5 member cyclic ring. In yet embodiments, the 3-7 member cyclic ring is a 6 member cyclic ring. In yet embodiments, the 3-7 member cyclic ring is a 7 member cyclic ring.

In some embodiments, the 3-7 member cyclic ring is hydrocarbon 3-7 member cyclic ring. In other embodiments, the 3-7 member cyclic ring is a heterocyclic ring. For example, the heterocyclic ring can comprise one or more N atom.

In some embodiments, the present disclosure provides for a compound selected from the group consisting of compound I-10, I-11, I-26, I-27, I-28, I-29, I-30, I-31, I-32, I-33, I-34, I-35, I-36, I-37, I-38, I-39, I-40, I-24a, I-26a, I-27a, I-36a, I-37a, I-40a, I-41a, I-46a, I-47a, I-48a, I-49a, I-61a, I-62a, I-63a, I-64a, I-65a, I-67a, I-68a, I-69a, and I-71a.

Pharmaceutical Compositions, Combinations, and Other Related Uses

In still another aspect, the present disclosure provides for a pharmaceutical composition comprising a compound described above admixed with at least one pharmaceutically acceptable carrier or excipient.

The above described compounds can be used for any suitable purpose. For example, the present compounds can be used in therapy and/or testing.

In yet another aspect, the present disclosure provides for a method for treating and/or preventing a proliferation disorder, a cancer, a tumor, an inflammatory disease, an autoimmune disease, psoriasis, dry eye or an immunologically related disease, or lupus, which comprises administering to a subject in need thereof an effective amount of a compound described above or a pharmaceutical composition described above.

In yet another aspect, the present disclosure provides for a use of a compound described above for the manufacture of a medicament.

In yet another aspect, the present disclosure provides for a combination for treating and/or preventing a proliferation disorder, a cancer, a tumor, an inflammatory disease, an autoimmune disease, psoriasis, dry eye or an immunologically related disease or lupus in a subject, which combination comprises an effective amount of a compound described above, or a pharmaceutically acceptable salt thereof, and an effective amount of a second prophylactic or therapeutic agent for treating and/or preventing a proliferation disorder, a cancer, a tumor, an inflammatory disease, an autoimmune disease, psoriasis, dry eye or an immunologically related disease or lupus in a subject.

In yet another aspect, the present disclosure provides for a method for treating and/or preventing a proliferation disorder, a cancer, a tumor, an inflammatory disease, an autoimmune disease, psoriasis, dry eye or an immunologically related disease or lupus in a subject, which methods comprises administering to a subject in need thereof an effective amount of the combination described above.

In yet another aspect, the present disclosure provides for a method for inhibiting an activity of a Bruton's tyrosine kinase (Btk or BTK) or a Janus kinase (JAK) EGFR (including HER), Alk, PDGFR, BLK, BMX/ETK, FLT3 (D835Y), ITK, TEC, TXK, and the respective pathways, in a cell or subject, which methods comprises administering to a cell or subject in need thereof an effective amount of a compound described above, or a pharmaceutical composition described above, or a combination described above.

The present methods can be used to inhibit an activity of any suitable Btk, BTK or JAK. In some embodiments, the present methods can be used to inhibit an activity of JAK1, JAK2 or JAK3.

The present methods can be used for any suitable purpose. In some embodiments, the present methods can be used to treat and/or prevent a proliferation disorder, a cancer, a tumor, an inflammatory disease, an autoimmune disease, psoriasis, dry eye or an immunologically related disease or lupus in the subject. The present methods can be used to treat and/or prevent any suitable proliferation disorder. Exemplary proliferation disorders include sarcoma, epidermoid cancer, fibrosarcoma, cervical cancer, gastric carcinoma, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancers, and pancreatic cancer.

In some embodiments, any of the compound selected from the group consisting of compound I-1, I-2, I-3, I-4, I-5, I-6, I-7, I-8, I-9, I-12, I-13, I-14, I-15, I-16, I-17, I-18, I-19, I-20, I-21, I-22, I-23, I-24, I-25, I-41, I-23a, I-25a, I-28a, I-29a, I-30a, I-31a, I-32a, I-33a, I-34a, I-35a, I-38a, I-39a, I-42a, I-43a, I-44a, I-45a, I-51a, I-52a, I-59a, I-60a, I-66a, I-70a, I-72a, I-10, I-11, I-26, I-27, I-28, I-29, I-30, I-31, I-32, I-33, I-34, I-35, I-36, I-37, I-38, I-39, I-40, I-24a, I-26a, I-27a, I-36a, I-37a, I-40a, I-41a, I-46a, I-47a, I-48a, I-49a, I-61a, I-62a, I-63a, I-64a, I-65a, I-67a, I-68a, I-69a, and I-71a can be used in the above pharmaceutical compositions, combinations and other related uses or methods.

Formulations

Any suitable formulation of the compounds described herein can be prepared. See generally, Remington's Pharmaceutical Sciences, (2000) Hoover, J. E. editor, 20 th edition, Lippincott Williams and Wilkins Publishing Company, Easton, Pa., pages 780-857. A formulation is selected to be suitable for an appropriate route of administration. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example, by a sufficiently basic compound such as an amine with a suitable acid, affording a physiologically acceptable anion. Alkali metal (e.g., sodium, potassium or lithium) or alkaline earth metal (e.g., calcium) salts of carboxylic acids also are made.

Where contemplated compounds are administered in a pharmacological composition, it is contemplated that the compounds can be formulated in admixture with a pharmaceutically acceptable excipient and/or carrier. For example, contemplated compounds can be administered orally as neutral compounds or as pharmaceutically acceptable salts, or intravenously in a physiological saline solution. Conventional buffers such as phosphates, bicarbonates or citrates can be used for this purpose. Of course, one of ordinary skill in the art may modify the formulations within the teachings of the specification to provide numerous formulations for a particular route of administration. In particular, contemplated compounds may be modified to render them more soluble in water or other vehicle, which for example, may be easily accomplished with minor modifications (salt formulation, esterification, etc.) that are well within the ordinary skill in the art. It is also well within the ordinary skill of the art to modify the route of administration and dosage regimen of a particular compound in order to manage the pharmacokinetics of the present compounds for maximum beneficial effect in a patient.

The compounds having formula I-III as described herein are generally soluble in organic solvents such as chloroform, dichloromethane, ethyl acetate, ethanol, methanol, isopropanol, acetonitrile, glycerol, N,N-dimethylformamide, N,N-dimetheylaceatmide, dimethylsulfoxide, etc. In one embodiment, the present invention provides formulations prepared by mixing a compound having formula I-III with a pharmaceutically acceptable carrier. In one aspect, the formulation may be prepared using a method comprising: a) dissolving a described compound in a water-soluble organic solvent, a non-ionic solvent, a water-soluble lipid, a cyclodextrin, a vitamin such as tocopherol, a fatty acid, a fatty acid ester, a phospholipid, or a combination thereof, to provide a solution; and b) adding saline or a buffer containing 1-10% carbohydrate solution. In one example, the carbohydrate comprises dextrose. The pharmaceutical compositions obtained using the present methods are stable and useful for animal and clinical applications.

Illustrative examples of water soluble organic solvents for use in the present methods include and are not limited to polyethylene glycol (PEG), alcohols, acetonitrile, N-methyl-2-pyrrolidone, N,N-dimethylformamide, N,N-dimethylacetamide, dimethyl sulfoxide, or a combination thereof. Examples of alcohols include but are not limited to methanol, ethanol, isopropanol, glycerol, or propylene glycol.

Illustrative examples of water soluble non-ionic surfactants for use in the present methods include and are not limited to CREMOPHOR® EL, polyethylene glycol modified CREMOPHOR® (polyoxyethyleneglyceroltrirircinoleat 35), hydrogenated CREMOPHOR® RH40, hydrogenated CREMOPHOR® RH60, PEG-succinate, polysorbate 20, polysorbate 80, SOLUTOL® HS (polyethylene glycol 660 12-hydroxystearate), sorbitan monooleate, poloxamer, LABRAFIL® (ethoxylated persic oil), LABRASOL® (capryl-caproyl macrogol-8-glyceride), GELUCIRE® (glycerol ester), SOFTIGEN® (PEG 6 caprylic glyceride), glycerin, glycol-polysorbate, or a combination thereof.

Illustrative examples of water soluble lipids for use in the present methods include but are not limited to vegetable oils, triglycerides, plant oils, or a combination thereof. Examples of lipid oils include but are not limited to castor oil, polyoxyl castor oil, corn oil, olive oil, cottonseed oil, peanut oil, peppermint oil, safflower oil, sesame oil, soybean oil, hydrogenated vegetable oil, hydrogenated soybean oil, a triglyceride of coconut oil, palm seed oil, and hydrogenated forms thereof, or a combination thereof.

Illustrative examples of fatty acids and fatty acid esters for use in the present methods include but are not limited to oleic acid, monoglycerides, diglycerides, a mono- or di-fatty acid ester of PEG, or a combination thereof.

Illustrative examples of cyclodextrins for use in the present methods include but are not limited to alpha-cyclodextrin, beta-cyclodextrin, hydroxypropyl-beta-cyclodextrin, or sulfobutyl ether-beta-cyclodextrin.

Illustrative examples of phospholipids for use in the present methods include but are not limited to soy phosphatidylcholine, or distearoyl phosphatidylglycerol, and hydrogenated forms thereof, or a combination thereof.

One of ordinary skill in the art may modify the formulations within the teachings of the specification to provide numerous formulations for a particular route of administration. In particular, the compounds may be modified to render them more soluble in water or other vehicle. It is also well within the ordinary skill of the art to modify the route of administration and dosage regimen of a particular compound in order to manage the pharmacokinetics of the present compounds for maximum beneficial effect in a patient.

Drug Combinations

The methods of the embodiments comprise administering an effective amount of at least one exemplary compound of the present disclosure; optionally the compound may be administered in combination with one or more additional therapeutic agents, particularly therapeutic agents known to be useful for treating a proliferation disorder, a cancer, a tumor, an inflammatory disease, an autoimmune disease, psoriasis, dry eye or an immunologically related disease afflicting the subject.

The additional active ingredients may be administered in a separate pharmaceutical composition from at least one exemplary compound of the present disclosure or may be included with at least one exemplary compound of the present disclosure in a single pharmaceutical composition. The additional active ingredients may be administered simultaneously with, prior to, or after administration of at least one exemplary compound of the present disclosure.

Methods of Using the Exemplary Compounds and Pharmaceutical Compositions Thereof The present invention also provides pharmaceutical compositions for the treatment and/or prevention of a proliferation disorder, a cancer, a tumor, an inflammatory disease, an autoimmune disease, psoriasis, dry eye or an immunologically related disease, comprising any compound having formula I or II, or any of the compounds of I-1 to I-41.

To practice the method of the present invention, compounds having formula and pharmaceutical compositions thereof may be administered orally, parenterally, by inhalation, topically, rectally, nasally, buccally, vaginally, via an implanted reservoir, or other drug administration methods. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, such as a sterile injectable aqueous or oleaginous suspension, may be formulated according to techniques known in the art using suitable dispersing or wetting agents and suspending agents. The sterile injectable preparation may also be a sterile injectable solution or suspension in a non-toxic parenterally acceptable diluent or solvent. Among the acceptable vehicles and solvents that may be employed include mannitol, water, Ringer's solution and isotonic sodium chloride solution. Suitable carriers and other pharmaceutical composition components are typically sterile.

In addition, sterile, fixed oils are conventionally employed as a solvent or suspending medium (e.g., synthetic mono- or diglycerides). Fatty acids, such as oleic acid and its glyceride derivatives, are useful in the preparation of injectables, as are pharmaceutically acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Various emulsifying agents or bioavailability enhancers which are commonly used in the manufacture of pharmaceutically acceptable solid, liquid, or other dosage forms can also be used for the purpose of formulation.

A composition for oral administration may be any orally acceptable dosage form including, but not limited to, tablets, capsules, emulsions and aqueous suspensions, dispersions and solutions. In the case of tablets for oral use, commonly used carriers include lactose and corn starch. Lubricating agents, such as magnesium stearate, can also be added. For oral administration in a capsule form, useful diluents include lactose and dried corn starch. When aqueous suspensions or emulsions are administered orally, the active ingredient can be suspended or dissolved in an oily phase combined with emulsifying or suspending agents. If needed, certain sweetening, flavoring, or coloring agents can be added. A nasal aerosol or inhalation compositions can be prepared according to techniques well-known in the art of pharmaceutical formulation and can be prepared as solutions in, for example saline, employing suitable preservatives (for example, benzyl alcohol), absorption promoters to enhance bioavailability, and/or other solubilizing or dispersing agents known in the art.

In addition, the compounds having formula I or II, or any of the compounds of I-1 to I-41, may be administered alone or in combination with other therapeutic agents, e.g., anti-cancer agents, for the treatment of various proliferation disorder, cancer, tumor, inflammatory disease, autoimmune disease, psoriasis, dry eye or immunologically related disease. Combination therapies according to the present invention comprise the administration of at least one exemplary compound of the present disclosure and at least one other pharmaceutically active ingredient. The active ingredient(s) and pharmaceutically active agents may be administered separately or together. The amounts of the active ingredient(s) and pharmaceutically active agent(s) and the relative timings of administration will be selected in order to achieve the desired combined therapeutic effect.

Biological Screening and Anticancer Activity:

Some exemplary assays and examples for assessing therapeutic efficacy, e.g., anticancer effects, of exemplary compounds of the invention are described as below.

In Vitro Cell-Based Screening Using Real-Time Cell Electronic Sensing (RT-CES) System Some of the exemplary heterocyclic compounds in the present invention are developed for the anticancer activities for cancer cells with certain molecular targets, i.e., EGFR (epidermal growth factor receptor). The anticancer efficacy of these heterocyclic compounds and their analogues described above may be preliminarily screened in vitro using a penal of EGFR cancer cell lines by real time electronic cell sensing (RT-CES) system from ACEA Biosciences, Inc. (or xCELLigence system from Roche Applied Sciences/ACEA Biosciences Inc.), which provides dynamic cell response information after exposing to an anticancer agent.

The details of this cell electronic sensing technology, called real-time cell electronic sensing (RT-CES®) and associated devices, systems and methods of use are described in U.S. Pat. No. 7,732,127; U.S. Pat. No. 7,192,752; U.S. Pat. No. 7,459,303; U.S. Pat. No. 7,468,255; U.S. Pat. No. 7,470,533; U.S. Pat. No. 7,560,269; U.S. provisional application No. 60/397,749, filed on Jul. 20, 2002; U.S. provisional application No. 60/435,400, filed on Dec. 20, 2002; U.S. Provisional application 60/469,572, filed on May 9, 2003, PCT application number PCT/US03/22557, filed on Jul. 18, 2003; PCT application number PCT/US03/22537, filed on Jul. 18, 2003; PCT application number PCT/US04/37696, filed on Nov. 12, 2004; PCT application number PCT/US05/04481, filed on Feb. 9, 2005; U.S. patent application Ser. No. 10/705,447, filed on Nov. 10, 2003; U.S. patent application Ser. No. 10/705,615, filed on Nov. 10, 2003; U.S. patent application Ser. No. 10/987,732, filed on Nov. 12, 2004; U.S. patent application Ser. No. 11/055,639, filed on Feb. 9, 2005, each of which is incorporated by reference. Additional details of RT-CES technology is further disclosed in U.S. provisional application No. 60/519,567, filed on Nov. 12, 2003, and U.S. provisional application No. 60/542,927, filed on Feb. 9, 2004, U.S. provisional application No. 60/548,713, filed on Feb. 27, 2004, U.S. provisional application No. 60/598,608, filed on Aug. 4, 2004; U.S. provisional application No. 60/598,609, filed on Aug. 4, 2004; U.S. provisional application No. 60/613,749, filed on Sep. 27, 2004; U.S. provisional application No. 60/613,872, filed on Sep. 27, 2004; U.S. provisional application No. 60/614,601, filed on Sep. 29, 2004; U.S. provisional application No. 60/630,071, filed on Nov. 22, 2004; U.S. provisional application No. 60/630,131, filed on Nov. 22, 2004, each of which is incorporated herein by reference.

For measurement of cell-substrate or cell-electrode impedance using RT-CES technology, microelectrodes having appropriate geometries are fabricated onto the bottom surfaces of microtiter plate or similar device, facing into the wells. Cells are introduced into the wells of the devices, and make contact to and attach to the electrode surfaces. The presence, absence or change of properties of cells affects the electronic and ionic passage on the electrode sensor surfaces. Measuring the impedance between or among electrodes provides important information about biological status of cells present on the sensors. When there are changes to the biological status of the cells analogue, electronic readout signals are measured automatically and in real time, and are converted to digital signals for processing and analysis.

In a RT-CES system, a cell index is automatically derived and provided based on measured electrode impedance values. The cell index obtained for a given well reflects: 1) how many cells are attached to the electrode surfaces in this well; 2) how well cells are attached to the electrode surfaces in this well. Thus, the more the cells of same type in similar physiological conditions attach the electrode surfaces, the larger the cell index. And, the better the cells attach to the electrode surfaces (e.g., the cells spread-out more to have larger contact areas, or the cells attach tighter to electrode surfaces), the larger the cell index. We have found that the cMet-addictive cell lines would produce a transient impedance response profile when treated with positive-control EGFR (epidermal growth factor receptor) inhibitors.

Through the use of the RT-CES system, the heterocyclic compounds described in the examples above have been shown to produce a similar cell response impedance profile on RT-CES system to that generated by positive control inhibitors. In addition, these compounds have been shown to inhibit EGFR (epidermal growth factor receptor)-induced cell migration in several cell lines. In addition, these compounds have shown no or negligible effects when they were used to treat non-cMet addictive cancer cell lines.

The RT-CES system (or xCELLigence RTCA system) comprises three components, an electronic sensor analyzer, a device station and 16× or 96× microtiter plate devices (i.e. E-Plate 16 or E-Plate 96). Microelectrode sensor array was fabricated on glass slides with lithographical microfabrication methods and the electrode-containing slides are assembled to plastic trays to form electrode-containing wells. Each 16× (or 96×) microtiter plate device used in RT-CES system comprises up to 16 (or 96) such electrode-containing wells. The device station receives the 16× or 96× microtiter plate devices and is capable of electronically switching any one of the wells to the sensor analyzer for impedance measurement. In operation, the devices with cells cultured in the wells are placed into a device station (xCELLigence RTCA SP station or RT-CES SP station) that is located inside an incubator. Electrical cables connect the device station to the sensor analyzer (xCELLigence RTCA analyzer or RT-CES analyzer). Under the RT-CES or xCELLigence RTCA software control, the sensor analyzer can automatically select wells to be measured and continuously conduct impedance measurements. The impedance data from the analyzer is transferred to a computer, analyzed and processed by the integrated software.

Impedance measured between electrodes in an individual well depends on electrode geometry, ionic concentration in the well and whether there are cells attached to the electrodes. In the absence of the cells, electrode impedance is mainly determined by the ion environment both at the electrode/solution interface and in the bulk solution. In the presence of the cells, cells attached to the electrode sensor surfaces will alter the local ionic environment at the electrode/solution interface, leading to an increase in the impedance. The more cells there are on the electrodes, the larger the increase in cell-electrode impedance. Furthermore, the impedance change also depends on cell morphology and the extent to which cells attach to the electrodes.

To quantify cell status based on the measured cell-electrode impedance, a parameter termed Cell Index is derived, according to $$CI = \max_{i=1,\ldots,N}\left(\frac{R_{cell}(f_i)}{R_b(f_i)} - 1\right)$$

where $R_b(f)$ and $R_{cell}(f)$ are the frequency dependent electrode resistances (a component of impedance) without cells or with cell present, respectively. N is the number of the frequency points at which the impedance is measured. Thus, Cell Index is a quantitative measure of the status of the cells in an electrode-containing well. Under the same physiological conditions, more cells attached on to the electrodes leads to larger $R_{cell}(f)$ value, leading to a larger value for Cell Index. Furthermore, for the same number of cells present in the well, a change in the cell status such as morphology will lead to a change in the Cell Index. For example, an increase in cell adhesion or cell spreading leads to larger cell-electrode contact area which will lead to an increase in $R_{cell}(f)$ and thus a larger value for Cell Index. The Cell Index may also be calculated using a formula different from the one described here. Other methods for calculating the Cell Index based on impedance measurement can be found in U.S. Pat. No. 7,732,127; U.S. Pat. No. 7,192,752; U.S. Pat. No. 7,459,303; U.S. Pat. No. 7,468,255; U.S. Pat. No. 7,470,533; U.S. Pat. No. 7,560,269; PCT application number PCT/US04/37696, fined on Nov. 12, 2004, PCT application number PCT/US05/04481, filed on Feb. 9, 2005, U.S. patent application Ser. No. 10/987,732, filed on Nov. 12, 2004, and U.S. patent application Ser. No. 11/055,639, filed on Feb. 9, 2005.

Control Compounds for Testing

The following compounds can be used as comparison compounds for testing the compounds in the present disclosure.

WZ4002 is an irreversible inhibitor against EGFR T790M. (Nature 2009 Dec. 24; 462(7276): 1070-1074) The structure of WZ4002 is shown below:

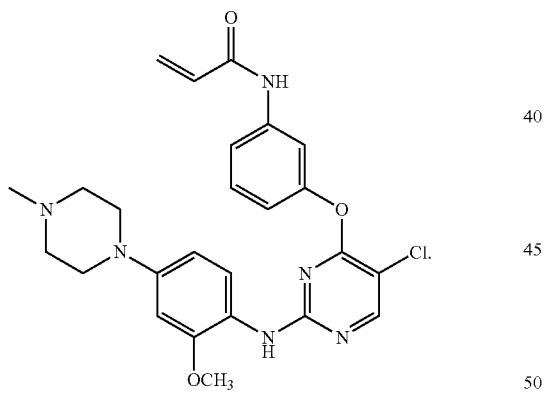

BIB W2992 (Afatinib) is an irreversible EGFR/HER2 inhibitor. (*Oncogene* 2008; 27:4702-4711) The structure of BIBW2992 is shown below:

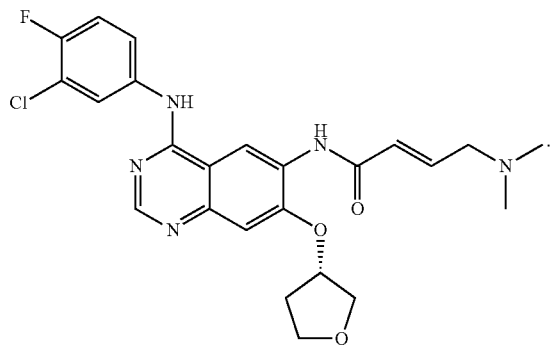 [SMILES: CN(C)C/C=C/C(=O)Nc1cc2c(Nc3ccc(F)c(Cl)c3)ncnc2cc1O[C@H]1CCOC1]

Erlotinib is a reversible tyrosine kinase inhibitor which acts on EGFR. (Drugs 2000, 60 Suppl 1: 15-23; discussion 41-2.) The structure of erlotinib is shown below:

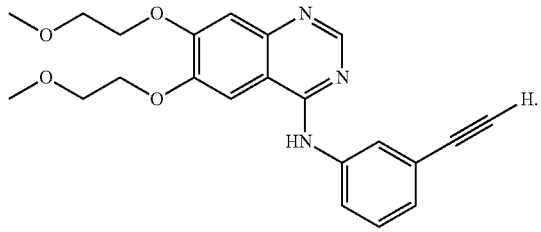

EXAMPLES

Example 1

Synthesis of N-(3-(5-methoxy-2-(4-(4-methylpiperazin-1-yl)phenylamino) pyrimidin-4-yloxy) phenyl) acrylamide (I-1) and N-(3-((2-((3-fluoro-4-(4-methylpiperazin-1-yl)phenyl)amino)pyrimidin-4-yl)oxy) phenyl)acrylamide (I-2)

The synthetic scheme for compounds I-1 and I-2 are shown below:

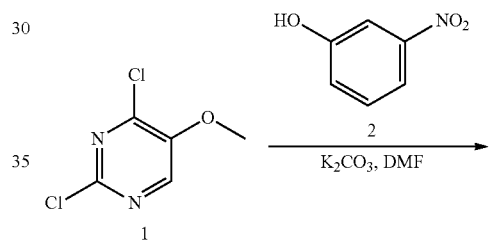

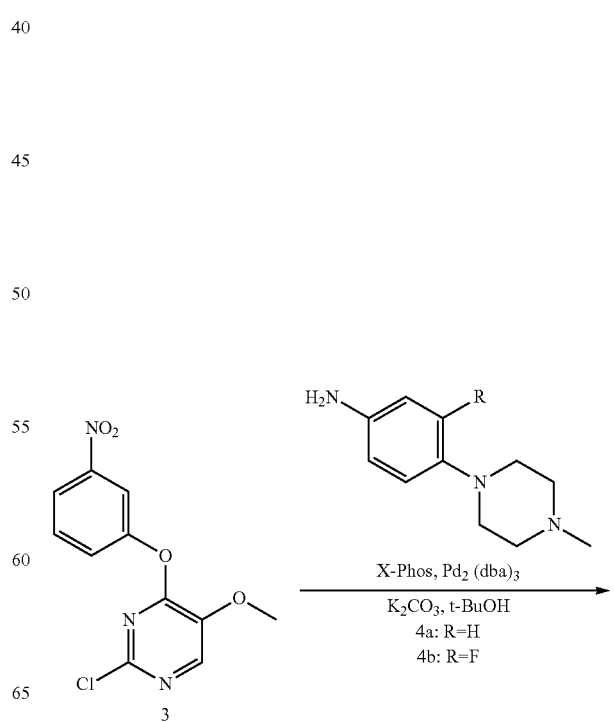

-continued

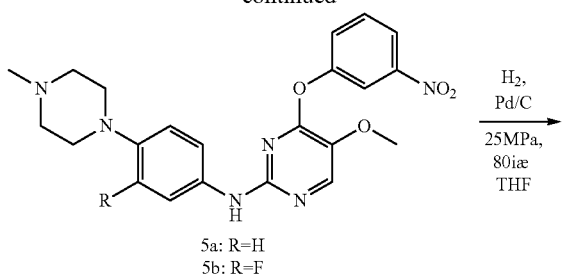

5a: R=H
5b: R=F

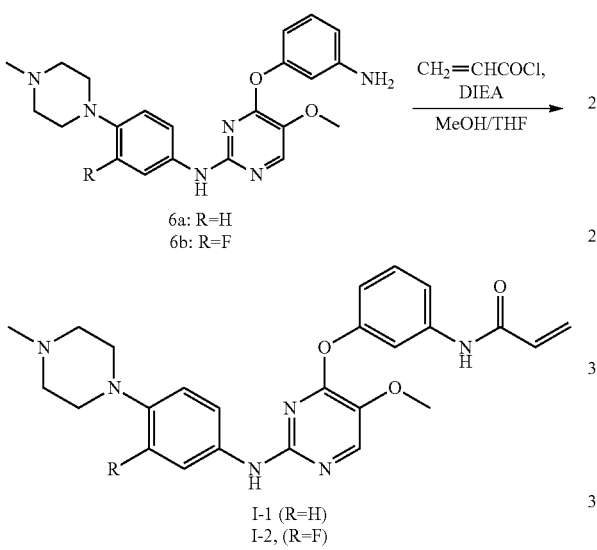

6a: R=H
6b: R=F

I-1 (R=H)
I-2, (R=F)

Step 1: Synthesis of
2-chloro-5-methoxy-4-(3-nitrophenoxy) pyrimidine
(3)

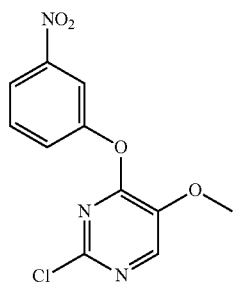

A mixture of 2,4-dichloro-5-methoxypyrimidine 1 (130.0 g, 726.3 mmol), 3-nitrophenol 2 (106.7 g, 767.0 mmol), and $K_2CO_3$ (193 g, 1.40 mol) in DMF (625 mL) was stirred at 30° C. for 24 h. Water (3.12 L) was then added into the reaction mixture. The mixture was stirred for 10 min. The precipitation was collected, washed with water (200 mL×3), and dried overnight to afford compound 3 (196.0 g, $M+H^+$= 282.6) as white solid.

Step 2: Synthesis of 5-methoxy-N-(4-(4-methylpiperazin-1-yl)phenyl)-4-(3-nitrophenoxy)pyrimidin-2-amine (5a)

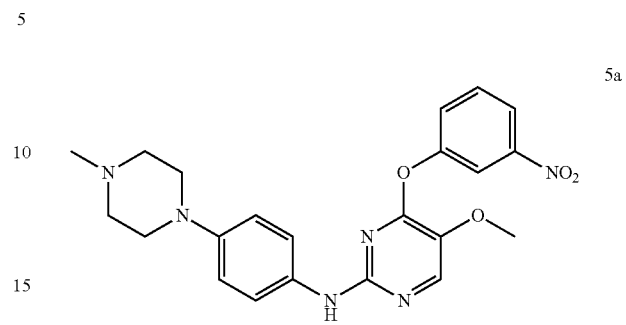

A mixture of compound 3 (80.0 g, 284.0 mmol), 4-(4-methylpiperazin-1-yl)aniline 4 (54.3 g, 284.0 mmol), X-Phos (8.0 g, 56.8 mmol), $Pd_2(dba)_3$ (8.0 g, 28.4 mmol), $K_2CO_3$ (78.5 g, 568.1 mmol) in t-BuOH (1.0 L) was stirred at refluxing for 4 h. The mixture was allowed to cool down to room temperature and then filtered. The solvent was evaporated under reduced pressure. To the residue, water (400 mL) was added. The mixture was extracted with DCM (400 mL×3). The organic layers were combined, and treated with activated charcoal (for de-colorization), and then filtered. The filtrate was concentrated down under reduced pressure. The crude was further purified by crystallization from ethyl acetate to afford yellow crystals 6 (92.0 g, $M+H^+$=437.5).

Step 3: Synthesis of 4-(3-aminophenoxy)-5-methoxy-N-(4-(4-methylpiperazin-1-yl)phenyl)pyrimidin-2-amine (6a)

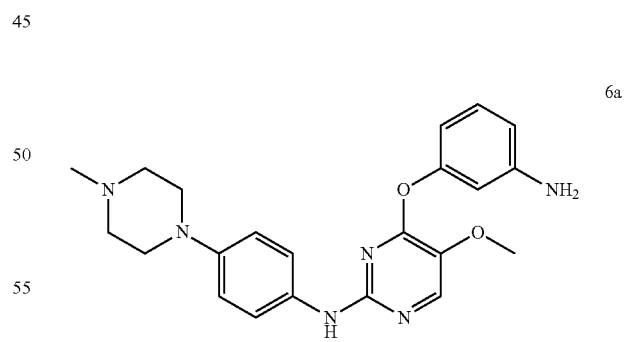

A solution of 5a (65.0 g, 143.0 mmol) in THF (150 mL) and 10% Pd/C (3.4 g, 5%) were stirred at 25 MPA hydrogen gas at 80° C. for 12 h. The mixture was cooled and filtered, and the organic solvent was removed under reduced pressure. The crude was further purified by crystallization from ethyl acetate to afford 6a (42.0 g, $M+H^+$=407.5).

Synthesis of N-(3-(5-methoxy-2-(4-(4-methylpiperazin-1-yl)phenylamino)pyrimidin-4-yloxy) phenyl) acrylamide (I-1)

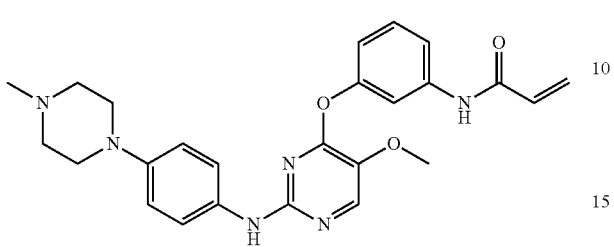

I-1

To a mixture of 6a (42.0 g, 103.3 mmol), DIEA (22.4 g, 173.6 mmol) in MeOH (420 mL) and THF (150 mL) was added acryloyl chloride (15.7 g, 173.6 mmol) at 0° C. The mixture was stirred for 1 h. The organic solvent was removed under reduced pressure. The residue was re-dissolved in DCM (800 mL) and washed with saturated aqueous sodium bicarbonate (400 ml). The organic layer was separated and the solvent was removed under reduced pressure. The crude was further purified by crystallization from THF/H$_2$O (3:10) to afford compound I-1 (25.0 g, M+H$^+$=461.5). $^1$H NMR (500 MHz, DMSO-d$_6$) δ 10.34 (s, 1H), 9.01 (s, 1H), 8.17 (s, 1H), 7.64-7.59 (m, 2H), 7.43 (t, J=8.4 Hz, 1H), 7.28 (d, J=9.0 Hz, 2H), 6.95 (m, 1H), 6.64 (d, J=9.1 Hz, 2H), 6.44 (dd, J=17.0, 10.1 Hz, 1H), 6.35-6.19 (m, 1H), 5.78 (dd, J=10.1, 1.9 Hz, 1H), 3.87 (s, 3H), 3.02-2.91 (m, 4H), 2.48-2.39 (m, 4H), 2.23 (s, 3H). $^{13}$C NMR (126 MHz, DMSO-d$_6$) δ 165.32 (s), 161.43 (s), 155.79 (s), 154.79 (s), 147.52 (s), 145.95 (s), 142.27 (s), 136.62 (s), 135.09 (s), 133.70 (s), 131.87 (s), 129.25 (s), 121.10 (s, 2C), 118.76 (s), 118.17 (s), 117.71 (s, 2C), 114.94 (s), 59.63 (s), 56.65 (s, 2C), 50.92 (s, 2C), 47.71 (s).

Compound (I-2) N-(3-(2-(3-fluoro-4-(4-methylpiperazin-1-yl)phenyl amino)-5-methoxypyrimidin-4-yloxy)phenyl) acrylamide was synthesized using similar procedures as Compound I-1 with similar yield. Compound (I-2): M+H$^+$= 479.5. $^1$H NMR (500 MHz, MeOD) δ 8.07 (s, 1H), 7.69 (t, J=2.0 Hz, 1H), 7.57 (dd, J=8.2, 1.0 Hz, 1H), 7.43 (t, J=8.2 Hz, 1H), 7.30 (dd, J=15.2, 2.5 Hz, 1H), 7.03-6.88 (m, 2H), 6.78 (t, J=9.5 Hz, 1H), 6.45 (dd, J=17.0, 9.9 Hz, 1H), 6.37 (dd, J=17.0, 2.0 Hz, 1H), 5.78 (dd, J=9.9, 2.0 Hz, 1H), 3.94 (s, 3H), 2.99 (hr s, 4H), 2.62 (hr s, 4H), 2.35 (s, J=6.2 Hz, 3H). $^{13}$C NMR (126 MHz, MeOD) δ 166.29 (s), 162.07 (s), 158.04 (s), 156.11 (s), 155.29 (s), 154.60 (s), 144.75 (s), 141.44 (s), 138.09 (d, J=11.1 Hz), 137.15 (s), 134.70 (d, J=9.8 Hz), 132.55 (s), 131.07 (s), 128.26 (s), 120.31 (d, J=4.1 Hz), 118.88 (s), 118.28 (s), 115.45-115.14 (m), 107.96 (d, J=26.4 Hz), 58.81 (s), 56.19 (s, 2C), 51.83 (s, J=2.6 Hz, 2C), 46.25 (s).

Example 2

Synthesis of Key Intermediates (I, II, III, IV and V)

Intermediate I (the Synthetic Scheme is Shown Below)

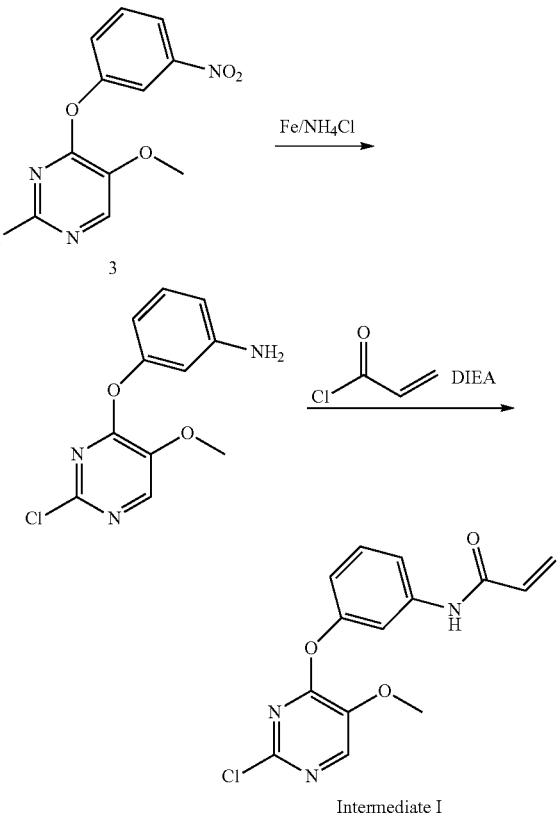

Intermediate I

Step 1: Synthesis of 3-(2-chloro-5-methoxypyrimidin-4-yloxy) aniline

To a solution of compound 3 (35 g) in THF (200 mL), water (30 mL), NH4Cl (17 g) and Fe (15 g) were added. The reaction mixture was heated to reflux with stirring for 3 h. The reaction mixture was cooled down and filtered, and the THF layer was concentrated under reduced pressure. The crude was re-dissolved in ethyl acetate (200 mL) and the pH was adjusted with aqueous sodium bicarbonate solution, and then washed with water (100 mL×3). The organic layer was separated and the solvent was removed under reduced pressure to obtain the title product (13 g, M+H$^+$=252.5).

Step 2: Synthesis of N-(3-(2-chloro-5-methoxypyrimidin-4-yloxy)phenyl) acryl amide (I)

To a solution of 3-(2-chloro-5-methoxypyrimidin-4-yloxy) aniline (7.5 g) and DIEA (6 g) in THF (150 mL), acryloyl chloride (2.7 g) in THF (10 mL) was drop-wise added at 0° C. with an ice-bath over 20 mm. After the reaction mixture was stirred overnight, aqueous NaOH (1M, 40 mL) was added. The reaction mixture was stirred at room temperature for another 0.5 h. The THF layer was separated, and the aqueous layer was extracted with ethyl acetate (100 mL). The combined organic layer was concentrated under reduced pressure. The residue was re-dissolved in ethyl acetate (200 mL), washed with water (100 mL×3). The organic layer was separated and the solvent was removed under reduced pressure to yield the crude, which was further purified by flash column chromatography to give the desired intermediate 1 (4 g, M+H$^+$=306.5).

Intermediate II (the synthetic scheme is shown below):

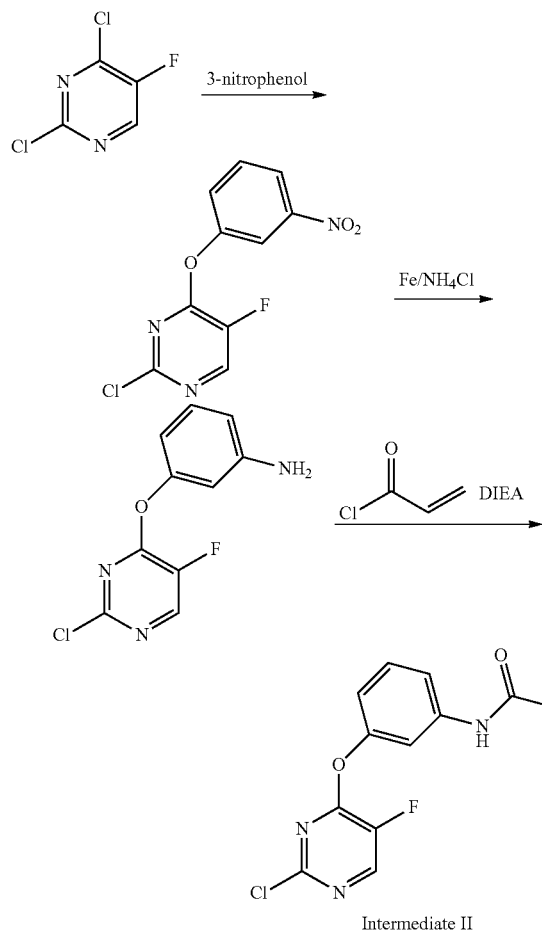

Step 1: the Synthesis of 2-chloro-5-fluoro-4-(3-nitrophenoxy) pyrimidine

A mixture of 2,4-dichloro-5-fluoropyrimidine (10.20 g), 3-nitrophenol (8.6 g), and K$_2$CO$_3$ (15.30 g) in DMF (80 mL) was stirred overnight at room temperature. Water (300 mL) was added. The reaction mixture was stirred for 30 mm and then filtered. The precipitate was collected, washed with water (100 mL×2) and dried. The solid was re-dissolved in ethyl acetate (200 mL), washed with water (100 mL×3). The organic layer was separated and the solvent was removed under reduced pressure. The crude was further purified by crystallization from ethyl acetate/petroleum ether (20 ml) to afford yellow crystals 3 (9.8 g, M+H$^+$=270.6).

Step 2: the Synthesis of 3-(2-chloro-5-fluoropyrimidin-4-yloxy) aniline

To a solution of 2-chloro-5-fluoro-4-(3-nitrophenoxy) pyrimidine (6.8 g) in THF (100 mL) water (20 mL), NH4Cl (6.5 g) and Fe (6.5 g) were added. The reaction mixture was stirred at refluxing for 5 h, cooled to room temperature and then filtered. The filtrate was concentrated under reduced pressure. The residue was re-dissolved in ethyl acetate (200 mL) and the PH was adjusted with aqueous sodium bicarbonate solution. The mixture was washed with water (100 mL×3). The organic layer was separated and the solvent was removed under reduced pressure to yield the desired product with, 66.2% yield (4 g, M+H$^+$=240.5).

Step 3: the synthesis of N-(3-(2-chloro-5-fluoropyrimidin-4-yloxy)phenyl)acrylamide (II)

To a solution of 3-(2-chloro-5-fluoropyrimidin-4-yloxy) aniline (3.9 g) and DIEA (3 g) in THF (60 mL), acryloyl chloride (1.6 g) in THF (5 mL) was added drop-wise at 0° C. (an ice-bath) over 15 mm After the reaction mixture was stirred for 4 h, aqueous sodium bicarbonate Aqueous (50 mL) was added drop-wise. The reaction mixture was stirred for another 0.5 h. The organic layer was separated. The aqueous layer was extracted with ethyl acetate (100 mL). The combined organic layers were concentrated down under reduced pressure. The residue was re-dissolved in ethyl acetate (200 mL), washed with water (100 mL×3). The organic layer was separated and the solvent was removed under reduced pressure. The crude was further purified by flash column chromatography to yield the desired intermediated II (4 g, M+H$^+$=294.5).

Intermediate III (the synthetic scheme is shown below):

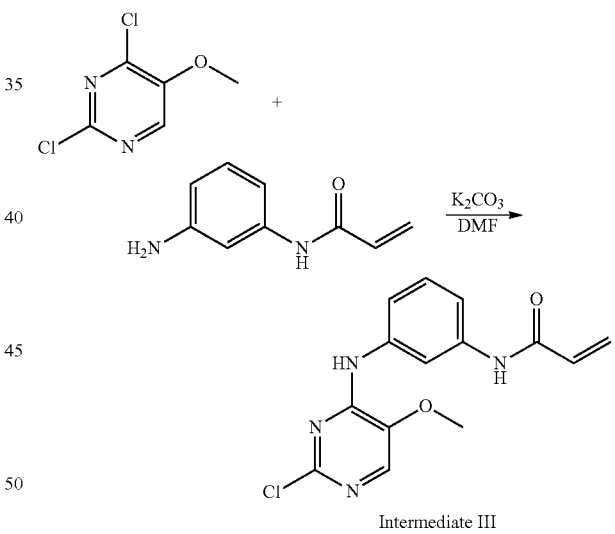

Synthesis of N-(3-(2-chloro-5-methoxypyrimidin-4-ylamino)phenyl)acrylamide (III)

To a solution of 2,4-dichloro-5-methoxypyrimidine 1 (2.55 g) and N-(3-aminophenyl) acrylamide (2.32 g) in DMF (30 mL), K$_2$CO$_3$ (4.14 g) was added. The reaction mixture was stirred at 50° C. for 16 h. TLC (petroleum ether:ethyl acetate=1:1 as elution) indicated the completion of the reaction. Ethyl acetate (200 mL) was added, washed with water (200 mL×3). The organic layer was separated, and the solvent was removed under reduced pressure. The crude was further purified by flash column chromatography to yield the desired product III (3.5 g, M+H$^+$=305.7).

Intermediate IV (the synthetic scheme is shown below):

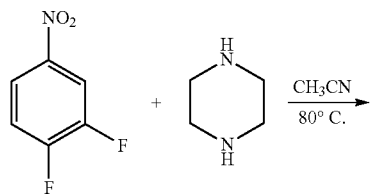

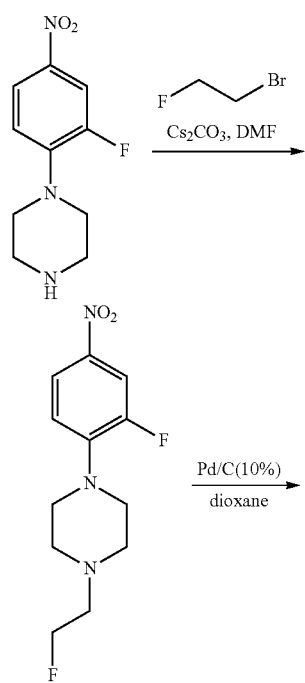

Intermediate IV

Step 1: the synthesis of
1-(2-fluoro-4-nitrophenyl)piperazine

In a round-bottom flask, 1,2-difluoro-4-nitrobenzene (23 g, 144.57 mmol) was added to a solution of piperazine (21.66 g, 251.46 mmol) in MeCN (200 mL). The mixture was stirred at 80° C. for 3 h until the reaction was complete indicated by TLC (petroleum ether:ethyl acetate=3:1). The mixture was concentrated followed by adding water (300 mL), extracted by ethyl acetate (200 mL×3). Organic layers were combined, dried over $Na_2SO_4$ and concentrated under reduced pressure to yield yellow crude product (30 g, $M+H^+=226.5$).

Step 2: the synthesis of 1-(2-fluoro-4-nitrophenyl)-4-(2-fluoroethyl)piperazine 1-bromo-2-fluoroethane (5.4 g, 42.63 mmol), DMF (48 mL), 1-(2-fluoro-4-nitrophenyl)piperazine (8 g, 35.52 mmol) and Cs2CO3 (25.2 g, 77.34 mmol) was sequentially added to the flask. The reaction mixture was stirred at 80° C. for 7 h until the reaction was complete indicated by TLC (ethyl acetate:petroleum ether=1:3). After cooled to room temperature, the mixture was filtered. The filtrate was poured into water (700 mL) with stirring vigorously. The precipitate was collected, washed with water, and dried to yield the crude product (9 g, $M+H^+=272.5$).

Step 3: the synthesis of 3-fluoro-4-(4-(2-fluoroethyl)piperazin-1-yl)aniline (IV)

A solution of 1-(2-fluoro-4-nitrophenyl)-4-(2-fluoroethyl) piperazine (1.1 g, 4.06 mmol) and Pd/C (10%) (0.2 g, 1.87 mmol) in 1,4-dioxane (10 mL) was hydrogenated for 12 h at room temperature until the reaction was complete indicated by TLC (MeOH:DCM=1:4). The mixture was filtered through Celite-bed, and washed with 1,4-dioxane (5 mL). The filtrate was concentrated under reduced pressure to give the crude product IV (1 g, $M+H^+=242.5$), which was used for next step without further purification.

Intermediate V (the synthetic scheme is shown below):

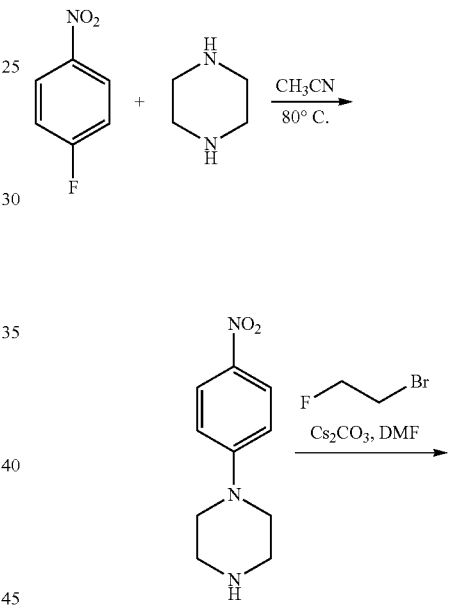

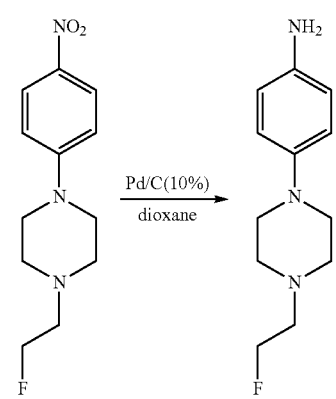

Using a similar chemistry as for intermediate IV, the intermediate (V) 4-(4-(2-fluoroethyl)piperazin-1-yl)aniline was synthesized.

Example 3

Synthesis of N-(3-(2-(3-fluoro-4-(4-(2-fluoroethyl)piperazin-1-yl)phenylamino)-5-methoxypyrimidin-4-yloxy)phenyl)acrylamide (I-3)

The synthetic scheme for compound I-3 is shown below:

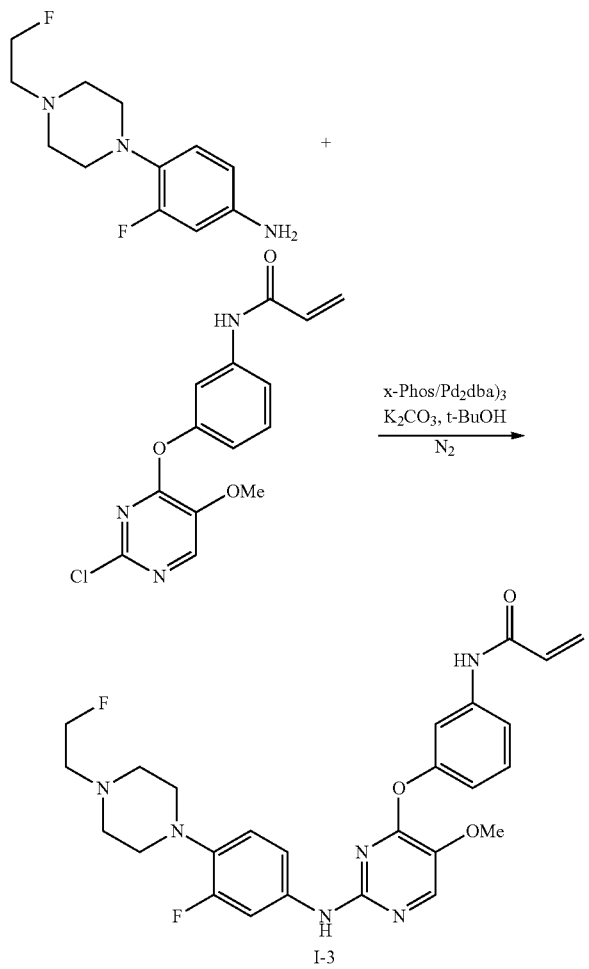

N-(2-(2-chloro-5-methoxypyrimidin-4-yloxy)phenyl)acrylamide (300 mg, 0.981 mmol), 3-fluoro-4-(4-(2-fluoroethyl)piperazin-1-yl)aniline (236.8 mg, 0.981 mmol), potassium carbonate (175 mg, 1.27 mmol), tris(dibenzylideneacetone)dipalladium (35 mg, 0.07 mmol) and dicyclohexyl (2',4',6'-triisopropylbiphenyl-2-yl) phosphine (35 mg, 0.038 mmol) and t-BuOH (3 mL) were sequentially added to a 10 mL round bottom flask with a magnetite. The flask was placed on an oil bath and stirred under $N_2$. The reaction mixture was heated to reflux for 5~7 h until reaction was complete indicated by TLC (ethyl acetate/petroleum ether/TEA=1/1/0.1 as elution). The mixture was concentrated under reduced pressure, followed by addition of EtOAc (10 mL) and activated charcoal (0.1 g). After stirred for 15 min, the mixture was filtered through Celite®, and the filter cake was washed with ethyl acetate (10 mL). The filtrate was concentrated under reduced pressure. The crude was further purified by flash column chromatography (ethyl acetate/petroleum ether=1/1 to 100% EtOAc as elution) to give the title compound I-3 (120 mg, yield 26%, purity 97.35%, M+H$^+$=511.5) as white solid. $^1$H NMR (500 MHz, DMSO-d$_6$) δ 10.32 (s, 1H), 9.28 (s, 1H), 8.22 (s, 1H), 7.67 (t, J=2.1 Hz, 1H), 7.56 (dd, J=8.2, 1.0 Hz, 1H), 7.43 (t, J=8.1 Hz, 1H), 7.35 (dd, J=15.5, 1.9 Hz, 1H), 7.11 (dd, J=8.7, 1.9 Hz, 1H), 6.97 (m, 1H), 6.79-6.71 (m, 1H), 6.43 (dd, J=17.0, 10.2 Hz, 1H), 6.26 (dd, J=17.0, 1.9 Hz, 1H), 5.77 (dd, J=10.1, 1.9 Hz, 1H), 4.61 (t, J=4.9 Hz, 1H), 4.51 (t, J=4.9 Hz, 1H), 3.89 (s, 3H), 2.93-2.81 (m, 4H), 2.69 (t, J=4.9 Hz, 1H), 2.63 (t, J=4.9 Hz, 1H), 2.57 (br s, 4H). $^{13}$C NMR (126 MHz, DMSO-d$_6$) δ 165.32 (s), 161.39 (s), 157.66 (s), 155.73 (s), 154.92 (d, J=65.0 Hz), 145.45 (s), 142.39 (s), 138.17 (d, J=11.0 Hz), 137.16 (s), 135.13 (d, J=9.3 Hz), 133.71 (s), 131.94 (s), 129.23 (s), 120.92 (s), 118.70 (s), 118.25 (s), 115.73 (s), 114.68 (s), 107.96 (d, J=26.1 Hz), 83.84 (d, J=164.5 Hz), 59.62 (s), 59.46 (s), 55.05 (s, 2C), 52.54 (s, 2C).

Example 4

Synthesis of N-(3-((5-fluoro-2-((3-fluoro-4-(4-(2-fluoroethyl)piperazin-1yl)phenyl)amino)pyrimidin-4-yl)amino)phenyl)acrylamide (I-4)

The synthetic scheme for compound I-4 is shown below:

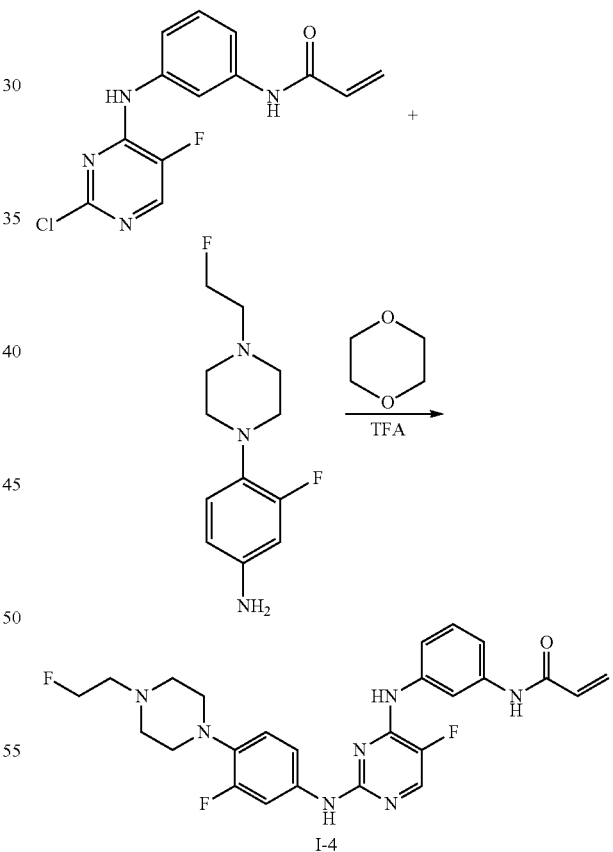

N-(3-(2-chloro-5-fluoropyrimidin-4-ylamino)phenyl)acrylamide (878 mg), 1,4-dioxane (30 mL), 3-fluoro-4-(4-(2-fluoroethyl)cyclohexyl)aniline (730 mg) and TFA (0.7 mL) were sequentially added to the flask. The reaction mixture was stirred at refluxing for 24 h. TLC (petroleum ether:ethyl acetate=2:1 as elution) indicated the completion of the reaction. The reaction mixture was concentrated under reduced pressure. The crude was re-dissolved in ethyl acetate (100 mL), adjusted the pH to 8 with aqueous solution of sodium bicarbonate, and washed by water (100 mL×3). The organic layer was separated, and the solvent was removed under reduced pressure. The crude was further purified by flash column chromatography to yield the title compound I-4 (480 mg, M+H$^+$=498.5 32% yield). $^1$H NMR (500 MHz, MeOD) 8.08 (s, 1H), 7.93 (d, J=3.8 Hz, 1H), 7.57 (dd, J=15.1, 2.5 Hz, 1H), 7.48-7.39 (m, 2H), 7.32 (t, J=8.1 Hz, 1H), 7.23-7.13 (m, 1H), 6.90 (t, J=9.2 Hz, 1H), 6.46 (dd, J=17.0, 9.9 Hz, 1H), 6.38 (dd, J=17.0, 1.9 Hz, 1H), 5.79 (dd, J=9.9, 1.9 Hz, 1H), 4.68 (t, J=4.5 Hz, 1H), 4.58 (t, J=4.5 Hz, 1H), 3.11-3.03 (m, 4H), 2.81 (t, J=4.5 Hz, 1H), 2.76-2.70 (m, 5H). $^{13}$C NMR (126 MHz, MeOD) δ 166.30 (s), 158.11 (s), 157.14 (s), 156.17 (s), 152.12 (d, J=10.7 Hz), 143.43 (s), 141.61-140.82 (m), 140.37 (d, J=35.4 Hz), 138.06 (d, J=10.8 Hz), 135.17 (d, J=9.7 Hz), 132.75 (s), 130.22 (s), 128.07 (s), 120.36 (d, J=4.0 Hz), 119.38 (s), 117.04 (s), 116.11 (s), 115.41 (s), 108.84 (d, J=25.9 Hz), 82.71 (d, J=166.3 Hz), 59.44 (d, J=19.8 Hz), 54.75 (s, 2C), 51.95 (d, J=2.6 Hz, 2C).

Example 5

Synthesis of N-(3-(2-(4-(4-(2-fluoroethyl)piperazin-1-yl)phenylamino)-5-methoxypyrimidin-4-yloxy)phenyl)acrylamide (I-5)

The synthetic scheme for compound I-5 is shown below:

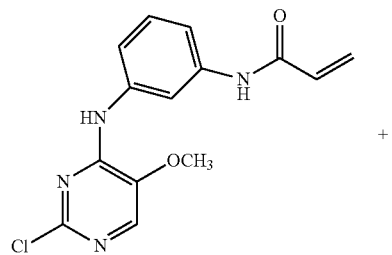

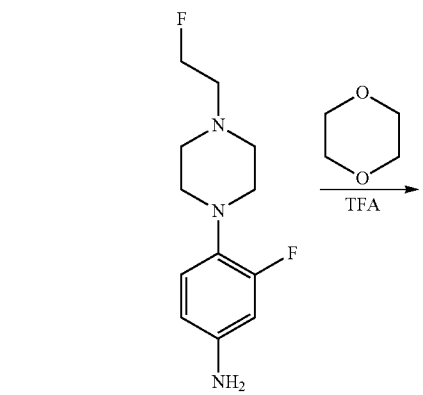

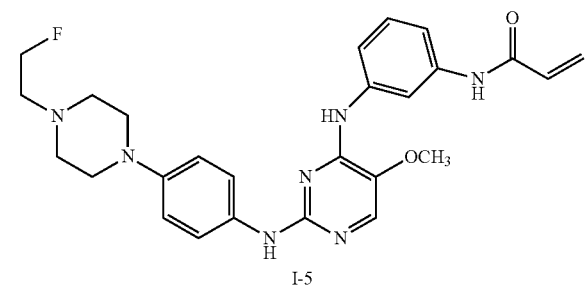

I-5

N-(3-(2-chloro-5-methoxypyrimidin-4-ylamino)phenyl) acrylamide (1.089 g), 4-(4-(2-fluoroethyl)piperazin-1-yl) aniline (0.800 g), potassium carbonate (1.231 g), tris(dibenzylideneacetone) dipalladium (0.300 g) and dicyclohexyl (2',4',6'-triisopropylbiphenyl-2-yl) phosphine (0.300 g) and t-BuOH (30 mL) were sequentially added to a 100 mL round bottom flask with a magnetite. The flask was placed on an oil bath and stirred under a N$_2$ flow. The reaction mixture was heated to refluxing for 5~7 h until reaction was complete indicated by TLC (ethyl acetate/petroleum ether/TEA=1/1/0.1 as elution). The mixture was concentrated under reduced pressure, followed by addition of EtOAc (50 mL) and activated charcoal (0.5 g). After stirred for 15 min, the mixture was filtered through Celite®. The filter cake was washed with ethyl acetate (50 mL). The filtrate was concentrated under reduced pressure and the crude was further purified by flash column chromatography (ethyl acetate/petroleum ether=1/1 to 100% ethyl acetate as elution) to give the title compound I-5 (750 mg, yield 42.65%, purity 95.8%, M+H$^+$=492.5) as white solid. $^1$H NMR (500 MHz, DMSO-d$_6$) δ 10.09 (s, 1H), 8.69 (s, 1H), 8.58 (s, 1H), 7.98 (t, J=1.8 Hz, 1H), 7.82 (s, 1H), 7.55-7.49 (m, 3H), 7.42 (d, J=8.6 Hz, 1H), 7.26 (t, J=8.1 Hz, 1H), 6.77 (d, J=9.1 Hz, 2H), 6.47 (dd, J=17.0, 10.2 Hz, 1H), 6.27 (dd, J=17.0, 2.0 Hz, 1H), 5.76 (dd, J=10.1, 2.0 Hz, 1H), 4.65-4.59 (m, 1H), 4.56-4.50 (m, 1H), 3.85 (s, 3H), 3.05-2.95 (m, 4H), 2.70 (t, J=4.9 Hz, 1H), 2.64 (t, J=4.9 Hz, 1H), 2.62-2.54 (m, 4H). $^{13}$C NMR (126 MHz, DMSO-d$_6$) δ 165.06 (s), 156.09 (s), 153.81 (s), 147.29 (s), 141.66 (s), 140.88 (s), 139.29 (s), 136.26 (s), 135.95 (s), 134.03 (s), 130.53 (s), 128.76 (s), 121.28 (s), 119.17 (s), 118.00 (s), 116.38 (s), 115.43 (s), 83.91 (d, J=164.3 Hz), 59.58 (d, J=19.5 Hz), 59.00 (s), 55.05 (s, 2C), 51.30 (s, 2C).

Example 6

Synthesis of N-(2-(5-fluoro-2-(4-(4-(2-fluoroethyl)piperazin-1-yl)phenylamino)pyrimidin-4-ylamino)phenyl)acrylamide (I-6)

The synthetic scheme for compound I-6 is shown below:

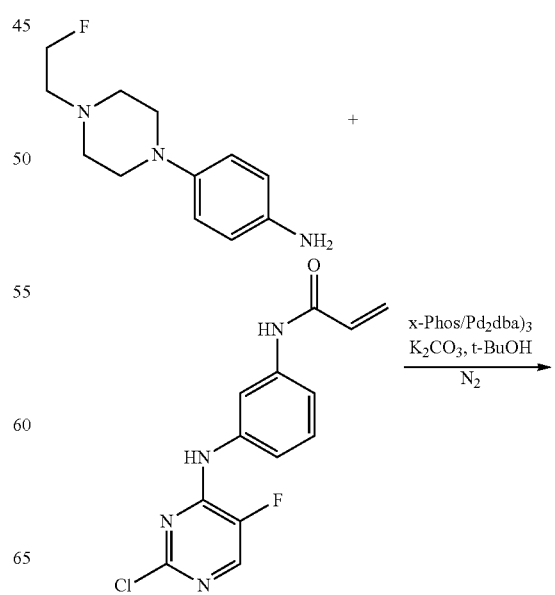

-continued

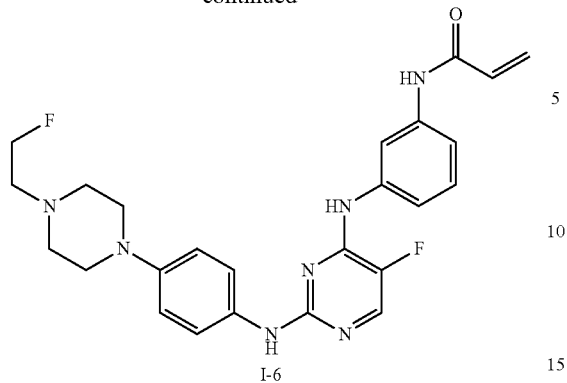

I-6

N-(2-(2-chloro-5-fluoropyrimidin-4-ylamino)phenyl) acrylamide (2.010 g, 6.849 mmol), 4-(4-(2-fluoroethyl)piperazin-1-yl)aniline (2.008 g, 8.969 mmol), potassium carbonate (1.880 g, 13.698 mmol), tris(dibenzylideneacetone) dipalladium (630 mg, 0.685 mmol) and dicyclohexyl (2',4',6'-triisopropylbiphenyl-2-yl) phosphine (627 mg, 1.370 mmol) and t-BuOH (20 mL) were sequentially added into a 100 mL round bottom flask with a magnetite. The flask was placed on an oil bath and stirred under a $N_2$ flow. The reaction mixture was heated to refluxing for 5~7 h until reaction was complete indicated by TLC (EtOAc/petroleum ether/TEA=3/1/0.1 as elution). The mixture was concentrated under reduced pressure, followed by addition of EtOAc (50 mL) and activated charcoal (0.5 g). After stirred for 15 min, the mixture was filtered through Celite®. The filter cake was washed with ethyl acetate (50 mL). The filtrate was concentrated under reduced pressure. The crude was further purified by flash column chromatography (EtOAc/petroleum ether=3/1 to EtOAc as elution) to give the title compound I-6 (1.85 g, yield 56.23%, purity 95%, M+H$^+$=480.2) as light yellow solid. $^1$H NMR (500 MHz, MeOD) δ 8.07 (s, 1H), 7.88 (d, J=3.7 Hz, 1H), 7.50-7.39 (m, 4H), 7.29 (t, J=8.1 Hz, 1H), 6.92-6.85 (m, 2H), 6.46 (dd, J=17.0, 9.8 Hz, 1H), 6.39 (dd, J=17.0, 2.1 Hz, 1H), 5.80 (dd, J=9.8, 2.1 Hz, 1H), 4.71-4.65 (m, 1H), 4.61-4.55 (m, 1H), 3.17-3.10 (m, 4H), 2.84-2.78 (m, 1H), 2.78-2.69 (m, 5H). $^{13}$C NMR (126 MHz, MeOD) δ 166.25 (s), 157.72 (s), 152.10 (d, J=10.7 Hz), 148.08 (s), 143.16 (s), 141.20 (s), 141.12 (s), 140.96 (s), 140.66 (s), 140.07 (s), 135.13 (s), 132.74 (s), 130.13 (s), 128.15 (s), 122.40 (s), 119.20 (s), 118.27 (s), 116.94 (s), 115.33 (s), 82.76 (d, J=166.4 Hz), 59.42 (d, J=19.7 Hz), 54.71 (s, 2C), 51.15 (s, 2C).

Example 7

Synthesis of N-(2-(2-(3-fluoro-4-(4-(2-fluoroethyl) piperazin-1-yl)phenylamino)-5-methoxypyrimidin-4-ylamino)phenyl)acrylamide (I-7)

The synthetic scheme for compound I-7 is shown below:

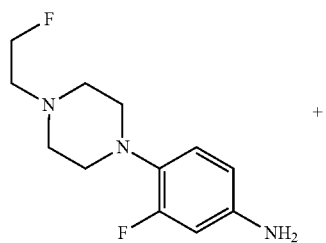

+

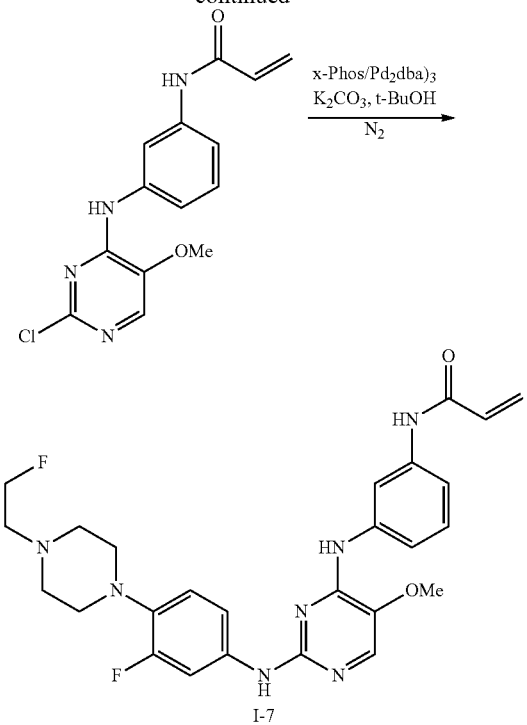

I-7

N-(2-(2-chloro-5-methoxypyrimidin-4-ylamino)phenyl) acrylamide (1.521 g, 5 mmol), 3-fluoro-4-(4-(2-fluoroethyl) piperazin-1-yl)aniline (1.210 g, 5 mmol), potassium carbonate (1.383 g, 10 mmol), tris(dibenzylideneacetone) dipalladium (460 mg, 0.5 mmol) and dicyclohexyl (2',4',6'-triisopropylbiphenyl-2-yl) phosphine (475 mg, 1 mmol) and t-BuOH (50 mL) were sequentially added into a 100 mL round bottom flask with a magnetite. The flask was placed on an oil bath and stirred under a $N_2$ flow. The reaction mixture was heated to refluxing for 5~7 h until the reaction was complete indicated by TLC (EtOAc/petroleum ether/ TEA=1/1/0.1 as elution). The mixture was concentrated under reduced pressure, followed by addition of EtOAc (50 mL) and activated charcoal (0.5 g). After stirred for 15 min, the mixture was filtered through Celite®, and the filter cake was washed with ethyl acetate (50 mL). The filtrate was concentrated and the crude was further purified by flash column chromatography (EtOAc/petroleum ether=1/1 to EtOAc as elution) to yield the title compound I-7 (1.537 g, yield 60.2%, purity 95.33%, M+H$^+$=510.3) as light yellow solid. $^1$H NMR (500 MHz, DMSO-d$_6$) δ 10.08 (s, 1H), 8.89 (s, 1H), 8.77 (s, 1H), 7.96 (t, J=1.8 Hz, 1H), 7.86 (s, 1H), 7.67 (dd, J=15.7, 2.4 Hz, 1H), 7.51 (d, J=8.0 Hz, 1H), 7.44 (d, J=8.7 Hz, 1H), 7.31 (dd, J=8.7, 2.0 Hz, 1H), 7.27 (t, J=8.1 Hz, 1H), 6.84 (dd, J=9.8, 9.1 Hz, 1H), 6.46 (dd, J=17.0, 10.2 Hz, 1H), 6.25 (dd, J=17.0, 2.0 Hz, 1H), 5.75 (dd, J=10.1, 2.0 Hz, 1H), 4.61 (t, J=4.9 Hz, 1H), 4.52 (t, J=4.9 Hz, 1H), 3.87 (s, 3H), 2.97-2.86 (m, 4H), 2.70 (t, J=4.9 Hz, 1H), 2.64 (t, J=4.9 Hz, 1H), 2.59 (s, 4H). $^{13}$C NMR (126 MHz, DMSO-d$_6$) δ 165.07 (s), 157.89 (s), 155.97 (s), 155.49 (s), 153.84 (s), 141.51 (s), 141.07 (s), 139.06 (d, J=11.0 Hz), 138.82 (s), 136.67 (s), 134.63 (d, J=9.4 Hz), 134.06 (s), 130.60 (s), 128.67 (s), 121.06 (d, J=4.0 Hz), 119.34 (s), 116.48 (s), 115.75-115.32 (m), 107.95 (d, J=26.1 Hz), 83.85 (d, J=164.4 Hz), 59.57 (d, J=19.6 Hz), 58.89 (s), 55.11 (s, 2C), 52.65 (s, 2C).

Example 8

Synthesis of N-(2-(5-fluoro-2-(3-fluoro-4-(4-(2-fluoroethyl)piperazin-1-yl)phenylamino)pyrimidin-4-yloxy)phenyl)acrylamide (I-8)

The synthetic scheme for compound I-8 is shown below:

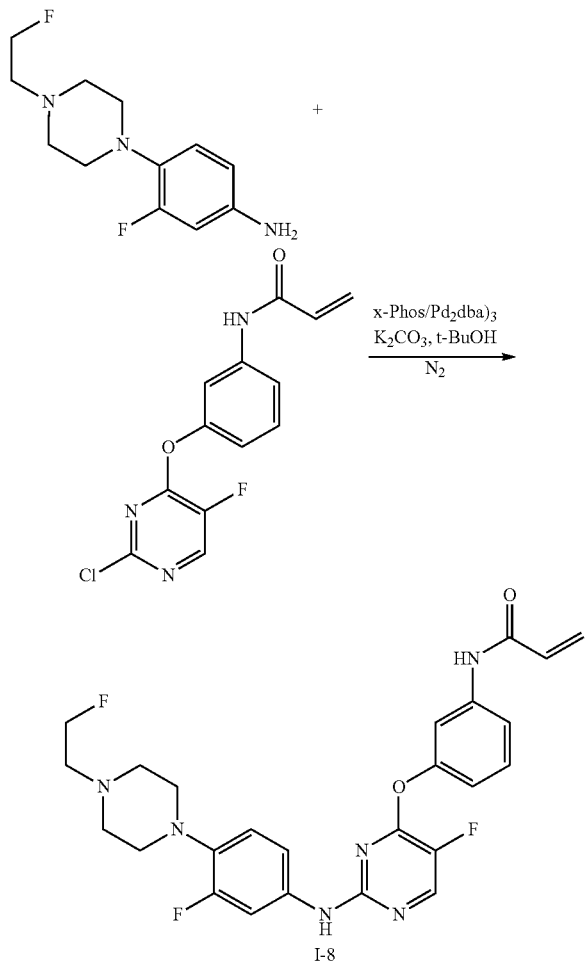

N-(2-(2-chloro-5-fluoropyrimidin-4-yloxy)phenyl)acrylamide (1.461 g, 5 mmol), 3-fluoro-4-(4-(2-fluoroethyl)piperazin-1-yl)aniline (1.210 g, 5 mmol), potassium carbonate (1.380 g, 10 mmol), tris(dibenzylideneacetone)dipalladium (460 mg, 0.5 mmol) and dicyclohexyl (2',4',6'-triisopropyl-biphenyl-2-yl) phosphine (475 mg, 1 mmol) and t-BuOH (50 mL) were sequentially added into a 100 mL round bottom flask with a magnetite. The flask was placed on an oil bath and stirred under a $N_2$ flow. The reaction mixture was heated to refluxing for 5~7 h until reaction was complete indicated by TLC (EtOAc/petroleum ether/TEA=1/1/0.1 as elution). The mixture was concentrated under reduced pressure, followed by addition of EtOAc (50 mL) and activated charcoal (0.5 g). After stirred for 15 min, the mixture was filtered through Celite®, and the filter cake was washed with ethyl acetate (50 mL). The filtrate was concentrated under reduced pressure, and the crude was further purified by flash column chromatography (EtOAc/petroleum ether=1/1 to EtOAc as elution) to give the title compound I-8 (1.72 g, yield 69.1%, purity 98.67%, M+H⁺=499.3) as light yellow solid. ¹H NMR (500 MHz, DMSO-d₆) δ 10.35 (s, 1H), 9.60 (s, 1H), 8.49 (d, J=3.0 Hz, 1H), 7.74 (t, J=2.0 Hz, 1H), 7.61-7.55 (m, 1H), 7.46 (t, J=8.2 Hz, 1H), 7.32 (d, J=15.1 Hz, 1H), 7.10 (d, J=8.2 Hz, 1H), 7.04 (m, 1H), 6.77 (t, J=9.4 Hz, 1H), 6.44 (dd, J=17.0, 10.2 Hz, 1H), 6.27 (dd, J=17.0, 1.9 Hz, 1H), 5.78 (dd, J=10.1, 1.9 Hz, 1H), 4.61 (t, J=4.9 Hz, 1H), 4.51 (t, J=4.9 Hz, 1H), 2.94-2.83 (m, 4H), 2.69 (t, J=4.9 Hz, 1H), 2.63 (t, J=4.9 Hz, 1H), 2.57 (s, 4H). ¹³C NMR (126 MHz, DMSO-d₆) δ 165.36 (s), 159.02 (d, J=11.0 Hz), 157.52 (s), 156.87 (d, J=3.4 Hz), 155.59 (s), 153.97 (s), 147.89 (d, J=22.1 Hz), 142.88 (s), 142.47 (s), 140.90 (s), 137.36 (d, J=10.9 Hz), 135.82 (d, J=9.3 Hz), 133.67 (s), 132.04 (s), 129.30 (s), 120.86 (d, J=3.9 Hz), 118.70 (s), 116.34 (s), 114.68 (s), 108.54 (d, J=26.0 Hz), 83.83 (d, J=164.4 Hz), 59.53 (d, J=19.5 Hz), 55.01 (s, 2C), 52.46 (d, J=2.4 Hz, 2C).

Example 9

Synthesis of N-(2-(2-(3-fluoro-4-(4-(2-fluoroethyl)piperazin-1-yl)phenylamino)-5-methoxypyrimidin-4-yloxy)phenyl)acrylamide (I-9)

The synthetic scheme for compound I-9 is shown below:

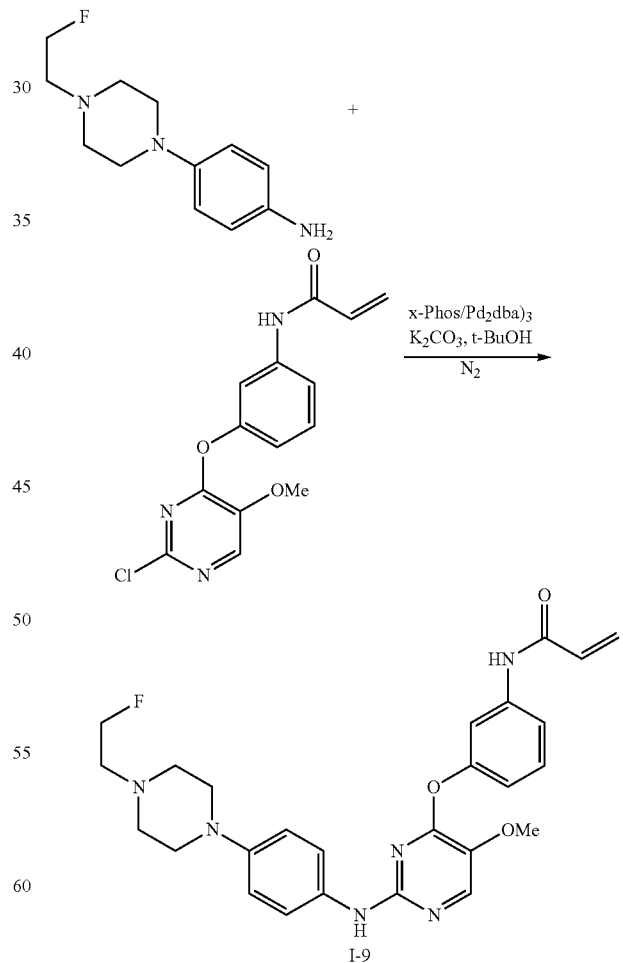

N-(2-(2-chloro-5-methoxypyrimidin-4-yloxy)phenyl)acrylamide (1.360 g, 4.48 mmol), 4-(4-(2-fluoroethyl)piperazin-1-yl)aniline 1 (1.002 g, 4.48 mmol), potassium carbonate (1.380 g, 10 mmol), tris(dibenzylideneacetone) dipalladium (460 mg, 0.5 mmol) and dicyclohexyl (2',4',6'-triisopropylbiphenyl-2-yl) phosphine (475 mg, 1 mmol) and t-BuOH (50 mL) were sequentially added into a 100 mL round bottom flask with a magnetite. The flask was placed on an oil bath and stirred under a $N_2$ flow. The reaction mixture was heated to refluxing for 5~7 h until reaction was complete indicated by TLC (EtOAc/petroleum ether/TEA=1/1/0.1 as elution). The mixture was concentrated under reduced pressure, followed by addition of EtOAc (50 mL) and activated charcoal (0.5 g). After stirred for 15 min, the mixture was filtered through Celite®, and the filter cake was wash with EA (50 mL). The filtrate was concentrated and the crude was further purified by flash column chromatography (EtOAc/petroleum ether=1/1 to EtOAc as elution) to yield the title compound I-9 (840 mg, yield 38%, purity 96.93%, M+H$^+$=493.5) as white solid. $^1$H NMR (500 MHz, DMSO-d$_6$) δ 10.32 (s, 1H), 9.00 (s, J=24.8 Hz, 1H), 8.17 (s, 1H), 7.59-7.63 (m, 2H), 7.43 (t, J=8.4 Hz, 1H), 7.29 (d, J=9.0 Hz, 2H), 7.03-6.89 (m, 1H), 6.65 (d, J=9.1 Hz, 2H), 6.44 (dd, J=17.0, 10.1 Hz, 1H), 6.28 (dd, J=17.0, 1.9 Hz, 1H), 5.78 (dd, J=10.1, 1.9 Hz, 1H), 4.62 (t, J=4.9 Hz, 1H), 4.52 (t, J=4.9 Hz, 1H), 3.87 (s, J=15.8 Hz, 3H), 3.05-2.89 (m, 4H), 2.69 (t, J=4.9 Hz, 1H), 2.63 (t, J=4.9 Hz, 1H), 2.61-2.53 (m, 4H). $^{13}$C NMR (126 MHz, DMSO-d$_6$) δ 165.32 (s), 161.44 (s), 155.80 (s), 154.79 (s), 147.56 (s), 145.97 (s), 142.27 (s), 136.63 (s), 135.12 (s), 133.70 (s), 131.88 (s), 129.26 (s), 121.13 (s, 2C), 118.76 (s), 118.16 (s), 117.74 (s, 2C), 114.95 (s), 83.90 (d, J=164.3 Hz), 59.64 (s), 59.48 (s), 54.99 (s, 2C), 51.13 (s, 2C).

Example 10

Synthesis of N-(3-(2-(4-(2-methoxyethoxy)phenylamino)-7H-pyrrolo[2,3-d]pyrimidin-4-yloxy)phenyl)acrylamide (I-10)

The synthetic scheme for compound I-10 is shown below:

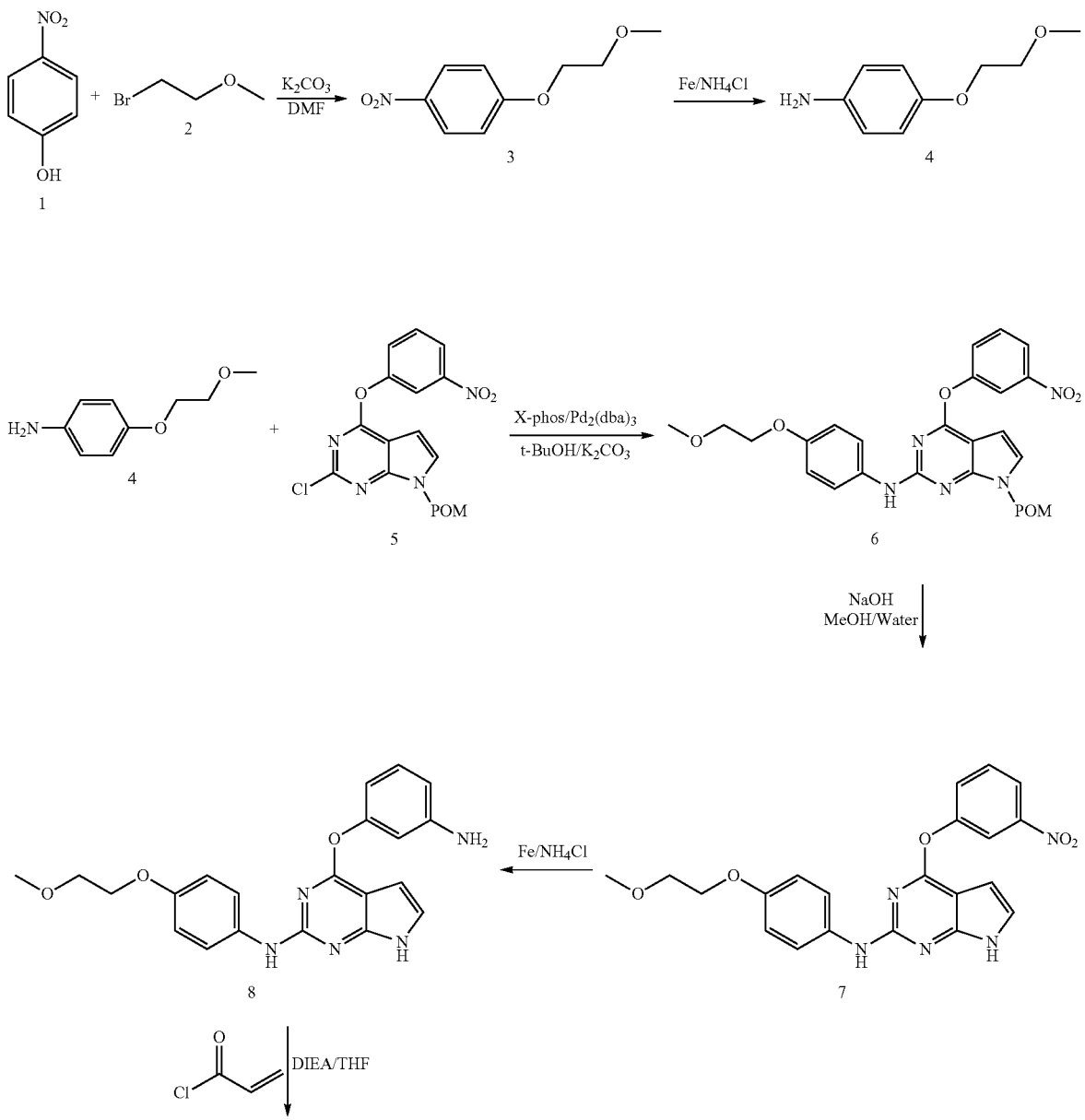

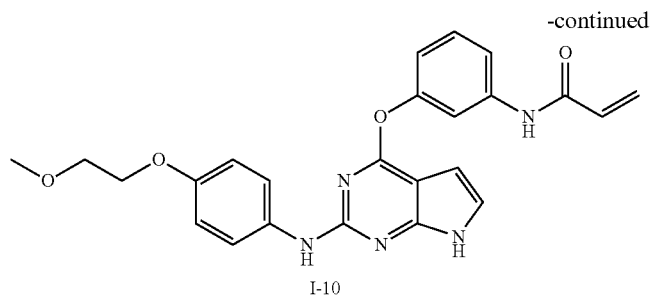

I-10

Step 1: Synthesis of 1-(2-methoxyethoxy)-4-nitrobenzene (3)

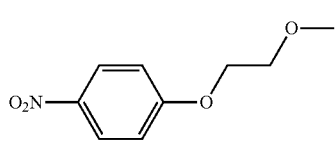

To a solution of 4-nitrophenol (18.2 g, 130 mmol) and 1-bromo-2-methoxyethane (20 g, 144 mmol) in DMF (60 ml), $K_2CO_3$ (36 g, 260 mmol) was added. The reaction mixture was stirred at 65~70° C. for 4 h and then cooled to room temperature. Water (200 mL) was added and the mixture was extracted with ethyl acetate (200 mL×3). The combined organic layers were washed with water (200 ml×3), dried over $Na_2SO_4$. The solvent was removed under reduced pressure to yield the desired product (3) as white solid (25 g, 97.6% yield), which was used for the next step without further purification.

Step 2: Synthesis of 4-(2-methoxyethoxy)aniline (4)

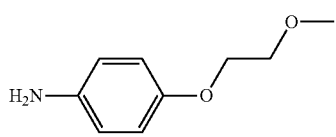

To a solution of compound 3 (25 g, 127 mmol) in THF (180 mL), water (60 mL) was added. After stirred for ~5 mM, $NH_4Cl$ (28 g, 523 mmol) and Fe (36 g, 635 mmol) were sequentially added. The reaction mixture was heated to refluxing and stirred for 4 h. After cooled to room temperature, the mixture was filtered through Celite® and washed with ethyl acetate (200 mL). The filtrate was concentrated under reduced pressure. The crude was re-dissolved in ethyl acetate (500 mL), washed with saturated $NaHCO_3$ (200 mL) and water (200 mL). The organic layer was concentrated under reduced pressure. The crude was further purified by flash column chromatography to yield the desired product 4 (12 g, 56.7% yield, M+H$^+$=168.5).

Step 3: Synthesis of (2-(4-(2-methoxyethoxy)phenylamino)-4-(3-nitrophenoxy)-7H-pyrrolo[2,3-d]pyrimidin-7-yl)methyl pivalate (6)

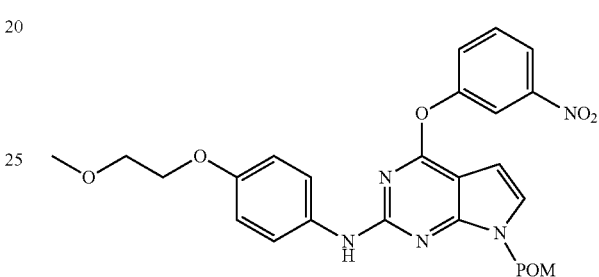

To a solution of (2-chloro-4-(3-nitrophenoxy)-7H-pyrrolo[2,3-d]pyrimidin-7-yl)methyl pivalate (4 g, 10 mmol), compound 4 (1.67 g, 10 mmol) in t-BuOH (40 mL), potassium carbonate (2.8 g, 20 mmol), tris(dibenzylideneacetone)dipalladium (500 mg) and dicyclohexyl (2',4',6'-triisopropyl-biphenyl-2-yl) phosphine (500 mg) were sequentially added. The reaction mixture was stirred under $N_2$ flow and heated to refluxing. After stirred for 3~4, TLC (DCM/MeOH=10/1 as elution) indicated the completion of the reaction. The mixture was cooled to 40~50° C., filtered through Celite®. The filter cake was washed with t-BuOH. The filtrate was concentrated under reduced pressure. The residue was re-dissolved in ethyl acetate (200 mL) washed with water, and concentrated under reduced pressure. The crude was further purified by flash column chromatography to yield the desired product 6 (5.9 g, M+H$^+$=536.5).

Step 4: Synthesis of N-(4-(2-methoxyethoxy)phenyl)-4-(3-nitrophenoxy)-7H-pyrrolo[2,3-d]pyrimidin-2-amine (7)

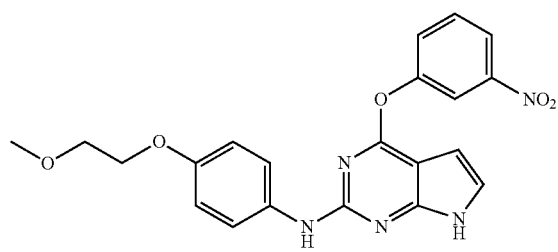 [SMILES: COCCOc1ccc(Nc2nc(Oc3cccc([N+](=O)[O-])c3)c3cc[nH]c3n2)cc1]

To a reactor (250 mL) was charged with 6 (5.9 g, 0.01 mol) and MeOH (120 mL). When 6 was completely dissolved, the solution was cooled with ice-bath to ~10° C.

NaOH solution (2.5 M, 8 mL) was then added over 45 min, maintaining the temperature under 16° C. throughout the addition. When addition was complete, the reaction mixture was stirred for 4~5 h at ~16° C. The completion of the reaction was monitored by TLC and LC-MS which indicated the consumption of 6 and low content (less than 8%) of an intermediate (MW: 493). Water (300 mL) was added to the reaction over 90 min, maintaining the temperature below 20° C. The desired product 8 was precipitated during the addition of the water. The mixture was stirred for another 15 min after the addition of the water. The precipitate (crude) was collected and washed with water (200 mL). The crude was re-dissolved in ethyl acetate (200 mL) and washed with water (200 mL×3). The mixture was passed through Celite® to remove un-soluble solid. The solvent was removed under reduced pressure. The residue was further purified by re-crystallization from ethyl acetate/petroleum ether (5:4) to yield the desired product 7 (3 g, 71.2% yield, M+H$^+$=422.5).

Step 5: Synthesis of 4-(3-aminophenoxy)-N-(4-(2-methoxyethoxy)phenyl)-7H-pyrrolo[2,3-d]pyrimidin-2-amine (8)

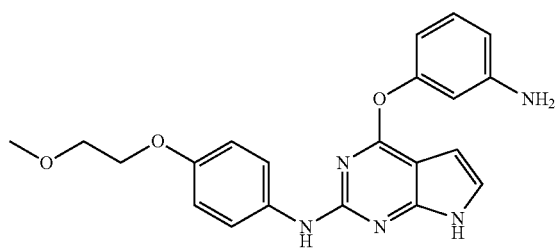 [SMILES: COCCOc1ccc(Nc2nc(Oc3cccc(N)c3)c3cc[nH]c3n2)cc1]

To a solution of compound 7 (3 g, 7.1 mmol) in THF (40 mL), water (15 mL), NH4Cl (1.5 g, 28.4 mmol) and Fe (2 g, 35.5 mmol) were added. The reaction mixture was heated to refluxing for 4 h and then cooled to room temperature. The reaction mixture was filtered. The filtrate was concentrated under reduced pressure. The residue was re-dissolved in ethyl acetate (50 mL) and washed with saturated NaHCO$_3$ (30 mL) and water (50 mL×3). The organic solvent was removed under reduced pressure. The crude was further purified by re-crystallization from ethyl acetate/PE (1:1) to yield the desired product 8 (2.4 g, 86.2% yield, M+H$^+$=392.5).

Step 6: Synthesis of N-(3-(2-(4-(2-methoxyethoxy)phenylamino)-7H-pyrrolo[2,3-d]pyrimidin-4-yloxy)phenyl)acrylamide (I-10)

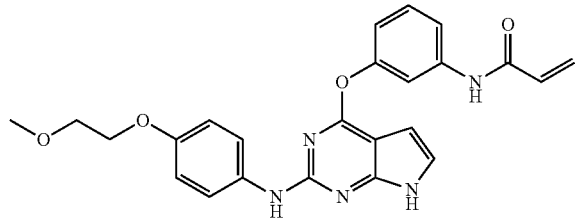 [SMILES: C=CC(=O)Nc1cccc(Oc2nc(Nc3ccc(OCCOC)cc3)nc3[nH]ccc23)c1]

To a solution of compound 8 (328 mg, 0.83 mmol) and DIEA (112 mg, 0.87 mmol) in THF (5 mL) with ice-bath at −20° C., acryloyl chloride (79 mg, 0.87 mmol) was added over 5 min, maintaining the temperature around −10° C. throughout the addition. The reaction mixture was stirred for another 30 min at the same temperature after the addition. After warmed up to room temperature, ethyl acetate (50 mL) was added. The mixture was washed with water (50 mL×3). The organic solvent was removed under reduced pressure. The crude was further purified by flash column chromatography to yield the desired product I-10 (350 mg, 94.6% yield, M+H$^+$=446.5). $^1$H NMR (500 MHz, DMSO-d$_6$) δ 11.51 (s, J=26.7 Hz, 1H), 10.31 (s, 1H), 8.92 (s, J=7.3 Hz, 1H), 7.66 (t, J=2.1 Hz, 1H), 7.61-7.56 (m, 1H), 7.51 (d, J=8.9 Hz, 2H), 7.43 (t, J=8.1 Hz, 1H), 7.06 (dd, J=3.5, 2.3 Hz, 1H), 7.00 (m, 1H), 6.70 (d, J=9.0 Hz, 2H), 6.44 (dd, J=17.0, 10.2 Hz, 1H), 6.30-6.23 (m, 2H), 5.77 (dd, J=10.1, 1.9 Hz, 1H), 4.02-3.96 (m, 2H), 3.66-3.60 (m, 2H), 3.31 (s, J=2.3 Hz, 3H). $^{13}$C NMR (126 MHz, DMSO-d$_6$) δ 165.33 (s), 163.90 (s), 157.42 (s), 157.35 (s), 155.32 (s), 154.64 (s), 142.24 (s), 136.59 (s), 133.71 (s), 131.81 (s), 129.26 (s), 123.61 (s), 121.74 (s), 118.97 (s), 117.98 (s), 116.07 (s), 114.95 (s), 100.28 (s, 2C), 72.53 (s), 69.00 (s), 60.17 (s).

Example 11

Synthesis of N-(3-(2-(4-(2-methoxyethoxy)phenylamino)-7H-pyrrolo[2,3-d]pyrimidin-4-ylamino)phenyl)acrylamide (I-11)

The synthetic scheme for compound I-11 is shown below:

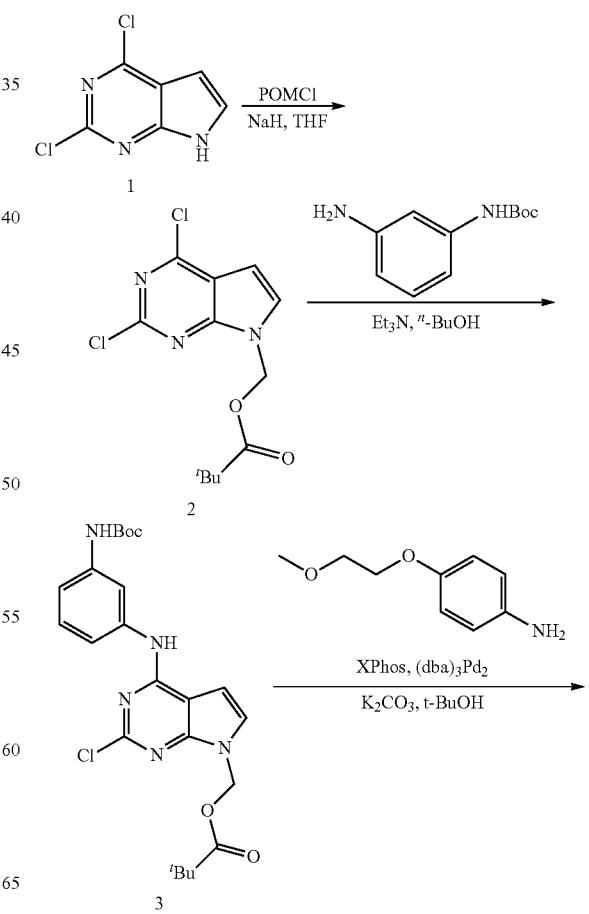

-continued

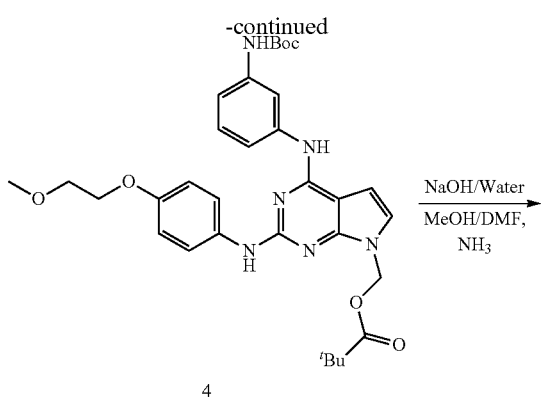

4

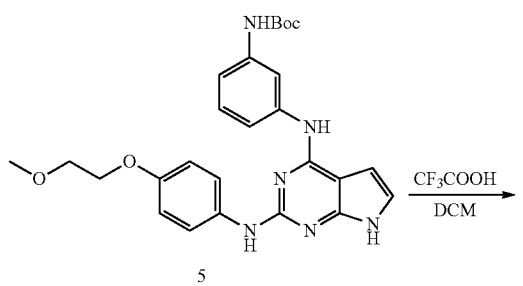

5

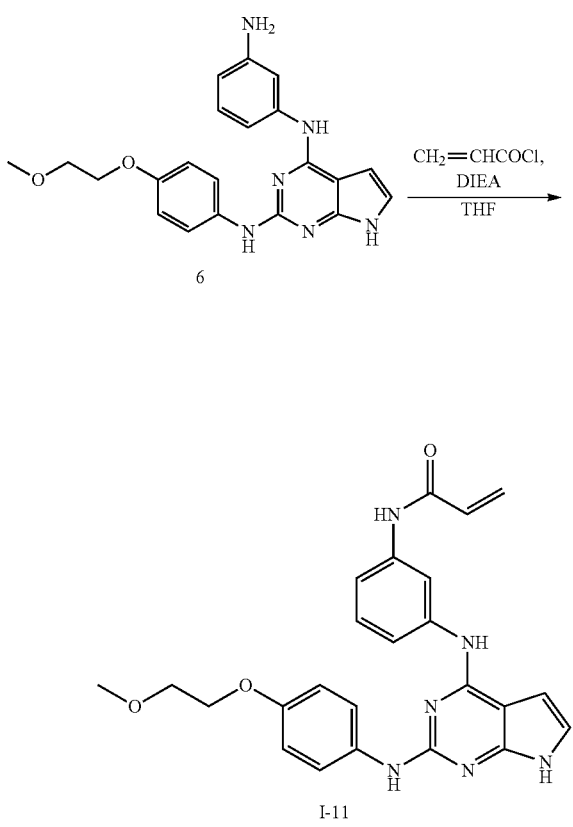

I-11

Step 1: Synthesis of (2,4-dichloro-7H-pyrrolo[2,3-d]pyrimidin-7-yl)methyl pivalate (2)

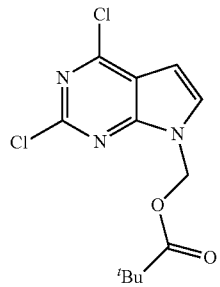 [SMILES: CC(C)(C)C(=O)OCn1ccc2c(Cl)nc(Cl)nc21]

NaH (80%, 3.54 g, 0.117 mol) was added slowly to a solution of 2,4-dichloro-7H-pyrrolo[2,3-d]pyrimidine 1 (20.03 g, 0.106 mol) in THF (200 mL), and maintained the temperature between 0~–5° C. The mixture was stirred for another 15 min until the evolution of hydrogen ceased. A solution of POMCl (18.96 g, 0.12 mol) in THF (70 mL) was added over 30 min. The reaction mixture was allowed to warm to room temperature and stirred for 3~4 h. When HPLC indicated that 1 was consumed, the reaction mixture was filtered through Celite®, washed with ethyl acetate (100 mL). The combined organic layers were concentrated under reduced pressure. The residue was re-dissolved in ethyl acetate (300 mL), washed with water (100 mL×2) and brine (100 mL). The organic layer was separated and the solvent was removed under reduced pressure to afford the desired product 2 as yellow solid, which was used directly for the next step without further purification.

Step 2: Synthesis of (4-(3-(tertbutoxycarbonylamino)-2-chloro-7H-pyrrolo[2,3-d]pyrimidin-7-yi)methyl pivalate (3)

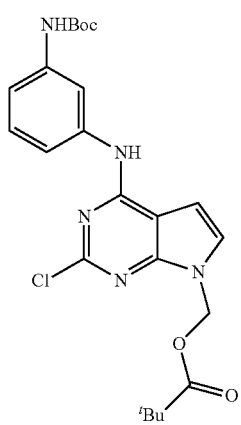 [SMILES: CC(C)(C)OC(=O)Nc1cccc(Nc2nc(Cl)nc3c2ccn3COC(=O)C(C)(C)C)c1]

To a mixture of pyrimidine 2 (6.1 g, 0.02 mol) and tert-butyl 3-aminophenylcarbamate (4.3 g, 0.019 mol) in n-BuOH (110 mL) was added TEA (7 mL). The reaction mixture was heated to refluxing and stirred for 12~18 h. When HPLC indicated that compound 2 was consumed, the mixture was cooled to room temperature. Water (200 mL) and ethyl acetate (100 mL) were added into this mixture, which was agitated and separated layers. The organic layer was washed with 1N HCl (20 mL), then 5% NaHCO₃ (50 mL), dried over sodium sulfate. The organic solvent was removed under reduced pressure to give a light oil, in which hexane (60 mL) was added and stirred for 2-3 h. The precipitate was collected and dried to yield the desired product (3.92 g, M+H⁺=474.5) as white solid.

Step 3: Synthesis of (4-(3-tert-butoxycarbonylamino)phenylamino)-2-(4-(2-methoxyethoxy)phenylamino)-7H-pyrrolo[2,3-d]pyrimidin-7-yl) methyl pivalate (4)

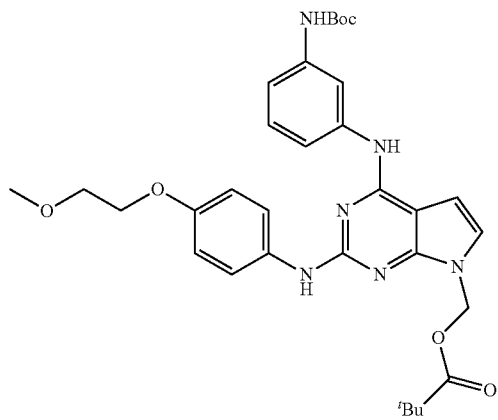 [SMILES: COCCOc1ccc(Nc2nc(Nc3cccc(NC(=O)OC(C)(C)C)c3)c3ccn(COC(=O)C(C)(C)C)c3n2)cc1]

t-BuOH (80 mL) was added to a RBF (250 mL) equipped with magic stirring. Compound 3 (3.92 g, 8.3 mmol) and 4-(2-methoxyethoxy)aniline (1.5 g, 9 mmol) were sequentially added and stirred for 5~10 mm Potassium carbonate (2.28 g, 16.5 mmol), tris(dibenzylideneacetone)dipalladium (750 mg, 0.9 mmol) and dicyclohexyl (2',4',6'-triisopropyl-biphenyl-2-yl) phosphine (750 mg, 18 mmol) were sequentially added and one more portion of t-BuOH (20 mL) was added. The flask was placed on an oil-bath and stirred under a N₂ flow. The reaction mixture was heated to refluxing. After stirred for 3~4 h, the reaction was complete indicated by TLC (DCM/MeOH=10/1 as elution). The mixture was cooled to 40~50° C. and filtered through Celite®. The filter cake was washed with ethyl acetate (50 mL). The filtrate was concentrated under reduced pressure. The crude was then purified with Flash column chromatography (ethyl acetate:Hexane=1:10~1:3) to yield the desired product 4 (1.74 g, M+H⁺=605.5) as brown solid.

Step 4: tert-butyl 3-(2-(4-(2-methoxyethoxy)phenylamino)-7H-pyrrolo[2,3-d]pyrimidin-4-ylamino) phenylcarbamate (5)

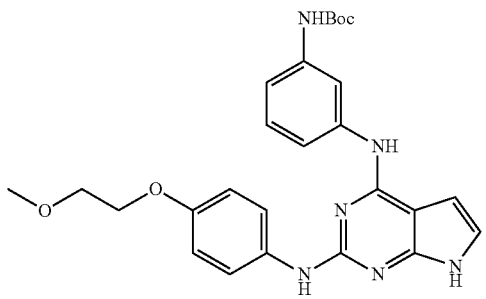 [SMILES: COCCOc1ccc(Nc2nc(Nc3cccc(NC(=O)OC(C)(C)C)c3)c3cc[nH]c3n2)cc1]

To a solution of compound 4 (1.74 g) in MeOH (25 mL) and THF (15 mL) in an ice-bath, NaOH solution (2.5 M, 2.3 mL) was added over 5 min(the temperature was kept around 6~10° C. throughout the addition). After the reaction mixture was stirred for 4~5 h at the same temperature, NH3 (gas) was bubbled into this reaction for 2~3 h. Once the reaction was complete indicated by TLC and LC-MS with the consumption of 4 and low content (less than 2%) of an intermediate (MW=521). Water (100 mL), and ethyl acetate (60 mL) were added. The mixture was agitated. Organic phase was separated and dried over sodium sulfate. The solvent was removed under reduced pressure to give the desired product 5 (1.35 g, M+H⁺=491.5) as brown oil, which was used directly for the next step without further purification.

Step 5: Synthesis of N-(3-aminophenyl)-N-(4-(2-methoxyethoxy)phenyl)-7H-pyrrolo[2,3-d]pyrimidine-2,4-diamine (6)

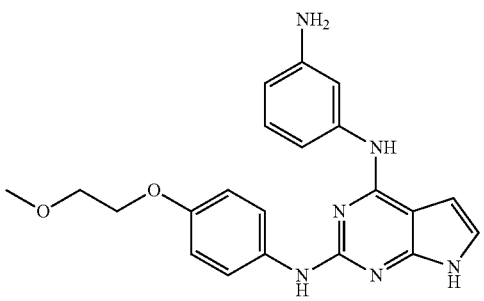 [SMILES: COCCOc1ccc(Nc2nc(Nc3cccc(N)c3)c3cc[nH]c3n2)cc1]

To a solution of 5 in DCM (49 mL) was added TFA (5.6 mL). The mixture was stirred at room temperature for 4 h. At this point the reaction was complete indicated by HPLC showing that compound 5 was consumed. The organic solvent was removed under reduced pressure. The crude was treated with cold (0° C.) saturated sodium bicarbonate (30 mL) and ethyl acetate (60 mL). The mixture was agitated. Organic phase was separated and dried over sodium sulfate. The organic solvent was removed under reduced pressure. The crude (brown oil) was further purified by flash column chromatography (Hexane:ethyl acetate=1:5) to yield the desired product (918 mg, M+H⁺=391.5) as brown solid.

Step 6: Synthesis of N-(3-(2-(4-(2-methoxyethoxy)phenylamino)-7H-pyrrolo[2,3-d]pyrimidin-4-ylamino)phenyl)acrylamide (I-11)

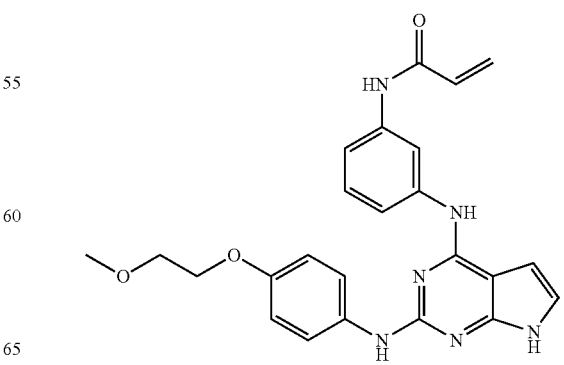

To a solution of 6 (918 mg, 2.35 mmol) and DIEA (320 mg, 2.48 mmol) in THF (20 mL) cooled with an ice bath (~−10° C.), acryloyl chloride (226 mg, 2.48 mmol) was added dropwise. The reaction mixture was stirred for 20 min. At this point, TLC (DCM/MeOH=8/1 as elution) indicated the completion of the reaction. Saturated NaHCO3 solution (8 mL) was added to quench the reaction. THF was removed, and the residue was re-dissolved in ethyl acetate (50 mL) and water (20 mL). The mixture was agitated. The organic phase was separated and dried over sodium sulfate. The organic solvent was removed under reduced pressure. The crude (orange oil) was further purified by flash column chromatography (100% ethyl acetate) to yield the desired product I-11 (652 mg, M+H$^+$=445.5) as white solid. $^1$H NMR (500 MHz, DMSO-d$_6$) δ 11.15 (s, 3H), 10.07 (s, 3H), 9.18 (s, 3H), 8.51 (s, 3H), 8.13 (s, 3H), 7.77 (d, J=8.0 Hz, 3H), 7.73-7.66 (m, 6H), 7.33 (d, J=8.5 Hz, 3H), 7.27 (t, J=8.0 Hz, 3H), 6.88 (dd, J=3.4, 2.2 Hz, 3H), 6.85-6.79 (m, 6H), 6.67 (dd, J=3.5, 2.0 Hz, 3H), 6.48 (dd, J=17.0, 10.2 Hz, 3H), 6.29 (dd, J=17.0, 2.0 Hz, 3H), 5.77 (dd, J=10.1, 2.0 Hz, 3H), 4.04-4.01 (m, 7H), 3.67-3.63 (m, 6H), 3.32 (s, 9H). $^{13}$C NMR (126 MHz, DMSO-d$_6$) δ 165.08 (s), 157.81 (s), 155.89 (s), 154.61 (s), 154.48 (s), 142.86 (s), 140.98 (s), 137.20 (s), 134.07 (s), 130.62 (s), 128.71 (s), 121.86 (s, 2C), 120.80 (s), 118.30 (s), 116.24 (s, 2C), 115.39 (s), 114.09 (s), 101.24 (s), 100.12 (s), 72.59 (s), 69.08 (s), 60.19 (s).

Example 12

Synthesis of N-(2-(5-fluoro-2-((4-(4-(2-fluoroethyl)piperazin-1-yl)phenylamino)pyrimidin-4-yloxy)phenyl)acrylamide (I-12)

The synthetic scheme for compound I-12 is shown below:

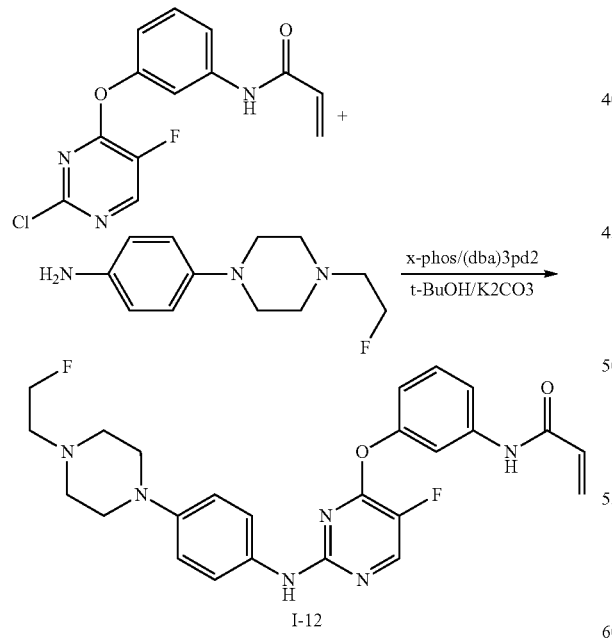

To a solution of N-(3-(2-chloro-5-fluoropyrimidin-4-yloxy)phenyl)acrylamide (1.3 g, 4.4 mmol), 4-(4-(2-fluoroethyl)piperazin-1-yl)aniline (1 g, 4.4 mmol) in t-BuOH (15 mL), potassium carbonate (1.2 g, 8.8 mmol), tris(dibenzylideneacetone)dipalladium (400 mg) and dicyclohexyl (2',4',6'-triisopropylbiphenyl-2-yl) phosphine (400 mg) were sequentially added. The reaction mixture was heated to refluxing and stirred under N$_2$ flow for 2 h. At this point, TLC (petroleum ether:ethyl acetate=1:1 as elution) indicated the completion of the reaction. The mixture was allowed to cool to 40~50° C., filtered through Celite®, and washed with t-BuOH. The filtrate was concentrated under reduced pressure. The residue was re-dissolved in ethyl acetate (100 mL), washed with water. The organic solvent was removed under reduced pressure. The crude was further purified by flash column chromatography to yield the desired product I-12 (1.2 g, 56.8% yield, M+H$^+$=481.5). $^1$H NMR (500 MHz, DMSO-d$_6$) δ 10.36 (s, 1H), 9.33 (s, 1H), 8.43 (d, J=3.0 Hz, 1H), 7.68 (t, J=2.1 Hz, 1H), 7.63 (d, J=8.2 Hz, 1H), 7.45 (t, J=8.1 Hz, 1H), 7.27 (d, J=8.4 Hz, 2H), 7.02 (m, 1H), 6.66 (d, J=8.8 Hz, 2H), 6.45 (dd, J=17.0, 10.1 Hz, 1H), 6.28 (dd, J=17.0, 1.9 Hz, 1H), 5.79 (dd, J=10.1, 1.9 Hz, 1H), 4.66-4.58 (m, 1H), 4.56-4.49 (m, 1H), 3.04-2.93 (m, 4H), 2.69 (t, J=4.9 Hz, 1H), 2.63 (t, J=4.9 Hz, 1H), 2.60-2.54 (m, 4H). $^{13}$C NMR (126 MHz, DMSO-d$_6$) δ 165.37 (s), 158.94 (s), 158.86 (s), 157.34 (s), 157.31 (s), 154.09 (s), 148.11 (s), 142.33 (s), 134.28 (s), 133.65 (s), 131.99 (s), 129.34 (s), 121.74 (s), 118.76 (s), 118.63 (s), 117.59 (s), 114.94 (s), 83.90 (d, J=164.4 Hz), 59.55 (d, J=19.5 Hz), 54.96 (s, 2C), 50.96 (s, 2C).

Synthesis of intermediates (S-1 and R-1)

Intermediate S-1: (S)—N-(1-(2-fluoroethyl)pyrrolidin-3-yl)benzene-1,4-diamine

The synthetic scheme is shown below:

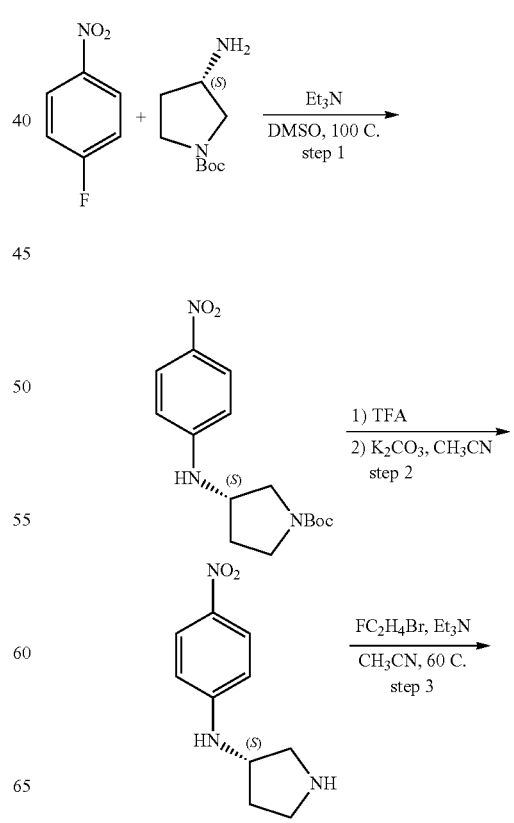

75
-continued

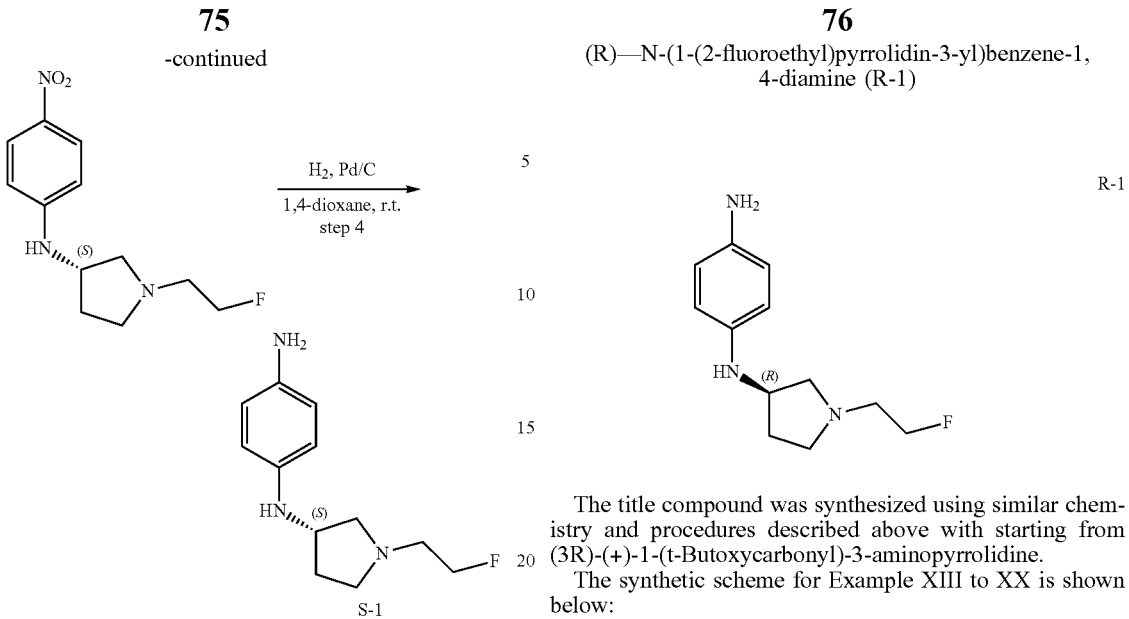

Step 1
A 3-neck round-bottom-flask (250 mL) equipped with a condenser was charged with 4-fluoro-1-nitrobenzene (7.3 g), (3S)-(−)-1-(t-Butoxycarbonyl)-3-aminopyrrolidine (11.2 g) and TEA (19 g) in dimethyl sulfoxide (58 mL). The reaction was heated at 100° C. overnight. After completion of the reaction, the reaction mixture was poured into water. The mixture was extracted with ethyl acetate. Organic layer was washed with brine and dried over sodium sulfate. Organic solvent was removed under reduce pressure. The resulting crude product (22.75 g) was used directly for the next step reaction without further purification.

Step 2
To the crude product from step 1 (22.7 g) in a 3-neck round-bottom-flask (250 mL) was added TEA (74 mL) at room temperature. The reaction mixture was stirred for 2 h at room temperature. After completion of the reaction, the reaction mixture was concentrated under reduced pressure to remove un-reacted TEA. The residue was re-dissolved in MeGH and then basified using: $K_2CO_3$ under 0° C. The crude product (29.95 g) was obtained after removal of un-reacted $K_2CO_3$ and solvent.

Step 3
To the crude from step 2 (27 g) in MeCN (170 mL) was added TEA (35 mL) and 1,2-bromofluoroethane (12 g). The reaction mixture was heated at 60° C. for 25 hours. After completion of the reaction, the reaction mixture was poured into water. The mixture was extracted with ethyl acetate. The organic layer was separated, washed with brine, and dried over sodium sulfate. The organic solvent was removed under reduce pressure. The resulted crude was purified by flash chromatography to afford the desired product (11.3 g, 86% yield over 3 steps) as yellow solid.

Step 4
A solution of above product from step 3 (2.183 g) and Pd/C (0.798 g) in 1,4-dioxane (43 mL) was hydrogenated for 22 hours at room temperature. After completion of the reaction, the reaction mixture was filtered through Celite-bed. The Celite bed was washed with 1,4-dioxane. The filtrate was concentrated to provide the desired amine (2.022 g) as dark oil which was used directly for the next step reaction without further purification.

76
(R)—N-(1-(2-fluoroethyl)pyrrolidin-3-yl)benzene-1,4-diamine (R-1)

The title compound was synthesized using similar chemistry and procedures described above with starting from (3R)-(+)-1-(t-Butoxycarbonyl)-3-aminopyrrolidine.

The synthetic scheme for Example XIII to XX is shown below:

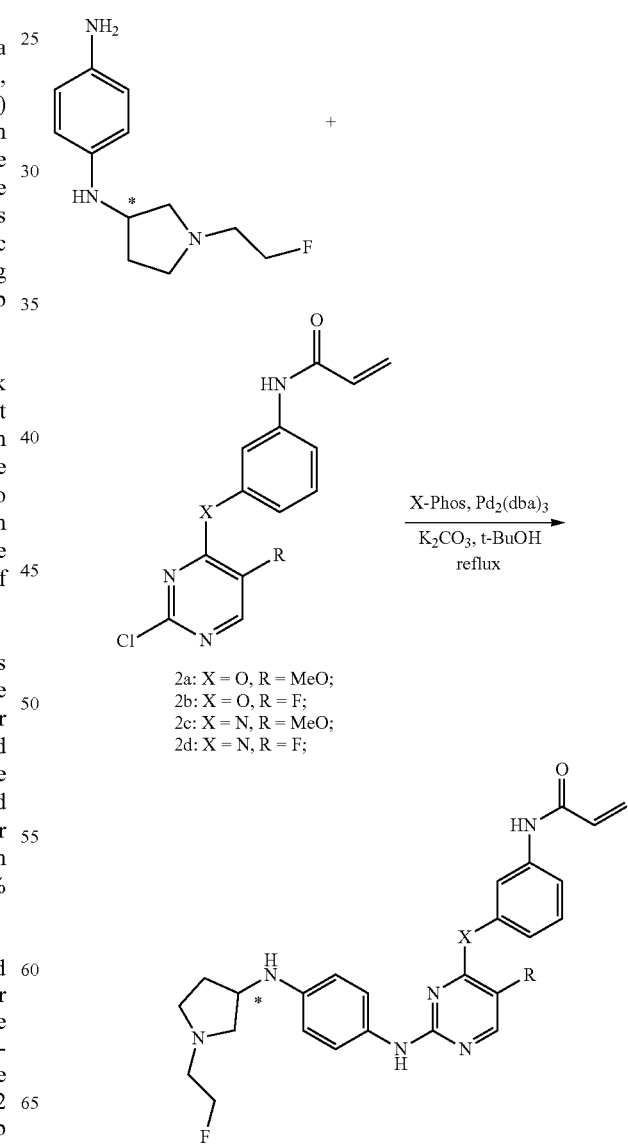

2a: X = O, R = MeO;
2b: X = O, R = F;
2c: X = N, R = MeO;
2d: X = N, R = F;

Example 13

Synthesis of (S)—N-(3-(2-(4-(1-(2-fluoroethyl)pyr-rolidin-3-ylamino)phenylamino)-5-methoxypyrimi-din-4-yloxy)phenyl)acrylamide (I-13)

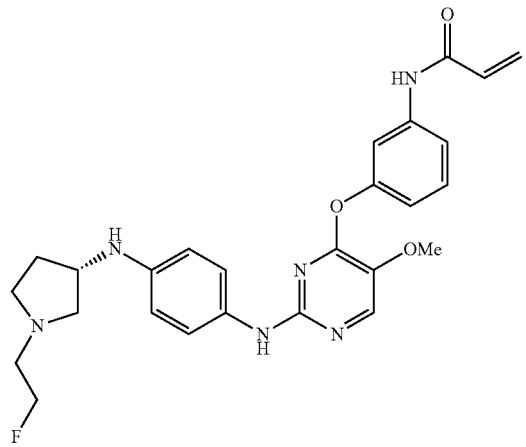

I-13

A mixture of above 2a (828 mg, 2.71 mmol), S-1 (630 mg, 2.82 mmol), tris(dibenzylideneacetone)dipalladium (79 mg, 0.086 mmol), dicyclohexyl (2',4',6'-triisopropylbiphenyl-2-yl) phosphine (84 mg, 0.176 mmol) and potassium carbonate (758 mg, 5.48 mmol) in tert-butanol (26 mL) was stirred under argon at refluxing temperature for 3.5 h. After cooling to RT, the reaction mixture was filtered through Celite. The Celite was washed with ethyl acetate. The combined filtrate was concentrated under reduced pressure. The residue was purified by flash column chromatography (DCM/MeOH=50/1) to give the title compound (1.07 g, yield 81%, M+H$^+$=493.5). $^1$H NMR (500 MHz, DMSO-d$_6$) δ 10.32 (s, 1H), 8.80 (s, 1H), 8.13 (s, 1H), 7.65-7.53 (m, 2H), 7.41 (t, J=8.1 Hz, 1H), 7.13 (d, J=8.7 Hz, 2H), 6.94 (m, 1H), 6.44 (dd, J=17.0, 10.1 Hz, 1H), 6.35-6.20 (m, 3H), 5.78 (dd, J=10.1, 1.9 Hz, 1H), 5.23 (d, J=7.0 Hz, 1H), 4.56 (t, J=5.0 Hz, 1H), 4.46 (t, J=5.0 Hz, 1H), 3.85 (s, 3H), 3.79-3.71 (m, 1H), 2.82 (dd, J=9.2, 6.9 Hz, 1H), 2.77-2.60 (m, 3H), 2.55-2.47 (m, 2H), 2.36 (dd, J=9.3, 4.6 Hz, 1H), 2.20-2.10 (m, 1H), 1.57-1.43 (m, 1H). $^{13}$C NMR (126 MHz, DMSO-d$_6$) δ 165.30 (s), 161.44 (s), 156.14 (s), 154.83 (s), 146.15 (s), 145.00 (s), 142.28 (s), 136.28 (s), 133.69 (s), 132.06 (s), 131.79 (s), 129.28 (s), 122.07 (s), 118.79 (s), 117.96 (s), 114.70 (s), 114.33 (s), 84.85 (d, J=164.4 Hz), 62.73 (s), 59.70 (s), 57.21 (d, J=19.5 Hz), 55.14 (s), 53.86 (s), 33.88 (s).

Example 14

Synthesis of (R)—N-(3-(2-(4-(1-(2-fluoroethyl)pyr-rolidin-3-ylamino)phenylamino)-5-methoxypyrimi-din-4-yloxy)phenyl)acrylamide (I-14)

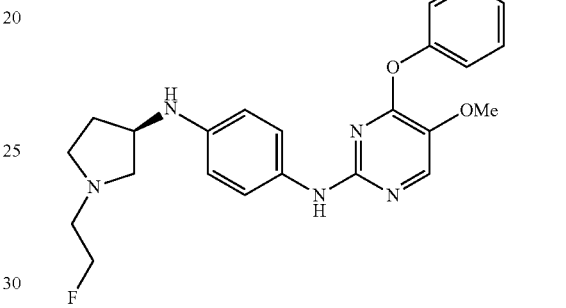

I-14

A mixture of above 2a (1.5 g, 4.91 mmol), R-1 (1.1 g, 4.91 mmol), tris(dibenzylideneacetone)dipalladium (400 mg, 0.437 mmol), dicyclohexyl (2',4',6'-triisopropylbiphenyl-2-yl) phosphine (400 mg, 5.87 mmol) and potassium carbonate (1.36 g, 9.84 mmol) in tert-butanol (100 mL) was stirred under argon at reflux temperature for 5 h. After cooling to RT, the reaction mixture was filtered through Celite. The Celite was washed with ethyl acetate, and the combined filtrate was concentrated under reduced pressure. The residue was purified by flash column chromatography (EA/PE=10/1) to give the title compound (0.94 g, 40%, M+H$^+$=493.5). $^1$H NMR (500 MHz, DMSO-d$_6$) δ 10.32 (s, 1H), 8.80 (s, 1H), 8.13 (s, 1H), 7.65-7.53 (m, 2H), 7.41 (t, J=8.1 Hz, 1H), 7.13 (d, J=8.7 Hz, 2H), 6.94 (m, 1H), 6.44 (dd, J=17.0, 10.1 Hz, 1H), 6.35-6.20 (m, 3H), 5.78 (dd, J=10.1, 1.9 Hz, 1H), 5.23 (d, J=7.0 Hz, 1H), 4.56 (t, J=5.0 Hz, 1H), 4.46 (t, J=5.0 Hz, 1H), 3.85 (s, 3H), 3.79-3.71 (m, 1H), 2.82 (dd, J=9.2, 6.9 Hz, 1H), 2.77-2.60 (m, 3H), 2.55-2.47 (m, 2H), 2.36 (dd, J=9.3, 4.6 Hz, 1H), 2.20-2.10 (m, 1H), 1.57-1.43 (m, 1H). $^{13}$C NMR (126 MHz, DMSO-d$_6$) δ 165.30 (s), 161.44 (s), 156.14 (s), 154.83 (s), 146.15 (s), 145.00 (s), 142.28 (s), 136.28 (s), 133.69 (s), 132.06 (s), 131.79 (s), 129.28 (s), 122.07 (s), 118.79 (s), 117.96 (s), 114.70 (s), 114.33 (s), 84.85 (d, J=164.4 Hz), 62.73 (s), 59.70 (s), 57.21 (d, J=19.5 Hz), 55.14 (s), 53.86 (s), 33.88 (s).

Example 15

Synthesis of (S)—N-(3-(5-fluoro-2-(4-(1-(2-fluoro-ethyl)pyrrolidin-3-ylamino)phenylamino)pyrimidin-4-ylamino)phenyl)acrylamide (I-15)

I-15

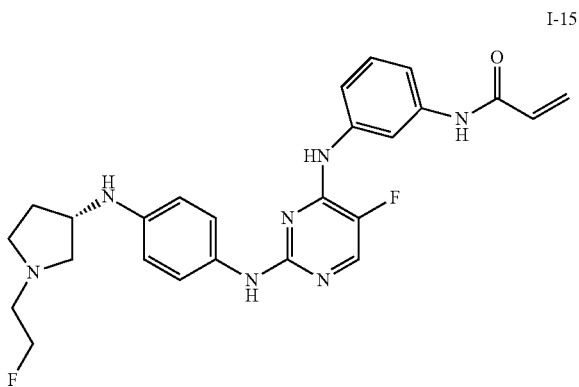 [SMILES: C=CC(=O)Nc1cccc(Nc2nc(Nc3ccc(N[C@H]4CCN(CCF)C4)cc3)ncc2F)c1]

A mixture of above 2d (812 mg), S-1 (627 mg), tris(dibenzylideneacetone)dipalladium (262 mg), dicyclohexyl (2',4',6'-triisopropylbiphenyl-2-yl) phosphine (271 mg,) and potassium carbonate (818 mg,) in tert-butanol (20 mL) was stirred under argon at refluxing temperature for 3.5 h. After cooling to RT, the reaction mixture was filtered through Celite and the Celite was washed with ethyl acetate. The combined filtrate was concentrated under reduced pressure. The residue was purified by flash column chromatography (ethyl acetate/EtOH=10/1) to give the title compound (100 mg, yield 7.4%, M+H$^+$=480.5). $^1$H NMR (500 MHz, DMSO-d$_6$) δ 10.12 (s, J=14.4 Hz, 1H), 9.30 (s, 1H), 8.67 (s, 1H), 8.02 (d, J=3.7 Hz, 1H), 7.94 (s, 1H), 7.55 (d, J=7.9 Hz, 1H), 7.42 (d, J=8.1 Hz, 1H), 7.31 (d, J=8.8 Hz, 2H), 7.24 (t, J=8.1 Hz, 1H), 6.53-6.39 (m, 3H), 6.28 (dd, J=17.0, 2.0 Hz, 1H), 5.84-5.69 (m, 1H), 5.30 (d, J=7.1 Hz, 1H), 4.56 (t, J=5.0 Hz, 1H), 4.47 (t, J=5.0 Hz, 1H), 3.87-3.74 (m, 1H), 2.84 (dd, J=9.2, 6.9 Hz, 1H), 2.77-2.71 (m, 1H), 2.71-2.62 (m, 2H), 2.57-2.48 (m, 2H), 2.40 (dd, J=9.3, 4.5 Hz, 1H), 2.22-2.11 (m, 1H), 1.61-1.48 (m, 1H). $^{13}$C NMR (126 MHz, DMSO-d$_6$) δ 163.53 (s), 156.57 (s), 150.06 (d, J=10.5 Hz), 143.84 (s), 141.73-141.13 (m), 139.74 (s), 139.55 (s), 139.48 (s), 132.41 (s), 130.46 (s), 129.00 (s), 127.25 (s), 121.71 (s), 117.51 (s), 114.88 (s), 113.42 (s), 112.86 (s), 83.31 (d, J=164.4 Hz), 61.21 (s), 55.66 (d, J=19.5 Hz), 53.60 (s), 52.33 (s), 32.35 (s).

Example 16

Synthesis of (S)—N-(3-(2-(4-(1-(2-fluoroethyl)pyrrolidin-3-ylamino)phenylamino)-5-methoxypyrimidin-4-ylamino)phenyl)acrylamide (I-16)

I-16

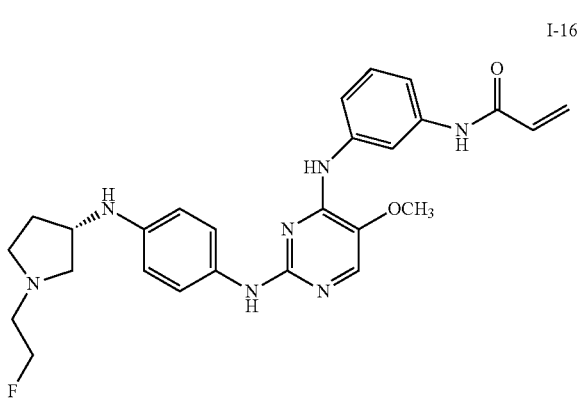 [SMILES: C=CC(=O)Nc1cccc(Nc2nc(Nc3ccc(N[C@H]4CCN(CCF)C4)cc3)ncc2OC)c1]

A mixture of above 2c (873 mg, 2.87 mmol), S-1 (640 mg, 2.87 mmol), tris(dibenzylideneacetone)dipalladium (250 mg, 0.272 mmol), dicyclohexyl (2',4',6'-triisopropylbiphenyl-2-yl) phosphine (250 mg, 0.544 mmol) and potassium carbonate (795 mg, 5.84 mmol) in tert-butanol (20 mL) was stirred under argon at reflux temperature for 3.5 h. After cooling to RT, the reaction mixtures was filtered through Celite and the Celite was washed with ethyl acetate. The combined filtrate was concentrated under reduced pressure. The residue was purified by flash column chromatography (DCM/MeOH=50/1) to give the title compound (407 mg, yield 28.89%, M+H$^+$=492.6). $^1$H NMR (500 MHz, DMSO-d$_6$) δ 10.06 (s, 1H), 8.63 (s, 1H), 8.32 (s, 1H), 7.97 (s, 1H), 7.78 (s, J=5.0 Hz, 1H), 7.59 (d, J=8.1 Hz, 1H), 7.40 (d, J=8.3 Hz, 1H), 7.35 (d, J=8.9 Hz, 2H), 7.23 (t, J=8.1 Hz, 1H), 6.53-6.38 (m, 3H), 6.27 (dd, J=17.0, 2.0 Hz, 1H), 5.76 (dd, J=10.1, 2.0 Hz, 1H), 5.21 (d, J=6.2 Hz, 1H), 4.57 (t, J=5.0 Hz, 1H), 4.47 (t, J=5.0 Hz, 1H), 3.83 (s, 3H), 3.81 (br s, 1H), 2.84 (dd, J=9.2, 6.9 Hz, 1H), 2.77-2.71 (m, 1H), 2.71-2.62 (m, 2H), 2.56-2.47 (m, 2H), 2.40 (dd, J=9.3, 4.6 Hz, 1H), 2.16 (qd, J=13.4, 7.9 Hz, 1H), 1.55 (dq, J=7.7, 6.3 Hz, 1H). $^{13}$C NMR (126 MHz, DMSO-d$_6$) δ 165.06 (s), 156.50 (s), 153.76 (s), 144.87 (s), 141.82 (s), 140.91 (s), 139.47 (s), 136.04 (s), 134.03 (s), 132.85 (s), 130.46 (s), 128.74 (s), 122.60 (s, 2C), 118.91 (s), 116.05 (s), 114.92 (s), 114.56 (s, 2C), 84.88 (d, J=164.4 Hz), 62.81 (s), 59.08 (s), 57.24 (d, J=19.5 Hz), 55.16 (s), 53.98 (s), 33.94 (s).

Example 17

Synthesis of (R)—N-(3-(2-(4-(1-(2-fluoroethyl)pyrrolidin-3-ylamino)phenylamino)-5-methoxypyrimidin-4-ylamino)phenyl)acrylamide (I-17)

I-17

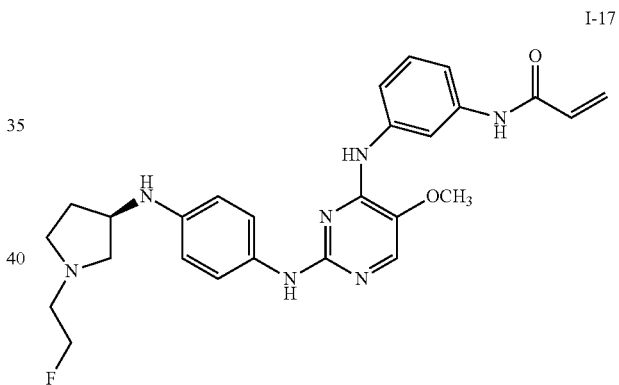

A mixture of above 2c (1412 mg), R-1 (1048 mg), tris(dibenzylideneacetone)dipalladium (312 mg), dicyclohexyl (2',4',6'-triisopropylbiphenyl-2-yl) phosphine (324 mg,) and potassium carbonate (1246 mg,) in tert-butanol (40 mL) was stirred under argon at reflux temperature for 3.5 h. After cooling to RT, the reaction mixture was filtered through Celite, and the Celite was washed with EA. The combined filtrate was concentrated under reduced pressure. The residue was purified by flash column chromatography (ethyl acetate/EtOH=10/1) to give the title compound (800 mg, yield 34.6%, M+H$^+$=492.5). $^1$H NMR (500 MHz, DMSO-d$_6$) δ 10.06 (s, 1H), 8.63 (s, 1H), 8.32 (s, 1H), 7.97 (s, 1H), 7.78 (s, J=5.0 Hz, 1H), 7.59 (d, J=8.1 Hz, 1H), 7.40 (d, J=8.3 Hz, 1H), 7.35 (d, J=8.9 Hz, 2H), 7.23 (t, J=8.1 Hz, 1H), 6.53-6.38 (m, 3H), 6.27 (dd, J=17.0, 2.0 Hz, 1H), 5.76 (dd, J=10.1, 2.0 Hz, 1H), 5.21 (d, J=6.2 Hz, 1H), 4.57 (t, J=5.0 Hz, 1H), 4.47 (t, J=5.0 Hz, 1H), 3.83 (s, 3H), 3.81 (br s, 1H), 2.84 (dd, J=9.2, 6.9 Hz, 1H), 2.77-2.71 (m, 1H), 2.71-2.62 (m, 2H), 2.56-2.47 (m, 2H), 2.40 (dd, J=9.3, 4.6 Hz, 1H), 2.16 (qd, J=13.4, 7.9 Hz, 1H), 1.55 (dq, J=7.7, 6.3 Hz, 1H). $^{13}$C NMR (126 MHz, DMSO-d$_6$) δ 165.06 (s), 156.50 (s), 153.76 (s), 144.87 (s), 141.82 (s), 140.91 (s), 139.47 (s), 136.04 (s), 134.03 (s), 132.85 (s), 130.46 (s), 128.74 (s), 122.60 (s, 2C), 118.91 (s), 116.05 (s), 114.92 (s), 114.56 (s, 2C), 84.88 (d, J=164.4 Hz), 62.81 (s), 59.08 (s), 57.24 (d, J=19.5 Hz), 55.16 (s), 53.98 (s), 33.94 (s).

Example 18

Synthesis of (R)—N-(3-(5-fluoro-2-(4-(1-(2-fluoroethyl)pyrrolidin-3-ylamino)phenylamino)pyrimidin-4-yloxy)phenyl)acrylamide (I-18)

I-18

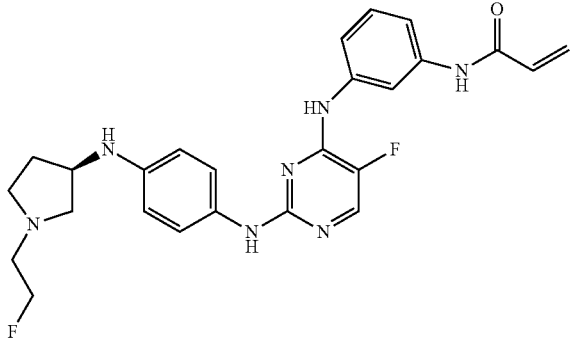

A mixture of above 2d (870 mg, 2.97 mmol), R-1 (660 mg, 2.96 mmol) tris(dibenzylideneacetone)dipalladium (172 mg, 0.188 mmol), dicyclohexyl (2',4',6'-triisopropylbiphenyl-2-yl) phosphine (172 mg, 0.360 mmol) and potassium carbonate (800 mg, 5.79 mmol) in tert-butanol (50 mL) was stirred under argon at reflux temperature for 5 h. After cooling to RT, the reaction mixture was filtered through Celite, and the Celite was washed with ethyl acetate. The combined filtrate was concentrated under reduced pressure. The residue was purified by flash column chromatography (ethyl acetate/petroleum ether=10/1) to give the title compound (0.58 g, yield 41%, M+H$^+$=480.5). $^1$H NMR (500 MHz, DMSO-d$_6$) δ 10.12 (s, J=14.4 Hz, 1H), 9.30 (s, 1H), 8.67 (s, 1H), 8.02 (d, J=3.7 Hz, 1H), 7.94 (s, 1H), 7.55 (d, J=7.9 Hz, 1H), 7.42 (d, J=8.1 Hz, 1H), 7.31 (d, J=8.8 Hz, 2H), 7.24 (t, J=8.1 Hz, 1H), 6.53-6.39 (m, 3H), 6.28 (dd, J=17.0, 2.0 Hz, 1H), 5.84-5.69 (m, 1H), 5.30 (d, J=7.1 Hz, 1H), 4.56 (t, J=5.0 Hz, 1H), 4.47 (t, J=5.0 Hz, 1H), 3.87-3.74 (m, 1H), 2.84 (dd, J=9.2, 6.9 Hz, 1H), 2.77-2.71 (m, 1H), 2.71-2.62 (m, 2H), 2.57-2.48 (m, 2H), 2.40 (dd, J=9.3, 4.5 Hz, 1H), 2.22-2.11 (m, 1H), 1.61-1.48 (m, 1H). $^{13}$C NMR (126 MHz, DMSO-d$_6$) δ 163.53 (s), 156.57 (s), 150.06 (s, J=10.5 Hz), 143.84 (s), 141.73-141.13 (m), 139.74 (s), 139.55 (s), 139.48 (s), 132.41 (s), 130.46 (s), 129.00 (s), 127.25 (s), 121.71 (s), 117.51 (s), 114.88 (s), 113.42 (s), 112.86 (s), 83.31 (d, J=164.4 Hz), 61.21 (s), 55.66 (d, J=19.5 Hz), 53.60 (s), 52.33 (s), 32.35 (s).

Example 19

Synthesis of (R)—N-(3-(5-fluoro-2-(4-(1-(2-fluoroethyl)pyrrolidin-3-ylamino)phenylamino)pyrimidin-4-yloxy)phenyl)acrylamide (I-19)

I-19

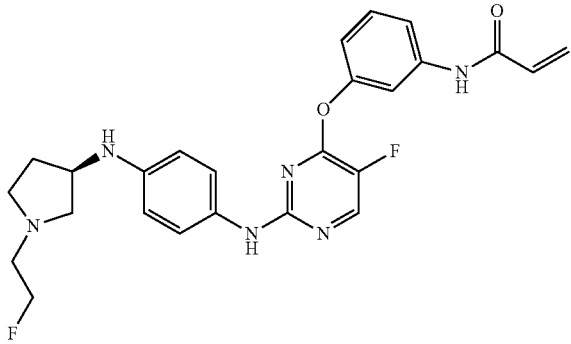

A mixture of above 2b (1408 mg), R-1 (1062 mg), tris(dibenzylideneacetone)dipalladium (353 mg), dicyclohexyl (2',4',6'-triisopropylbiphenyl-2-yl) phosphine (359 mg,) and potassium carbonate (1260 mg,) in tert-butanol (35 mL) was stirred under argon at reflux temperature for 4.5 h. After cooling to RT, the reaction mixture was filtered through Celite, and the Celite was washed with ethyl acetate. The combined filtrate was concentrated under reduced pressure. The residue was purified by flash column chromatography (ethyl acetate/EtOH=10/1) to give the title compound (987 mg, yield 42.9%, M+H$^+$=481.5). $^1$H NMR (500 MHz, DMSO-d$_6$) δ 10.35 (s, 1H), 9.13 (s, 1H), 8.38 (d, J=3.0 Hz, 1H), 7.67 (t, J=1.9 Hz, 1H), 7.61 (d, J=8.2 Hz, 1H), 7.43 (t, J=8.2 Hz, 1H), 7.12 (d, J=7.8 Hz, 2H), 7.02 (m, 1H), 6.45 (dd, J=17.0, 10.1 Hz, 1H), 6.35-6.24 (m, 3H), 5.79 (dd, J=10.1, 1.9 Hz, 1H), 5.32 (d, J=6.8 Hz, 1H), 4.56 (t, J=5.0 Hz, 1H), 4.46 (t, J=5.0 Hz, 1H), 3.83-3.69 (m, 1H), 2.82 (dd, J=9.1, 7.0 Hz, 1H), 2.77-2.71 (m, 1H), 2.71-2.60 (m, 2H), 2.55-2.47 (m, 2H), 2.37 (dd, J=9.2, 4.5 Hz, 1H), 2.19-2.10 (m, 1H), 1.59-1.45 (m, 1H). $^{13}$C NMR (126 MHz, DMSO-d$_6$) δ 165.35 (s), 158.84 (d, J=11.0 Hz), 157.58 (d, J=2.8 Hz), 154.14 (s), 147.88 (d, J=21.9 Hz), 145.58 (s), 142.35 (s), 140.31 (s), 133.66 (s), 131.90 (s), 131.24 (s), 129.34 (s), 122.68 (s), 118.78 (s), 118.43 (s), 114.69 (s), 114.23 (s), 84.84 (d, J=164.5 Hz), 62.69 (s), 57.19 (d, J=19.5 Hz), 55.13 (s), 53.80 (s), 33.85 (s).

Example 20

Synthesis of (S)—N-(3-(5-fluoro-2-(4-(1-(2-fluoroethyl)pyrrolidin-3-ylamino)phenylamino)pyrimidin-4-yloxy)phenyl)acrylamide (I-20)

I-20

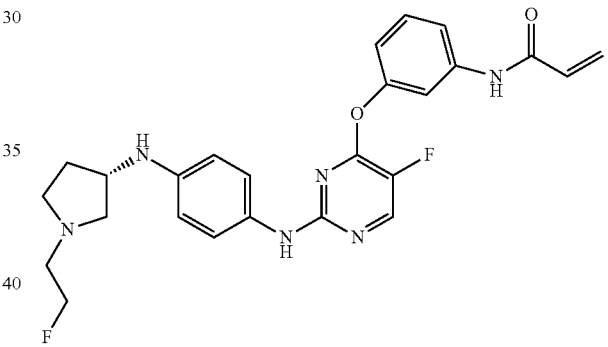

A mixture of above 2b (791 mg), S-1 (607 mg), tris (dibenzylideneacetone)dipalladium (193 mg), dicyclohexyl (2',4',6'-triisopropylbiphenyl-2-yl) phosphine (200 mg,) and potassium carbonate (758 mg,) in tert-butanol (30 mL) was stirred under argon at reflux temperature for 7 h. After cooling to RT, the reaction mixture was filtered through Celite, and the Celite was washed with ethyl acetate. The combined filtrate was concentrated under reduced pressure. The residue was purified by flash column chromatography (ethyl acetate/EtOH=10/1) to give the title compound (441 mg, yield 34.1%, M+H$^+$=481.5). $^1$H NMR (500 MHz, DMSO-d$_6$) δ 10.35 (s, 1H), 9.13 (s, 1H), 8.38 (d, J=3.0 Hz, 1H), 7.67 (t, J=1.9 Hz, 1H), 7.61 (d, J=8.2 Hz, 1H), 7.43 (t, J=8.2 Hz, 1H), 7.12 (d, J=7.8 Hz, 2H), 7.02 (m, 1H), 6.45 (dd, J=17.0, 10.1 Hz, 1H), 6.35-6.24 (m, 3H), 5.79 (dd, J=10.1, 1.9 Hz, 1H), 5.32 (d, J=6.8 Hz, 1H), 4.56 (t, J=5.0 Hz, 1H), 4.46 (t, J=5.0 Hz, 1H), 3.83-3.69 (m, 1H), 2.82 (dd, J=9.1, 7.0 Hz, 1H), 2.77-2.71 (m, 1H), 2.71-2.60 (m, 2H), 2.55-2.47 (m, 2H), 2.37 (dd, J=9.2, 4.5 Hz, 1H), 2.19-2.10 (m, 1H), 1.59-1.45 (m, 1H). $^{13}$C NMR (126 MHz, DMSO-d$_6$) δ 165.35 (s), 158.84 (d, J=11.0 Hz), 157.58 (d, J=2.8 Hz), 154.14 (s), 147.88 (d, J=21.9 Hz), 145.58 (s), 142.35 (s), 140.31 (s), 133.66 (s), 131.90 (s), 131.24 (s), 129.34 (s), 122.68 (s), 118.78 (s), 118.43 (s), 114.69 (s), 114.23 (s), 84.84 (d, J=164.5 Hz), 62.69 (s), 57.19 (d, J=19.5 Hz), 55.13 (s), 53.80 (s), 33.85 (s).

Example 21
Synthesis of Biotin Substituted Compound (I-42)
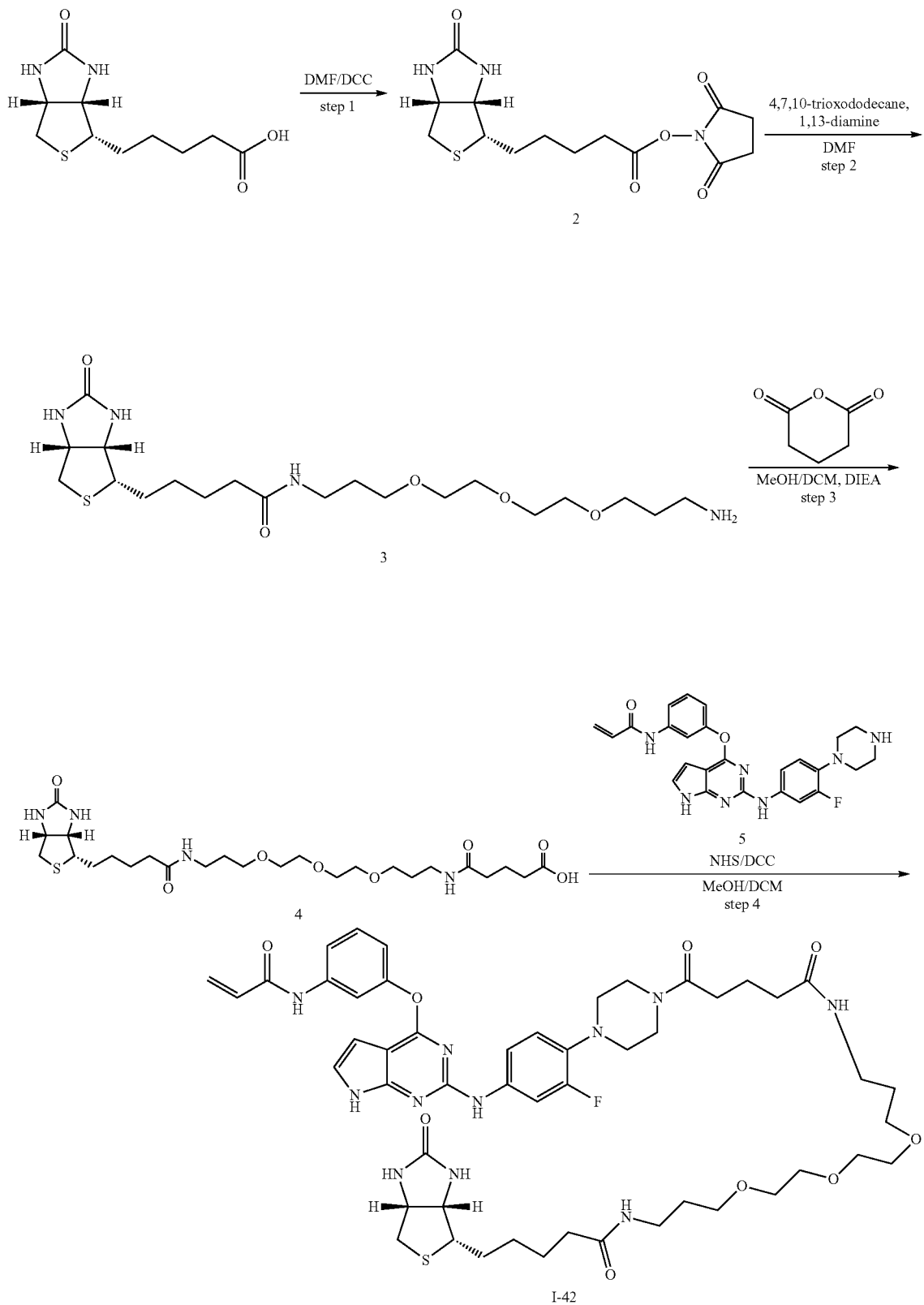

Step 1:

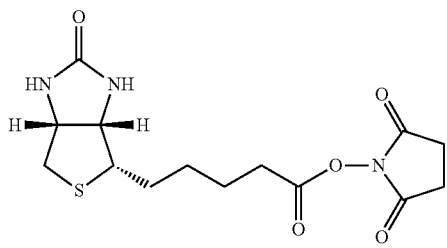 [SMILES: O=C1N[C@H]2[C@H](CS[C@H]2CCCCC(=O)ON2C(=O)CCC2=O)N1]

To a round bottom flask with a stirring bar, biotin (2.0 g, 8.2 mmol) and DMF (60 mL) were added. After the solid was dissolved with heat, N-hydroxysuccinimide (0.944 g, 8.2 mmol) and DCC (2.2 g, 10.7 mmol) were added. The reaction mixture was stirred at room temperature overnight. The white solid was filtered, and the DMF was evaporated under reduced pressure. The resulting residue was further purified by re-crystallization from isopropanol to give the desired product 2 (2.7 g, M+H$^+$=342.5) as white crystals.

Step 2:

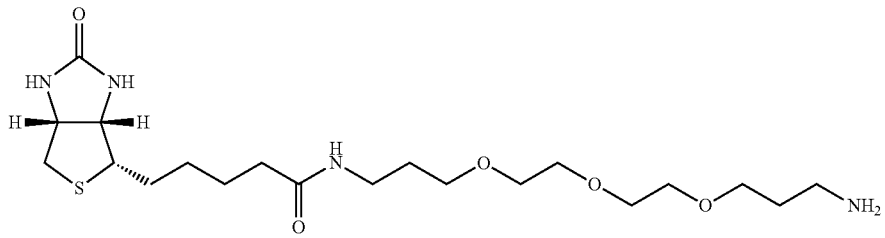 [SMILES: NCCCOCCOCCOCCCNC(=O)CCCC[C@@H]1SC[C@@H]2NC(=O)N[C@@H]21]

To a solution of 4,7,10-trioxododecane 1,13-diamine (6.7 g, 30.4 mmol) in anhydrous DMF (100 mL) was drop-wise added a solution of 2 (2.0 g, 5.86 mmol) in dry DMF (50 mL) over a period of 30 mm under N$_2$. The resulting thick white suspension was stirred for 30 min. The precipitate was filtered and washed with DMF. The combined filtrate was concentrated and diethyl ester was added. The precipitate (sticky solid) was collected and purified by flash chromatography (DCM/MeOH=5/1) to give desired compound 3 (2.44 g, yield 93%, M+H$^+$=448.5).

Step 3:

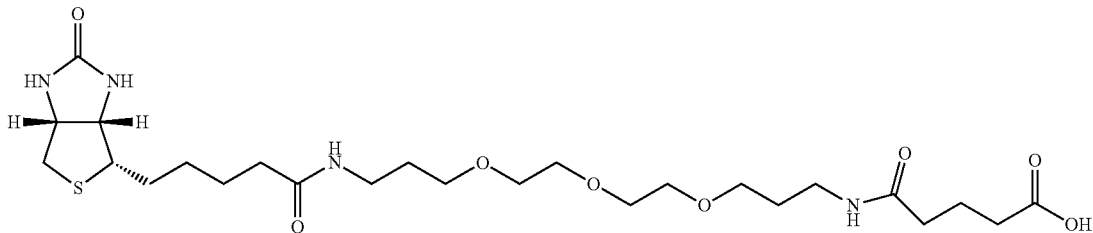 [SMILES: O=C(O)CCCC(=O)NCCCOCCOCCOCCCNC(=O)CCCC[C@@H]1SC[C@@H]2NC(=O)N[C@@H]21]

To a solution of 3 (2.44 g, 5.44 mmol) in dry methanol/DCM (1:1, 60 mL) were added glutaric anhydride (0.61 g, 5.35 mmol) and anhydrous diisopropyl ethylamine (2.5 g, 19 mmol). The reaction mixture was stirred at room temperature for 3 h, and then solvent was removed under reduced pressure. The resulting residue was purified by flash column chromatography (DCM/MeOH=5/1) to give desired compound 4 (1.3 g, yield 43%, M+H$^+$=561.5).

Step 4:

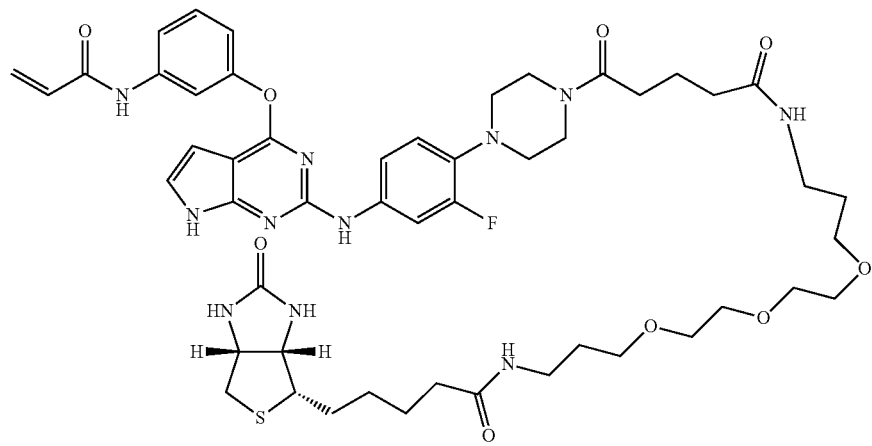 [SMILES: C=CC(=O)Nc1cccc(Oc2nc(Nc3ccc(N4CCN(C(=O)CCCC(=O)NCCCOCCOCCOCCCNC(=O)CCCC[C@@H]5SC[C@@H]6NC(=O)N[C@@H]65)CC4)c(F)c3)nc3[nH]ccc23)c1]

To a solution of 4 (290 mg, 0.516 mmol) in dry methanol/DCM (3:5, 16 mL) were added N-hydroxysuccinimide (89 mg, 0.775 mmol) and DCC (160 mg, 0.775 mmol). The mixture was stirred at room temperature for 3 h, and then a solution of 5 (synthesized separated) in dry methanol/DCM (1:1, 6 mL) was added. The reaction mixture was stirred overnight, and concentrated under reduced pressure. The resulting residue was purified by flash column chromatography (DCM/MeOH=from 50/1 to 15/1) to give the desired product I-42 (174 mg, yield 44%, M+H$^+$=1017.6).

Example 22

Synthesis of N-(3-(2-(3-fluoro-4-(4-methylpiperazin-1-yl)phenylamino)-5-hydroxypyrimidin-4-yloxy)phenyl)acrylamide (I-23a)

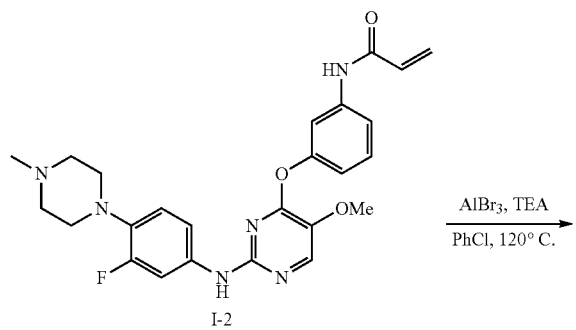

-continued

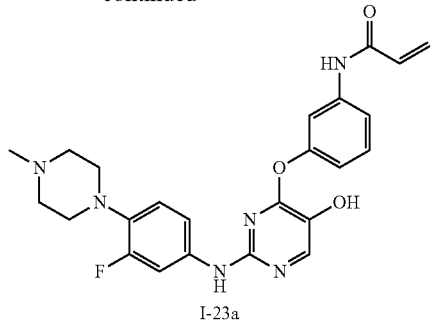

I-23a

To a solution of AlBr$_3$ (2.733 g) in chlorobenzene (20 mL) was drop-wise added TEA (0.434 g, 4.8 mmol). Compound I-2 (0.518 g) was then added. The reaction mixture was stirred at 120° C. for 4.5 h. MeOH (10 mL) was then added in to quench the reaction. Water was added in, and the mixture was extracted with ethyl acetate. The organic layers were combined, dried and concentrated under reduced pressure. The crude was purified by column chromatography (DCM/MeOH=15/1 as mobile phase) to give desired product I-23a (0.07 g, 13.88%, M+H+=465.5).

Example 23

Synthesis of N-(3-(2-(3-fluoro-4-(2-methoxyethoxy)phenylamino)-7H-pyrrolo[2,3-d]pyrimidin-4-yloxy)phenyl)acrylamide (I-24a)

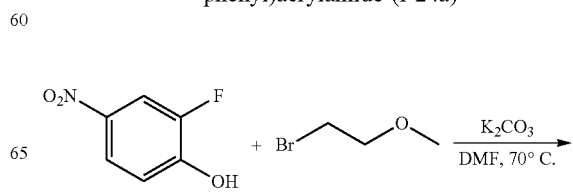

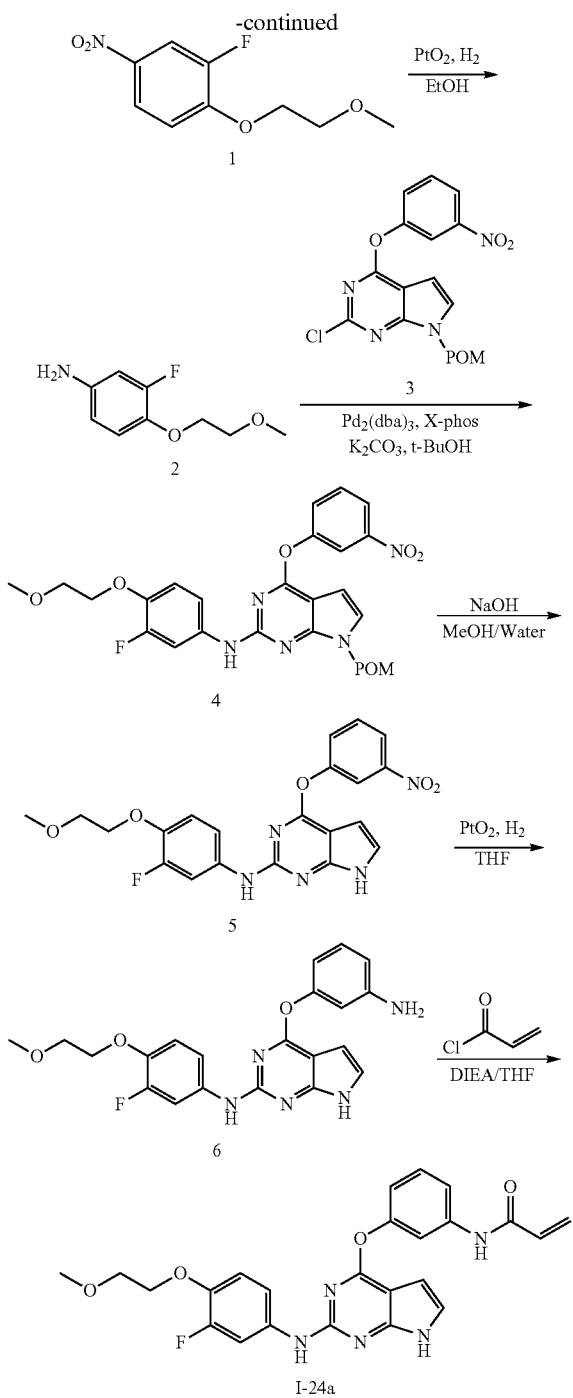

vacuum for 5 hours to afford 2-fluoro-1-(2-methoxyethoxy)-4-nitrobenzene 1 (10.33 g, 95.81%).

Synthesis of 3-fluoro-4-(2-methoxyethoxy)aniline (2)

A mixture of 1 (5.15 g, 23.93 mmol) and PtO$_2$ (0.143 g, 0.63 mmol) in EtOH (100 mL) was stirred at room temperature with hydrogen balloon overnight. After completion of the reaction, the reaction mixture was filtered through Celite®. The Celite layer was washed with EtOH. The combined filtrate was concentrated under reduced pressure to afford 2 (4 g, 91%, M+H$^+$=186.5) without further purification.

Synthesis of (2-(3-fluoro-4-(2-methoxyethoxy)phenylamino)-4-(3-nitrophenoxy)-7H-pyrrolo[2,3-d]pyrimidin-7-yl)methyl pivalate (4)

Compound 2 (4.432 g, 23.95 mmol), compound 3 (9.752 g, 24 mmol), K$_2$CO$_3$ (6.659 g, 48.25 mmol), tris(dibenzylideneacetone)dipalladium (1.027 g, 1.12 mol), dicyclohexyl (2',4',6'-triisopropylbiphenyl-2-yl) phosphine (1.121 g, 2.36 mmol) and t-BuOH (50 mL) were sequentially added to a round-bottom flask. The reaction mixture was stirred at refluxing under N$_2$ flow. After reaction for 3~4 h, TLC (DCM/MeOH=10/1 as mobile phase) indicated the reaction to be complete. The reaction mixture was allowed to cool down to 40~50° C. and then filtered through Celite®. The celite layer was washed with ethyl acetate (30 mL). The combined filtrate was concentrated under reduced pressure. The crude was purified by column chromatography (Ethyl acetate:Petroleum ether=from 50% to 100% as mobile phase) to give 4 (9.61 g, 72.39%, M+H$^+$=554.5) as a slight yellow solid.

Synthesis of N-(3-fluoro-4-(2-methoxyethoxy)phenyl)-4-(3-nitrophenoxy)-7H-pyrrolo[2,3-d]pyrimidin-2-amine (5)

To a round-bottom flask (250 mL) was charged with compound 4 (9.608 g, 17.36 mmol) and MeOH (60 mL). After compound 4 was completely dissolved, the solution was cooled down to ~10° C. with an ice-bath. NaOH aqu solution (2.5 M, 20 mL) was slowly added into the flask with maintaining of the temperature around 16° C. during the addition. The mixture was continued to stir for another 2 h at this temperature. Water (150 mL) was added slowly to the flask over 45 mm with maintaining of the temperature below 20° C. during the addition of water. The precipitate was collected, washed with water (50 mL) and dried under vacuum to afford the desired product 5 (4.232 g, 55%, M+H$^+$=440.6), which was used for next step without further purification.

Synthesis of 4-(3-aminophenoxy)-N-(3-fluoro-4-(2-methoxyethoxy)phenyl)-7H-pyrrolo[2,3-d]pyrimidin-2-amine (6)

A mixture of 5 (4.232 g, 9.6 mmol) and PtO$_2$ (0.101 g, 0.45 mmol) in THF (40 mL) was stirred at room temperature with hydrogen balloon overnight. After completion of the reaction, the reaction mixture was filtered through Cane®, The filtrate was concentrated under reduced pressure to afford the desired product 6 (3.35 g, 85%, M+H$^+$=410.5) as a white solid.

Synthesis of N-(3-(2-(3-fluoro-4-(2-methoxyethoxy)phenylamino)-7H-pyrrolo[2,3-d]pyrimidin-4-yloxy)phenyl)acrylamide (I-24a)

To a solution of compound 6 (2.05 g, 4 mmol) and DIEA (1.341 g, 10.4 mmol) in THF (50 mL) at 0° C., acryloyl chloride (0.434 g, 4.8 mmol) was dropwise added over 5 min. The reaction mixture was stirred for 1 h at 0° C. At this point, TLC indicated the reaction to be complete. NaOH aq. solution (1 M, 4 mL) and water (20 mL) were added to quench the reaction. The resulting mixture was continued to stir for another 10 min. The upper THF phase was separated and the solvent was removed under reduced pressure. The resulting crude was purified by column chromatography (Ethyl acetate:Petroleum ether from 50% to 100% as mobile phase) to give I-24a (1.420 g, 76.67%, M+H$^+$=464.6) as a white solid.

Example 24

Synthesis of N-(3-(5-methoxy-2-(4-(4-(2-methoxyethyl)piperazin-1-yl)phenylamino)pyrimidin-4-yloxy)phenyl)acrylamide (I-25a)

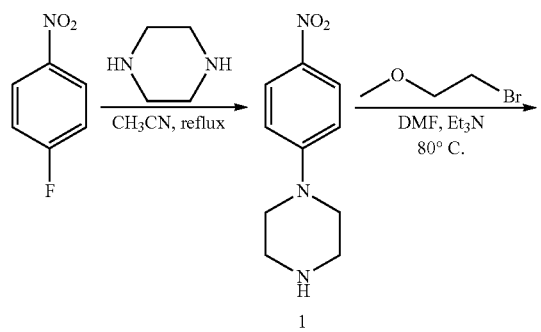

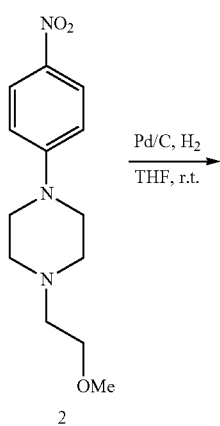

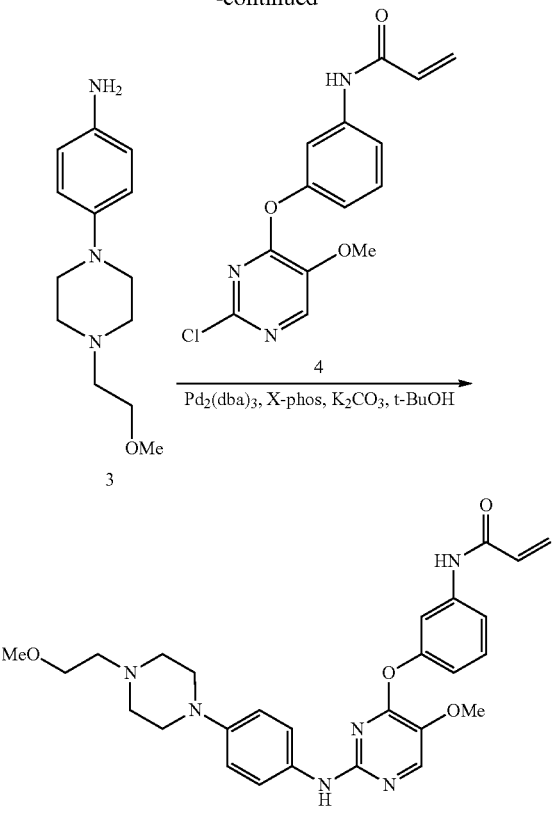

Synthesis of 1-(4-nitrophenyl)piperazine (1)

A mixture of 4-nitrofluorobenzene (70.7 g), piperazine (49.8 g) and acetonitrile (400 mL) was stirred at refluxing overnight. The reaction was monitored by TLC. After the reaction was complete, the reaction mixture was allowed to cool down to room temperature, basified with saturated K$_2$CO$_3$ solution (500 mL), and then extracted with ethyl acetate. The combined organic layers was washed with water and brine, dried over Na$_2$SO$_4$, and concentrated under reduced pressure to afforded 1-(4-nitrophenyl)piperazine 2 (88.4 g, 85.1%, M+H$^+$=208.5) as a yellow solid.

Synthesis of 1-(2-methoxyethyl)-4-(4-nitrophenyl)piperazine (2)

To a solution of 1-bromo-2-methoxyethane (60.5 g) and 1 (78.5 g) in DMF (400 mL) at room temperature was added Et$_3$N (65.6 g). The mixture was then heated up at 80 T and stirred for 4.5 h. At this point, TLC indicated the reaction to be complete. The reaction mixture was poured onto ice-water (1 L). The yellow precipitate was collected and dissolved with ethyl acetate. The solution was washed with water, brine and dried over Na$_2$SO$_4$. The organic solvent was removed under reduced pressure. The crude residue was re-dissolved with ethyl acetate (300 mL), and petroleum ether (250 mL) was then added. The resulting precipitate was removed (undesired product). The filtrate was concentrated under reduced pressure to afforded desired product 2 (65.4 g, 65.1%, M+H$^+$=266.6) as a yellow solid.

Synthesis of 4-(4-(2-methoxyethyl)piperazin-1-yl)aniline (3)

A solution of 2 (63.4 g) and Pd/C (4.634 g, 10% activated on carbon) in THF (500 mL) was stirred at room temperature with hydrogen balloon overnight. After completion of the reaction, the reaction mixture was filtered through Celite®. The celite was washed with ethyl acetate. The combined filtrate was concentrated under reduced pressure to afford the crude compound 3 (54.0 g, 96.0%, M+H$^+$=236.6) without further purification.

Synthesis of N-(3-(5-methoxy-2-(4-(4-(2-methoxyethyl)piperazin-1-yl)phenylamino)pyrimidin-4-yloxy)phenyl)acrylamide (I-25a)

Compound 3 (0.835 g), compound 4 (1.1 g), K$_2$CO$_3$ (0.964 g), tris(dibenzylideneacetone)dipalladium (0.164 g), dicyclohexyl (2',4',6'-triisopropylbiphenyl-2-yl) phosphine (0.157 g) and t-BuOH (20 mL) were sequentially added to a round-bottom flask. The reaction mixture was stirred at refluxing under N$_2$ flow. After reaction for 3~4 h, TLC (DCM/MeOH=10/1 as mobile phase) indicated the reaction to be complete. The reaction mixture was allowed to cool down to 40~50° C., and was filtered through Celite®. The celite layer was washed with ethyl acetate (30 mL). The combined filtrate was concentrated under reduced pressure. The crude was further purified by column chromatography (EtOAc:EtOH=20:1 as mobile phase) to give I-25a (0.923 g, 98.37%, M+H$^+$=505.6) as a white solid.

Example 25

Synthesis of (S)—N-(3-(2-(4-(((1-(2-fluoroethyl)pyrrolidin-3-yl)(methyl)amino)phenylamino)-7H-pyrrolo[2,3-d]pyrimidin-4-yloxy)phenyl)acrylamide (I-26a)

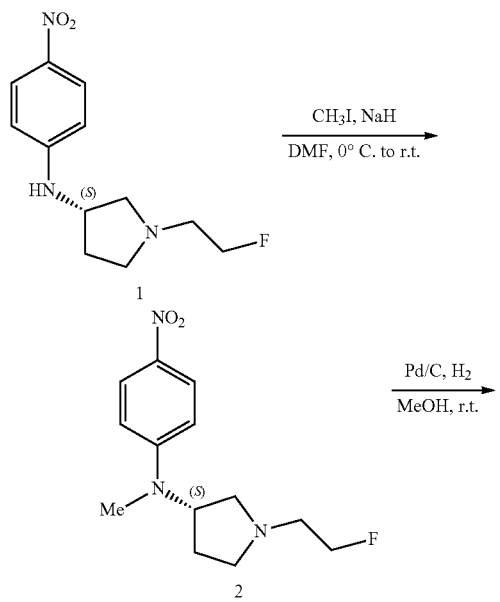

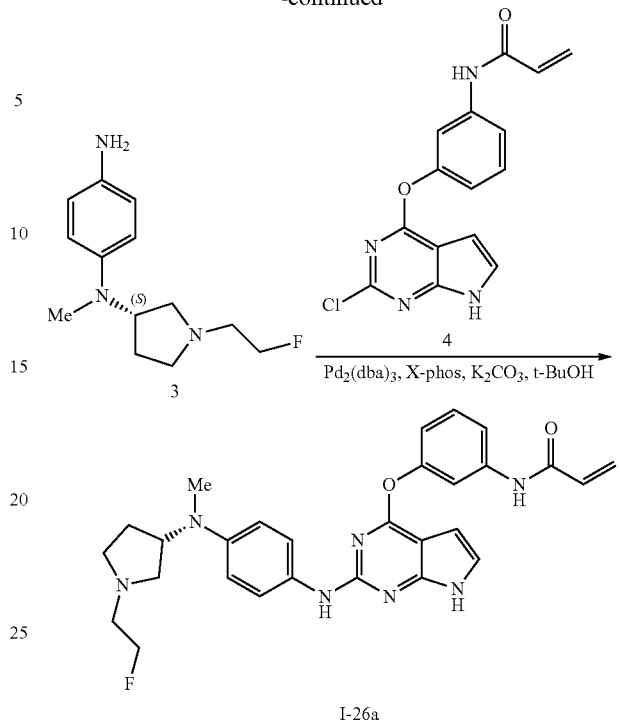

Synthesis of (S)-1-(2-fluoroethyl)-N-methyl-N-(4-nitrophenyl)pyrrolidin-3-amine (2)

To a solution of 1 (see the previous section of intermediate S-1, 2.572 g) in DMF (28 mL) at 0° C. was sequentially added NaH (0.35 g, 80% dispersion in mineral oil) and CH$_3$I (1.65 g). The resulting mixture was allowed to warm up to room temperature and stirred for 1 h. At this point, TLC indicated the reaction to be complete. The reaction mixture was then quenched with water and extracted with ethyl acetate. The combined organic layers was washed with water and dried over Na$_2$SO$_4$. The organic solvent was removed under reduced pressure to afford crude product 2 (2.501 g, 91.1%, M+H$^+$=268.5), which was used directly in next step without further purification.

Synthesis of (S)—N$^1$-(1-(2-fluoroethyl)pyrrolidin-3-yl)-N$^1$-methylbenzene-1,4-diamine (3)

A mixture of 2 (2.501 g) and Pd/C (0.495 g, 10% activated on carbon) in MeOH (39 mL) was stirred at room temperature with hydrogen balloon for 4.5 h. At this point, TLC showed the reaction to be complete. The reaction mixture was filtered through Celite®. The celite layer was washed with MeOH. The combined filtrate was concentrated under reduced pressure to afford dark oil. The oil residue was redissolved in ethyl acetate. The resulting mixture was washed with water and dried over Na$_2$SO$_4$. The organic solvent was removed under reduced pressure to afford the crude compound 3 (1.4 g, 63.1%, M+H$^+$=238.5), which was used in next step without further purification.

Synthesis of (S)—N-(3-(2-(4-(((1-(2-fluoroethyl)pyrrolidin-3-yl)(methyl)amino)phenylamino)-7H-pyrrolo[2,3-d]pyrimidin-4-yloxy)phenyl)acrylamide (I-26a)

Compound 3 (1.401 g), compound 4 (1.985 g), K$_2$CO$_3$ (1.460 g), tris(dibenzylideneacetone)dipalladium (0.65 g), dicyclohexyl (2',4',6'-triisopropylbiphenyl-2-yl) phosphine (0.65 g) and t-BuOH (32 mL) were sequentially added into a round-bottom flask. The reaction mixture was stirred at refluxing under N₂ flow for 3-4 h. At this point, TLC (DCM/MeOH=10/1 as mobile phase) indicated the reaction to be complete. The mixture was allowed to cool down to 40~50° C. and then filtered through Celite®. The celite layer was washed with ethyl acetate (30 mL). The combined filtrate was concentrated under reduced pressure to give crude product, which was further purified by column chromatography to afford I-26a (415 mg, 13.16%, M+H⁺=516.6).

Example 26

Synthesis of (S)—N-(3-(2-(4-(1-(2-fluoroethyl)pyrrolidin-3-ylamino)phenylamino)-7H-pyrrolo[2,3-d]pyrimidin-4-yloxy)phenyl)acrylamide (I-27a)

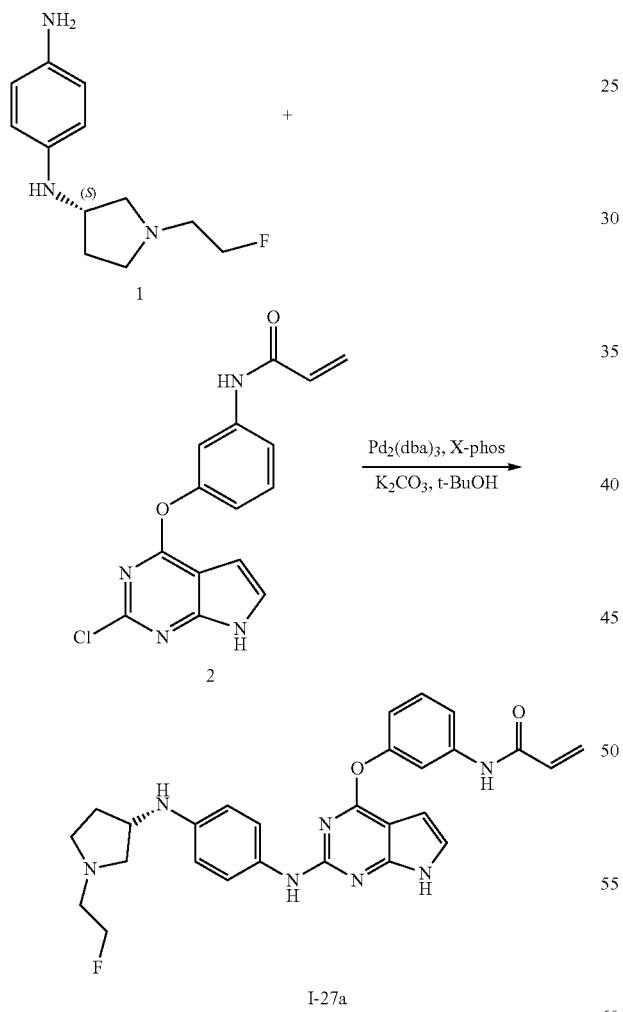

Compound 1 (see the previous section of intermediate S-1, 1.010 g), compound 2 (1.415 g), K₂CO₃ (1.30 g), tris(dibenzylideneacetone)dipalladium (0.602 g), dicyclohexyl (2',4',6'-triisopropylbiphenyl-2-yl) phosphine (0.601 g) and t-BuOH (28 mL) were sequentially added to a round-bottom flask. The reaction mixture was stirred at refluxing under N₂ flow for 3~4 h. At this point TLC (DCM/MeOH=10/1 as mobile phase) indicated the reaction to be complete. The reaction mixture was allowed to cool down to 40~50° C. and filtered through Celite®. The celite layer was washed with ethyl acetate (30 mL). The combined filtrate was concentrated under reduced pressure to give a crude product, which was further purified by column chromatography to afford I-27a (400 mg, 17.81%, M+H⁺=502.6) as a gray solid.

Example 27

Synthesis of N-(3-(5-methoxy-2-(1-(2-methoxyethyl)indolin-4-ylamino)pyrimidin-4-yloxy)phenyl)acrylamide (I-28a)

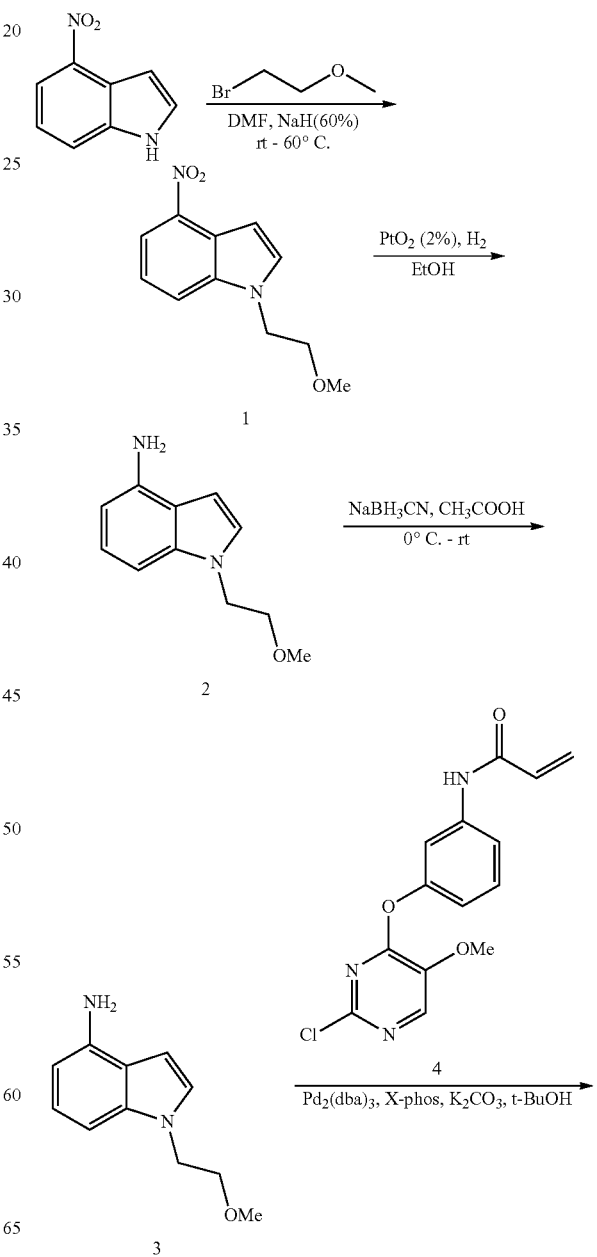

Synthesis of 1-(2-methoxyethyl)-4-nitro-1H-indole (1)

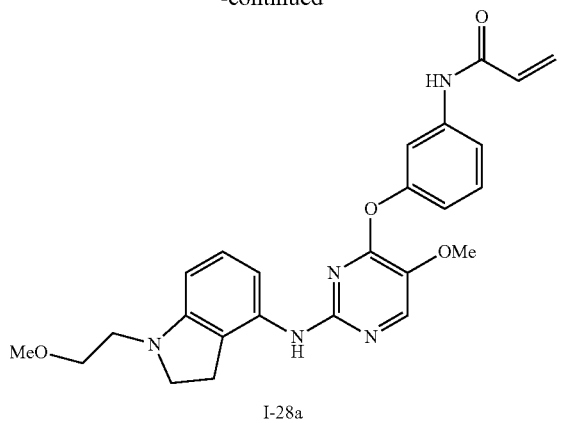

I-28a

To a solution of 4-nitro-1H-indole (5.1 g, 30.77 mmol), 1-bromo-2-methoxyethane (5.134 g, 37 mmol) in DMF (30 mL), NaH (1.610 g, 80% dispersion in mineral oil, 40 mmol) was added portion-wise at room temperature. The mixture was stirred at 60° C. for 3 h until TLC (petroleum ether:ethyl acetate=6:1 as mobile phase) indicated the completion of the reaction. The mixture was allowed to cool down to room temperature, and then poured onto water (60 mL) and extracted with ethyl acetate (50 mL×4). The combined organic layers was washed with water and brine, dried and concentrated. The residue was purified by column chromatography (ethyl acetate/petroleum ether from 1/10 to 1/3 as mobile phase) to give compound 1 (4.778 g, 21.5 mmol, 69%) as a yellow solid.

Synthesis of 1-(2-methoxyethyl)-1H-indol-4-amine (2)

A mixture of 1-(2-methoxyethyl)-4-nitro-1H-indole 1 (4.778 g, 21 mmol) and $PtO_2$ (0.091 g, 0.40 mmol) in EtOH (40 mL) was stirred at room temperature with hydrogen balloon overnight. TLC indicated the reaction to be complete. The reaction mixture was filtered through Celite®. The celite layer was washed with EtOH. The combined filtrate was concentrated under reduced pressure to afford compound 2 (3.67 g, 91%, M+H$^+$=191.2), which was used for next step reaction without further purification.

Synthesis of 1-(2-methoxyethyl)indolin-4-amine (3)

To a solution of 1-(2-methoxyethyl)-1H-indol-4-amine 2 (1.590 g, 7.16 mmol) in $CH_3COOH$ (10 mL) at 0° C. was added $NaBH_3CN$ (1.286 g, 20.74 mmol) portion-wise. The mixture was stirred for 3 h until TLC (petroleum ether/ethyl acetate=1/2 as mobile phase) indicated the reaction to be complete. After the solvent was removed, the residue was basified with saturated $NaHCO_3$ (50 mL) and then extracted with ethyl acetate (30 mL×4). The organic layers were combined, dried over $Na_2SO_4$, and concentrated under reduced pressure. The crude was purified by column chromatography (ethyl acetate/petroleum ether from 1/3 to 3/1 as mobile phase) to give compound 3 (0.96 g, 4.37 mmol, 61%, M+H$^+$=193.5) as a yellow solid.

Synthesis of N-(3-(5-methoxy-2-(1-(2-methoxyethyl)indolin-4-ylamino)pyrimidin-4-yloxy)phenyl)acrylamide (I-28a)

Compound 3 (0.430 g, 2.24 mmol), compound 4 (0.936 g, 3.063 mmol), $K_2CO_3$ (0.660 g, 4.783 mmol), tris(dibenzylideneacetone)dipalladium (0.270 g, 0.295 mmol), dicyclohexyl (2',4',6'-triisopropylbiphenyl-2-yl) phosphine (0.243 mg, 0.512 mmol) and t-BuOH (30 mL) were sequentially added to the flask. The reaction mixture was stirred at refluxing under $N_2$ flow. After 5~7 h, TLC (Ethyl acetate: Petroleum ether:TEA=1:1:0.1 as mobile phase) indicated the reaction to be complete. The reaction mixture was allowed to cool down to 40~50° C. and filtered through Celite®. The Celite layer was washed with ethyl acetate (50 mL). The filtrate was concentrated under reduced pressure. The crude was purified by column chromatography (Ethyl acetate:Petroleum ether from 50% to 100% as mobile phase) to give I-28a (773 mg, 79.89%, M+H$^+$=462.5) as a white solid.

$^1$H NMR (500 MHz, $CDCl_3$) δ 7.98 (s, 1H), 7.92 (s, 1H), 7.54 (s, 1H), 7.48 (d, J=7.9 Hz, 1H), 7.36 (t, J=8.1 Hz, 1H), 7.04 (t, J=14.6 Hz, 1H), 6.97 (d, J=7.8 Hz, 1H), 6.84 (t, J=8.0 Hz, 1H), 6.57 (s, 1H), 6.42 (d, J=16.8 Hz, 1H), 6.23 (dd, J=16.8, 10.2 Hz, 1H), 6.16 (d, J=7.8 Hz, 1H), 5.74 (d, J=10.8 Hz, 1H), 3.94 (s, 3H), 3.60 (t, J=5.7 Hz, 2H), 3.42 (s, 3H), 3.36 (t, J=8.3 Hz, 2H), 3.23 (t, J=5.7 Hz, 2H), 2.74 (t, J=8.3 Hz, 2H).

Example 28

Synthesis of N-(3-(5-methoxy-2-(1-(2-methoxyethyl)indolin-4-ylamino)pyrimidin-4-ylamino)phenyl)acrylamide (I-29a)

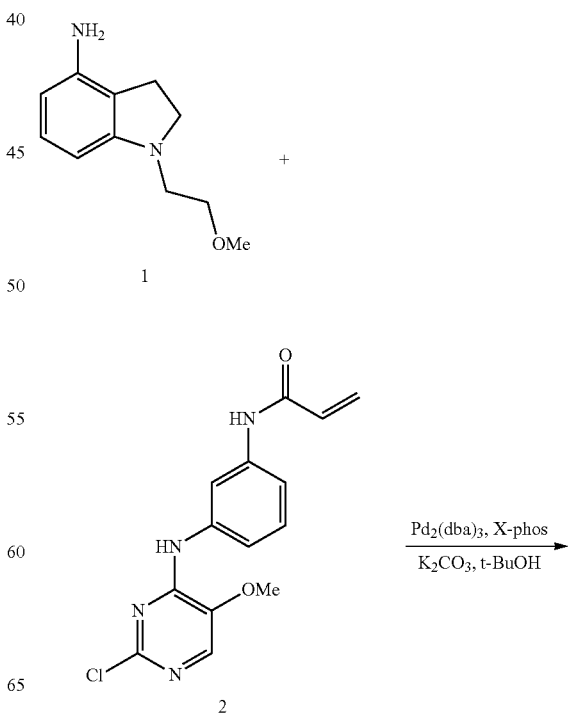

-continued

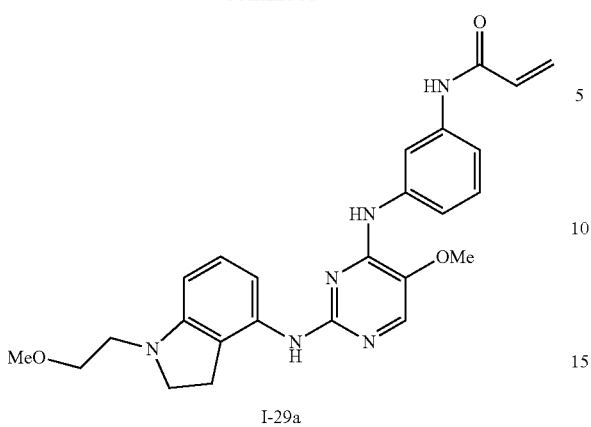

I-29a

Compound 1 (0.403 g, 2.099 mmol), compound 2 (0.880 g, 2.890 mmol), K$_2$CO$_3$ (0.643 g, 4.659 mmol), tris(dibenzylideneacetone)dipalladium (0.233 g, 0.255 mmol), dicyclohexyl (2',4',6'-triisopropylbiphenyl-2-yl) phosphine (0.243 mg, 0.512 mmol) and t-BuOH (30 mL) were sequentially added to a flask. The reaction mixture was stirred at refluxing under N$_2$ flow. After 5~7 h, TLC (Ethyl acetate: Petroleum ether:TEA=1:1:0.1 as mobile phase) indicated the reaction to be complete. The reaction mixture was allowed to cool down to 40~50° C. and filtered through Celite®. The Celite layer was washed with ethyl acetate (50 mL). The filtrate was concentrated under reduced pressure. The crude was purified by column chromatography (Ethyl acetate:Petroleum ether from 50% to 100% as mobile phase) to give I-29a (646 mg, 62.7%, M+H$^+$=461.5) as a white solid.

$^1$H NMR (500 MHz, CDCl$_3$) δ 8.24 (s, 1H), 7.68 (s, 1H), 7.58 (s, 1H), 7.57 (d, J=7.0 Hz, H), 7.26 (dt, J=10.6, 4.1 Hz, 3H), 7.13 (d, J=6.8 Hz, 1H), 7.08 (t, J=7.9 Hz, 1H), 6.68 (s, 1H), 6.45 (d, J=16.9 Hz, 1H), 6.32-6.19 (m, 2H), 5.78 (d, J=10.3 Hz, 1H), 3.89 (s, 3H), 3.62 (t, J=5.8 Hz, 2H), 3.45 (t, J=8.3 Hz, 2H), 3.41 (s, 3H), 3.30 (t, J=5.7 Hz, 2H), 2.95 (t, J=8.3 Hz, 2H).

Example 29

Synthesis of (S)—N-(3-(5-methoxy-2-(4-(1-(2-methoxyethyl)pyrrolidin-3-ylamino)phenylamino)pyrimidin-4-yloxy)phenyl)acrylamide (I-30a)

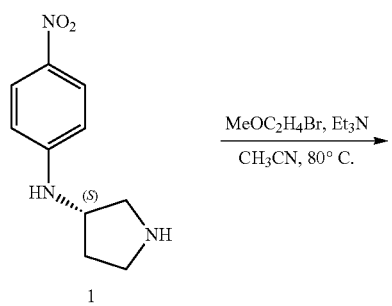

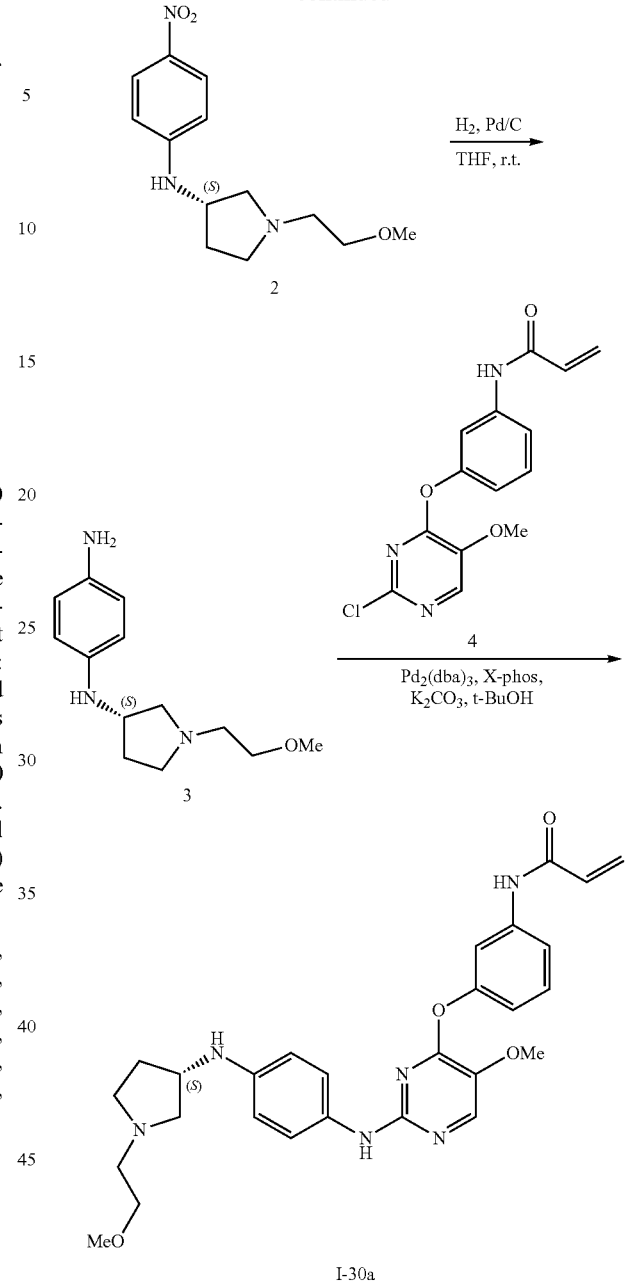

I-30a

Synthesis of (S)-1-(2-methoxyethyl)-N-(4-nitrophenyl)pyrrolidin-3-amine (2)

To compound 1 (10 g) in MeCN (70 mL) was added Et$_3$N (6.5 g) and 2-bromoethyl methyl ether (6.5 g). The reaction was stirred at 80° C., for 28 h. Once the reaction was complete, organic solvent was removed under reduced pressure. The residue was re-dissolved in ethyl acetate, and a small amount of saturated K$_2$CO$_3$ aqueous solution was added. After stirred for a few minutes, the organic layer was separated, washed with brine and dried over Na$_2$SO$_4$. The solution was concentrated under reduced pressure. The resulting crude was purified by flash chromatography to afford the desired product 2 (6.213 g, 48%, M+H$^+$=266.5) as a yellow solid.

Synthesis of (S)—N¹-(1-(2-methoxyethyl)pyrrolidin-3-yl)benzene-1,4-diamine (3)

A solution of 2 (6.213 g) and Pd/C (0.584 g, 10% activated on carbon) in THF (50 mL) was hydrogenated with hydrogen balloon at room temperature overnight. At this point. TLC was indicated the reaction to be complete. The reaction mixture was filtered through Celite®. The celite layer was washed with MeOH. The combined layers was concentrated under reduced pressure to afford the desired product 3 (4.8 g, 87.3%, M+H$^+$=236.5) without further purification.

Synthesis of (S)—N-(3-(5-methoxy-2-(4-(1-(2-methoxyethyl)pyrrolidin-3-ylamino)phenylamino)pyrimidin-4-yloxy)phenyl)acrylamide (I-30a)

Compound 3 (0.786 g), compound 4 (1.083 g), K$_2$CO$_3$ (1.154 g), tris(dibenzylideneacetone)dipalladium (0.117 g), dicyclohexyl (2',4',6'-triisopropylbiphenyl-2-yl) phosphine (0.120 g) and t-BuOH (20 mL) were sequentially added to a flask. The reaction mixture was stirred at refluxing under N$_2$ flow. After 6 h, TLC (DCM:MeOH=10:1 as mobile phase) indicated the reaction to be complete. The reaction mixture was allowed to cool down to 40~50° C. and filtered through Celite®. The Celite layer was washed with ethyl acetate (30 mL). The filtrate was concentrated under reduced pressure. The crude was purified by column chromatography (Ethyl acetate:MeOH=9:1 as mobile phase) to give I-30a (1.2 g, 72.56%, M+H$^+$=505.6).

Example 30

Synthesis of (S)—N-(3-(5-methoxy-2-(4-(1-(2-methoxyethyl)pyrrolidin-3-ylamino)phenylamino)pyrimidin-4-ylamino)phenyl)acrylamide (I-31a)

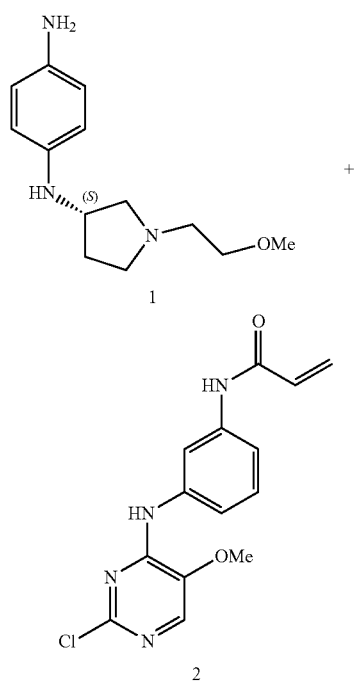

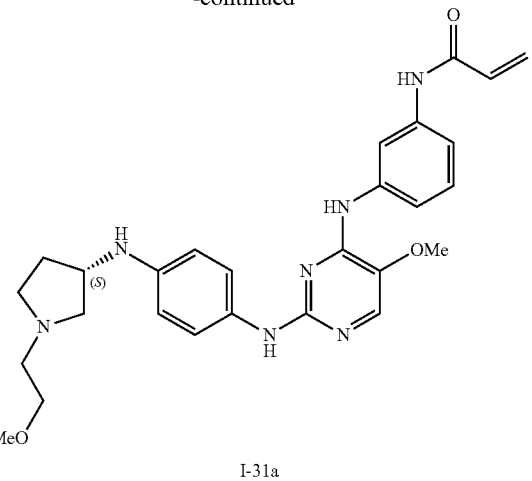

I-31a

Compound 1 (0.789 g), compound 2 (1.041 g), K$_2$CO$_3$ (0.686 g), tris(dibenzylideneacetone)dipalladium (0.148 g), dicyclohexyl (2',4',6'-triisopropylbiphenyl-2-yl) phosphine (0.156 g) and t-BuOH (30 mL) were sequentially added to a flask. The reaction mixture was stirred at refluxing under N$_2$ flow. After 18 h, TLC (DCM:MeOH=10:1 as mobile phase) indicated the reaction to be complete. The reaction mixture was allowed to cool down to 40~50° C. and filtered through Celite®. The Celite layer was washed with ethyl acetate (30 mL). The filtrate was concentrated under reduced pressure. The resulting crude was purified by column chromatography (Ethyl acetate:MeOH=10:1 as mobile phase) to give I-31a (0.2 g, 12%, M+H$^+$=504.6).

Example 31

Synthesis of N-(3-(5-methoxy-2-(4-(2-methoxyethylamino)phenylamino)pyrimidin-4-yloxy)phenyl)acrylamide (I-32a)

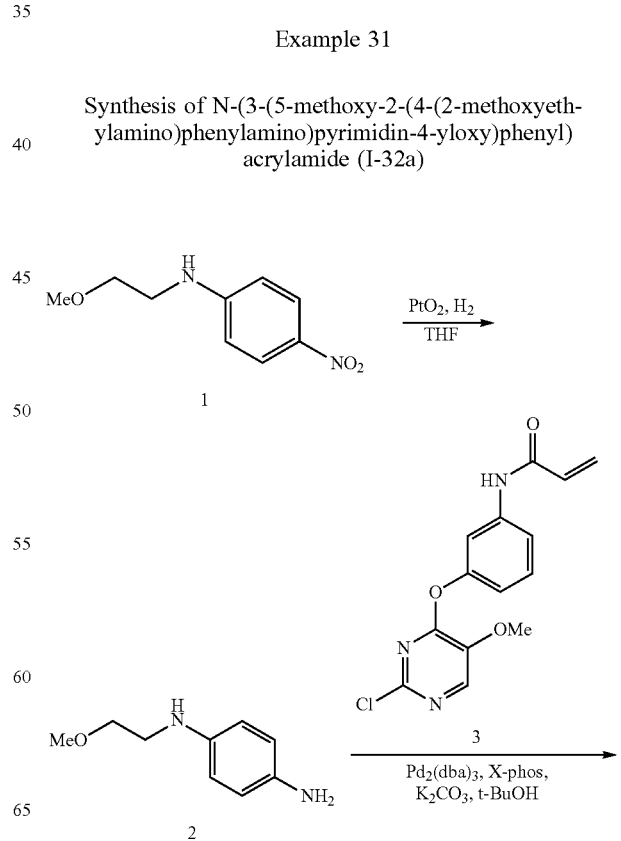

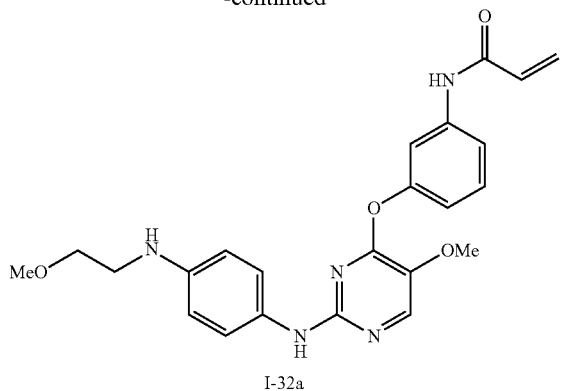

I-32a

Synthesis of N¹-(2-methoxyethyl)benzene-1,4-diamine (2)

A mixture of compound 1 (1.496 g) and PtO₂ (0.060 g) in THF (15 mL) was hydrogenated at room temperature overnight. At this point, TLC was indicated the reaction to be complete. The reaction mixture was filtered through Celite®. The celite layer was washed with ethyl acetate. The combined layers were concentrated under reduced pressure to afford the desired product 2 (1.201 g, 94.43%, M+H+= 236.5) without further purification.

Synthesis of N-(3-(5-methoxy-2-(4-(2-methoxyethylamino)phenylamino)pyrimidin-4-yloxy)phenyl)acrylamide (I-32a)

Compound 2 (0.532 g), compound 3 (0.925 g), K₂CO₃ (0.931 g), tris(dibenzylideneacetone)dipalladium (0.145 g), dicyclohexyl (2',4',6'-triisopropylbiphenyl-2-yl) phosphine (0.150 g) and t-BuOH (10 mL) were sequentially added to the flask. The reaction mixture was stirred at refluxing under N₂ flow. After 2 h, TLC (DCM:MeOH=10:1 as mobile phase) indicated the reaction to be complete. The reaction mixture was allowed to cool down to 40~50° C. and filtered through Celite®. The Celite layer was washed with ethyl acetate (50 mL). The filtrate was concentrated under reduced pressure. The resulting crude was purified by column chromatography (Ethyl acetate:MeOH=10:1 as mobile phase) to give I-32a (0.672 g, 48.2%, M+H⁺=436.2).

¹H NMR (500 MHz, CDCl₃) δ 7.96 (s, 1H), 7.79 (s, 1H), 7.58 (d, J=7.7 Hz, 1H), 7.45 (s, 1H), 7.36 (t, J=8.1 Hz, 1H), 7.11 (d, J=8.8 Hz, 2H), 6.97 (d, J=7.0 Hz, 1H), 6.78 (s, 1H), 6.47 (d, J=8.8 Hz, 2H), 6.43 (dd, J=16.9, 1.0 Hz, 1H), 6.23 (dd, J=16.8, 10.2 Hz, 1H), 5.75 (dd, J=10.3, 1.0 Hz, 1H), 3.92 (s, 3H), 3.58 (t, J=5.2 Hz, 2H), 3.39 (s, 3H), 3.22 (t, J=5.2 Hz, 2H).

Example 32

Synthesis of N-(3-(5-methoxy-2-(6-((2-methoxyethyl)(methyl)amino)pyridin-3-ylamino)pyrimidin-4-yloxy)phenyl)acrylamide (I-33a)

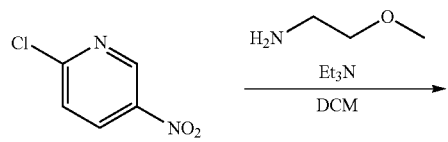

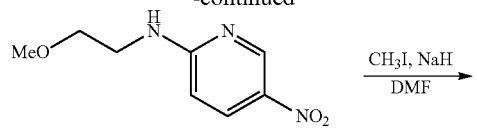

1

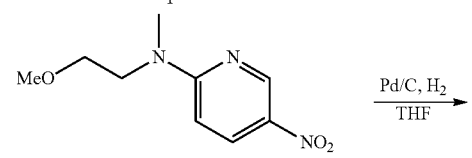

2

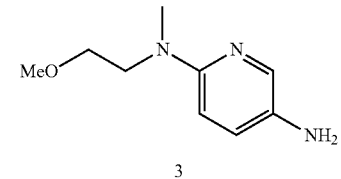

3

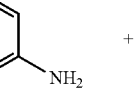

3

+

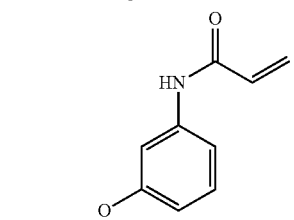

4

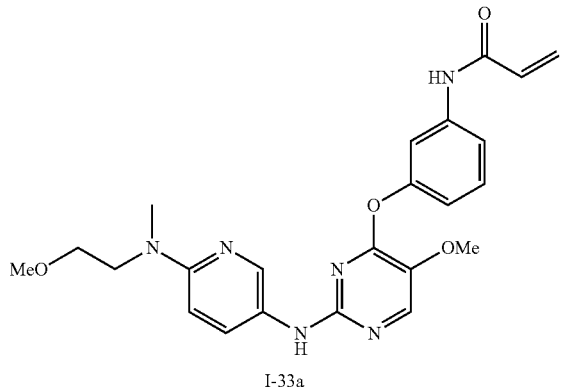

I-33a

Synthesis of N-(2-methoxyethyl)-5-nitropyridin-2-amine (1)

A mixture of 2-chloro-5-nitropyridine (1.578 g), 2-methoxyethylamine (1.522 g) and Et₃N (2.070 g) in DCM (10 mL) was stirred at room temperature for 6 h. Then the mixture was heated up and stirred at refluxing for another 2 h. CH₃CN (5 mL) was added in, and refluxed overnight. At this point, TLC indicated the reaction to be complete. The reaction was quenched with water, and then extracted with ethyl acetate. Organic layers was combined, washed with brine, dried over $Na_2SO_4$, filtered and concentrated under reduced pressure to give desired compound 1 (1.868 g, 95%, $M+H^+=198.2$).

Synthesis of N-(2-methoxyethyl)-N-methyl-5-nitro-pyridin-2-amine (2)

To a solution of 1 (1.648 g) in DMF (15 mL) with ice-water bath was sequentially added NaH (0.302 g, 80% dispersion in mineral oil) and $CH_3I$ (1.418 g). The resulting mixture was then stirred at 0° C. for 10 rain. The reaction mixture was quenched with water and extracted with ethyl acetate. The combined organic layer was washed with water, dried over $Na_2SO_4$, filtered and concentrated under reduced pressure. The resulting crude product 2 (2.0 g, $M+H^+=212.2$) was used directly in next step without further purification.

Synthesis of $N^2$-(2-methoxyethyl)-$N^2$-methylpyri-dine-2,5-diamine (3)

A solution of 2 (2.0 g) and Pd/C (0.300 g, 10% activated on carbon) in TITLE' (20 mL) was hydrogenated at 40° C. overnight. At this point, TLC indicated the reaction to be complete. The reaction mixture was filtered through Celite®. The celite layer was washed with MeOH. The combined filtrate was concentrated under reduced pressure to afford desired product 3 (1.687 g, 98%, $M+H^+=182.3$) without further purification.

Synthesis of N-(3-(5-methoxy-2-(6-((2-methoxy-ethyl)(methyl)amino)pyridin-3-ylamino)pyrimidin-4-yloxy)phenyl)acrylamide (I-33a)

Compound 3 (1.687 g), compound 4 (2.827 g), $K_2CO_3$ (2.570 g), tris(dibenzylideneacetone)dipalladium (0.6 g), dicyclohexyl (2',4',6'-triisopropylbiphenyl-2-yl) phosphine (0.6 g) and t-BuOH (60 mL) were sequentially added to a flask. The reaction mixture was stirred at refluxing under $N_2$ flow. After 3 h, TLC (Ethyl acetate:EtOH=10:1 as mobile phase) indicated the reaction to be complete. The reaction mixture was allowed to cool down to 40~50° C. and filtered through Celite®. The Celite layer was washed with ethyl acetate (50 mL). The combined filtrate was concentrated under reduced pressure. The resulting crude was purified by column chromatography (Ethyl acetate as mobile phase) to give I-33a (2.591 g, 62.4%, $M+H^+=451.5$).

Example 33

Synthesis of N-(3-(5-methoxy-2-(1-(2-methoxy-ethyl)indolin-5-ylamino)pyrimidin-4-yloxy)phenyl) acrylamide (I-34a)

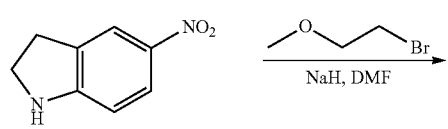

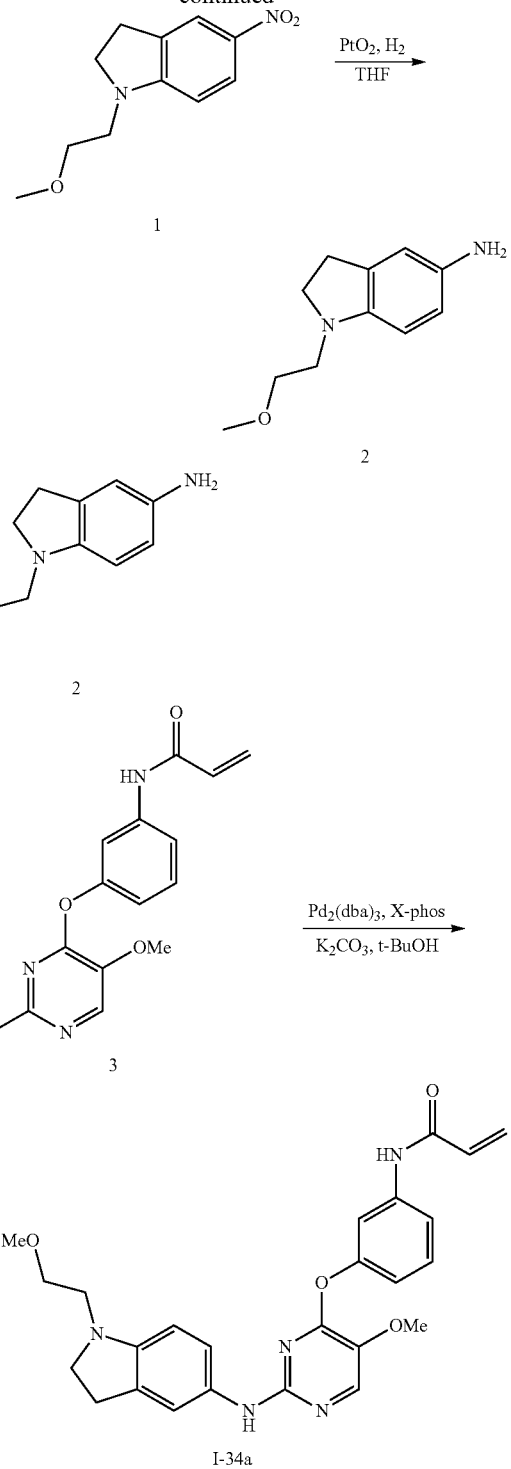

Synthesis of 1-(2-methoxyethyl)-5-nitroindoline (1)

To a solution of 5-nitroindoline (5.718 g) in DMF (60 mL) at 0° C. was sequentially added NaH (1.348 g, 60% dispersion in mineral oil) and 1-bromo-2-methoxyethane (5.368 g). The mixture was stirred at 0° C. for 2 h, and then was allowed to warm up to room temperature and stirred for another 3 h. At this point, TLC indicated the reaction to be complete. The reaction mixture was poured onto ice-water.

The precipitate was collected, and re-dissolved in ethyl acetate. The organic layer was washed with water, brine and concentrated under reduced pressure to afford the desired product 1 (7.292 g, 94%, M+H$^+$=223.3) as a yellow solid.

Synthesis of 1-(2-methoxyethyl)indolin-5-amine (2)

A solution of 1 (7.272 g) and PtO$_2$ (0.202 g) in THF (100 mL) was hydrogenated at room temperature overnight. At this point, TLC indicated the reaction to be complete. The reaction mixture was filtered through Celite®. The celite layer was washed with ethyl acetate. The combined filtrate was concentrated under reduced pressure to afford desired product 2 (6.247 g, 99.3%, M+H$^+$=193.5) which was used for next step without further purification.

Synthesis of N-(3-(5-methoxy-2-(1-(2-methoxy-ethyl)indolin-5-ylamino)pyrimidin-4-yloxy)phenyl) acrylamide (I-34a)

Compound 2 (1.059 g), compound 3 (1.813 g), K$_2$CO$_3$ (1.037 g), tris(dibenzylideneacetone)dipalladium (0.146 g), dicyclohexyl (2',4',6'-triisopropylbiphenyl-2-yl) phosphine (0.152 g) and t-BuOH (50 mL) were sequentially added to a flask. The reaction mixture was stirred at refluxing under N$_2$ flow. After 5 h, TLC (Ethyl acetate:petroleum ether=1:1 as mobile phase) indicated the reaction to be complete. The reaction mixture was allowed to cool down to 40~50° C. and filtered through Celite®. The Celite layer was washed with ethyl acetate (50 mL). The combined filtrate was concentrated under reduced pressure. The resulting crude was purified by column chromatography (Ethyl acetate:petroleum ether=1:3 as mobile phase) to give desired product I-34a (1.368 g, 53.9%, M+H$^+$=462.6).

Example 34

Synthesis of N-(3-(5-methoxy-2-(4-((2-methoxy-ethyl)(methyl)amino)phenylamino)pyrimidin-4-yloxy)phenyl)acrylamide (I-35a)

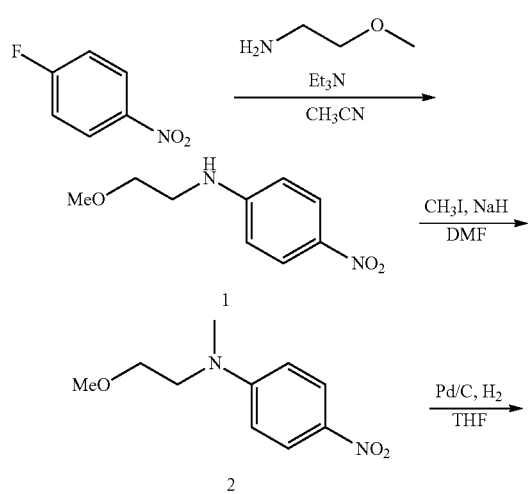

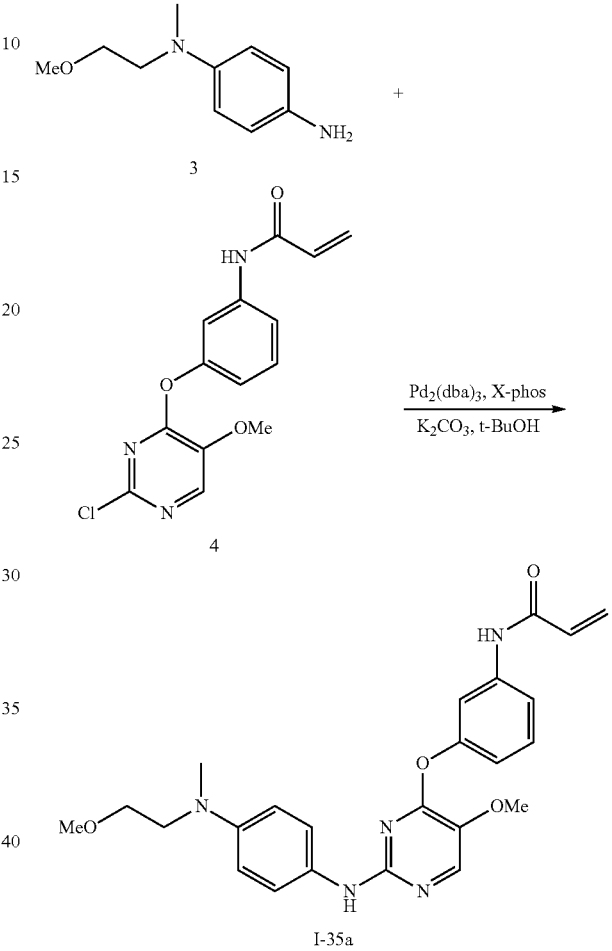

Synthesis of N-(2-methoxyethyl)-4-nitroaniline (1)

A mixture of 1-fluoro-4-nitrobenzene (2.820 g), 2-methoxyethylamine (3.00 g) and Et$_3$N (4.04 g) in CH$_3$CN (20 mL) was stirred at 50° C. overnight. The reaction was quenched with water, then extracted with ethyl acetate. Organic layers were combined, washed with brine, dried over Na$_2$SO$_4$, filtered and then concentrated under reduced pressure to give desired compound 1 (3.9 g, 99%, M+H$^+$= 197.3), which was used for next step without further purification.

Synthesis of N-(2-methoxyethyl)-N-methyl-4-nitroaniline (2)

To a solution of 1 (1.047 g) in DMF (1.5 mL) with ice-water bath was sequentially added NaH (0.200 g) and CH$_3$I (0.906 g). The resulting mixture was then stirred at 0° C. 10 min. The reaction mixture was quenched with water and extracted with ethyl acetate. The combined organic layer was washed with water, dried over Na₂SO₄, filtered and concentrated under reduced pressure. The resulting crude 2 (1.0 g, 89%, M+H⁺=211.3) was used directly in next step without further purification.

Synthesis of N¹-(2-methoxyethyl)-N¹-methylbenzene-1,4-diamine (3)

A mixture of 1 (1.0 g) and Pd/C (0.100 g, 10% activated on carbon) in THF (20 mL) was hydrogenated at 40° C. overnight. At this point. TLC indicated the reaction to be complete. The reaction mixture was filtered through Celite®. The celite layer was washed with ethyl acetate. The combined filtrate was concentrated under reduced pressure to afford desired product 3 (1.058, M+H⁺=181.3) without farther purification.

Synthesis of N-(3-(5-methoxy-2-(4-((2-methoxyethyl)(methyl)amino)phenylamino)pyrimidin-4-yloxy)phenyl)acrylamide (I-35a)

Compound 3 (1.058 g), compound 80 (4 g), K₂CO₃ (1.630 g), tris(dibenzylideneacetone)dipalladium (0.3 g), dicyclohexyl (2',4',6'-triisopropylbiphenyl-2-yl) phosphine (0.3 g) and t-BuOH (50 mL) were sequentially added to the flask. The reaction mixture was stirred at refluxing under N₂ flow. After 5 h, TLC (Ethyl acetate:Ethanol=10:1 as mobile phase) indicated the reaction to be complete. The reaction mixture was allowed to cool down to 40~50° C. and filtered through Celite®. The Celite layer was washed with ethyl acetate (50 mL). The combined filtrate was concentrated under reduced pressure. The resulting crude was purified by column chromatography (Ethyl acetate as mobile phase) to give desired product I-35a (1.8 g, 68.7%, M+H⁺=450.6).

Example 35

Synthesis of N-(3-(2-(1-(2-methoxyethyl)indolin-5-ylamino)-7H-pyrrolo[2,3-d]pyrimidin-4-yloxy)phenyl)acrylamide (I-36a)

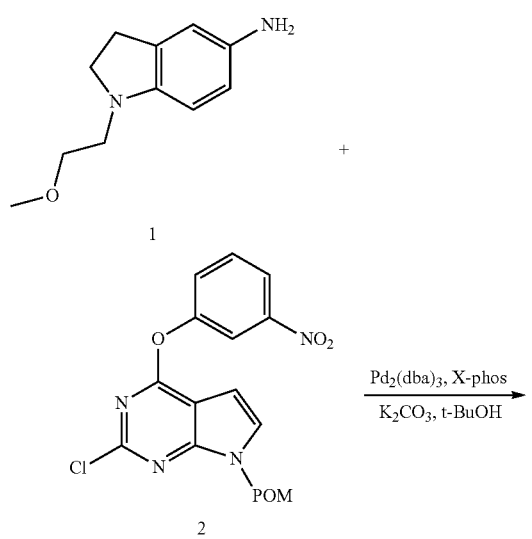

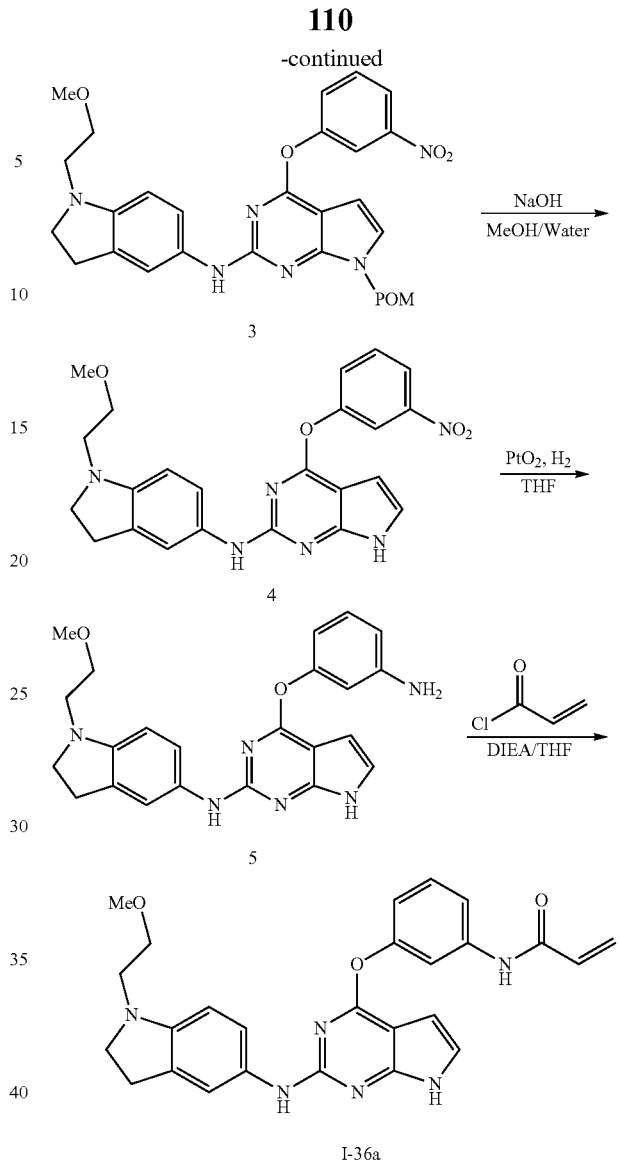

Synthesis of (2-(1-(2-methoxyethyl)indolin-5-ylamino)-4-(3-nitrophenoxy)-7H-pyrrolo[2,3-d]pyrimidin-7-yl)methyl pivalate (3)

Compound 1 (0.7 g), compound 2 (1.780 g), K₂CO₃ (1.01 g), tris(dibenzylideneacetone)dipalladium (0.4 g), dicyclohexyl (2',4',6'-triisopropylbiphenyl-2-yl) phosphine (0.401 g) and t-BuOH (16 mL) were sequentially added to the flask. The reaction mixture was stirred at refluxing under N₂ flow. After 3.5 h, TLC (Ethyl acetate:Ethanol=10:1 as mobile phase) indicated the reaction to be complete. The reaction mixture was allowed to cool down to 40~50° C. and filtered through Celite®. The Celite layer was washed with ethyl acetate (50 mL). The combined filtrate was concentrated under reduced pressure. The resulting crude was purified by column chromatography to give compound 3 (0.7 g, 34.2%).

Synthesis of N-(1-(2-methoxyethyl)indolin-5-yl)-4-(3-nitrophenoxy)-7H-pyrrolo[2,3-d]pyrimidin-2-amine (4)

To a round-bottom flask (250 mL) was charged with compound 3 (700 mg), MeOH (6 mL) and THF (1 mL).

When compound 3 was completely dissolved, the reaction mixture was cooled down to ~10° C. with an ice-bath. NaOH solution (2.5 M, 2 mL) was then added into the flask slowly, maintaining the temperature ~16° C. throughout the addition. The mixture was stirred for 2 h at this temperature and then water (20 mL) was added. The mixture was extracted with ethyl acetate. The organic layers were combined and concentrated under reduced pressure. The resulting crude was purified by column chromatography to afford compound 4 (320 mg, 57.4%, M+H⁺=447.6).

Synthesis of 4-(3-aminophenoxy)-N-(1-(2-methoxyethyl)indolin-5-yl)-7H-pyrrolo[2,3-d]pyrimidin-2-amine (5)

A mixture of 4 (320 mg) and PtO₂ (8 mg) in THF (5 ml) was hydrogenated with hydrogen balloon at room temperature overnight. At this point, TLC indicated the reaction to be complete. The reaction mixture was filtered through Celite®. The celite layer was washed with ethyl acetate. The combined filtrate was concentrated under reduced pressure. The resulting crude was purified by column chromatography to afford desired compound 5 ((125 g, 83.75%).

Synthesis of N-(3-(2-(1-(2-methoxyethyl)indolin-5-ylamino)-7H-pyrrolo[2,3-d]pyrimidin-4-yloxy)phenyl)acrylamide (I-36a)

To a mixture of compound 5 (0.25 g) and DIEA (125 mg) in THF (4 mL) at 0° C. was dropwise added acryloyl chloride (82 mg) over 5 min. The mixture was stirred for 2 h at this temperature. NaOH solution (1M, 2 mL) was added to quench the reaction. The mixture was stirred for 30 min, and then diluted with water (30 mL) before being extracted with ethyl acetate (30 mL). The organic layer was separated and concentrated under reduced pressure. The resulting crude was purified by column chromatography to give I-36a (186 mg, 65.85%, M+H+=471.6).

Example 36

Synthesis of N-(3-(2-(3,5-difluoro-4-(2-methoxyethoxy)phenylamino)-7H-pyrrolo[2,3-d]pyrimidin-4-yloxy)phenyl)acrylamide (I-37a)

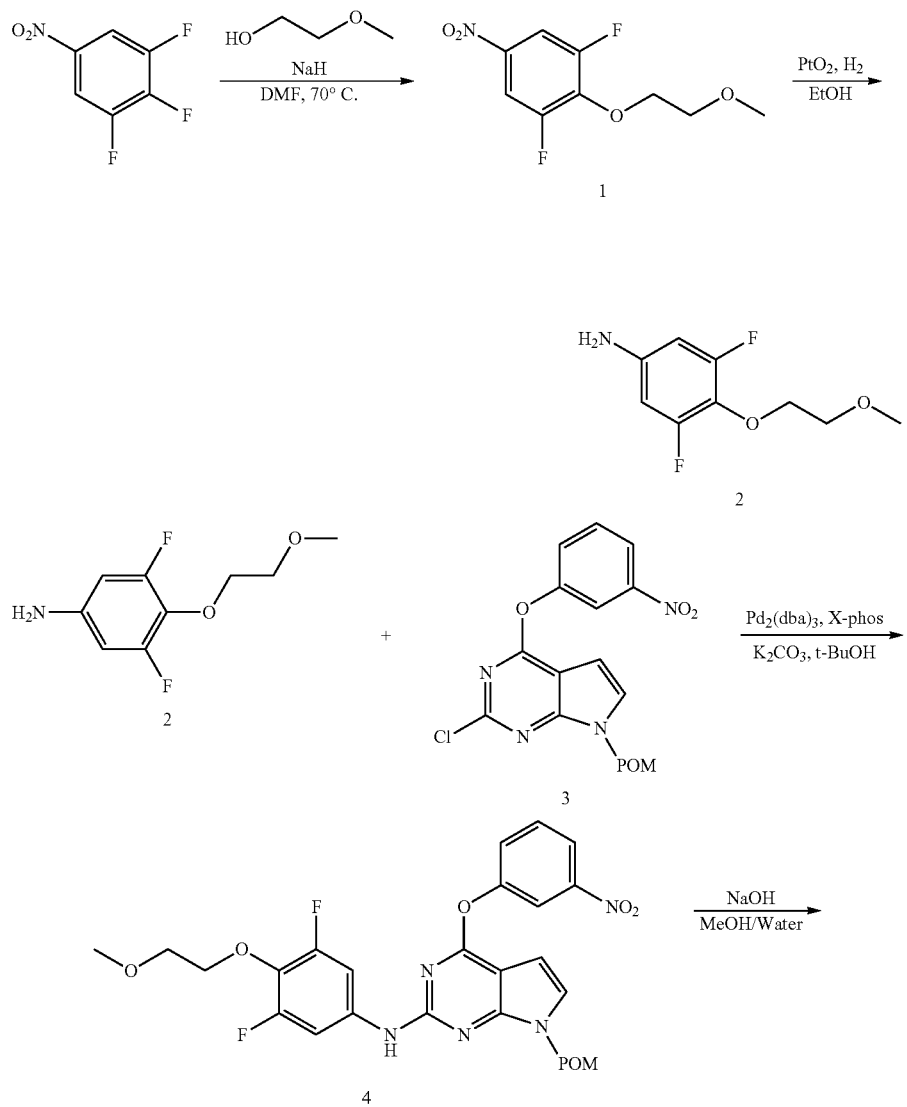

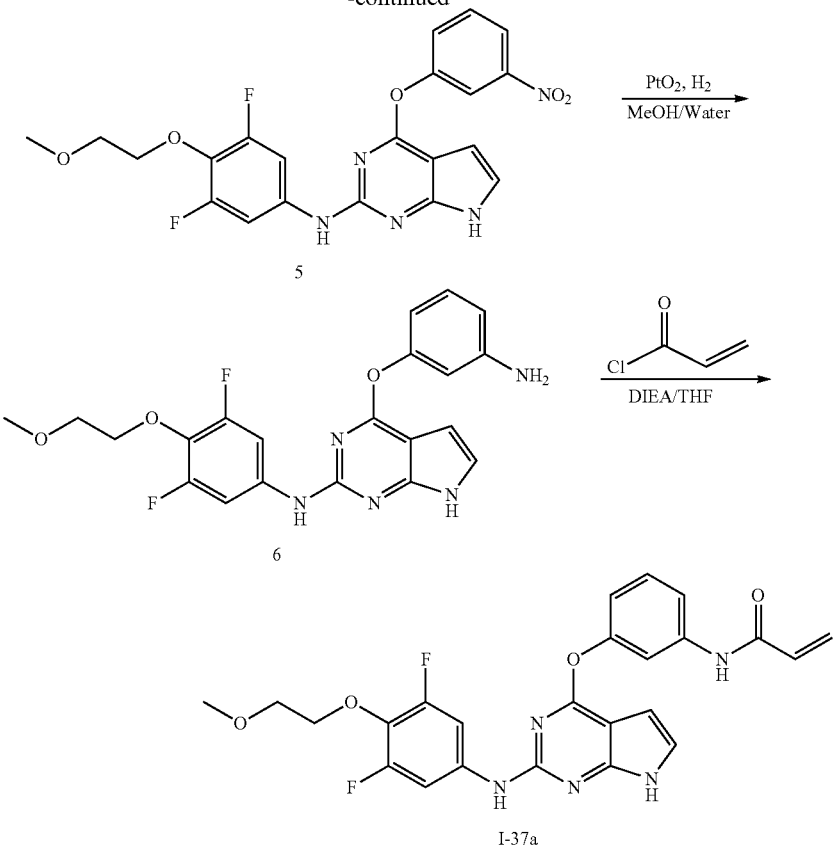

Synthesis of 1, 3-difluoro-2-(2-methoxyethoxy)-5-nitrobenzene (1)

To a solution of 1, 2, 3-trifluoro-5-nitrobenzene (2.625 g, 14 mmol) and 2-methoxyethanol (1.3 g, 17 mmol) in DMF (20 mL) was added NaH (0.815 g, 80% dispersion in mineral oil). The mixture was stirred at room temperature for 3 h until TLC (Petroleum:Ethyl acetate=1:6 as mobile phase) indicated the reaction to be complete. The mixture was poured into water (60 mL) and extracted with EA (40 mL×4). The organic layer was combined, dried over $Na_2SO_4$, filtered and concentrated under reduced pressure. The resulting crude was purified by column chromatography (EtOAc/Petroleum ether from 1/7 to 1/3 as mobile phase) to give 1 (2.609 g, 80%) as a dark yellow solid.

Synthesis of 3, 5-difluoro-4-(2-methoxyethoxy)aniline (2)

A mixture of 1 (3.88 g) and $PtO_2$ (0.9 g) in EtOH (30 mL) was hydrogenated at room temperature overnight. At this point, TLC indicated the reaction to be complete. The reaction mixture was filtered through Celite® and washed with ethyl acetate. The combined filtrate was concentrated under reduced pressure to afford the desired product 2 (2.7 g, 95%) without further purification.

Synthesis of (2-(3,5-difluoro-4-(2-methoxyethoxy) phenylamino)-4-(3-nitrophenoxy)-7H-pyrrolo[2,3-d] pyrimidin-7-yl)methyl pivalate (4)

Compound 2 (2.7 g, 13.3 mmol), compound 3 (6.075 g, 15 mmol), $K_2CO_3$ (4.140 g, 30 mmol), tris(dibenzylideneacetone)dipalladium (0.064 g, 0.07 mol), dicyclohexyl (2',4', 6'-triisopropylbiphenyl-2-yl) phosphine (0.065 g, 0.14 mmol) and t-BuOH (50 mL) were sequentially added to a flask. The reaction mixture was stirred at refluxing under $N_2$ flow. After 3-4 h, TLC (DCM:Methanol=10:1 as mobile phase) indicated the reaction to be complete. The reaction mixture was allowed to cool down to 40~50° C. and filtered through Celite®. The Celite layer was washed with ethyl acetate (30 mL). The combined filtrate was concentrated under reduced pressure. The resulting crude was purified by column chromatography (EtOAc/Petroleum ether from 50% to 100%) to give compound 4 (4.932 g, 65%) as a slight yellow solid.

Synthesis of N-(3,5-difluoro-4-(2-methoxyethoxy) phenyl)-4-(3-nitrophenoxy)-7H-pyrrolo[2,3-d]pyrimidin-2-amine (5)

To a round-bottom flask (250 mL) was charged with compound 4 (4.932 g, 8.64 mmol) and MeOH (40 mL). When compound 4 was completely dissolved, the solution was cooled down to ~10° C. with an ice-bath. NaOH solution (2.5 M, 10 mL) was then added into the flask slowly, maintaining the temperature ~16° C. during the addition. The mixture was stirred for 2 h at this temperature. Water (100 mL) was added to the flask over 15 min, maintaining the temperature below 20° C. The mixture was continuously stirred for another 15 min. The precipitate was collected, washed with water (50 mL) and dried under vacuum to afford compound 5 (1.579 g, 40%).

Synthesis of 4-(3-aminophenoxy)-N-(3,5-difluoro-4-(2-methoxyethoxy)phenyl)-7H-pyrrolo[2,3-d]pyrimidin-2-amine (6)

A mixture of 5 (1.579 g, 3.456 mmol) and PtO₂ (16 mg, 0.07 mmol) in THF (30 mL) was hydrogenated with hydrogen balloon at room temperature overnight. At this point, TLC indicated the reaction to be complete. The reaction mixture was filtered through Celite® and washed ethyl acetate. The combined filtrate was concentrated to afford the desired compound 6 (1.401 g, 95%) as a white solid.

Synthesis of N-(3-(2-(3,5-difluoro-4-(2-methoxyethoxy)phenylamino)-7H-pyrrolo[2,3-d]pyrimidin-4-yloxy)phenyl)acrylamide (I-37a)

To a solution of compound 6 (1.401 g, 3.28 mmol) and DIEA (0.464 g, 3.6 mmol) in THF (50 mL) at 0° C. was dropwise added acryloyl chloride (0.307 g, 3.4 mmol) over 5 min. The mixture was stirred for 1 h at this temperature. NaOH solution (1M, 3 mL) and water (20 mL) were added to quench the reaction. The mixture was stirred for additional 10 min, and the upper THF phase was separated and evaporated to under reduced pressure. The resulting crude was purified by column chromatography (EtOAc/Petroleum ether from 50% to 100% as mobile phase) to give I-37a (1.090 g, 63%, M+H⁺=482.2) as a white solid.

Example 37

Synthesis of N-(3-(5-methoxy-2-(4-((2-methoxyethyl)(propyl)amino)phenylamino)pyrimidin-4-yloxy)phenyl)acrylamide (I-38a)

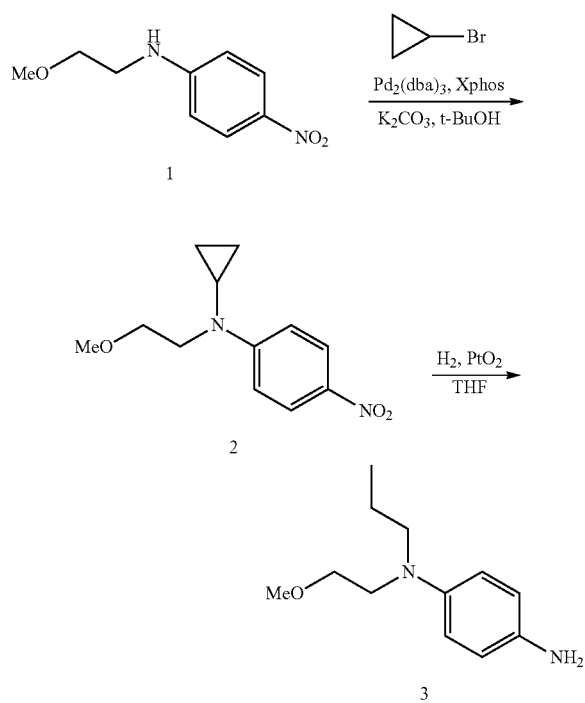

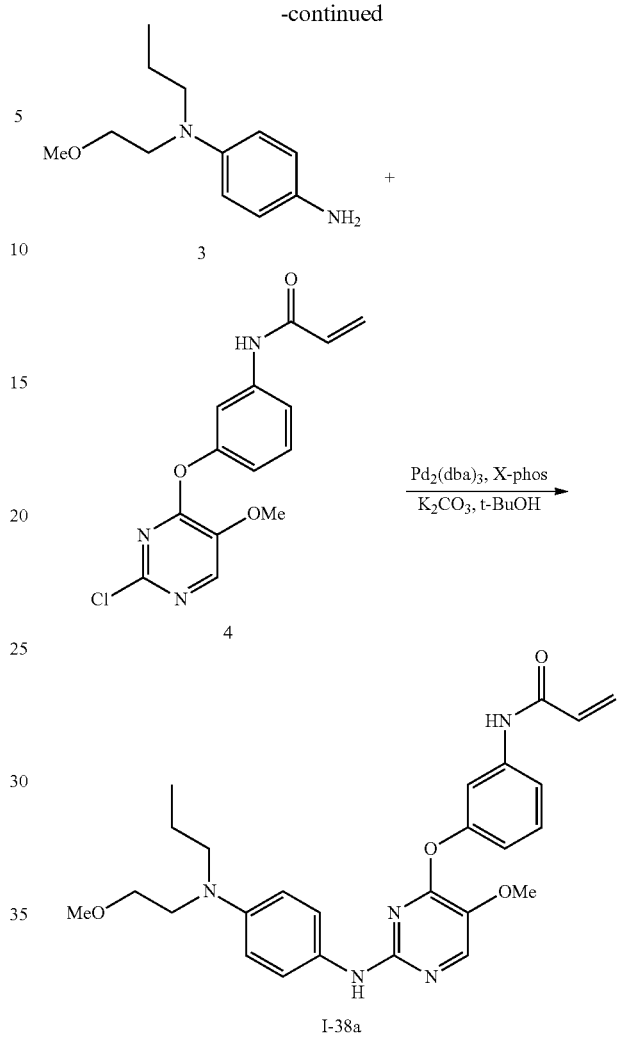

Synthesis of N-cyclopropyl-N-(2-methoxyethyl)-4-nitroaniline (2)

A mixture of compound 1 (1.001 g), cyclopropyl bromide (2.300 g), Pd₂(dba)₃ (0.132 g), X-Phos (0.100 g) and potassium carbonate (1.070 g) in t-butanol (20 mL) was stirred under argon at refluxing overnight. TLC indicated the reaction to be complete. After cooling to room temperature, the reaction mixture was filtered through Celite®, and washed with ethyl acetate. The combined filtrate was concentrated under reduced pressure. The resulting crude was purified by flash column chromatography to afford the desired compound 2 (700 mg, 58.13%).

Synthesis of N¹-(2-methoxyethyl)-N¹-propylbenzene-1,4-diamine (3)

A mixture of 2 (0.556 g) and PtO₂ (0.060 g) in THF (15 mL) was hydrogenated at room temperature overnight. TLC indicated the reaction to be complete. The reaction mixture was filtered through Celite®, and washed with ethyl acetate. The combined filtrate was concentrated under reduced pressure afford to the crude product 3 (0.55 g), which was used for next step without further purification.

Synthesis of N-(3-(5-methoxy-2-(4-((2-methoxyethyl)(propyl)amino)phenylamino)pyrimidin-4-yloxy)phenyl)acrylamide (I-38a)

Compound 3 (0.550 g), compound 4 (0.571 g), $K_2CO_3$ (0.075 g), tris(dibenzylideneacetone)dipalladium (0.075 g), dicyclohexyl (2',4',6'-triisopropylbiphenyl-2-yl) phosphine (0.071 g) and t-BuOH (15 mL) were sequentially added to the flask. The reaction mixture was stirred at refluxing under $N_2$ flow. After 3 h, TLC (Ethyl acetate:Ethanol=10:1 as mobile phase) indicated the reaction to be complete. The reaction mixture was allowed to cool down to 40~50° C. and filtered through Celite®. The celite layer was washed with ethyl acetate (10 mL). The combined filtrate was concentrated under reduced pressure. The resulting crude was purified by column chromatography (EtOAc/Petroleum ether from 50% to 100%) to give compound I-38a (0.182 g, 21.2%, M+H$^+$=478.6).

$^1$H NMR (500 MHz, CDCl$_3$) δ 7.94 (s, 1H), 7.65 (s, 1H), 7.54-7.46 (m, 2H), 7.36 (t, J=8.1 Hz, 1H), 7.12 (d, J=8.9 Hz, 2H), 6.96 ((dd, J=7.9, 1.0 Hz, 1H), 6.61 (s, 1H), 6.50 (d, J=8.9 Hz, 2H), 6.42 (dd, J=16.8, 1.2 Hz, 1H), 6.22 (dd, J=16.8, 10.2 Hz, 1H), 5.75 (dd, J=10.2, 1.1 Hz, 1H), 3.90 (s, 3H), 3.48 (t, J=5.8 Hz, 2H), 3.42 (t, J=6.0 Hz, 2H), 3.35 (s, 3H), 3.19 (t, J=6.0 Hz, 2H), 1.58-1.49 (m, 2H), 0.88 (t, J=7.4 Hz, 3H).

Example 38

Synthesis of N-(3-(2-(4-(cyclopropyl(2-methoxyethyl)amino)phenylamino)-5-methoxypyrimidin-4-yloxy)phenyl)acrylamide (I-39a)

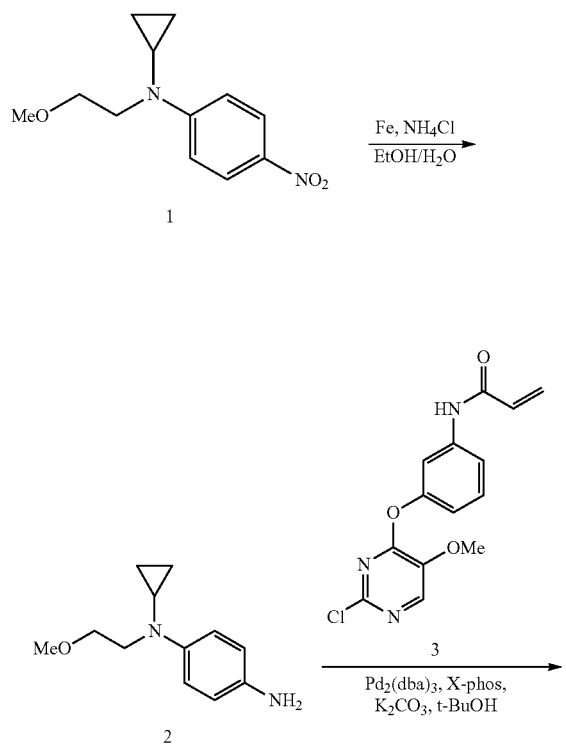

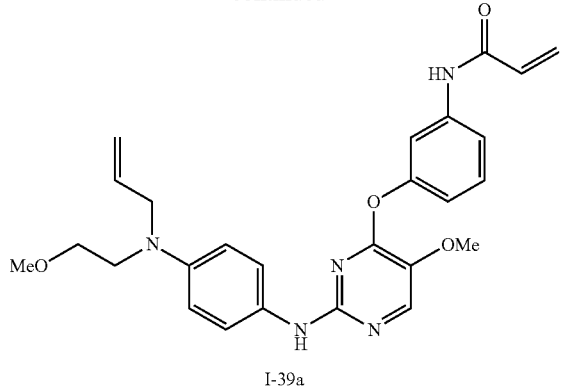

Synthesis of N$^1$-cyclopropyl-N$^1$-(2-methoxyethyl)benzene-1,4-diamine (2)

Compound 1 (0.580 g) in EtOH/H$_2$O (24 mL, 17:7) was treated with iron (0.62 g) followed by ammonium chloride (2.092 g). The mixture was stirred at refluxing for 2 h. The reaction mixture was filtered through Celite®. The filtrate was basified with NaHCO$_3$ (aq, 30 mL) and extracted with ethyl acetate (30 mL×4). The organic layer was combined, dried and concentrated to provide the crude compound 2 (0.545 g which was used in next step without further purification.

Synthesis of N-(3-(2-(4-(cyclopropyl(2-methoxyethyl)amino)phenylamino)-5-methoxypyrimidin-4-yloxy)phenyl)acrylamide (I-39a)

Compound 2 (0.5 g), compound 3 (0.745 g), K$_2$CO$_3$ (0.890 g), tris(dibenzylideneacetone)dipalladium (0.232 g), dicyclohexyl (2',4',6'-triisopropylbiphenyl-2-yl) phosphine (0.240 g) and t-BuOH (20 mL) were sequentially added to the flask. The reaction mixture was stirred at refluxing under N$_2$ flow. After 4 h, TLC (Ethyl acetate:Ethanol=10:1 as mobile phase) indicated the reaction to be complete. The reaction mixture was allowed to cool down to 40~50° C. and filtered through Celite®. The celite layer was washed with ethyl acetate (10 mL). The combined filtrate was concentrated under reduced pressure. The resulting crude was purified by column chromatography to give compound I-39a (0.228 g, 17.4%, M+H$^+$=476.6).

$^1$H NMR (500 MHz, DMSO) δ 10.33 (s, 1H), 8.86 (s, 1H), 8.13 (s, 1H), 7.60 (s, 1H), 7.59 (d, J=8.5 Hz, 1H), 7.39 (dd, J=26.8, 18.9 Hz, 1H), 7.18 (d, J=8.3 Hz, 2H), 6.94 (d, J=7.9 Hz, 1H), 6.44 (dd, J=19.2, 9.1 Hz, 3H), 6.27 (d, J=17.0 Hz, 1H), 5.76 (dd, J=17.6, 7.7 Hz, 2H), 5.09 (d, J=13.0 Hz, 2H), 3.85 (s, 3H), 3.89-3.80 (m, 2H), 3.47-3.32 (m, 4H), 3.25 (s, 3H).

$^{13}$C NMR (126 MHz, DMSO) δ 165.31 (s), 161.44 (s), 156.04 (s), 154.80 (s), 146.07 (s), 144.92 (s), 142.28 (s), 136.95 (s), 136.35 (s), 133.67 (s), 132.17 (s), 131.82 (s), 129.29 (s), 121.98 (s), 118.79 (s), 118.01 (s), 117.82 (s), 114.78 (s), 114.05 (s), 71.98 (s), 60.24 (s), 59.67 (s), 55.20 (s), 51.87 (s).

Example 39

Synthesis of (S)—N-(3-(2-(4-(1-(2-methoxyethyl)pyrrolidin-3-ylamino)phenylamino)-7H-pyrrolo[2,3-d]pyrimidin-4-yloxy)phenyl)acrylamide (I-40a)

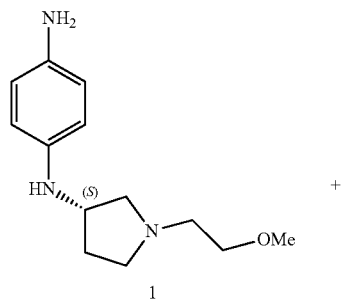

1

+

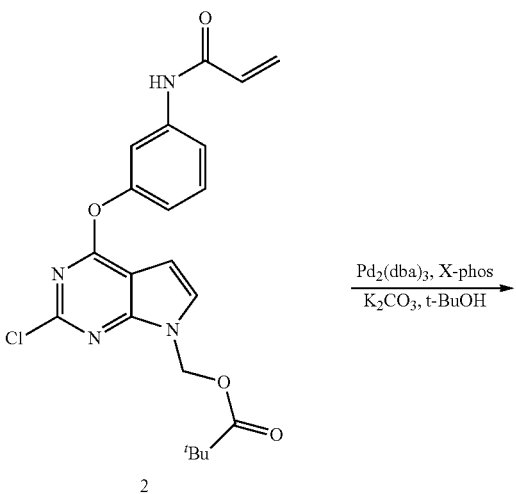

2

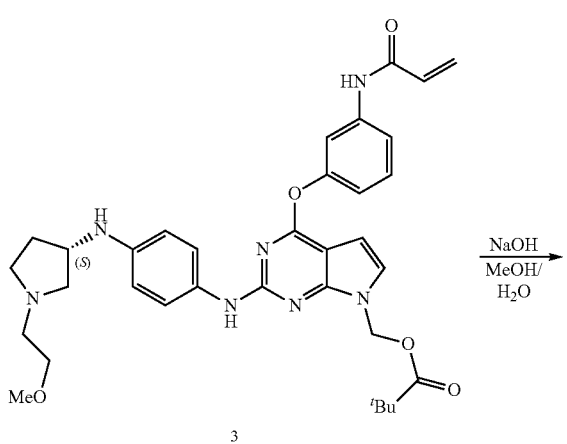

3

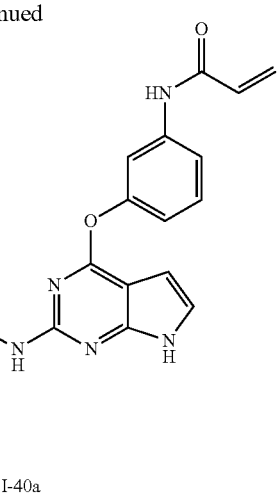

I-40a

Synthesis of (S)-(4-(3-acrylamidophenoxy)-2-(4-(1-(2-methoxyethyl)pyrrolidin-3-ylamino)phenylamino)-7H-pyrrolo[2,3-d]pyrimidin-7-yl)methyl pivalate (3)

Compound 1 (1.008 g, 4.289 mmol), compound 2 (2.143 g, 5.007 mmol), $K_2CO_3$ (1.455 g, 10.543 mmol), tris(dibenzylideneacetone)dipalladium (0.432 g, 0.472 mmol), dicyclohexyl (2',4',6'-triisopropylbiphenyl-2-yl) phosphine (0.434 g, 0.992 mmol) and t-BuOH (20 mL) were sequentially added to the flask. The reaction mixture was stirred at refluxing under $N_2$ flow. After 5-7 h, TLC (DCM:Methanol=10:1 as mobile phase) indicated the reaction to be complete. The reaction mixture was allowed to cool down to 40~50° C., concentrated under reduced pressure, and followed by addition of ethyl acetate (50 mL) and activated charcoal (0.5 g). The mixture was stirred for 15 min and then filtered through Celite®. The celite layer was washed with ethyl acetate (50 mL). The combined filtrate was concentrated under reduced pressure to afford crude 3 (1.723 g, 64%) as a white solid, which was used for next step without further purification.

Synthesis of (S)—N-(3-(2-(4-(1-(2-methoxyethyl)pyrrolidin-3-ylamino)phenylamino)-7H-pyrrolo[2,3-d]pyrimidin-4-yloxy)phenyl)acrylamide (I-40a)

To a round-bottom flask (250 mL) was charged with compound 3 (0.550 g, 0.877 mmol) and MeOH (20 mL). After compound 3 was completely dissolved, the mixture was cooled down to ~10° C. with an ice-bath. NaOH solution (2.5 M, 2 mL) was then added into the flask slowly, keeping the temperature below 16° C. during the addition. The mixture was stirred for 1 h at this temperature. Water (100 mL) was then added slowly to the flask over 15 min (maintaining the temperature below 20° C.). The mixture was extracted with ethyl acetate (30 mL×4). The combined organic layers were concentrated under reduced pressure. The resulting crude was purified by column chromatography (Ethyl acetate/Petroleum ether=from 10% to 100% as mobile phase) to give I-40a (0.17 g, 29%, M+H$^+$=514.5) as a yellow solid.

Example 40
Synthesis of N-(3-(2-(4-((2-methoxyethyl)(methyl)amino)phenylamino)-7H-pyrrolo[2,3-d]pyrimidin-4-yloxy)phenyl)acrylamide (I-41a)
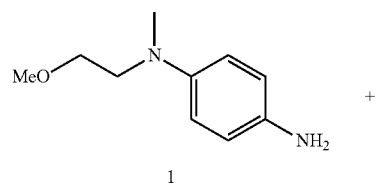
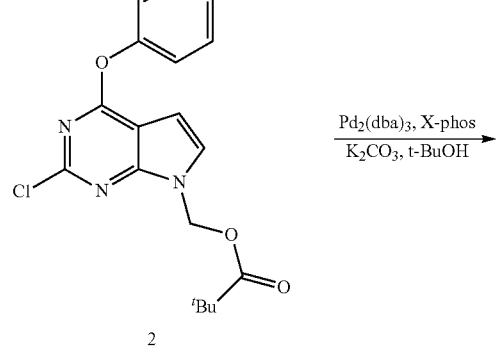
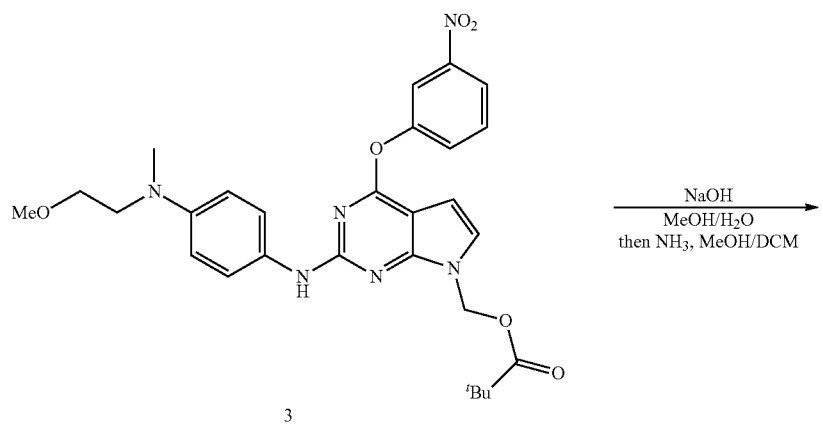
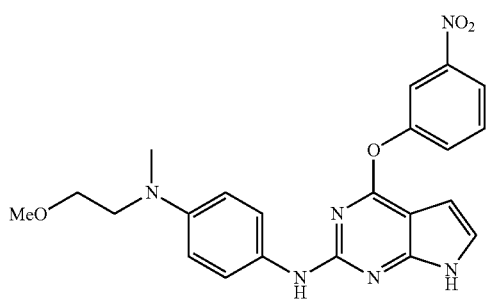

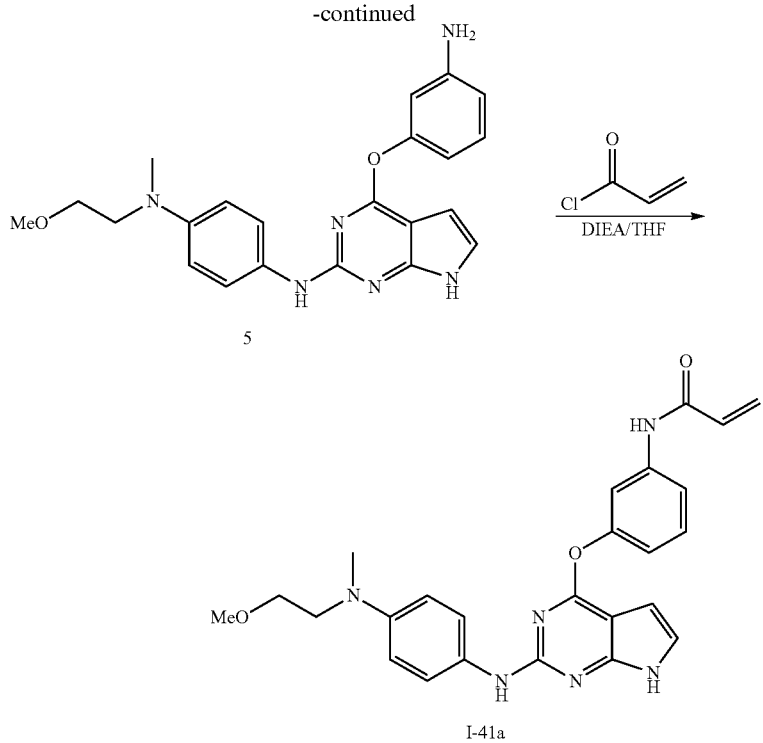

Synthesis of (2-(4-((2-methoxyethyl)(methyl)amino)phenylamino)-4-(3-nitrophenoxy)-7H-pyrrolo[2,3-d]pyrimidin-7-yl)methyl pivalate (3)

Compound 1 (3.0 g), compound 2 (7.1 g), K$_2$CO$_3$ (4.78 g), tris(dibenzylideneacetone)dipalladium (1.2 g), dicyclohexyl (2',4',6'-triisopropylbiphenyl-2-yl) phosphine (1.2 g) and t-BuOH (100 mL) were sequentially added to the flask. The reaction mixture was stirred at refluxing under N$_2$ flow. After 3 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound 3 (6.010 g, 65.8%).

Synthesis of N$^1$-(2-methoxyethyl)-N$^1$-methyl-N$^4$-(4-(3-nitrophenoxy)-7H-pyrrolo[2,3-d]pyrimidin-2-yl)benzene-1,4-diamine (4)

To a round-bottom flask (250 mL) was charged with compound 3 (6.01 g) and MeOH (50 mL). When compound 3 was completely dissolved, the solution was cooled down to ~10° C. with an ice-bath. NaOH solution (2.5 M, 10 mL) was then added slowly into the flask with the temperature remained below 16° C. during the addition. The mixture was stirred for 2.5 h at this temperature. Water (150 mL) was slowly added into the flask over 15 mm with the temperature remained below 20° C. during the addition. The mixture was extracted with ethyl acetate (100 mL×2). The organic layers were combined, and concentrated under reduced pressure. The resulting crude was re-dissolved in MeOH/DCM (1:1, 50 mL) and the resulting solution was bubbled with NH$_3$(g) at room temperature. After 7 hr, LC-MS indicated the reaction to be complete. The organic solvent was removed under reduced pressure to afford 4 (4.5 g, 94.7%), which was used in next step without further purification.

Synthesis of N$^1$-(4-(3-aminophenoxy)-7H-pyrrolo[2,3-d]pyrimidin-2-yl)-N$^4$-(2-methoxyethyl)-N$^4$-methylbenzene-1,4-diamine (5)

A mixture of 4 (4.5 g) and PtO$_2$ (50 mg) in THF (52 mL) was hydrogenated with hydrogen balloon at room temperature for 44 h. TLC and LC-MS indicated the incompletion of the reaction because of the slow conversion from hydroxylamine to amine. The reaction mixture was filtered through Celite®. The filtrate was concentrated. The residue was treated with iron/NH$_4$Cl aq/EtOH system for 24 h. The crude was purified by column chromatography to afford the desired compound 5 (2.1 g, 50%) as a white solid.

Synthesis of N-(3-(2-(4-((2-methoxyethyl)(methyl)amino)phenylamino)-7H-pyrrolo[2,3-d]pyrimidin-4-yloxy)phenyl)acrylamide (I-41a)

To a solution of compound 5 (2.1 g) and DIEA (1.01 g) in THF (30 mL) at 0° C. was added acryloyl chloride (0.810 g) drop-wise over 5 min. The mixture was stirred for 3 h at this temperature. NaOH solution (1M, 3 mL) and water (50 mL) were added to quench the reaction. The resulting mixture was stirred for another 10 mm, and then extracted with ethyl acetate. The organic layers were combined and concentrated under reduced pressure. The resulting crude was purified by column chromatography (DCM/MeOH=20/1 as mobile phase) to give compound I-41a (0.605 g, 95.9%, M+H$^+$=459.5).

Example 41

Synthesis of (S)—N-(3-(5-methoxy-2-(4-((1-(2-methoxyethyl)pyrrolidin-3-yl)(methyl)amino)phenylamino)pyrimidin-4-yloxy)phenyl)acrylamide (I-42a)

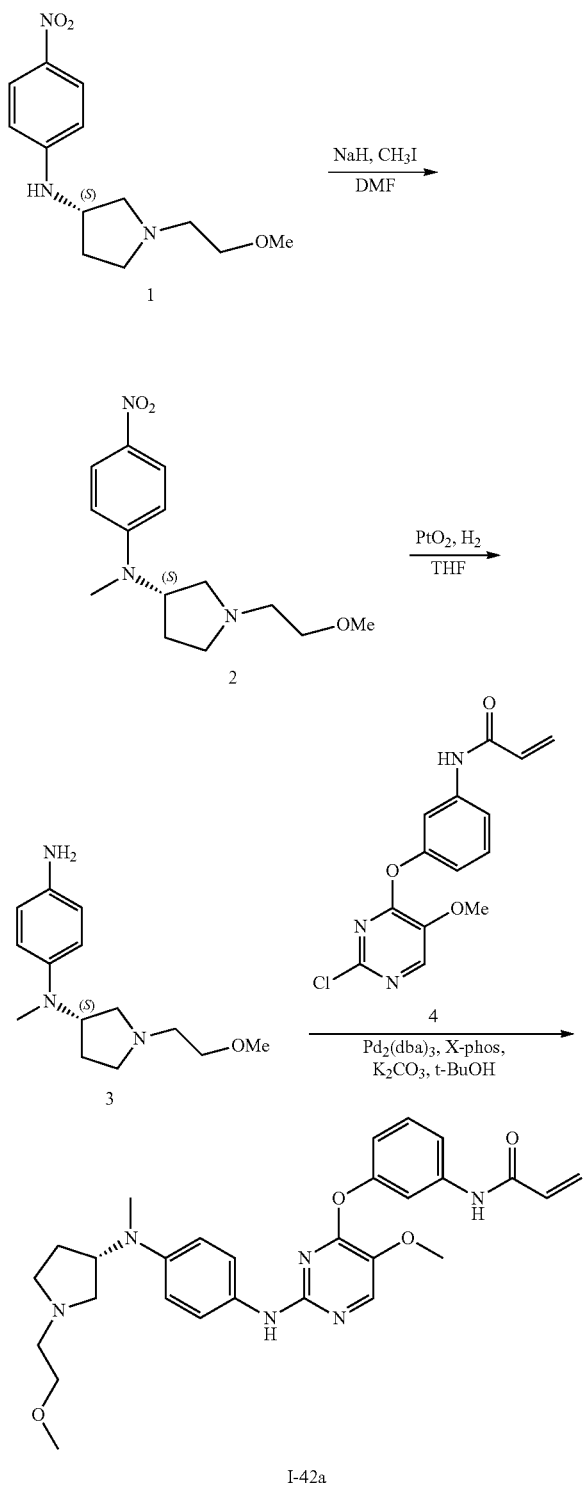

Synthesis of (S)-1-(2-methoxyethyl)-N-methyl-N-(4-nitrophenyl)pyrrolidin-3-amine (2)

To a solution of (2.7 g) in DMF (15 mL) at 0° C. was sequentially added NaH (0.611 g, 80% dispersion in mineral oil) and CH$_3$I (1.5 g). The resulting mixture was stirred for 3 h at this temperature. The reaction mixture was quenched with water and extracted with ethyl acetate. The combined organic layers were washed with water, dried over Na$_2$SO$_4$, filtered and concentrated under reduced pressure. The crude 2 (2.3 g) was used directly in next step without further purification.

Synthesis of (S)—N$^1$-(1-(2-methoxyethyl)pyrrolidin-3-yl)-N$^1$-methylbenzene-1,4-diamine (3)

A mixture of 2 (2.3 g) and PtO$_2$ (0.057 g) in THF (40 mL) was hydrogenated with hydrogen balloon at room temperature for 41 h. TLC showed the reaction to be complete. The reaction mixture was filtered through Celite®. The filtrate was concentrated under reduced pressure to afford the crude compound 3 (1.7 g) without further purification.

Synthesis of (S)—N-(3-(5-methoxy-2-(4-((1-(2-methoxyethyl)pyrrolidin-3-yl)(methyl)amino)phenylamino)pyrimidin-4-yloxy)phenyl)acrylamide (I-42a)

Compound 3 (0.7 g), compound 4 (0.905 g), K$_2$CO$_3$ (0.838 g), tris(dibenzylideneacetone)dipalladium (0.275 g), dicyclohexyl (2',4',6'-triisopropylbiphenyl-2-yl) phosphine (0.271 g) and t-BuOH (15 mL) were sequentially added to a flask. The reaction mixture was stirred at refluxing under N$_2$ flow. After 5 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound I-42a (0.66 g, 45.4%, M+H$^+$=519.6).

$^1$H NMR (500 MHz, DMSO) δ 10.36 (s, 1H), 8.94 (s, 1H), 8.15 (s, 1H), 7.74-7.53 (m, 2H), 7.42 (t, J=8.4 Hz, 1H), 7.23 (d, J=8.9 Hz, 2H), 7.09-6.85 (m, 1H), 6.55 (d, J=9.0 Hz, 2H), 6.45 (dd, J=16.9, 10.1 Hz, 1H), 6.28 (dd, J=17.0, 1.8 Hz, 1H), 5.78 (dd, J=10.1, 1.8 Hz, 1H), 4.24-4.08 (m, 1H), 3.86 (s, 3H), 3.47-3.37 (m, 2H), 3.24 (s, 3H), 2.71 (td, J=8.5, 4.3 Hz, 1H), 2.65 (s, 3H), 2.58 (dt, J=8.1, 6.0 Hz, 2H), 2.55-2.45 (m, 2H), 2.33 (q, J=7.7 Hz, 1H), 2.05-1.90 (m, 1H), 1.57 (td, J=13.4, 7.8 Hz, 1H).

$^{13}$C NMR (126 MHz, DMSO) δ 165.32 (s), 161.43 (s), 155.90 (s), 154.78 (s), 147.40 (s), 145.98 (s), 142.28 (s), 136.44 (s), 133.57 (d, J=18.4 Hz), 131.87 (s), 129.30 (s), 121.49 (s), 118.77 (s), 118.09 (s), 116.72 (s), 114.93 (s), 72.92 (s), 60.02 (s), 59.79 (s), 59.62 (s), 59.30 (s), 56.79 (s), 55.89 (s), 35.77 (s), 29.76 (s).

Example 42

Synthesis of N-(3-(2-(1-(2-fluoroethyl)-1H-indol-5-ylamino)-5-methoxypyrimidin-4-yloxy)phenyl)acrylamide (I-43a)

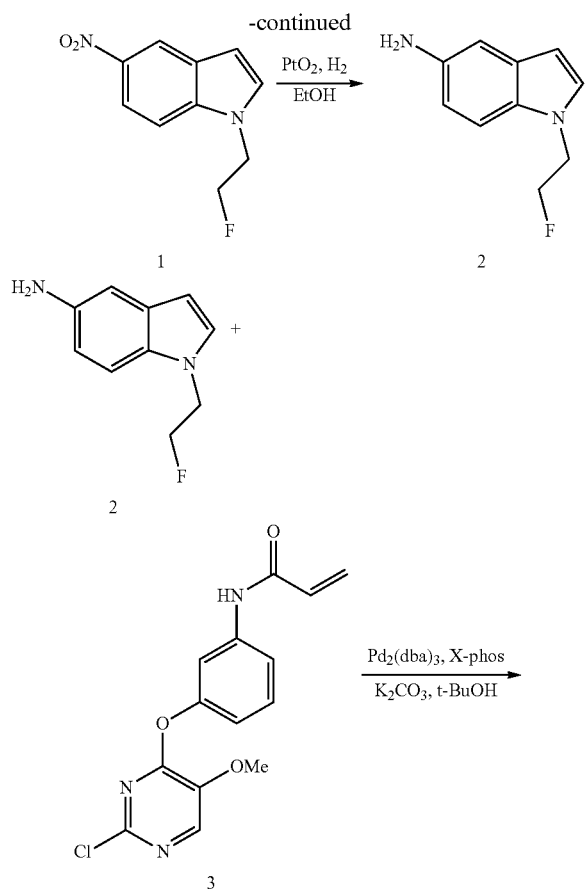

Synthesis of 1-(2-fluoroethyl)-5-nitro-1H-indole (1)

To a solution of 5-nitro-1H-indole (1.618 g, 10 mmol) in DMF (10 ml) at 0° C. was sequentially added NaH (0.805 g, 60% dispersion in mineral oil) and 1-bromo-2-methoxyethane (1.32 g). The mixture was stirred at 60° C. for 3 h until TLC (Petroleum ether:Ethyl acetate=5:1 as mobile phase) indicated the reaction to be complete. The mixture was allowed to cool down to room temperature, poured onto water (60 mL) and then extracted with ethyl acetate (50 mL×4). The organic layers were combined and the solvent was removed under reduced pressure. The resulting residue was purified by column chromatography (EtOAc/Petroleum ether from 1/10 to 1/3 as mobile phase) to give 1 (1.767 g, 8.5 mmol, 85%) as a yellow solid.

Synthesis of 1-(2-fluoroethyl)-1H-indol-5-amine (2)

A mixture of 1 (1.767 g, 8.5 mmol) and PtO$_2$ (0.046 g, 0.20 mmol) in EtOH (40 mL) was hydrogenated with hydrogen balloon at room temperature overnight. At this point, TLC indicated the reaction to be complete. The reaction mixture was filtered through Celite® and washed with small amount of ethanol. The combined filtrates was concentrated under reduced pressure to afford 2 (1.347 g, 89%), which was used in next step without further purification.

Synthesis of N-(3-(2-(1-(2-fluoroethyl)-1H-indol-5-ylamino)-5-methoxypyrimidin-4-yloxy)phenyl)acrylamide (I-43a)

Compound 2 (0.877 g, 4.867 mmol), compound 3 (1.902 g, 6.327 mmol), K$_2$CO$_3$ (1.347 g, 9.743 mmol), tris(dibenzylideneacetone)dipalladium (0.455 g, 0.487 mmol), dicyclohexyl (2',4',6'-triisopropylbiphenyl-2-yl) phosphine (0.471 g, 0.974 mmol) and t-BuOH (30 mL) were sequentially added to the flask. The reaction mixture was stirred at refluxing under N$_2$ flow. After 5 h, TLC (EtOAc/Petroleum ether/TEA=1:1:0.1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound I-43a (1.66 g, 74%, M+H$^+$=448.6) as a light yellow solid.

Example 43

Synthesis of N-(3-(5-methoxy-2-(4-(2-(methylsulfonyl)ethoxy)phenylamino)pyrimidin-4-yloxy)phenyl)acrylamide (I-44a)

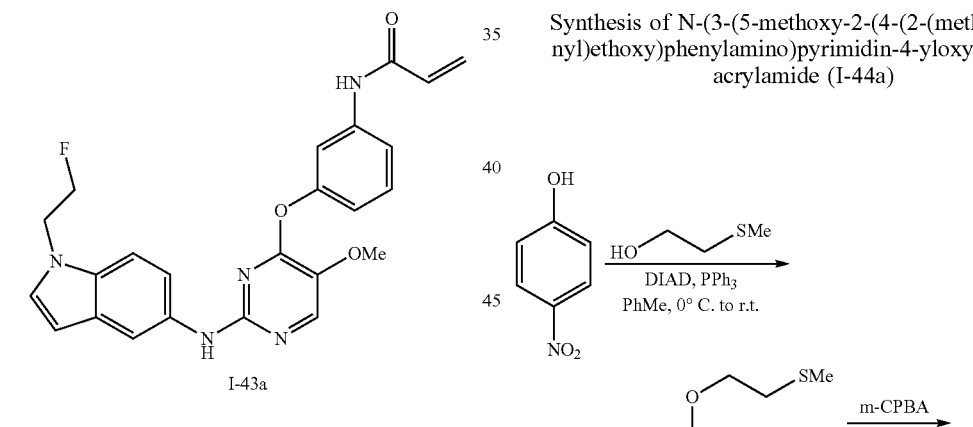

-continued

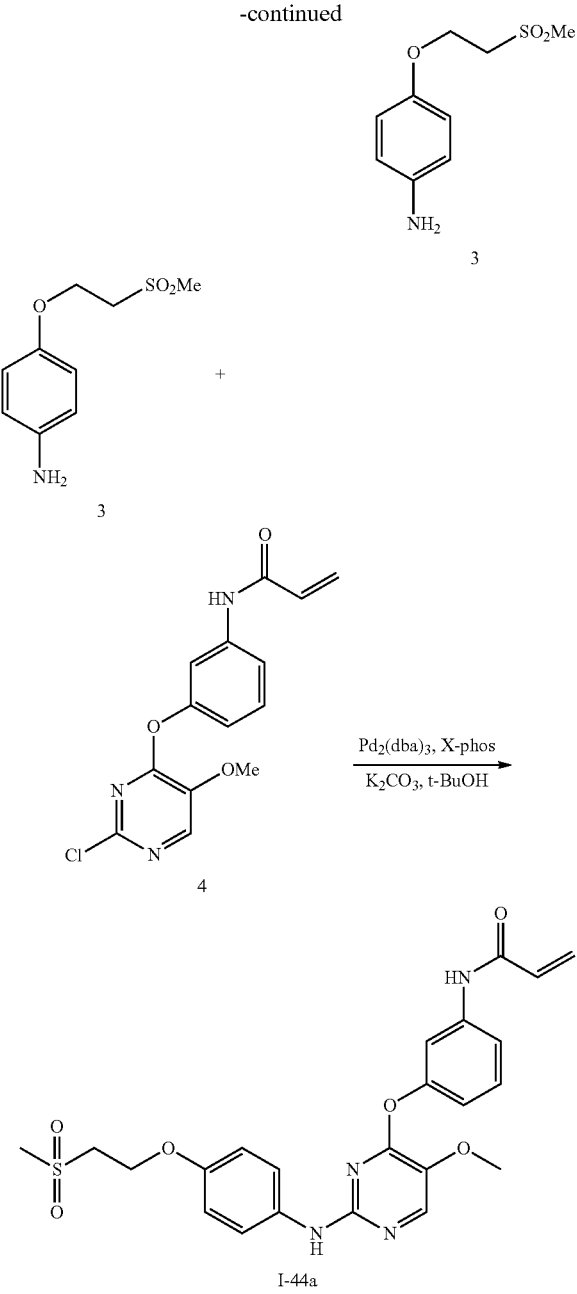

Synthesis of methyl(2-(4-nitrophenoxy)ethyl)sulfane (1)

To a solution of 4-nitrophenol (1.413 g), 2-(methylthio) ethanol (0.948 g) and PPh$_3$ (3.216 g) in toluene (30 mL) at 0° C. was slowly added DIAD (4 mL). The mixture was allowed to warm to room temperature and suited overnight. Solvent was evaporated under reduced pressure. The residue was purified by column chromatography (EtOAc/Petroleum ether from 1:20 to 1:10 as mobile phase) to afford compound 1 (1.879 g, 86.7%) as a yellow oil.

Synthesis of 1-(2-(methylsulfonyl)ethoxy)-4-nitrobenzene (2)

A solution of 1 (1.490 g) in DCM (10 mL) at 0° C. was treated with 3-chloroperbenzoic acid (2.511 g), The resulting mixture was stirred at ambient temperature overnight. The reaction was quenched with saturated aqueous NaHCO$_3$ solution, and then extracted with DCM. The organic layer was separated, dried over Na$_2$SO$_4$, filtered, and concentrated under reduced pressure to yield crude compound 2 (4.542 g), which was used directly in next step without further purification.

Synthesis of 4-(2-methylsulfonyl)ethoxy)amine (3)

A solution of 2 (4.542 g) in THF (50 mL) was treated with iron (5.823 g) and saturated aqueous ammonium chloride (5 mL). The mixture was stirred at refluxing for 2.5 h. After cooling to room temperature, the reaction mixture was filtered through Celite®. The filtrate was concentrated under reduced pressure to yield crude product 3 (2.785 g), which was used for next reaction without further purification.

Synthesis of N-(3-(5-methoxy-2-(4-(2-(methylsulfonyl)ethoxy)phenylamino)pyrimidin-4-yloxy)phenyl) acrylamide (I-44a)

Compound 3 (2.304 g), compound 4 (2.270 g), K$_2$CO$_3$ (3.270 g), tris(dibenzylideneacetone)dipalladium (0.517 g), dicyclohexyl (2',4',6'-triisopropylbiphenyl-2-yl) phosphine (0.512 g) and t-BuOH (60 mL) were sequentially added to a flask. The reaction mixture was stirred at refluxing under N$_2$ flow. After 3.5 h, TLC (EtOAc/Petroleum ether/TEA=1:1:0.1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound I-44a (1.8 g, 29.1%, M+H$^+$=485.5) as a light yellow solid.

$^1$H NMR (500 MHz, DMSO) δ 10.37 (s, 1H), 9.14 (s, 1H), 8.19 (s, 1H), 7.63 (t, J=2.0 Hz, 1H), 7.56 (d, J=9.1 Hz, 1H), 7.44 (t, J=8.1 Hz, 1H), 7.37 (d, J=9.0 Hz, 2H), 6.96 (ddd, J=8.1, 2.3, 0.8 Hz, 1H), 6.69 (d, J=9.1 Hz, 2H), 6.44 (dd, J=17.0, 10.1 Hz, 1H), 6.27 (dd, J=17.0, 1.9 Hz, 1H), 5.78 (dd, J=10.1, 1.9 Hz, 1H), 4.23 (t, J=5.6 Hz, 2H), 3.87 (s, 3H), 3.57 (t, J=5.6 Hz, 2H), 3.05 (s, 3H).

Example 44

Synthesis of N-(3-(5-methoxy-2-(1-(2-methoxyethyl)-1H-indol-5-ylamino)pyrimidin-4-yloxy)phenyl)acrylamide (I-45a)

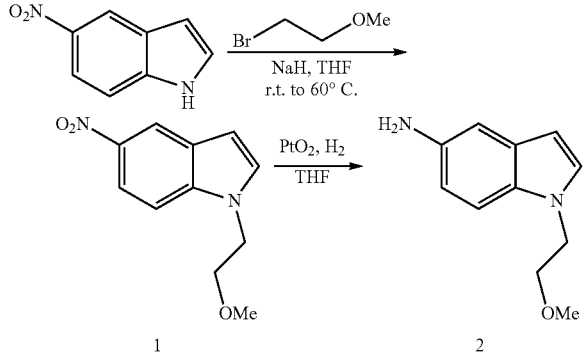

131

-continued

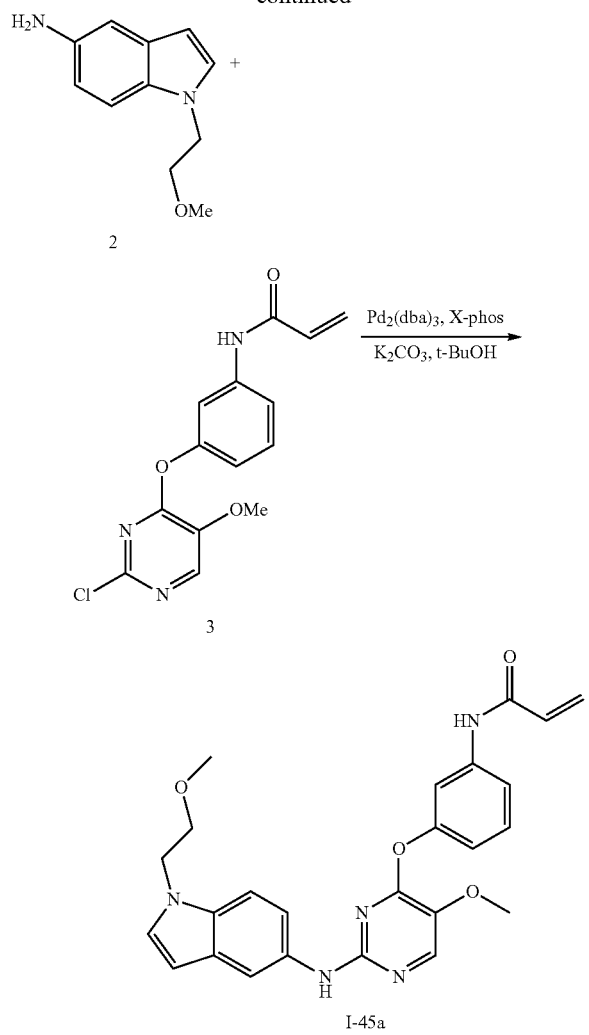

1-(2-methoxyethyl)-5-nitro-indole (1)

To a solution of 5-nitro-1H-indole (1.620 g) and 1-bromo-2-methoxyethane (1.412 g) in THF (15 mL) at room temperature was added NaH (0.420 g, 80% dispersion in mineral oil). The mixture was stirred at 60° C. for 6 h. Another portion of 1-bromo-2-methoxyethane (0.301 g) was added, and the mixture was continuously stirred at 60° C. overnight. The reaction mixture was cooled and poured onto ice-water. The precipitates was filtered, washed with water, and dried to afford 1 (2.10 g, 95.45%) as a yellow solid.

Synthesis of 1-(2-methoxyethyl)-1H-indol-5-amine (2)

A solution of 1 (2.052 g) and $PtO_2$ (0.062 g) in THF (20 mL) was hydrogenated with hydrogen balloon at room temperature overnight. At this point, TLC indicated the reaction to be complete. The reaction mixture was filtered through Celite®. The filtrate was concentrated under reduced pressure to afford 2 (1.600 g), which was used for next step without further purification.

132

Synthesis of N-(3-(5-methoxy-2-(1-(2-methoxyethyl)-1H-indol-5-ylamino)pyrimidin-4-yloxy)phenyl)acrylamide (I-45a)

Compound 2 (1.001 g), compound 3 (1.624 g), $K_2CO_3$ (1.495 g), tris(dibenzylideneacetone)dipalladium (0.456 g), dicyclohexyl (2',4',6'-triisopropylbiphenyl-2-yl) phosphine (0.480 g) and t-BuOH (15 mL) were sequentially added to a flask. The reaction mixture was stirred at refluxing under $N_2$ flow. After 6 h, TLC (EtOAc/Petroleum ether/TEA=1:1: 0.1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound I-45a (1.5 g, 62.5%, M+H$^+$=460.5) as a white solid.

$^1$H NMR (500 MHz, DMSO) δ 10.37 (s, 1H), 9.06 (s, 1H), 8.20 (s, 1H), 7.70-7.66 (m, 2H), 7.64 (d, J=8.2 Hz, 1H), 7.51-7.36 (m, 1H), 7.22-7.16 (m, 2H), 7.10 (dd, J=8.8, 1.9 Hz, 1H), 6.99 (ddd, J=8.1, 2.3, 0.7 Hz, 1H), 6.44 (dd, J=17.0, 10.1 Hz, 1H), 6.27 (dd, J=17.0, 1.9 Hz, 1H), 6.11 (d, J=2.9 Hz, 1H), 5.77 (dd, J=10.1, 1.9 Hz, 1H), 4.21 (t, J=5.3 Hz, 2H), 3.88 (s, 3H), 3.59 (t, J=5.4 Hz, 2H), 3.19 (s, 3H).

$^{13}$C NMR (126 MHz, DMSO) δ 165.36 (s), 161.45 (s), 156.17 (s), 154.90 (s), 146.13 (s), 142.38 (s), 136.38 (s), 134.91 (s), 133.62 (d, J=14.8 Hz), 131.92 (s), 130.87 (s), 129.95 (s), 129.31 (s), 118.93 (s), 118.06 (s), 116.55 (s), 114.68 (s), 111.23 (s), 111.10 (d, J=27.6 Hz), 102.25 (s), 73.05 (s), 60.05 (s), 59.67 (s), 47.31 (s).

Example 45

Synthesis of N-(3-(2-(6-((2-methoxyethyl)(methyl)amino)pyridin-3-ylamino)-7H-pyrrolo[2,3-d]pyrimidin-4-yloxy)phenyl)acrylamide (I-46a)

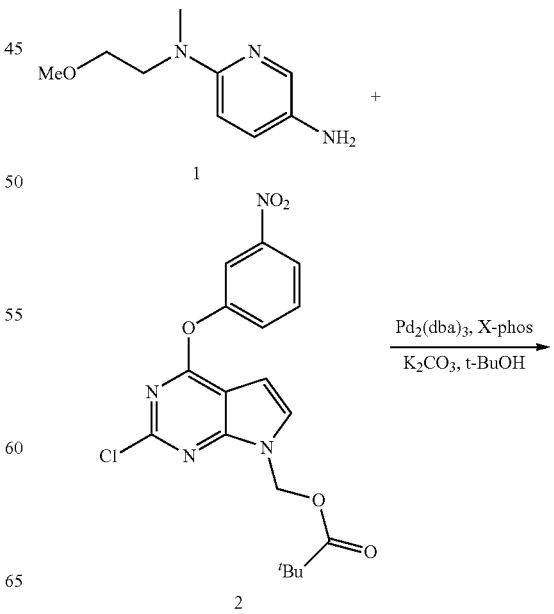

-continued

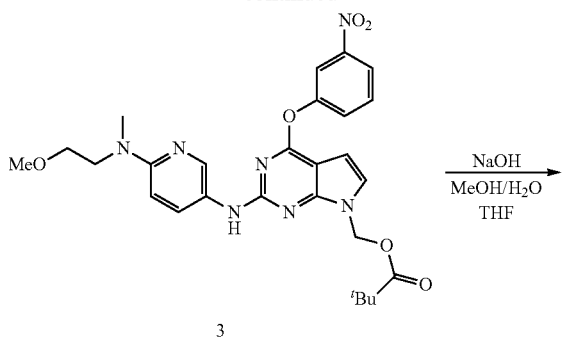

3

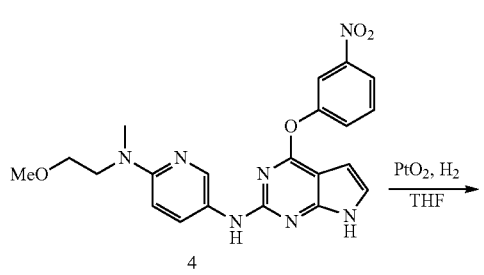

4

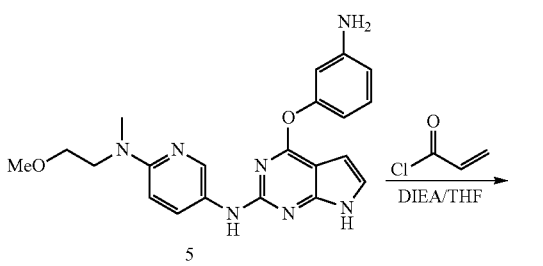

5

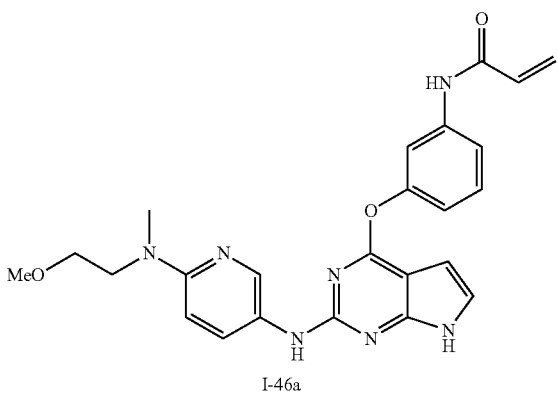 [SMILES: C=CC(=O)Nc1cccc(Oc2nc(Nc3ccc(N(C)CCOC)nc3)nc3[nH]ccc23)c1]

I-46a

Synthesis of (2-(6-((2-methoxyethyl)(methyl)amino)pyridin-3-ylamino)-4-(3-nitrophenoxy)-7H-pyrrolo[2,3-d]pyrimidin-7-yl)methyl pivalate (3)

Compound 1 (3.1 g), compound 2 (10.0 g), $K_2CO_3$ (5.2 g), tris(dibenzylideneacetone)dipalladium (1.2 g), dicyclohexyl (2',4',6'-triisopropylbiphenyl-2-yl) phosphine (1.2 g) and t-BuOH (100 mL) were sequentially added to a flask. The reaction mixture was stirred at refluxing under $N_2$ flow. After 3.5 h, TLC (DCM/MeOH=10/1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound 3 (6.875 g, 62.5).

Synthesis of $N^2$-(2-methoxyethyl)-$N^2$-methyl-$N^5$-(4-(3-nitrophenoxy)-7H-pyrrolo[2,3-d]pyrimidin-2-yl)pyridine-2,5-diamine (4)

To a round-bottom flask (250 mL) was charged with compound 3 (6.857 g) and MeOH (120 mL). When compound 3 was completely dissolved, the solution was cooled with ice-bath to around 10° C. NaOH solution (2.5 M, 10 ml) was then added into the flask slowly, maintaining the temperature below 16° C. during the addition. The mixture was stirred for 1 h at this temperature followed by addition of THF (50 mL). After 1.5 h, water (100 mL) was added to the flask over 15 min, maintaining the temperature below 20° C. The mixture was extracted with ethyl acetate. The combined organic layers were concentrated under reduced pressure. Solvents (50 mL, ethyl acetate/petroleum ether=1:4) were added into this crude product, and stirred for 2 h. The resulting solid was filtered and dried to afford 4 (5.13 g), which was used for next step without further purification.

Synthesis of $N^5$-(4-(3-aminophenoxy)-7H-pyrrolo[2,3-d]pyrimidin-2-yl)-$N^2$-(2-methoxyethyl)-$N^2$-methylpyridine-2,5-diamine (5)

A mixture of 4 (5.13 g) and $PtO_2$ (117 mg) in THF (50 mL) was hydrogenated with hydrogen balloon at 40° C. overnight. At this point, TLC indicated the reaction to be complete. The reaction mixture was filtered through Celite® and washed with ethyl acetate. The combined filtrate was concentrated under reduced pressure to afford the crude compound 5 (4.69 g), which was used for next step without further purification.

Synthesis of N-(3-(2-(6-((2-methoxyethyl)(methyl)amino)pyridin-3-ylamino)-7H-pyrrolo[2,3-d]pyrimidin-4-yloxy)phenyl)acrylamide (I-46a)

To a solution of compound 5 (3.734 g) and DIEA (1.480 g) in THF (30 mL) at 0° C. was drop-wise added acryloyl chloride (1.133 g) over 5 min. The mixture was stirred for 1 at this temperature. Saturated $NaHCO_3$ aqueous (10 mL) was added in to quench the reaction. The resulting mixture was stirred for 10 min, and then extracted with ethyl acetate. Organic layers were combined and concentrated under reduced pressure. The resulting crude was purified by column chromatography to afford compound I-46a (1.2 g, 28.4%, M+H$^+$=460.5).

$^1$H NMR (500 MHz, DMSO) δ 11.48 (s, 1H), 10.31 (s, 1H), 8.73 (s, 1H), 8.28 (s, 1H), 7.72 (dd, J=9.0, 2.4 Hz, 1H), 7.63 (t, J=2.0 Hz, 1H), 7.58 (d, J=8.2 Hz, 1H), 7.41 (t, J=8.1 Hz, 1H), 7.03 (dd, J=3.4, 2.3 Hz, 1H), 6.99 (dd, J=8.1, 1.5 Hz, 1H), 6.43 (dd, J=16.9, 10.1 Hz, 2H), 6.27 (dd, J=17.0, 1.9 Hz, 1H), 6.22 (dd, J=3.4, 1.9 Hz, 1H), 5.82-5.75 (m, 1H), 3.62 (t, J=5.8 Hz, 2H), 3.46 (t, J=5.8 Hz, 2H), 3.24 (s, 3H), 2.95 (s, 3H).

Example 46

Synthesis of N-(3-(2-(4-(4-(2-methoxyethyl)piperazin-1-yl)phenylamino)-7H-pyrrolo[2,3-d]pyrimidin-4-yloxy)phenyl)acrylamide (I-47a)

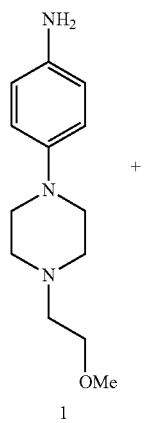

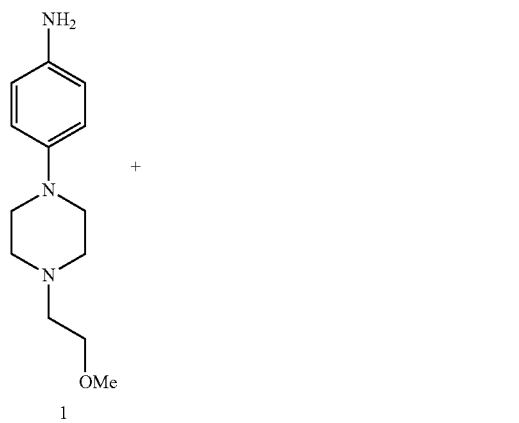

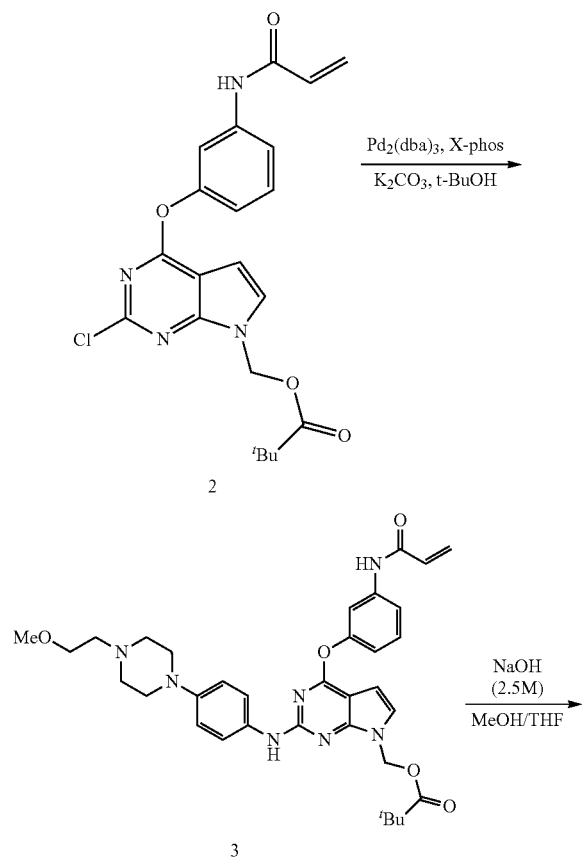

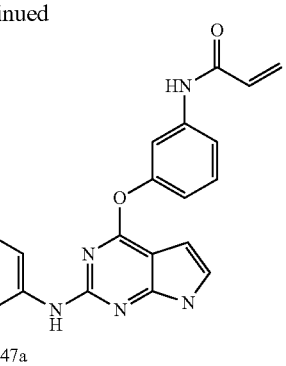

I-47a

Synthesis of (4-(3-acrylamidophenoxy)-2-(4-(4-(2-methoxyethyl)piperazin-1-yl)phenylamino)-7H-pyrrolo[2,3-d]pyrimidin-7-yl)methyl pivalate (3)

Compound 1 (2.445 g), compound 2 (4.325 g), $K_2CO_3$ (2.801 g), tris(dibenzylideneacetone)dipalladium (0.416 g), dicyclohexyl (2',4',6'-triisopropylbiphenyl-2-yl) phosphine (0.404 g) and t-BuOH (60 mL) were sequentially added to a flask. The reaction mixture was stirred at refluxing under $N_2$ flow. After 5 h, TLC (DCM/MeOH=10/1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound 3 (4.6 g, 72.7%).

Synthesis of N-(3-(2-(4-(4-(2-methoxyethyl)piperazin-1-yl)phenylamino)-7H-pyrrolo[2,3-d]pyrimidin-4-yloxy)phenyl)acrylamide (I-47a)

To a round-bottom flask (250 mL) was charged with compound 3 (4.5 g), MeOH (30 mL) and THF (30 mL). When compound 3 was completely dissolved, the solution was cooled down to around 10° C. with ice-bath. NaOH solution (2.5 M, 6 mL) was then added into the flask slowly, maintaining the temperature below 16° C. throughout the addition. The mixture was stirred for 1.5 h at this temperature. Then water (200 mL) was added to the flask over 15 min, maintaining the temperature below 20° C. The mixture was extracted with ethyl acetate (500 mL). the combined organic layers were separated, dried over $Na_2SO_4$ and concentrated under reduced pressure. The resulting crude was purified by column chromatography (EtOAc as mobile phase) to give I-47a (2.96 g, 80.4%, $M+H^+=514.6$) as a white solid.

Example 47

Synthesis of N-(3-(2-(3-fluoro-4-(4-(2-methoxyethyl)piperazin-1-yl)phenylamino)-7H-pyrrolo[2,3-d]pyrimidin-4-yloxy)phenyl)acrylamide (I-48a)

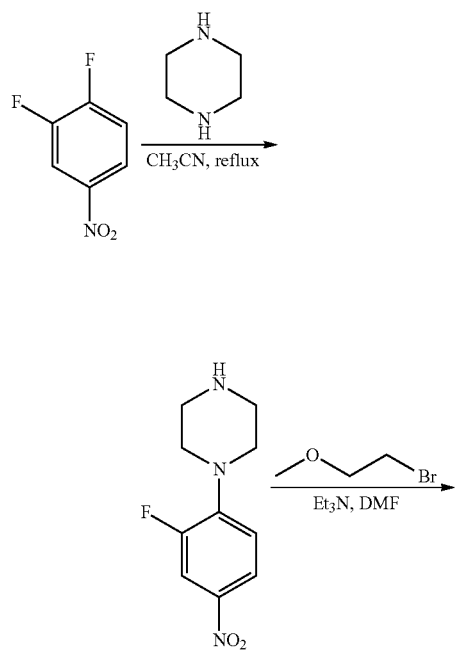

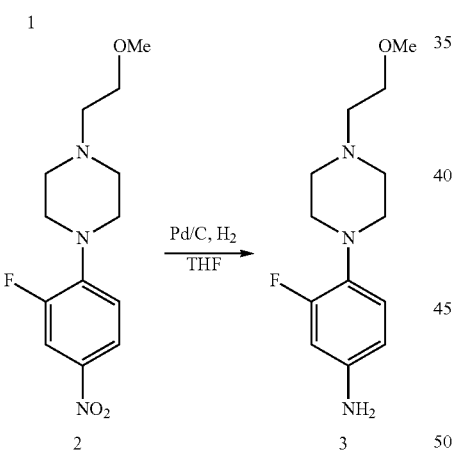

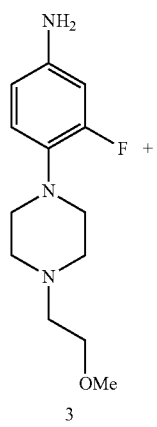

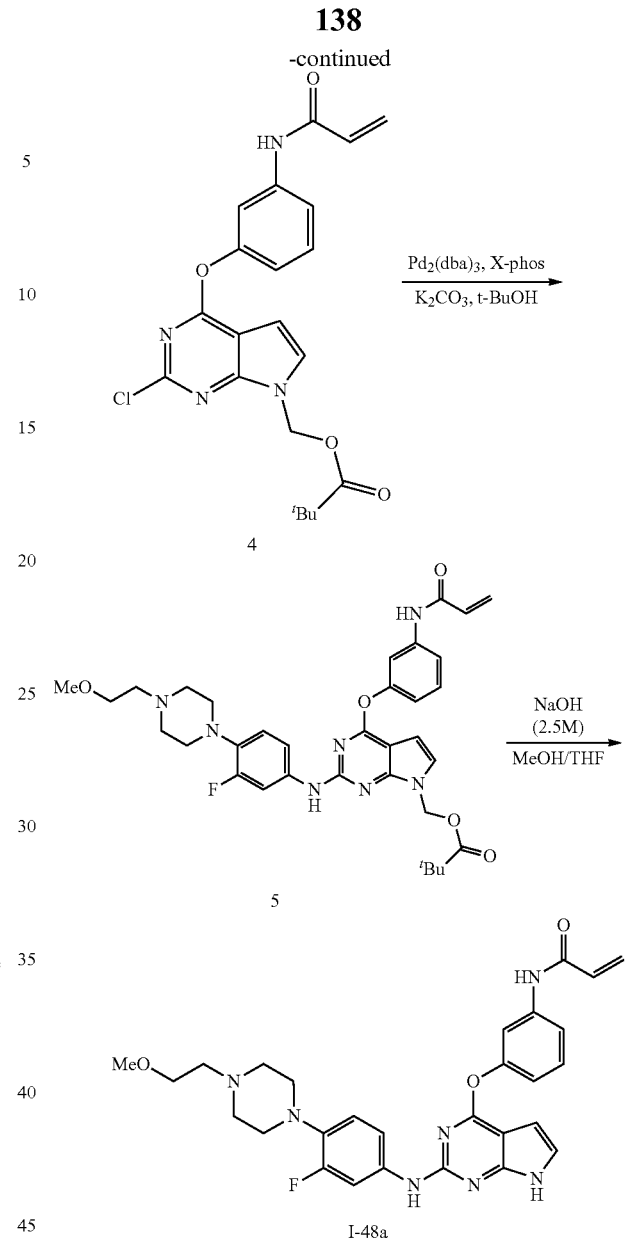

Synthesis of 1-(2-fluoro-4-nitrophenyl)piperazine (1)

A mixture of 1,2-difluoro-4-nitrobenzene (15.9 g), piperazine (10.39 g) and acetonitrile (100 mL) was stirred at refluxing for 7 h. TLC showed the reaction to be complete. After cooling, the mixture was basified with saturated $K_2CO_3$ aqueous solution (100 mL), and extracted with ethyl acetate. The combined organic layers was washed with water, dried over $Na_2SO_4$, and concentrated under reduced pressure. Solvents (40 mL, petroleum ether/ethyl acetate=1:1) were added in the clued and stirred overnight. The resulting precipitates was collected and dried to afford the desired product 1, (13.5 g) as a yellow solid.

Synthesis of 1-(2-fluoro-4-nitrophenyl)-4-(2-methoxyethyl)piperazine (2)

To a solution of 1-bromo-2-methoxyethane (8.7 g) and 1 (11.4 g) in DMF (100 mL) at room temperature was added $Et_3N$ (8.2 g). The mixture was stirred at 54° C., overnight.

The reaction mixture was poured onto ice-water (300 mL). The precipitate was collected and re-dissolved in ethyl acetate (200 mL). The organic layer was washed with brine and concentrated under reduced pressure to afford the desired compound 2 (14.0 g, 98%), which was used for next step without further purification.

Synthesis of 3-fluoro-4-(4-(2-methoxyethyl)piperazin-1-yl)aniline (3)

A mixture of 2 (7.0 g) and Pd/C (0.586 g, 10% activated on carbon) in THF (100 mL) was hydrogenated with hydrogen balloon at room temperature overnight. At this point, TLC indicated the reaction to be complete. The reaction mixture was filtered through Celite®. The filtrate was concentrated under reduced pressure to afford 3 (6.3 g), which was used for next step without further purification.

Synthesis of (4-(3-acrylamidophenoxy)-2-(3-fluoro-4-(4-(2-methoxyethyl)piperazin-1-yl)phenylamino)-7H-pyrrolo[2,3-d]pyrimidin-7-yl)methyl pivalate (5)

Compound 3 (1.051 g), compound 4 (1.806 g), $K_2CO_3$ (0.936 g), tris(dibenzylideneacetone)dipalladium (0.166 g), dicyclohexyl (2',4',6'-triisopropylbiphenyl-2-yl) phosphine (0.195 g) and t-BuOH (60 mL) were sequentially added to a flask. The reaction mixture was stirred at refluxing under $N_2$ flow. After 6 h, TLC (DCM/MeOH=10/1 as mobile phase) indicated the reaction to be complete. The mixture was allowed to cool down to 40~50° C., filtered through Celite®. The celite layer was washed with ethyl acetate (50 mL). The combined filtrate was concentrated under reduced pressure. The resulting crude was purified by column chromatography to afford compound 5 (2.316 g, 90.9%).

Synthesis of N-(3-(2-(3-fluoro-4-(4-(2-methoxyethyl)piperazin-1-yl)phenylamino)-7H-pyrrolo[2,3-d]pyrimidin-4-yloxy)phenyl)acrylamide (I-48a)

To a round-bottom flask (250 mL) was charged with compound 5 (2.3 g), MeOH (10 mL) and THF (10 mL). When compound 5 was completely dissolved, the solution was cooled down to around 10° C. with ice-bath. NaOH solution (2.5 M, 3.5 mL) was then added into the flask slowly, maintaining the temperature below 16° C. throughout the addition. The mixture was continuously stirred for another h at this temperature. Then water (40 mL) was added to the flask over 15 mm, maintaining the temperature below 20° C. The mixture was extracted with ethyl acetate (500 mL). The combined organic layers were separated, dried over $Na_2SO4$ and concentrated under reduced pressure. The resulting crude was purified by column chromatography to give I-48a (0.814 g, 42.5%, M+H$^+$=532.6).

$^1$H NMR (500 MHz, CDCl$_3$) δ 9.81 (s, 1H), 8.06 (s, 1H), 7.64 (s, 1H), 7.51-7.37 (m, 2H), 7.33 (t, J=8.0 Hz, 1H), 7.26 (s, 1H), 6.99 (d, J=7.3 Hz, 1H), 6.84 (d, J=8.0 Hz, 1H), 6.71 (t, J=9.1 Hz, 1H), 6.67 (s, 1H), 6.40 (d, J=16.8 Hz, 1H), 6.29-6.17 (m, 2H), 5.70 (d, J=10.2 Hz, 1H), 3.56 (dd, J=15.9, 11.0 Hz, 2H), 3.38 (s, 3H), 3.00 (s, 4H), 2.66 (d, J=4.7 Hz, 6H).

$^{13}$C NMR (126 MHz, CDCl$_3$) δ 171.28 (s), 163.75 (s), 162.68 (s), 156.59 (s), 155.11 (d, J=9.0 Hz), 154.65 (s), 153.45 (s), 138.98 (s), 135.62 (d, J=11.0 Hz), 134.26 (d, J=9.3 Hz), 130.98 (s), 129.75 (s), 128.04 (s), 120.68 (s), 119.07 (s), 117.96 (s), 116.88 (s), 114.53 (s), 114.08 (s), 107.60 (d, J=26.0 Hz), 99.56 (s), 99.39 (s), 69.91 (s), 58.91 (s), 57.96 (s), 53.63 (s), 50.69 (s).

Example 48

Synthesis of (S)—N-(3-(2-(4-((1-(2-methoxyethyl)pyrrolidin-3-yl)(methyl)amino)phenylamino)-7H-pyrrolo[2,3-d]pyrimidin-4-yloxy)phenyl)acrylamide (I-49a)

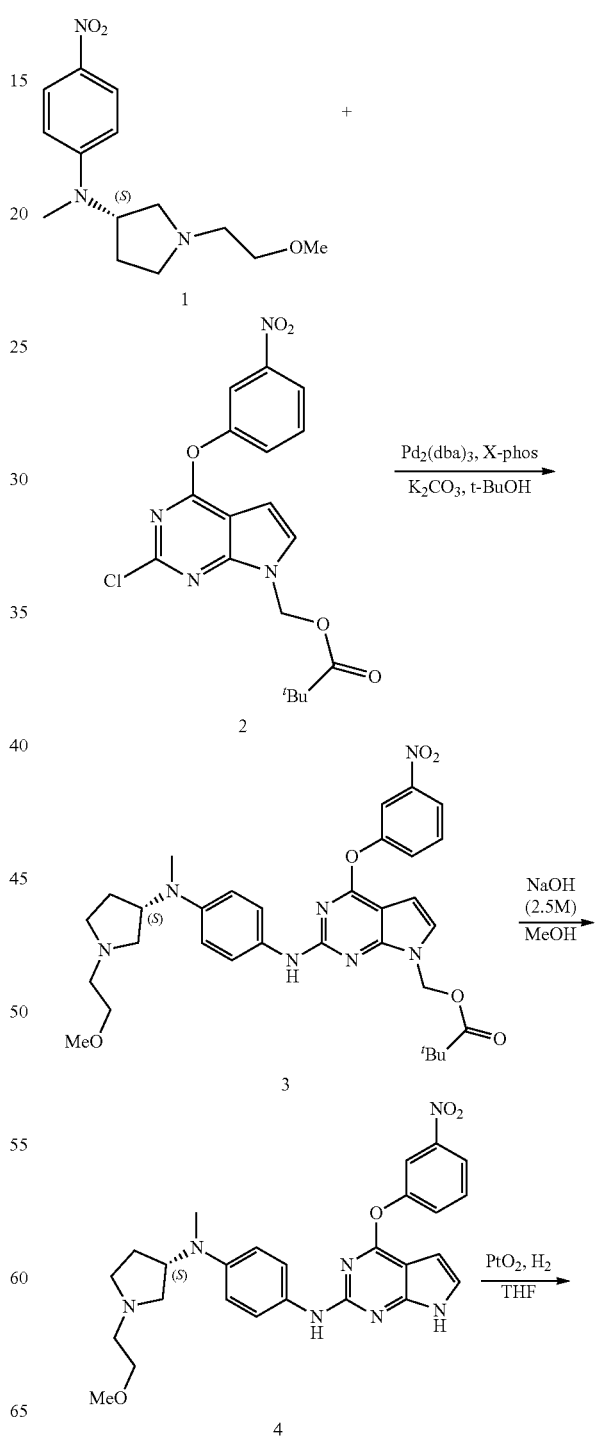

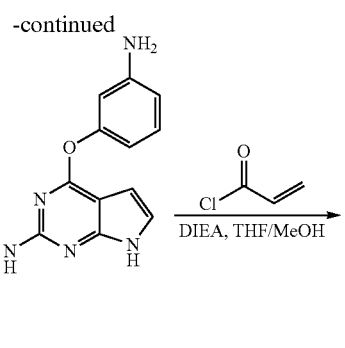

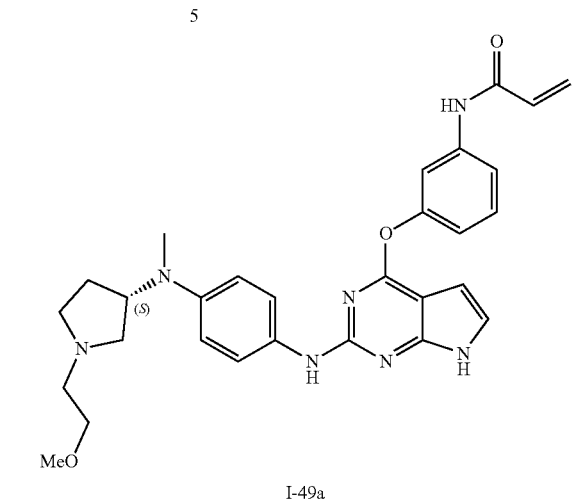

I-49a

Synthesis of (S)-(2-(4-((1-(2-methoxyethyl)pyrrolidin-3-yl)(methyl)amino)phenylamino)-4-(3-nitrophenoxy)-7H-pyrrolo[2,3-d]pyrimidin-7-yl)methyl pivalate (3)

Compound 1 (1.010 g), compound 2 (1.642 g), K$_2$CO$_3$ (1.262 g), tris(dibenzylideneacetone)dipalladium (0.371 g), dicyclohexyl (2',4',6'-triisopropylbiphenyl-2-yl) phosphine (0.367 g) and t-BuOH (15 mL) were sequentially added to a flask. The reaction mixture was stirred at refluxing under N$_2$ flow. After 22.5 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (30 mL). The combined filtrate was concentrated under reduced pressure. The resulting crude was further purified by column chromatography (Ethyl acetate/MeOH=20:1 as mobile phase) to afford compound 3 (1.74 g, 70.24%) as a brown oil.

Synthesis of (S)—N$^1$-(1-(2-methoxyethyl)pyrrolidin-3-yl)-N$^1$-methyl-N$^4$-(4-(3-nitrophenoxy)-7H-pyrrolo[2,3-d]pyrimidin-2-yl)benzene-1,4-diamine (4)

To a round-bottom flask (250 mL) was charged with compound 3 (1.74 g), THF (10 mL) and MeOH (20 mL). After compound 3 was completely dissolved, the solution was cooled to ~10° C. with ice-bath. NaOH solution (2.5 M, 3 mL) was then added into the flask slowly, maintaining the temperature below 16° C. during the addition. The mixture was stirred for 5.5 h at this temperature. Water (50 mL) was added slowly to the flask over 15 mm, maintaining the temperature below 20° C. during the addition. The mixture was extracted with ethyl acetate. The combined organic layers were concentrated under reduced pressure to afford compound 4 (1.2 g).

Synthesis of (S)—N$^1$-(4-(3-aminophenoxy)-7H-pyrrolo[2,3-d]pyrimidin-2-yl)-N$^4$-(1-(2-methoxyethyl)pyrrolidin-3-yl)-N$^4$-methylbenzene-1,4-diamine (5)

A mixture of 4 (1.2 g) and PtO$_2$ (33 mg) in THF (1.5 mL) was hydrogenated with hydrogen balloon at 50° C. for 40 h. TLC and LC-MS indicated that the reaction was not complete. The reaction mixture was filtered through Celite® and the filtrate was concentrated under reduced pressure. The resulting residue was treated with iron/NH$_4$Cl aq/EtOH system for 4 h. At this point. TLC and LC/MS indicated the reaction to be complete. The mixture was extracted with ethyl acetate. The combined organic layers were concentrated under reduced pressure to afford crude product 5 (1.1 g), which was used for next step without further purification.

Synthesis of (S)—N-(3-(2-(4-((1-(2-methoxyethyl)pyrrolidin-3-yl)(methyl)amino)phenylamino)-7H-pyrrolo[2,3-d]pyrimidin-4-yloxy)phenyl)acrylamide (I-49a)

To a solution of compound 5 (1.1 g) and DIEA (1.001 g) in THF/MeOH (4:1, 25 mL) at 0° C. was drop-wise added acryloyl chloride (0.462 g) over 5 min. The mixture was stirred for 1 h at this temperature. At this point, TLC and LC/MS indicated the reaction to be complete. Saturated Na$_2$CO$_3$ aqueous solution (50 mL) was added to quench the reaction. The resulting mixture was stirred for 10 mm, and extracted with ethyl acetate. The combined organic layers were combined and concentrated under reduced pressure. The resulting crude was further purified by column chromatography to give compound I-49a (0.7 g, 57.1%, M+H$^+$= 528.6).

Example 49

Synthesis of N-(3-(5-methoxy-2-(2-(2-methoxyethyl)isoindolin-5-ylamino)pyrimidin-4-yloxy)phenyl)acrylamide (I-50a)

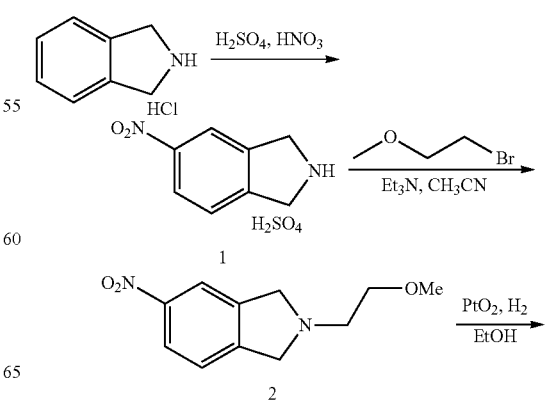

-continued

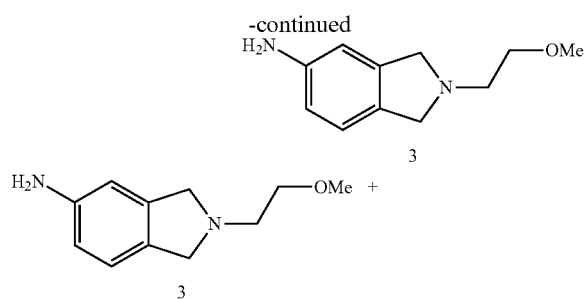

Synthesis of 2-(2-methoxyethyl)isoindolin-5-amine (3)

A mixture of 2 (650 mg) and PtO₂ (0.025 g) in THF (10 mL) was hydrogenated with hydrogen balloon at room temperature overnight. TLC indicated the reaction to be complete. The reaction mixture was filtered through Celite® and washed with ethyl acetate. The combined filtrates were concentrated under reduced pressure to afford the desired product 3 (0.50 g), which was used for next step without further purification.

Synthesis of N-(3-(5-methoxy-2-(2-(2-methoxyethyl)isoindolin-5-ylamino)pyrimidin-4-yloxy)phenyl)acrylamide (I-50a)

Compound 3 (0.5 g), compound 4 (0.8 g), K₂CO₃ (0.787 g), tris(dibenzylideneacetone)dipalladium (0.116 g), dicyclohexyl (2',4',6'-triisopropylbiphenyl-2-yl) phosphine (0.126 g) and t-BuOH (20 mL) were sequentially added to a flask. The reaction mixture was stirred at refluxing under N₂ flow. After 19 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound I-50a (0.512 g, 42.7%, M+H⁺=462.5).

Example 50

Synthesis of (S)—N-(3-(2-(4-(ethyl(1-(2-methoxyethyl)pyrrolidin-3-yl)amino)phenylamino)-5-methoxypyrimidin-4-yloxy)phenyl)acrylamide (I-51a)

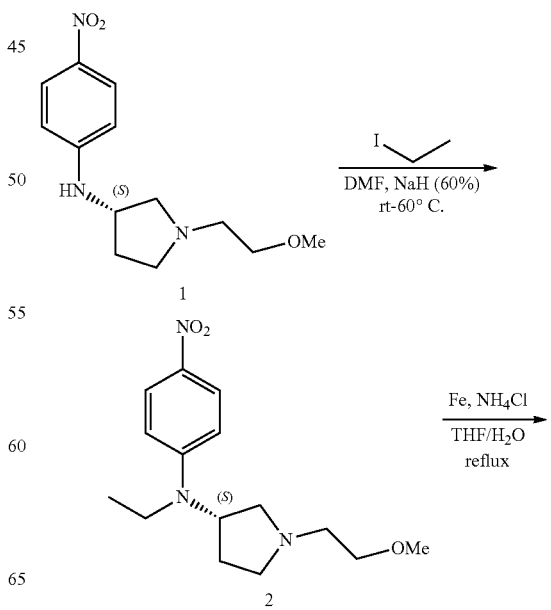

Synthesis of 5-nitroisoindoline (1)

To concentrated sulphuric acid (3 mL) at −10° C. was added isoindoline hydrochloride (1.569 g). The mixture was stirred at −10° C. for 15 mm Fuming nitric acid (3 mL) was added drop-wise. The resulting mixture was stirred for 35 mm at room temperature and then heated up and stirred at 50° C. for 35 mm After cooling to room temperature, the mixture was diluted with ethyl acetate (5 mL) and poured onto ice-water. The resulting precipitate was collected, washed with small amount of ethyl acetate and dried to afford 5-nitroisoindoline hydrosulfate 1 (1.644 g, 62.7%).

Synthesis of 2-(2-methoxyethyl)-5-nitroisoindoline (2)

To a solution of 1-bromo-2-methoxyethane (0.5 g) and 1 (0.5 g) in CH₃CN (15 mL) was added Et₃N (0.8 g). The mixture was then heated at 80° C. and stirred for 7 h. The reaction mixture was poured onto ice-water and extracted with ethyl acetate. The organic layer was washed with brine and concentrated under reduced pressure to afford the desired compound 2 (650 mg, 96%), which was used for next step without further purification.

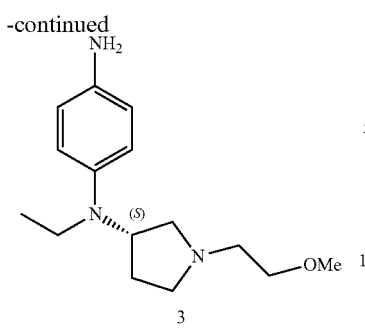

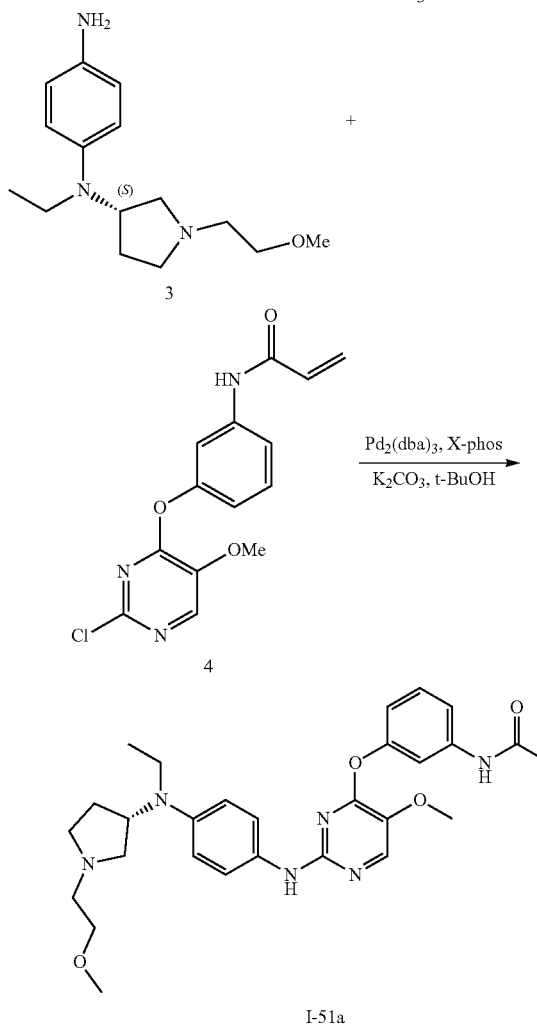

Synthesis of (S)—N-ethyl-1-(2-methoxyethyl)-N-(4-nitrophenyl)pyrrolidin-3-amine (2)

To a solution of 1 (1.969 g, 7.428 mmol) in DMF (10 ml) at 0° C. was sequentially added NaH (0.318 g, 80% dispersion in mineral oil, 13.25 mmol) and C₂H₅I (1.330 g, 8.52 mmol). The mixture was stirred at 60° C. for 3 h. The reaction mixture was quenched with water and extracted with ethyl acetate. The combined organic layers were washed with water, dried over Na₂SO₄, filtered and concentrated under reduced pressure. The resulting crude was further purified by column chromatography (ethyl acetate/petroleum ether from 33.3% to 100% as mobile phase) to give 2 (0.280 g, 0.9 mmol, 13%) as a yellow oil.

Synthesis of (S)—N$^1$-ethyl-N$^1$-(1-(2-methoxyethyl)pyrrolidin-3-yl)benzene-1,4-diamine (3)

To compound 2 (0.280 g, 0.9 mmol) in THF/H₂O (20 mL/3 mL) was added iron (0.280 g, 5 mmol) and NH₄Cl (0.535 g, 10 mmol). The mixture was stirred at refluxing for 2 h. At this point, TLC indicated the reaction to be complete. The mixture was filtered. The filtrate was diluted with ethyl acetate and washed with saturated NaHCO₃. The organic layer was dried over Na₂SO₄, filtered and concentrated under reduced pressure to afford desired compound 3 (0.191 g, 81%), which was used for next step without further purification.

Synthesis of (S)—N-(3-(2-(4-(ethyl(1-(2-methoxyethyl)pyrrolidin-3-yl)amino)phenylamino)-5-methoxypyrimidin-4-yloxy)phenyl)acrylamide (I-51a)

Compound 3 (0.191 g, 0.73 mmol), compound 4 (0.315 g, 1 mmol), K₂CO₃ (0.330 g, 2.5 mmol), tris(dibenzylideneacetone)dipalladium (0.096 g, 0.1 mmol), dicyclohexyl (2',4',6'-triisopropylbiphenyl-2-yl) phosphine (0.094 g, 0.2 mmol) and t-BuOH (20 mL) were sequentially added to the flask. The reaction mixture was stirred at refluxing under N₂ flow. After 5 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound I-51a (0.150 g, 32%, M+H⁺=433.6).

$^1$H NMR (500 MHz, CDCl₃) δ 8.33 (s, 1H), 7.96 (s, 1H), 7.66 (s, 1H), 7.47 (d, J=7.7 Hz, 1H), 7.33 (t, J=8.1 Hz, 1H), 7.16 (d, J=8.7 Hz, 2H), 7.01-6.91 (m, 2H), 6.69 (d, J=8.8 Hz, 2H), 6.41 (d, J=16.7 Hz, 1H), 6.28 (dd, J=16.8, 10.2 Hz, 1H), 5.71 (d, J=10.4 Hz, 1H), 4.21-4.00 (m, 1H), 3.93 (d, J=16.2 Hz, 3H), 3.51 (t, J=5.6 Hz, 2H), 3.37 (s, 3H), 3.20-3.11 (m, 2H), 2.85 (d, J=10.0 Hz, 1H), 2.79-2.67 (m, 2H), 2.67-2.52 (m, 2H), 2.43 (dd, J=9.0, 7.3 Hz, 1H), 2.17-2.01 (m, 1H), 1.80-1.63 (m, 1H), 0.99 (t, J=7.0 Hz, 3H).

$^{13}$C NMR (126 MHz, CDCl₃) δ 163.73 (s), 160.38 (s), 154.20 (s), 152.97 (s), 144.59 (s), 142.94 (s), 139.24 (s), 135.36 (s), 131.91 (s), 131.07 (s), 129.61 (s), 127.97 (s), 120.12 (s), 118.43 (s), 117.96 (s), 116.76 (s), 114.05 (s), 71.14 (s), 58.87 (s), 58.60 (s), 58.53 (s), 58.06 (s), 55.76 (s), 53.89 (s), 44.13 (s), 29.32 (s), 13.36 (s).

Example 51

Synthesis of N-(3-(5-methoxy-2-(1-(2-methoxyethyl)-2-oxoindolin-5-ylamino)pyrimidin-4-yloxy)phenyl)acrylamide (I-52a)

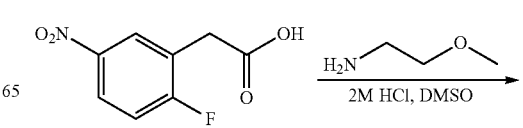

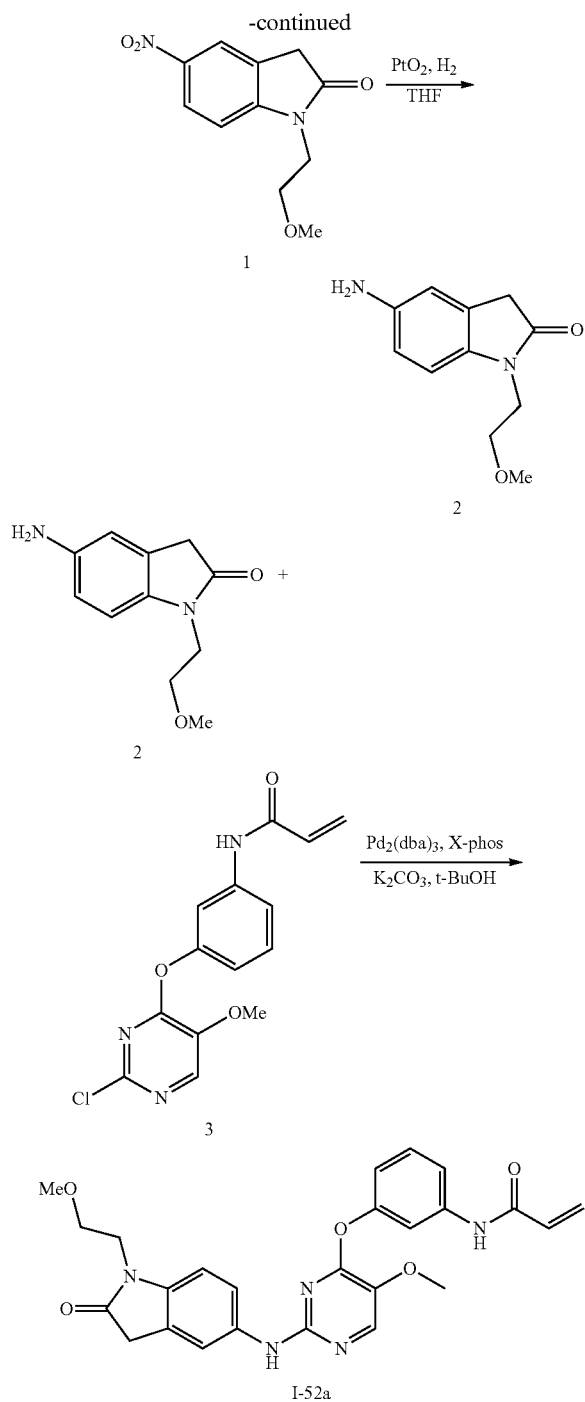

chromatography (DCM/petru=5/1 with drops of AcOH as mobile phase) to give 1 (0.720 g, yield 60.7%) as a yellow solid.

Synthesis of 5-amino-1-(2-methoxyethyl)indolin-2-one (2)

A mixture of 1 (0.401 g) and $PtO_2$ (0.019 g) in THF (15 mL) was hydrogenated with hydrogen balloon at room temperature overnight. After completion of the reaction, the reaction mixture was filtered through Celite®. The filtrate was concentrated under reduced pressure and the residue was re-dissolved with ethyl acetate. The solution was washed with water. The aqueous layer was separated and extracted with ethyl acetate (50 mL×3). The combined organic layers were dried over $Na_2SO_4$, filtered and concentrated under reduced pressure to afford the desired product 2 (0.345 g), which was used for next step without further purification.

Synthesis of N-(3-(5-methoxy-2-(1-(2-methoxyethyl)-2-oxoindolin-5-ylamino)pyrimidin-4-yloxy)phenyl)acrylamide (I-52a)

Compound 2 (0.360 g), compound 3 (0.650 g), $K_2CO_3$ (0.610 g), tris(dibenzylideneacetone)dipalladium (0.05 g), dicyclohexyl (2',4',6'-triisopropylbiphenyl-2-yl) phosphine (0.11 g) and t-BuOH (13 mL) were sequentially added to the flask. The reaction mixture was stirred at refluxing under $N_2$ flow. After 6 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound I-52a (0.47 g, 56.6%, M+H$^+$=476.5).

Example 52

Synthesis of (S)—N-(3-(2-(4-(cyclopropyl(1-(2-methoxyethyl)pyrrolidin-3-yl)amino)phenylamino)-5-methoxypyrimidin-4-yloxy)phenyl)acrylamide (I-53a)

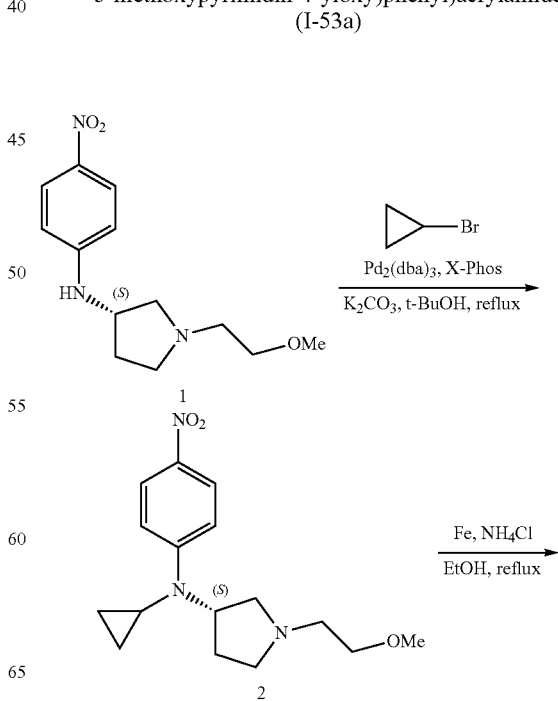

Synthesis of 1-(2-methoxyethyl)-5-nitroindolin-2-one (1)

A solution of 2-(2-fluoro-5-nitrophenyl) acetic acid (1.001 g) and 2-methoxyethanamine (1.892 g) in DMSO (5 nit) was stirred at 45° C. overnight. Excess 2-methoxyethanamine was removed under reduced pressure before HCl (2M, 3 mL) was added to the mixture. The mixture was stirred at 45° C. for 1 h. The reaction was quenched with water and extracted with ethyl acetate. The combined organic layers were dried over $Na_2SO_4$, filtered, and concentrated under reduced pressure. The residue was purified by column

149

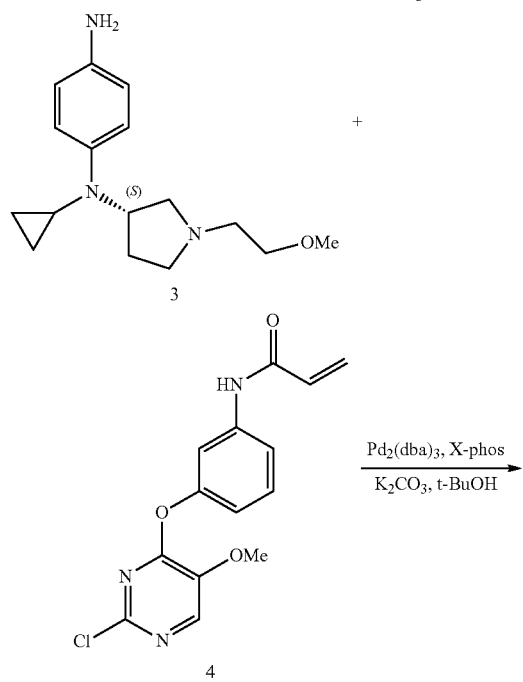

Synthesis of (S)—N-cyclopropyl-1-(2-methoxyethyl)-N-(4-nitrophenyl)pyrrolidin-3-amine (2)

A mixture of compound 1 (1.090 g), cyclopropyl bromide (1.825 g), Pd₂(dba)₃ (0.200 g), X-Phos (0.201 g) and potassium carbonate (2.032 g) in t-butanol (15 mL) was stirred under argon at refluxing overnight. After cooling to room temperature, the reaction mixture was filtered through Celite®, and washed with ethyl acetate. The combined filtrates were concentrated under reduced pressure. The residue was purified by flash column chromatography to afford the desired compound 2 (260 mg, 21.85%).

150

Synthesis of (S)—N¹-cyclopropyl-N¹-(1-(2-methoxyethyl)pyrrolidin-3-yl)benzene-1,4-diamine (3)

To compound 2 (260 ma) in EtOH/H₂O (5:2, 14 mL) was added iron (201 mg) and NH₄Cl (800 mg). The mixture was stirred at refluxing for 2 h. The reaction was filtered. The filtrate was diluted with ethyl acetate and washed with saturated NaHCO₃ aqueous solution. The organic layer was separated, dried over Na₂SO₄, and concentrated under reduced pressure to afford desired compound 3 (200 mg, 85.47%), which was used for next step without further purification.

Synthesis of (S)—N-(3-(2-(4-(cyclopropyl(1-(2-methoxyethyl)pyrrolidin-3-yl)amino)phenylamino)-5-methoxypyrimidin-4-yloxy)phenyl)acrylamide (I-53a)

Compound 3 (0.188 g), compound 4 (0.235 g), K₂CO₃ (0.250 g), tris(dibenzylideneacetone)dipalladium (0.076 g), dicyclohexyl (2',4',6'-triisopropylbiphenyl-2-yl) phosphine (0.085 g) and t-BuOH (10 mL) were sequentially added to the flask. The reaction mixture was stirred at refluxing under N₂ flow. After 5 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound I-53a (70 mg, 18.8%, M+H⁺=545.6).

Example 53

Synthesis of N-(3-(5-methoxy-2-(4-(4-(2-(methylsulfonyl)ethyl)piperazin-1-yl)phenylamino)pyrimidin-4-yloxy)phenyl)acrylamide (I-54a)

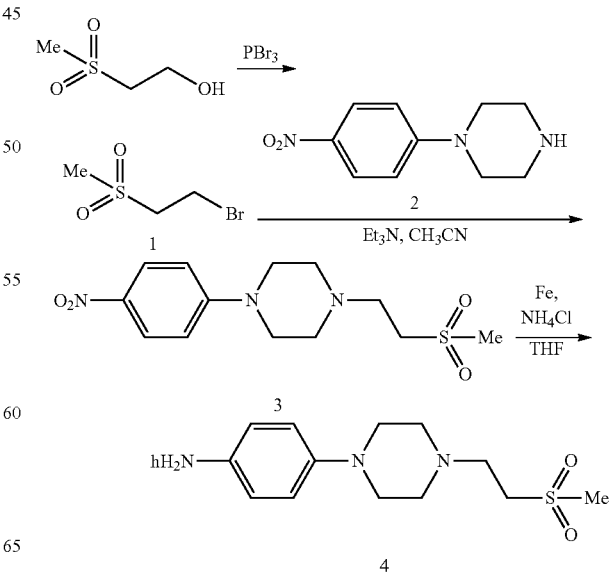

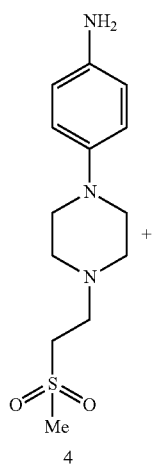

4

5

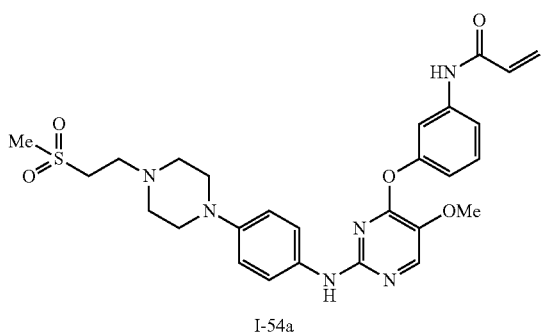 [SMILES: C=CC(=O)Nc1cccc(Oc2nc(Nc3ccc(N4CCN(CCS(C)(=O)=O)CC4)cc3)ncc2OC)c1]

I-54a

Synthesis of 1-bromo-2-(methylsulfonyl)ethane (1)

A solution of 2-(methylsulfonyl)ethanol (2.5 g) and pyridine (0.1 mL) in DCM (30 mL) at 0° C. was added PBr$_3$ (6.3 g). The mixture was warmed up and stirred at room temperature for 4 h. At this point, TLC indicated the reaction to be complete. The mixture was cooled to 0° C. and water was added to quench the reaction. The organic layer was separated, washed with saturated NaHCO$_3$ aqueous solution, dried over Na$_2$SO$_4$, and concentrated under reduced pressure to afford the crude product 1 (0.841 g, 22%), which was used for next step without further purification.

Synthesis of 1-(2-(methylsulfonyl)ethyl)-4-(4-nitrophenyl)piperazine (3)

To a solution of 1-bromo-2-(methylsulfonyl)ethane 1 (0.844 g) and 2 (1.212 g) in CH$_3$CN (20 mL) at room temperature was added Et$_3$N (1 mL). The mixture was then heated up and stirred at 70° C. overnight. Organic solvent was removed under reduced pressure. The residue was washed with ethyl acetate, THF and water. The resulting solid was collected and dried to afford the crude compound 3 (1 g, 85%), which was used for next step without further purification.

Synthesis of 4-(4-(2-(methylsulfonyl)ethyl)piperazin-1-yl)aniline (4)

A solution of 3 (1.2 g) in THF/H$_2$O (30 ml/5 ml) was treated with iron (2.1 g) and ammonium chloride (1.0 g). The mixture was stirred at refluxing for 2 h. The mixture was filtered through Celite® and washed with ethyl acetate (100 mL). The filtrate was washed with saturated aqueous NaHCO$_3$ solution and water and then dried over Na$_2$SO$_4$ and concentrated under reduced pressure to afford crude product 4 (0.380 g, 35%), which was used for next step without further purification.

Synthesis of N-(3-(5-methoxy-2-(4-(4-(2-(methylsulfonyl)ethyl)piperazin-1-yl)phenylamino)pyrimidin-4-yloxy)phenyl)acrylamide (I-54a)

Compound 4 (0.38 g), compound 5 (0.463 g), K$_2$CO$_3$ (0.440 g), tris(dibenzylideneacetone)dipalladium (0.913 g), dicyclohexyl (2',4',6'-triisopropylbiphenyl-2-yl) phosphine (0.860 g) and t-BuOH (10 mL) were sequentially added to the flask. The reaction mixture was stirred at refluxing under N$_2$ flow. After 5 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound I-54a (0.564 g, 74.1%, M+H$^+$=553.6).

Example 54

Synthesis of (S)—N-(3-(5-methoxy-2-(2-methoxy-4-((1-(2-methoxyethyl)pyrrolidin-3-yl)(methyl)amino)phenylamino)pyrimidin-4-yloxy)phenyl)acrylamide (I-55a)

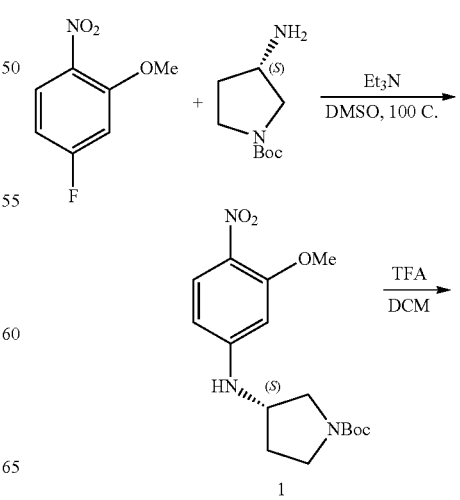

1

153

-continued

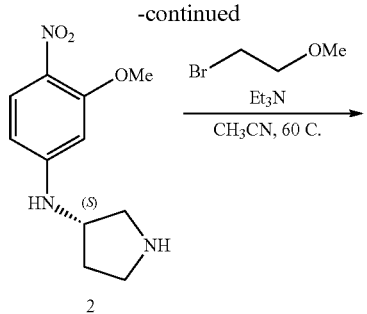

2

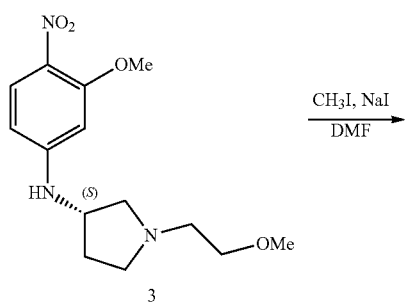

3

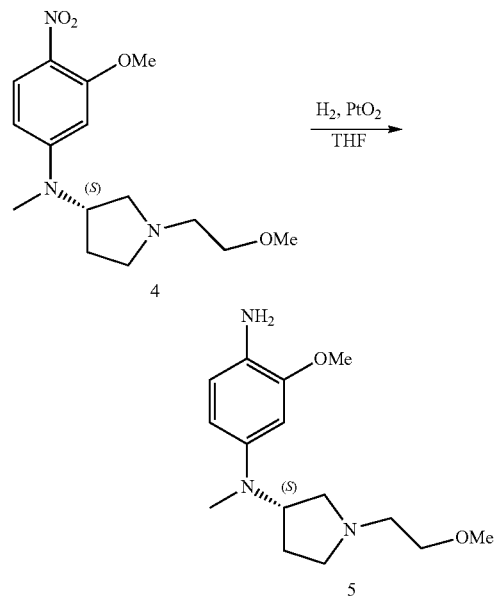

4

5

154

-continued

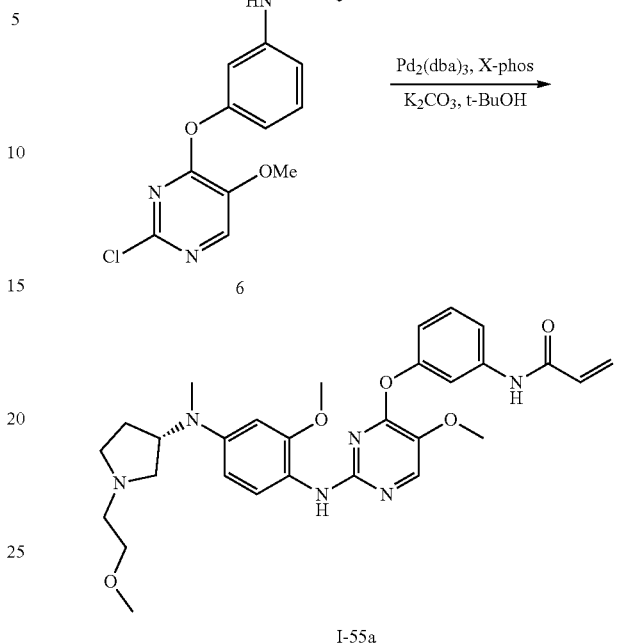

I-55a

Synthesis of (S)-tert-butyl 3-(3-methoxy-4-nitrophenylamino)pyrrolidine-1-carboxylate (1)

Into a 3-Neck round-bottom flask (250 mL) equipped with a refluxing condenser was charged 4-fluoro-2-methoxy-1-nitrobenzene (4.594 g) and (3S)-(−)-1-(t-Butoxycarbonyl)-3-aminopyrrolidine (5.0 g), TEA (3.030 g) in DMSO (50 mL). The reaction was heated up and stirred at 80° C. overnight. After TLC indicated the reaction to be complete, the reaction mixture was quenched with water and stirred for 0.5 h at room temperature. The resulting precipitation was filtered and dried to afford the crude compound 1 (10.0 g) which was used for next step without further purification.

Synthesis of (S)—N-(3-methoxy-4-nitrophenyl)pyrrolidin-3-amine (2)

To the crude compound 1 (10.0 g) in DCM (25 mL) was added TEA (10 mL). The reaction mixture was stirred at room temperature overnight. After TLC indicated that the reaction to be complete, the reaction mixture was concentrated under reduced pressure (to remove most of TFA). The residue was diluted with ethyl acetate and basified by addition of saturated NaHCO₃ (aq) at 0° C. The organic layer was separated, washed with brine, dried over Na₂SO₄, and concentrated under reduced pressure to afford the crude compound 2 (12 g), which was used for next step without further purification.

Synthesis of (S)—N-(3-methoxy-4-nitrophenyl)-1-(2-methoxyethyl)pyrrolidin-3-amine (3)

To a solution of 2-bromoethyl methyl ether (4.500 g) and 2 (3.512 g) in CH₃CN (100 mL) at room temperature was added Et₃N (6.0 g). The mixture was heated up and stirred at refluxing for 2.5 h. The reaction mixture was concentrated

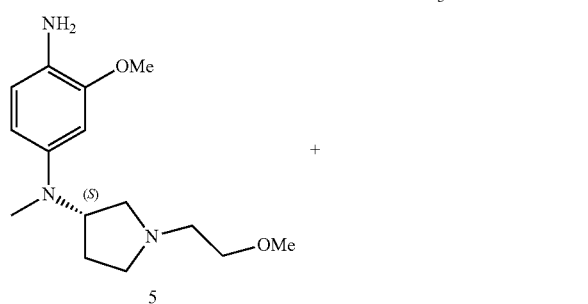

under reduced pressure. The residue was re-dissolved in ethyl acetate (200 mL) and the resulting solution was washed with water. The aqueous layer was separated and extracted with ethyl acetate. The organic layers were combined, dried over $Na_2SO_4$, and concentrated under reduced pressure. The crude material was washed with solvents (petroleum ether/ethyl acetate=2:1) to afford the desired compound 3 (8.59 g, 57.5%).

(S)—N-(3-methoxy-4-nitrophenyl)-1-(2-methoxyethyl)-N-methylpyrrolidin-3-amine (4)

To a solution of compound 3 (8.590 g) in DMF (5 mL) at 0° C. was sequentially added NaH (1.1 g, 80% dispersion in mineral oil) and $CH_3I$ (5.55 g). The resulting mixture was then stirred for 0.5 h. The reaction mixture was quenched with water and extracted with ethyl acetate. The combined organic layers were washed with water, dried over $Na_2SO_4$, and concentrated under reduced pressure. The crude material 4 (3.80 g, 42.2%) was used directly in next step without further purification.

Synthesis of (S)-3-methoxy-$N^1$-(1-(2-methoxyethyl)pyrrolidin-3-yl)-$N^1$-methylbenzene-1,4-diamine (5)

A mixture of 4 (3.8 g) and $PtO_2$ (0.130 g) in THF (30 hit) was hydrogenated with hydrogen balloon at room temperature overnight. Once the reaction was complete by TLC, the reaction mixture was filtered through Celite®. The filtrate was concentrated under reduced pressure. The residue was purified by column chromatography (ethyl acetate/EtOH=8/2, with 0.5% TEA as mobile phase) to afford the desired compound 5 (2.323 g, 67.7%).

Synthesis of (S)—N-(3-(5-methoxy-2-(2-methoxy-4-((1-(2-methoxyethyl)pyrrolidin-3-yl)(methyl)amino)phenylamino)pyrimidin-4-yloxy)phenyl)acrylamide (I-55a)

Compound 5 (2.323 g), compound 6 (3.036 g), $K_2CO_3$ (2.289 g), tris(dibenzylideneacetone)dipalladium (0.380 g), dicyclohexyl (2',4',6'-triisopropylbiphenyl-2-yl) phosphine (0.380 g) and t-BuOH (40 mL) were sequentially added to the flask. The reaction mixture was stirred at refluxing under $N_2$ flow. After 5 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound I-55a (2.845 g, 62.4%, M+H$^+$=549.6).

Example 55

Synthesis of N-(3-(2-(1-acetylindolin-5-ylamino)-5-methoxypyrimidin-4-yloxy)phenyl)acrylamide (I-56a)

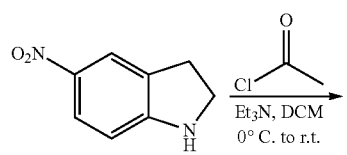

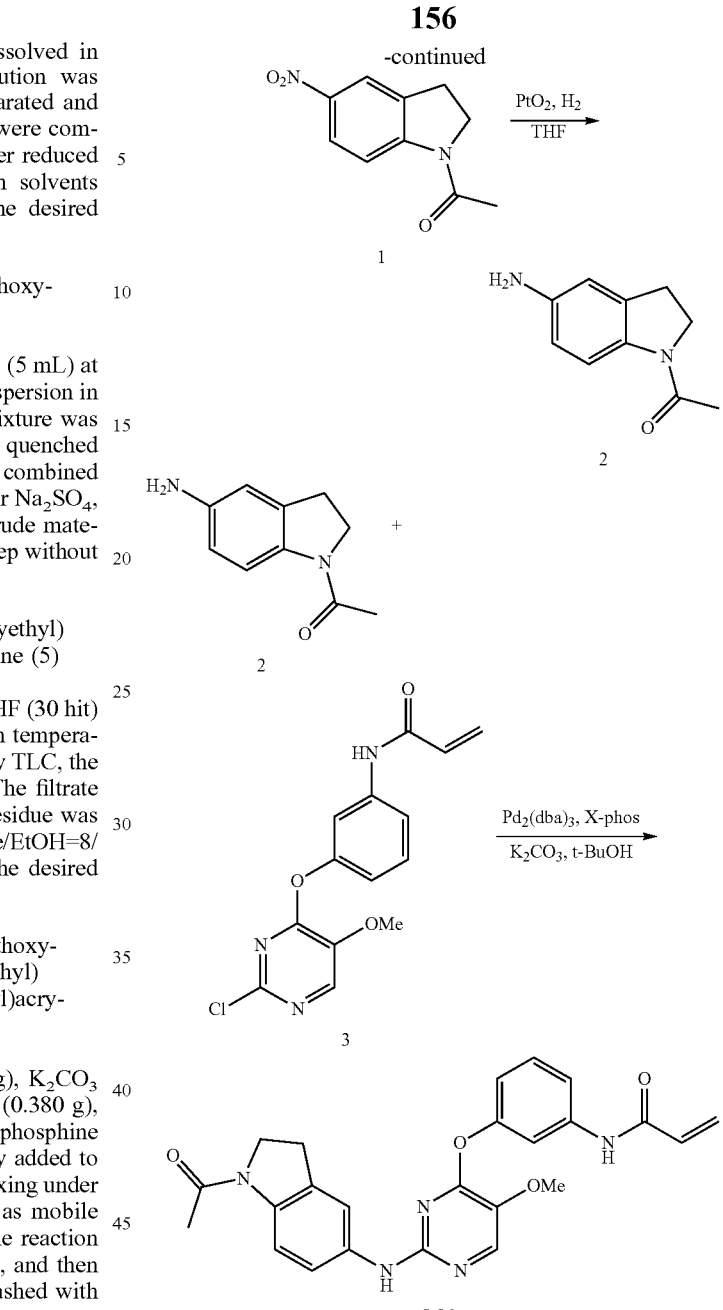

Synthesis of 1-(5-nitroindolin-1-yl)ethanone (1)

A solution of 5-nitroindoline (1.010 g, 6.159 mmol), TEA (0.810 g, 8.020 mmol) in DCM (30 mL) at 0° C. was slowly added acetyl chloride (0.610 g, 7.82 mmol). The mixture was warmed up and stirred at room temperature for 0.5 h. The reaction was quenched with water (30 mL) and extracted with DCM (25 mL×4). The organic layers were combined, dried and concentrated under reduced pressure to afford crude 1 (1.015 g, 4.927 mmol, 85%), which was used foe next step without further purification.

Synthesis of 1-(5-aminoindolin-1-yl)ethanone (2)

A mixture of 1 (1.015 g, 4.927 mmol) and $PtO_2$ (0.028 g, 0.14 mmol) in THF (30 mL) was hydrogenated with hydrogen balloon at room temperature overnight. Once the reaction was complete indicated by TLC, the reaction mixture was filtered through Celite®. The filtrate was concentrated under reduced pressure to afford the desired product 2 (0.798 g, 92%), which was used for next step without further purification.

Synthesis of N-(3-(2-(1-acetylindolin-5-ylamino)-5-methoxypyrimidin-4-yloxy)phenyl)acrylamide (I-56a)

Compound 2 (0.798 g, 4.531 mmol), compound 3 (1.956 g, 6.774 mmol), $K_2CO_3$ (1.553 g, 11 mmol), tris(dibenzylideneacetone)dipalladium (0.313 g, 0.34 mmol), dicyclohexyl (2',4',6'-triisopropylbiphenyl-2-yl) phosphine (0.360 g, 0.68 mmol) and t-BuOH (40 mL) were sequentially added to the flask. The reaction mixture was stirred at refluxing under $N_2$ flow. After 5 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound I-56a (1.71 g, 84.8%, M+H$^+$=446.6).

Example 56

Synthesis of (S)—N-(3-(5-methoxy-2-(4-(methyl(1-(2-(methylsulfonyl)ethyl)pyrrolidin-3-yl)amino)phenylamino)pyrimidin-4-yloxy)phenyl)acrylamide (I-57a)

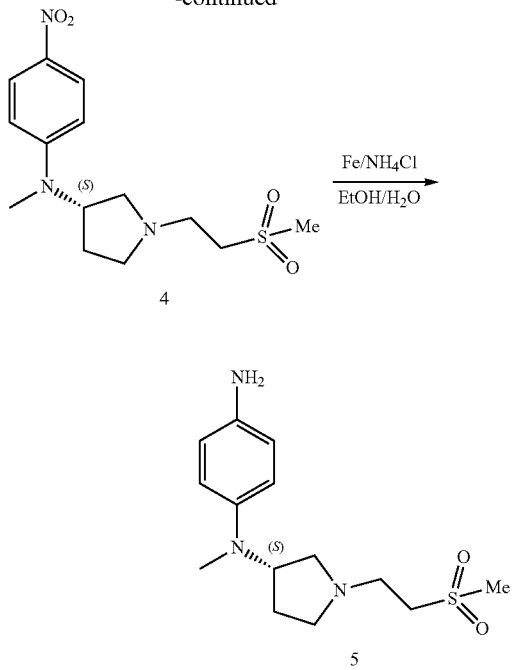

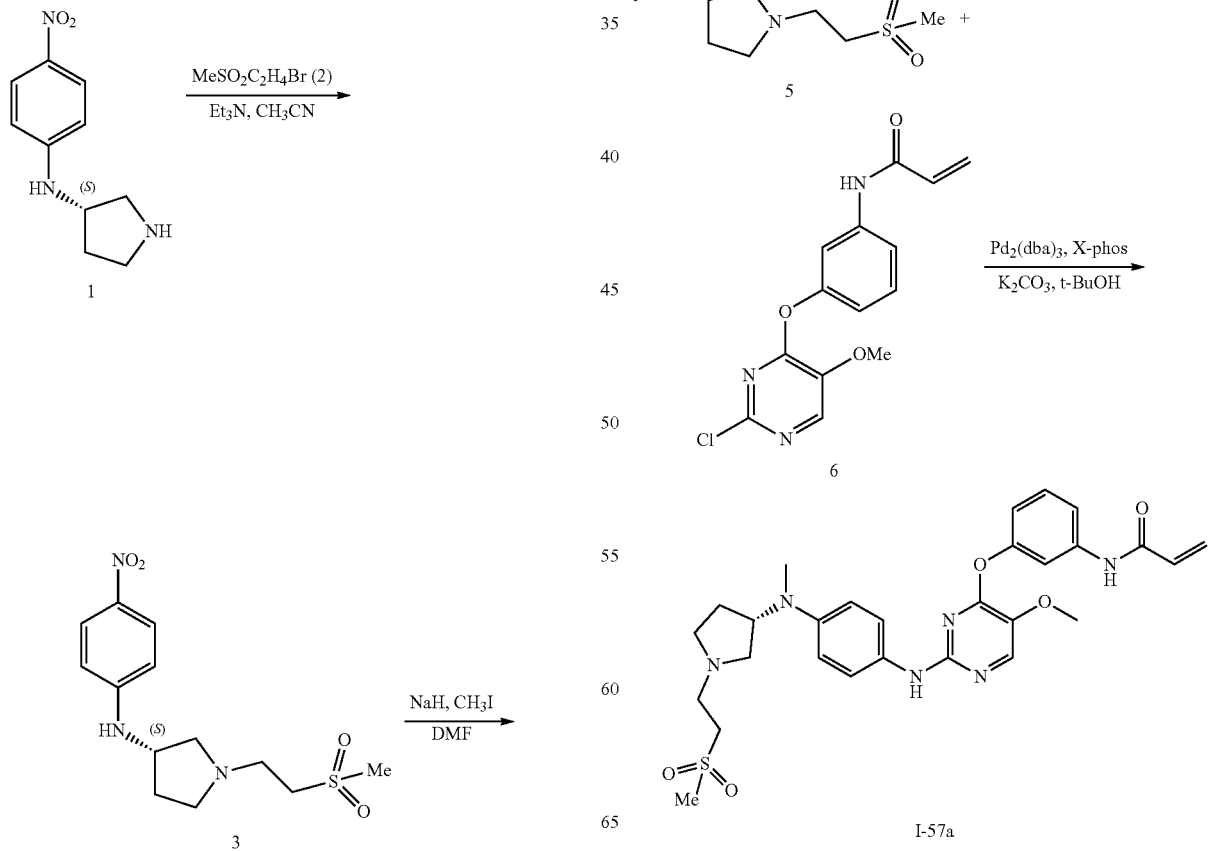

Synthesis of (S)-1-(2-(methylsulfonyl)ethyl)-N-(4-nitrophenyl)pyrrolidin-3-amine (3)

To a solution of 1-bromo-2-(methylsulfonyl)ethane (2, 3.824 g) and 1 (3.512 g) in CH₃CN (40 mL) at room temperature was added Et₃N (3.490 g). The mixture was heated up and stirred at refluxing for 5 h. The reaction mixture was then poured onto ice-water (150 mL). The resulting precipitate was collected, washed and dried to afford the desired compound 3 (3.484, 65.83%) as a yellow solid, which was used for next step without further purification.

(S)—N-methyl-1-(2-(methylsulfonyl)ethyl)-N-(4-nitrophenyl)pyrrolidin-3-amine (4)

To a solution of 3 (1.5 g) in DMF (10 mL) at 0° C. was sequentially added NaH (0.399 g, 80% dispersion in mineral oil) and CH₃I (0.924 g). The resulting mixture was then stirred for 1 h. The reaction mixture was quenched with water and extracted with ethyl acetate. The combined organic layers were washed with water, dried over Na₂SO₄, and concentrated under reduced pressure. The resulting crude material 4 (1.664 g) was used directly in the next step without further purification.

Synthesis of (S)—N¹-methyl-N¹-(1-(2-(methylsulfonyl)ethyl)pyrrolidin-3-yl)benzene-1,4-diamine (5)

A solution of 4 (1.664 g) in EtOH/H₂O (30 mL/1 mL) was treated with iron (1.143 g) and ammonium chloride (4.512 g). The mixture was stirred at refluxing for 2 h. The reaction was cooled to room temperature, and filtered through Celite®. The filtrate was extracted with ethyl acetate. The combined organic layers were washed with saturated aqueous K₂CO₃ solution, and concentrated under reduced pressure to afford crude product 5 (0.758 g, 50%), which was used for next step without further purification.

(S)—N-(3-(5-methoxy-2-(4-(methyl(1-(2-(methylsulfonyl)ethyl)pyrrolidin-3-yl)amino)phenylamino)pyrimidin-4-yloxy)phenyl)acrylamide (I-57a)

Compound 5 (0.654 g), compound 6 (0721 g), K₂CO₃ (0.702 g), tris(dibenzylideneacetone)dipalladium (0.182 g), dicyclohexyl (2',4',6'-triisopropylbiphenyl-2-yl) phosphine (0.191 g) and t-BuOH (30 ml) were sequentially added to the flask. The reaction mixture was stirred at refluxing under N₂ flow. After 4.5 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound I-57a (662 mg, 53.13%, M+H⁺=567.6).

Example 57

Synthesis of (S)—N-(3-(2-(4-((1-acetylpyrrolidin-3-yl)(methyl)amino)phenylamino)-5-methoxypyrimidin-4-yloxy)phenyl)acrylamide (I-58a)

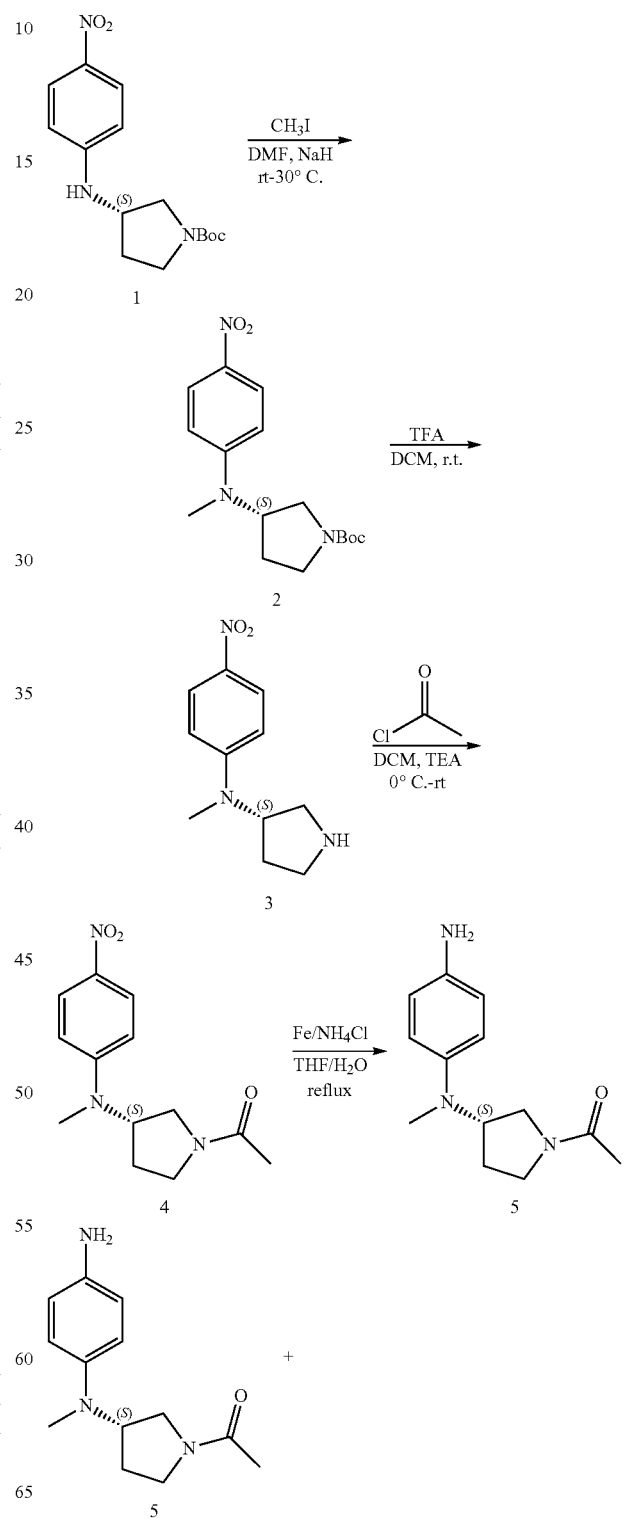

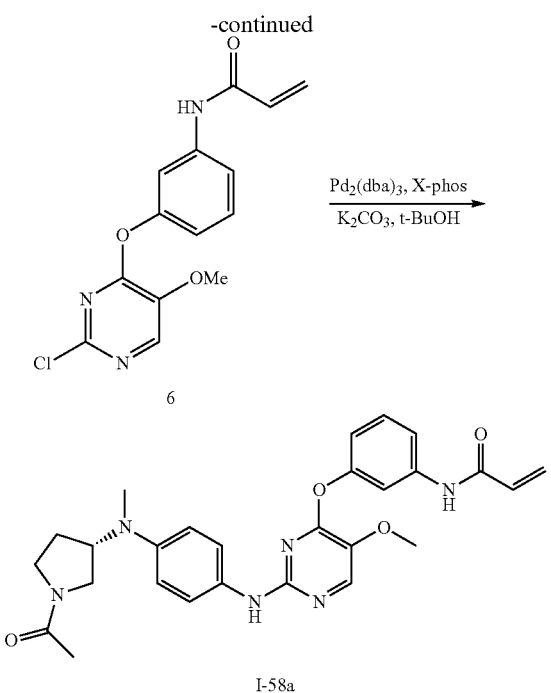

Synthesis of (S)-tert-butyl 3-(methyl(4-nitrophenyl) amino)pyrrolidine-1-carboxylate (2)

To a solution of (S)-tert-butyl 3-(4-nitrophenylamino) pyrrolidine-1-carboxylate (1, 0.995 g, 3.257 mmol) in DMF (5 mL) at 0° C. was sequentially added NaH (0.165 g, 80% dispersion in mineral oil) and CH₃I (0.705 g, 4.88 mmol). The resulting mixture was stirred for 0.5 h. The reaction mixture was quenched with water and extracted with ethyl acetate. The combined organic layers were washed with water, dried over Na₂SO₄, and concentrated under reduced pressure. The resulting crude material 2 (0.894 g, 2.931 mmol, 90%) was collected, washed, dried, and used directly in next step without further purification.

Synthesis of (S)—N-methyl-N-(4-nitrophenyl)pyrrolidin-3-amine (3)

To crude compound 2 (0.894 g, 2.931 mmol) in DCM (10 mL) was added TFA (2 mL). The reaction mixture was stirred at room temperature until TLC (petroleum ether/ethyl acetate=1/3 as mobile phase) indicated the reaction to be complete. The reaction mixture was concentrated under reduced pressure to remove most of TEA. The residue was basified with NaHCO₃ (aq, 30 mL) and extract with ethyl acetate (30 mL×4). The organic layers were combined, dried and concentrated under reduced pressure to afford crude 3 (0.504 g, 2.28 mmol, 78%), which was used in next step without further purification.

Synthesis of (S)-1-(3-(methyl(4-nitrophenyl)amino) pyrrolidin-1-yl)ethanone (4)

A solution of 3 (0.504 g, 2.28 mmol), TEA (0.303 g, 3 mmol) in DCM (20 mL) at 0° C. was slowly added acetyl chloride (0.610 g, 7.82 mmol). The mixture was warmed up and stirred at room temperature for 0.5 h. The reaction was quenched with water (30 mL) and extracted with DCM (25 mL×4). The organic layers were combined, dried and concentrated under reduced pressure to afford crude 4 (0.492 g, 1.87 mmol, 82%), which was used for next step without further purification.

Synthesis of (S)-1-(3-((4-aminophenyl)(methyl) amino)pyrrolidin-1-yl)ethanone (5)

A solution of 4 (0.320 g, 1.217 mmol) in THF/H₂O (20 mL/3 mL) was treated with iron (0.280 g, 5 mmol) and ammonium chloride (0.535 g, 10 mmol). The mixture was stirred at refluxing for 2 h. The reaction was filtered through Celite®. The filtrate was basified with NaHCO₃ (aq, 30 mL) and extracted with ethyl acetate (30 mL×4). The organic layers were combined, dried and concentrated under reduced pressure to afford crude product 5 (0.230 g, 1 mmol, 82%), which was used for next step without further purification.

Synthesis of (S)—N-(3-(2-(4-((1-acetylpyrrolidin-3-yl)(methyl)amino)phenylamino)-5-methoxypyrimidin-4-yloxy)phenyl)acrylamide (I-58a)

Compound 5 (0.230 g, 1 mmol), compound 6 (0.368 g, 1.217 mmol), K₂CO₃ (0.376 g, 2.5 mmol), tris(dibenzylideneacetone)dipalladium (0.058 g, 0.06 mmol), dicyclohexyl (2',4',6'-triisopropylbiphenyl-2-yl) phosphine (0.060 g, 0.12 mmol) and t-BuOH (20 mL) were sequentially added to the flask. The reaction mixture was stirred at refluxing under N₂ flow. After 4.5 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound I-58a (0.15 g, 30%, M+H⁺=503.6).

¹H NMR (500 MHz, DMSO) δ 10.35 (s, 1H), 8.99 (d, J=4.3 Hz, 1H), 8.16 (s, 1H), 7.67-7.56 (m, 2H), 7.49-7.37 (m, 1H), 7.28 (dd, J=9.0, 2.1 Hz, 2H), 6.95 (dd, J=8.0, 1.6 Hz, 1H), 6.65 (dd, J=9.1, 3.4 Hz, 2H), 6.44 (dd, J=16.9, 10.1 Hz, 1H), 6.27 (dd, J=17.0, 1.2 Hz, 1H), 5.77 (dd, J=10.1, 1.9 Hz, 1H), 4.24-3.99 (m, 1H), 3.87 (s, 3H), 3.63-3.46 (m, 2H), 3.33-3.07 (m, 2H), 2.63 (d, J=15.0 Hz, 3H), 1.93 (d, J=1.6 Hz, 3H), 2.06-1.80 (m, 2H).

¹³C NMR (126 MHz, DMSO) δ 168.77 (d, J=6.8 Hz), 163.80 (s), 159.89 (s), 154.25 (d, J=1.6 Hz), 153.24 (s), 145.45 (d, J=7.3 Hz), 144.39 (s), 140.70 (s), 135.05 (d, J=2.5 Hz), 133.41 (s), 133.13 (s), 132.07 (s), 130.33 (s), 127.75 (s), 119.79 (d, J=4.9 Hz), 117.23 (s), 116.62 (d, J=5.8 Hz), 113.41 (s), 59.72 (s), 58.58 (s), 58.07 (s), 48.76 (s), 47.70 (s), 45.94 (s), 44.16 (s), 35.59 (s), 34.90 (s), 29.04 (s), 27.37 (s), 22.73 (s), 22.19 (s).

Example 58

Synthesis of N-(3-(5-methoxy-2-(1-(methylsulfonyl) indolin-5-ylamino)pyrimidin-4-yloxy)phenyl)acrylamide (I-59a)

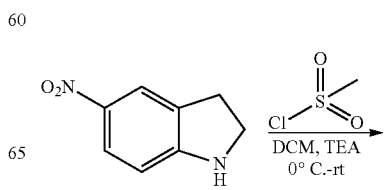

163

-continued

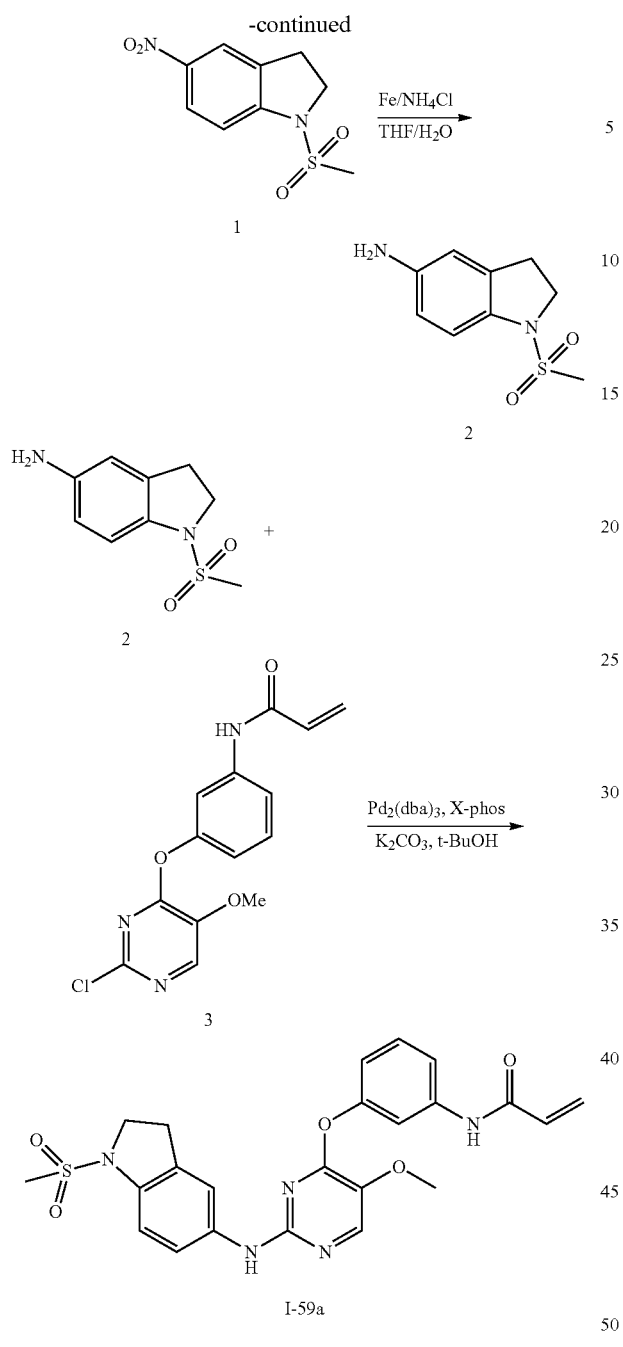

Synthesis of 1-(methylsulfonyl)-5-nitroindoline (1)

A solution of 5-nitroindoline (1.033 g, 6.30 mmol), TEA (0.827 g, 8.19 mmol) in DCM (30 mL) at 0° C. was slowly added methylsufonyl chloride (0.868 g, 7.56 mmol). The mixture was warmed up and stirred at room temperature for 0.5 h. The reaction was quenched with water (30 mL) and extracted with DCM (25 mL×4). The organic layers were combined, dried and concentrated under reduced pressure to afford crude 1 (1.427 g, 5.9 mmol, yield 95%), which was used for next step without further purification.

Synthesis of 1-(methylsulfonyl)indolin-5-amine (2)

A solution of 1 (1.427 g, 5.9 mmol) in THF/H$_2$O (20 mL/3 mL) was treated with iron (1.372 g, 24.5 mmol) and ammo-

164 nium chloride (2.621 g, 49 mmol). The mixture was stirred at refluxing for 2 h. The reaction was filtered through Celite®. The filtrate was basified with NaHCO$_3$ (aq, 30 mL) and extracted with ethyl acetate (30 mL×4). The organic layers were combined, dried and concentrated under reduced pressure to provide crude product 2 (0.742 g, 3.5 mmol, 59.3%), which was used for next step without further purification.

Synthesis of N-(3-(5-methoxy-2-(1-(methylsulfonyl)indolin-5-ylamino)pyrimidin-4-yloxy)phenyl)acrylamide (I-59a)

Compound 2 (0.420 g, 2 mmol), compound 3 (0.660 g, 2.3 mmol), K$_2$CO$_3$ (0.494 g, 3 mmol), tris(dibenzylideneacetone)dipalladium (0.093 g, 0.1 mmol), dicyclohexyl (2',4',6'-triisopropylbiphenyl-2-yl) phosphine (0.115 g, 0.22 mmol) and t-BuOH (20 mL) were sequentially added to the flask. The reaction mixture was stirred at refluxing under N$_2$ flow. After 5 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound I-59a (0.24 g, 25%, M+H$^+$=482.5).

Example 59

Synthesis of (S)—N-(3-(5-methoxy-2-(4-(methyl(1-(methylsulfonyl)pyrrolidin-3-yl)amino)phenylamino)pyrimidin-4-yloxy)phenyl)acrylamide (I-60a)

-continued

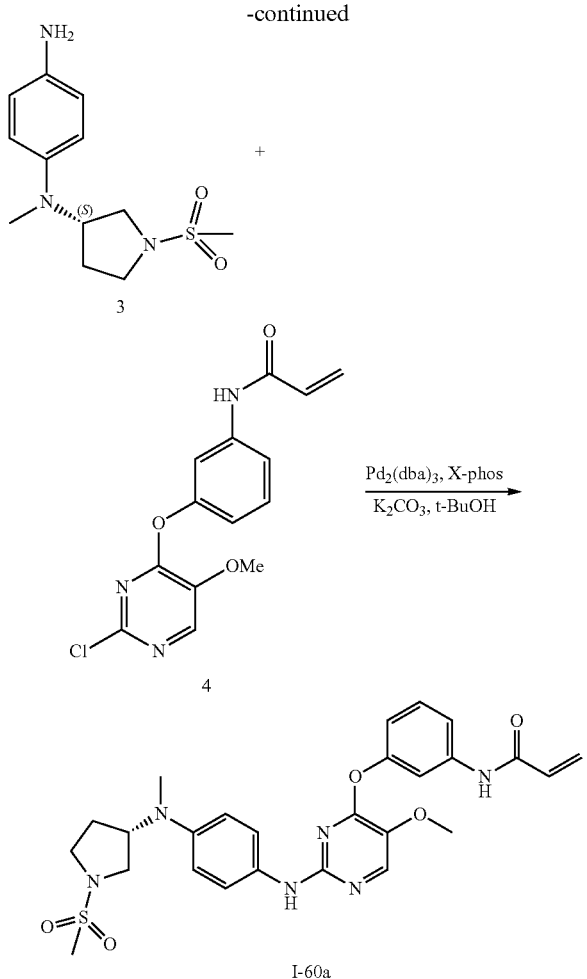

Synthesis of (S)—N-methyl-1-(methylsulfonyl)-N-(4-nitrophenyl)pyrrolidin-3-amine (2)

A solution of 1 (0.504 g, 3 mmol), TEA (0.404 g, 4 mmol) in DCM (20 mL) at 0° C. was slowly added methylsufonyl chloride (0.402 g, 3.5 mmol). The mixture was warmed up and stirred at room temperature for 0.5 h. The reaction was quenched with water (30 mL) and extracted with DCM (25 mL×4). The organic layers were combined, dried and concentrated under reduced pressure to afford crude 2 (0.762 g, 2.55 mmol, yield 85%), which was used for next step without further purification.

(S)—N¹-methyl-N¹-(1-(methylsulfonyl)pyrrolidin-3-yl)benzene-1,4-diamine (3)

A solution of 2 (0.762 g, 2.55 mmol) in THF/H$_2$O (20 mL/3 mL) was treated with iron (0.560 g, 10 mmol) and ammonium chloride (1.070 g, 20 mmol). The mixture was stirred at refluxing for 2 h. The reaction mixture was filtered through Celite®. The filtrate was basified with NaHCO$_3$ (aq, 30 mL) and extracted with ethyl acetate (30 mL×4). The organic layers were combined, dried and concentrated under reduced pressure to provide crude product 3 (0.511 g, 1.9 mmol, 75%), which was used for next step without further purification.

Synthesis of (S)—N-(3-(5-methoxy-2-(4-(methyl(1-(methylsulfonyl)pyrrolidin-3-yl)amino)phenylamino)pyrimidin-4-yloxy)phenyl)acrylamide (I-60a)

Compound 3 (0.340 g, 1.5 mmol), compound 4 (0.550 g, 1.8 mmol), K$_2$CO$_3$ (0.414 g, 3 mmol), tris(dibenzylideneacetone)dipalladium (0.137 g, 0.15 mmol), dicyclohexyl (2',4',6'-triisopropylbiphenyl-2-yl) phosphine (0.143 g, 0.3 mmol) and t-BuOH (20 mL) were sequentially added to the flask. The reaction mixture was stirred at refluxing under N$_2$ flow. After 5 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound I-60a (0.33 g, 41%, M+H$^+$=539.6).

$^1$H NMR (500 MHz, CDCl$_3$) δ 8.48 (s, 1H), 7.94 (s, 1H), 7.67 (s, 1H), 7.48 (d, J=7.8 Hz, 1H), 7.33 (t, J=8.1 Hz, 1H), 7.22 (s, J=14.5 Hz, 1H), 7.16 (d, J=8.8 Hz, 2H), 6.92 (d, J=7.1 Hz, 1H), 6.68 (d, J=8.8 Hz, 2H), 6.38 (dd, J=16.8, 1.3 Hz, 1H), 6.29 (dd, J=16.9, 10.0 Hz, 1H), 5.68 (dd, J=10.1, 1.3 Hz, 1H), 4.07-3.97 (m, 1H), 3.89 (s, 3H), 3.51-3.41 (m, 2H), 3.37-3.26 (m, 1H), 3.17 (dd, J=10.2, 6.7 Hz, 1H), 2.84 (s, 3H), 2.70 (s, 3H), 2.14-2.05 (m, 1H), 2.03-1.94 (m, 1H).

$^{13}$C NMR (126 MHz, CDCl$_3$) δ 163.90 (s), 160.47 (s), 153.91 (s), 152.97 (s), 145.41 (s), 142.83 (s), 139.37 (s), 135.46 (s), 133.38 (s), 131.13 (s), 129.61 (s), 127.92 (s), 119.96 (s, ×2), 118.61 (s, ×2), 117.87 (s), 116.88 (s), 114.16 (s), 60.56 (s), 58.04 (s), 49.98 (s), 46.60 (s), 37.28 (s), 34.79 (s), 29.24 (s).

Example 60

Synthesis of (S)—N-(3-(2-(4-(1-acetylpyrrolidin-3-ylamino)phenylamino)-7H-pyrrolo[2,3-d]pyrimidin-4-yloxy)phenyl)acrylamide (I-61a)

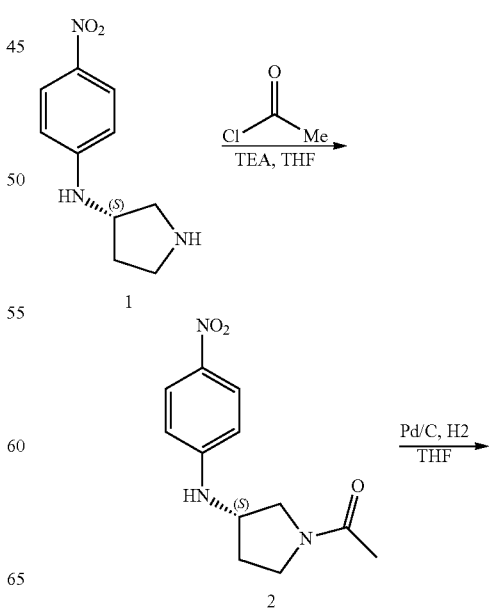

-continued

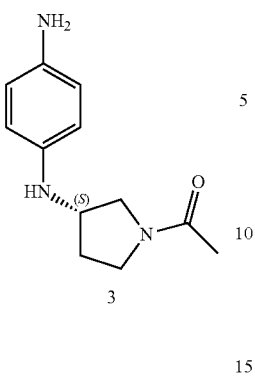

3

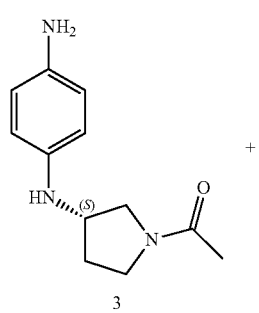

+

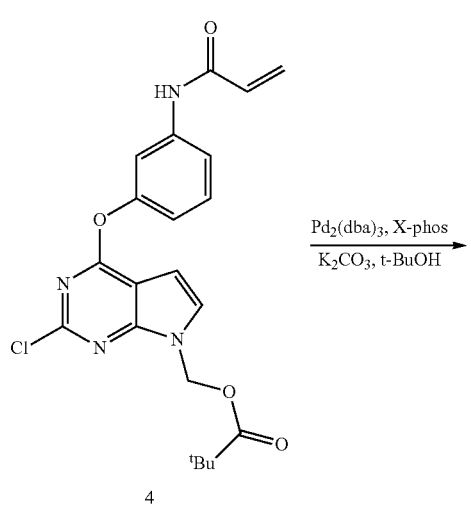

4

Pd₂(dba)₃, X-phos
―――――――→
K₂CO₃, t-BuOH

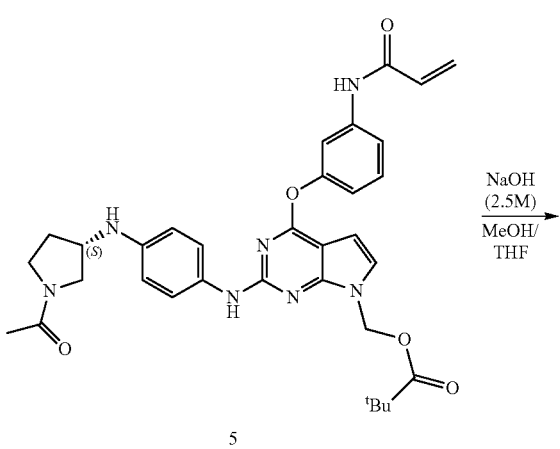

5

NaOH
(2.5M)
―――→
MeOH/
THF

-continued

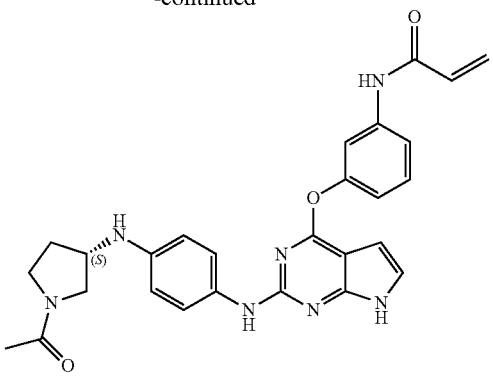

I-61a

Synthesis of (S)-1-(3-(4-nitrophenylamino)pyrrolidin-1-yl)ethanone (2)

A solution of compound 1 (2.139 g), TEA (1.568 g) in THF (40 mL) at −10° C. was slowly added acetyl chloride (0.806 g, dissolved in 4 mL THF). The mixture was stirred at this temperature for 4 h. The reaction was quenched with water and extracted with ethyl acetate. The organic layers were combined, dried and concentrated under reduced pressure to afford crude 2 (1.88 g, 73.2%), which was used for next step without further purification.

Synthesis of (S)-1-(3-(4-aminophenylamino)pyrrolidin-1-yl)ethanone (3)

A mixture of 2 (1.88 g) and Pd/C (0.198 g, 10% activated on carbon) in THF (30 mL) was hydrogenated with hydrogen balloon at room temperature overflight. Once the reaction was complete indicated by TLC, the reaction mixture was filtered through Celite®. The filtrate was concentrated under reduced pressure to afford 3 (1.65 g), which was used for next step) without further purification.

Synthesis of (S)-(2-(4-(1-acetylpyrrolidin-3-ylamino)phenylamino)-4-(3-acrylamidophenoxy)-7H-pyrrolo[2,3-d]pyrimidin-7-yl)methyl pivalate (5)

Compound 3 (1.6 g), compound 4 (3.1 g), K₂CO₃ (2.0 g), tris(dibenzylideneacetone)dipalladium (0.3 g), dicyclohexyl (2',4',6'-triisopropylbiphenyl-2-yl) phosphine (0.3 g) and t-BuOH (50 mL) were sequentially added to the flask. The reaction mixture was stirred at refluxing under N₂ flow. After 5 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound 5 (2.4 g, 54.2%).

Synthesis of (S)—N-(3-(2-(4-(1-acetylpyrrolidin-3-ylamino)phenylamino)-7H-pyrrolo[2,3-d]pyrimidin-4-yloxy)phenyl)acrylamide (I-61a)

To a round-bottom flask (250 mL) was charged with compound 5 (2.4 g), MeOH (15 mL) and THF (15 mL). After compound 5 was completely dissolved, the solution was cooled down to −5° C. NaOH aqueous solution (2.5 M, 3.1 mL) was then added into the flask slowly. The mixture was stirred for 2 h at this temperature. Water (80 mL) was then added in to quench the reaction. The mixture was extracted with ethyl acetate. The organic layers were combined, dried and concentrated under reduced pressure. The resulting crude was further purified by column chromatography to give I-61a (1.4 g, 71.8%, M+H$^+$=498.6).

Example 61

(S)—N-(3-(2-(4-(1-(methylsulfonyl)pyrrolidin-3-ylamino)phenylamino)-7H-pyrrolo[2,3-d]pyrimidin-4-yloxy)phenyl)acrylamide (I-62a)

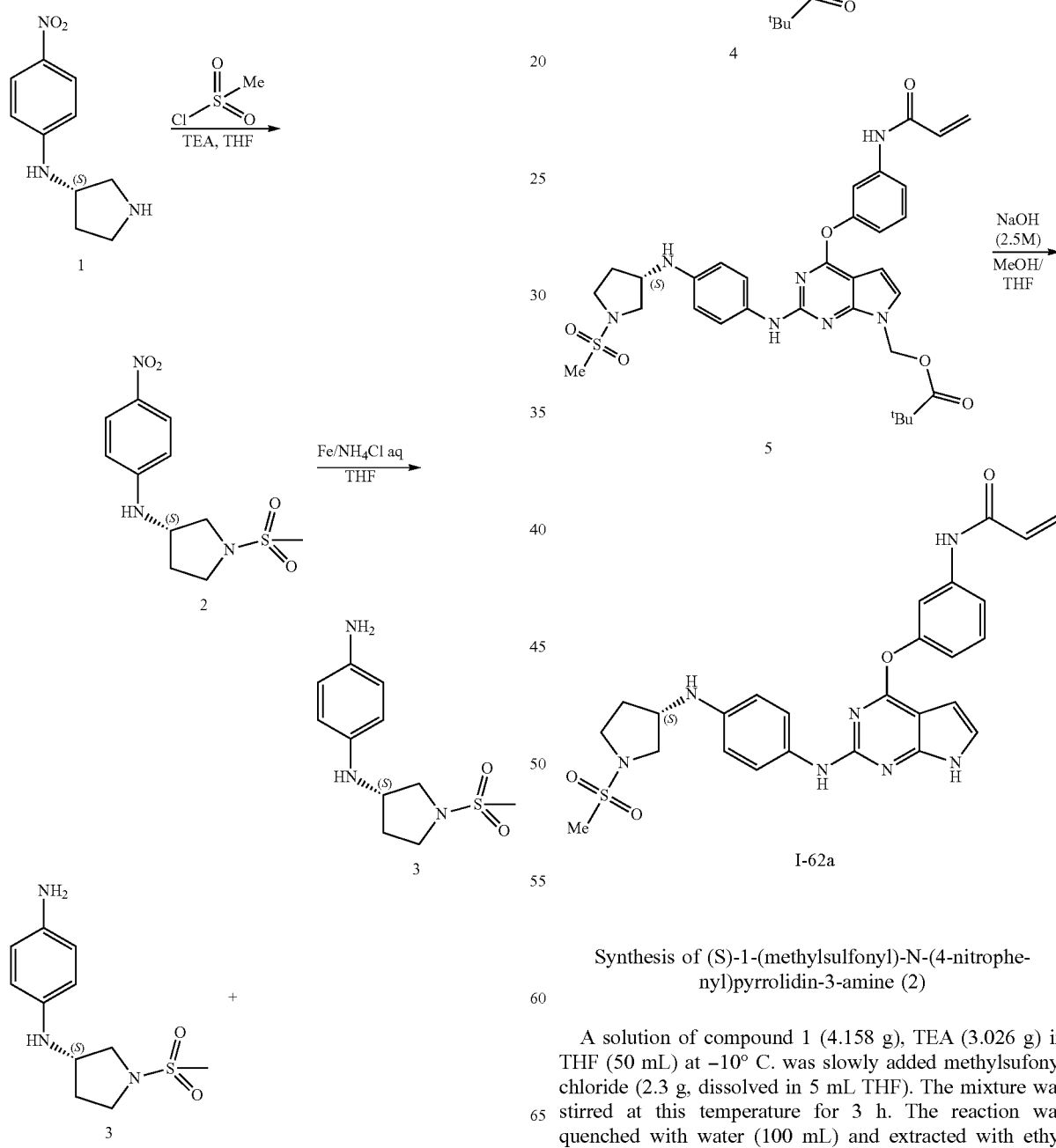

Synthesis of (S)-1-(methylsulfonyl)-N-(4-nitrophenyl)pyrrolidin-3-amine (2)

A solution of compound 1 (4.158 g), TEA (3.026 g) in THF (50 mL) at −10° C. was slowly added methylsufonyl chloride (2.3 g, dissolved in 5 mL THF). The mixture was stirred at this temperature for 3 h. The reaction was quenched with water (100 mL) and extracted with ethyl acetate (150 mL). The organic layers were combined, dried and concentrated under reduced pressure to afford crude 2 (4.3 g, 75.2%), which was used for next step without further purification.

Synthesis of (S)—$N^1$-(1-(methylsulfonyl)pyrrolidin-3-yl)benzene-1,4-diamine (3)

A solution of 2 (4.3 g) in THF/$H_2O$ (90 mL/30 mL) was treated with iron (3.3 g) followed by ammonium chloride (4.8 g). The mixture was stirred at refluxing for 4.5 h. After cooling down to room temperature, the reaction mixture was filtered through Celite®. The filtrate was basified with $NaHCO_3$ (aq, 30 mL) and extracted with ethyl acetate (30 mL×4). The organic layer were combined, dried and concentrated under reduced pressure to provide crude compound 3 (3.1 g, 80.7%), which was used for next step without further purification.

Synthesis of (S)-(4-(3-acrylamidophenoxy)-2-(4-(1-(methylsulfonyl)pyrrolidin-3-ylamino)phenylamino)-7H-pyrrolo[2,3-d]pyrimidin-7-yl)methyl pivalate (5)

Compound 3 (3.1 g), compound 4 (5.2 g), $K_2CO_3$ (2.5 g), tris(dibenzylideneacetone)dipalladium (0.6 g), dicyclohexyl (2',4',6'-triisopropylbiphenyl-2-yl) phosphine (0.6 g) and t-BuOH (80 mL) were sequentially added to the flask. The reaction mixture was stirred at refluxing under $N_2$ flow. After 4 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound 5 (4.1 g, 52.2%).

Synthesis of (S)—N-(3-(2-(4-(1-(methylsulfonyl) pyrrolidin-3-ylamino)phenylamino)-7H-pyrrolo[2,3-d]pyrimidin-4-yloxy)phenyl)acrylamide (I-62a)

To a round-bottom flask (250 mL) was charged with compound 5 (2.1 g), MeOH (12 mL) and THF (12 mL). After compound 5 was completely dissolved, the solution was cooled down to −5° C. NaOH solution (2.5 M, 3 mL) was then added into the flask slowly. The mixture was stirred for 1 h at this temperature. Water (40 mL) was then added in to quench the reaction. The mixture was extracted with ethyl acetate. The organic layers were combined, dried and concentrated under reduced pressure. The resulting crude was purified by column chromatography to give I-62a (1.0 g, 57.8%, M+H$^+$=498.6).

Example 62

(S)—N-(3-(2-(4-(methyl(1-(methylsulfonyl)pyrrolidin-3-yl)amino)phenylamino)-7H-pyrrolo[2,3-d] pyrimidin-4-yloxy)phenyl)acrylamide (I-63a)

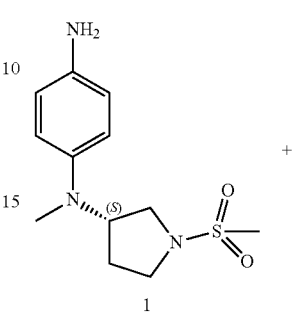

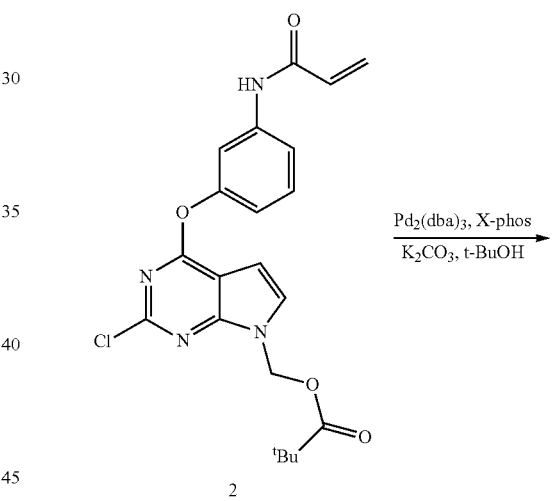

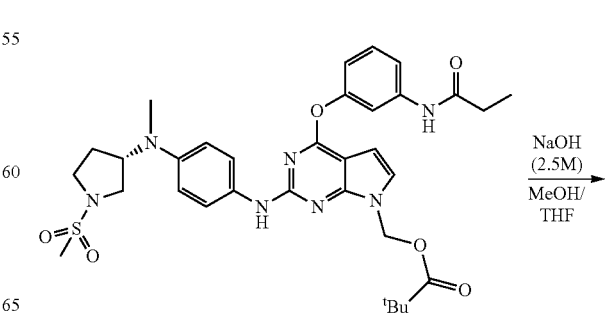

173

-continued

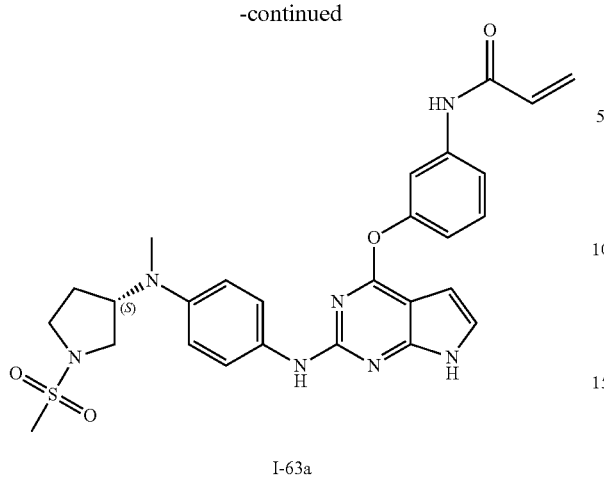

I-63a

Synthesis of (S)-(4-(3-acrylamidophenoxy)-2-(4-(methyl(1-(methylsulfonyl)pyrrolidin-3-yl)amino)phenylamino)-7H-pyrrolo[2,3-d]pyrimidin-7-yl) methyl tert-butyl carbonate (3)

Compound 1 (0.5 g), compound 2 (0.876 g), K$_2$CO$_3$ (0.512 g), tris(dibenzylideneacetone)dipalladium (0.102 g), dicyclohexyl (2',4',6'-triisopropylbiphenyl-2-yl) phosphine (0.104 g) and t-BuOH (30 mL) were sequentially added to the flask. The reaction mixture was stirred at refluxing under N$_2$ flow. After 3.5 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound 3 (0.8 g, 59.3%).

Synthesis of (S)—N-(3-(2-(4-(methyl(1-(methylsulfonyl)pyrrolidin-3-yl)amino)phenylamino)-7H-pyrrolo[2,3-d]pyrimidin-4-yloxy)phenyl)acrylamide (I-63a)

To a round-bottom flask (250 mL) was charged with compound 3 (0.8 g), MeOH (20 mL) and THF (2 mL). After compound 3 was completely dissolved, the solution was cooled down to −5° C. NaOH solution (2.5 M, 1.5 mL) was then added into the flask slowly. The mixture was stirred for 2 h at this temperature. Water (40 mL) was added in to quench the reaction. The mixture was extracted with ethyl acetate. The organic layers were combined, dried and concentrated under reduced. The resulting crude was purified by column chromatography to give I-63a (0.25 g, 37.8%, M+H$^+$=548.6).

174

Example 63

Synthesis of (S)—N-(3-(2-(4-((1-acetylpyrrolidin-3-yl)(methyl)amino)phenylamino)-7H-pyrrolo[2,3-d]pyrimidin-4-yloxy)phenyl)acrylamide (I-64a)

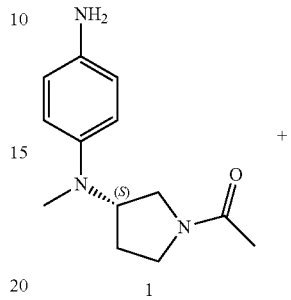

1

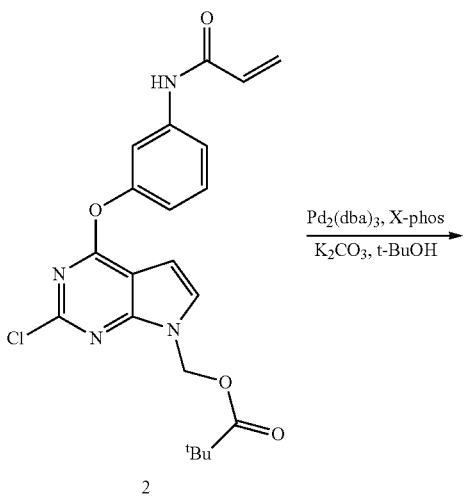

2

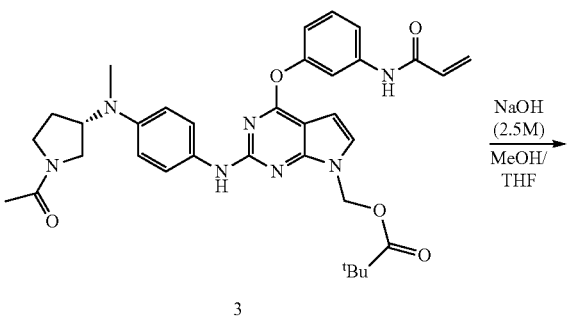

3

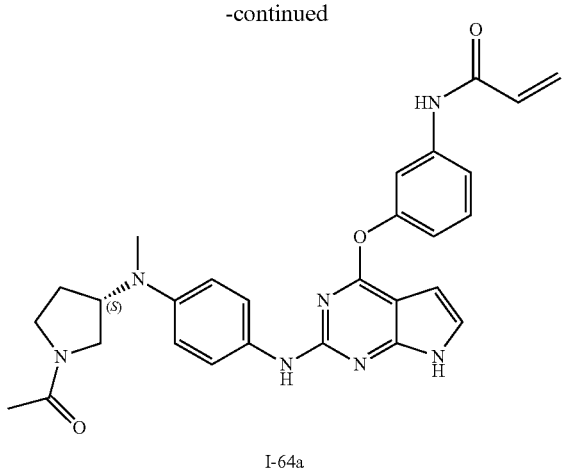

I-64a

Synthesis of (S)-(2-(4-((1-acetylpyrrolidin-3-yl)(methyl)amino)phenylamino)-4-(3-acrylamidophenoxy)-7H-pyrrolo[2,3-d]pyrimidin-7-yl)methyl tert-butyl carbonate (3)

Compound 1 (0.9 g), compound 2 (1.65 g), K$_2$CO$_3$ (1.07 g), tris(dibenzylideneacetone)dipalladium (0.35 g), dicyclohexyl (2',4',6'-triisopropylbiphenyl-2-yl) phosphine (0.35 g) and t-BuOH (20 mL) were sequentially added to the flask. The reaction mixture was stirred at refluxing under N$_2$ flow.

After 4 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography to afford compound 3 (1.24 g, 51.7%).

Synthesis of (S)—N-(3-(2-(4-((1-acetylpyrrolidin-3-yl)(methyl)amino)phenylamino)-7H-pyrrolo[2,3-d]pyrimidin-4-yloxy)phenyl)acrylamide (I-64a)

To a round-bottom flask (250 mL) was charged with compound 3 (1.24 g), MeOH (10 mL) and THF (5 mL). When compound 3 was completely dissolved, the solution was cooled down to −5° C. NaOH solution (2.5 M, 1.6 mL) was then added into the flask slowly. The mixture was stirred for 1 h at this temperature. Water (40 mL) was added in to quench the reaction. The mixture was extracted with ethyl acetate. The organic layers were combined, dried and concentrated under reduced pressure. The resulting crude was further purified by column chromatography to give I-64a (0.265 g, 26.2%, M+H$^+$=512.6).

Example 64

Synthesis of N-(3-(2-(4-(4-(2-methoxyethyl)piperazin-1-yl)phenylamino)-9H-purin-6-yloxy)phenyl)acrylamide (I-65a)

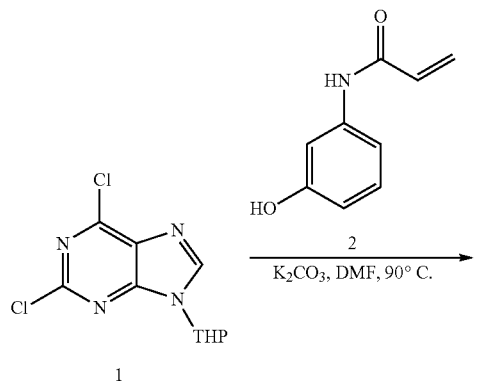

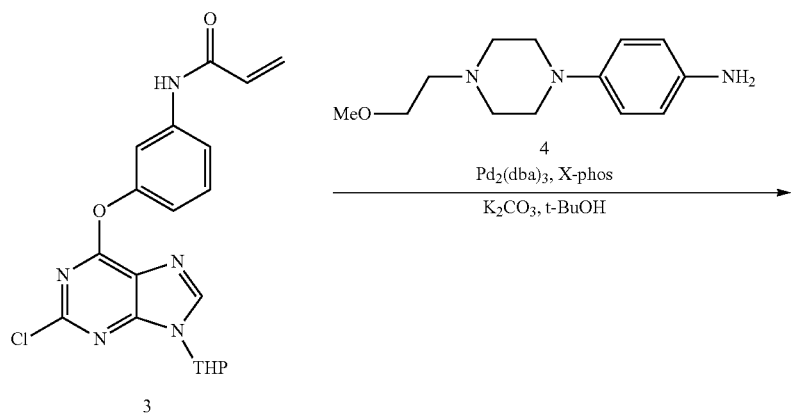

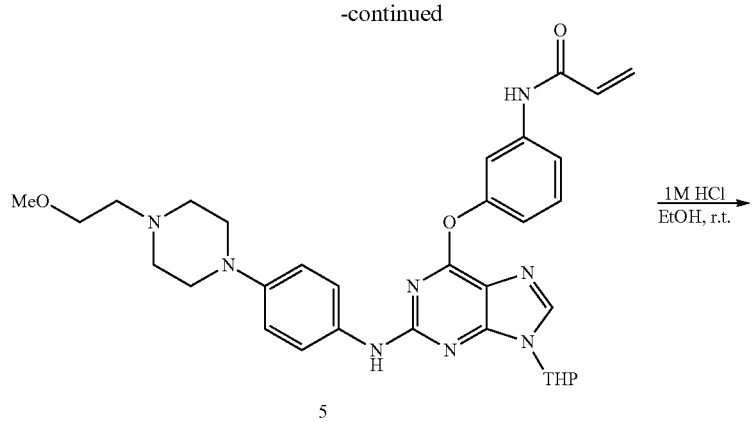

5

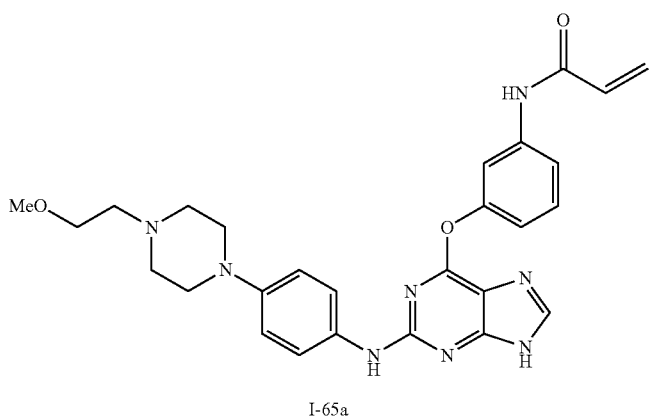

I-65a

Synthesis of N-(3-(2-chloro-9-(tetrahydro-2H-pyran-2-yl)-9H-purin-6-yloxy)phenyl)acrylamide (3)

To a mixture of purine 1 (2.7 g) and phenol 2 (1.6 g) in DMF (40 mL) was added $K_2CO_3$ (2.2 g). The reaction mixture was stirred at 90° C. for 4 h. Once TLC indicated the reaction to be complete, the mixture was poured onto water (150 mL). The resulting precipitate was collected, washed with water (100 ml), and dried under vacuum to afford desired compound 3 (3.2 g, 80%) as a white solid.

Synthesis of N-(3-(2-(4-(4-(2-methoxyethyl)piperazin-1-yl)phenylamino)-9-(tetrahydro-2H-pyran-2-yl)-9H-purin-6-yloxy)phenyl)acrylamide (5)

Compound 3 (1.6 g), compound 4 (0.8 g), $K_2CO_3$ (0.97 g), tris(dibenzylideneacetone)dipalladium (0.115 g), dicyclohexyl (2',4',6'-triisopropylbiphenyl-2-yl) phosphine (0.126 g) and t-BuOH (20 mL) were sequentially added to the flask. The reaction mixture was stirred at refluxing under $N_2$ flow. After 23 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography (EtOAc/MeOH=15:1 as mobile phase) to afford compound 5 (1.1 g, 54.2%, M+H$^+$=599) as a slight yellow solid.

Synthesis of N-(3-(2-(4-(4-(2-methoxyethyl)piperazin-1-yl)phenylamino)-9H-purin-6-yloxy)phenyl)acrylamide (I-65a)

To a solution of compound 5 (0.6 g) in EtOH (10 mL) was HCl aq. (2 mL, 1N). The mixture was stirred at room temperature for 3 h. another portion of HCl aq. (0.5 mL, ~12 M) was then added in and the reaction was stirred for another 3.5 h before being quenched and basified with $K_2CO_3$ (1.3 g in 10 mL water). The mixture was extracted with ethyl acetate. The organic layer was separated, dried over anhydrous sodium sulfate and concentrated under reduced pressure. To this crude material (600 mg) was added ethyl acetate (30 mL) and stirred for 1.5 h. The solution was concentrated till the volume was down to 10 mL. The resulting precipitate was collected, washed and dried to afford the desired compound I-65a (250 mg, 48.5%, M+H$^+$= 515.6)

Example 65
Synthesis of (S)—N-(3-(2-(4-((1-acetylpyrrolidin-3-yl)amino)phenylamino)-5-methoxypyrimidin-4-yloxy)phenyl)acrylamide (I-66a)
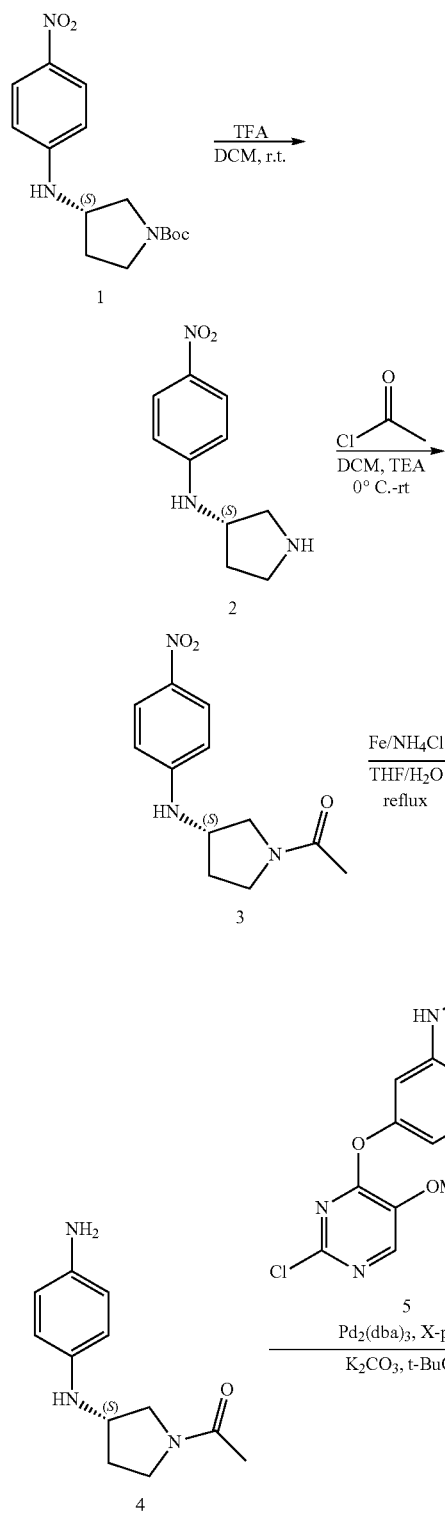
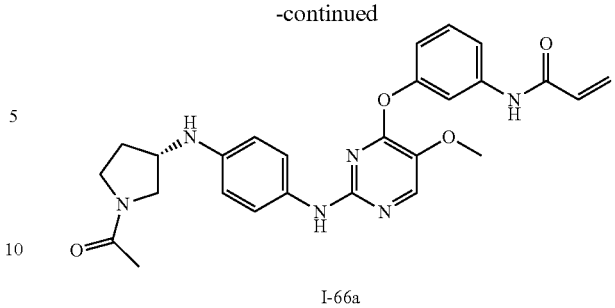
I-66 can be synthesized using above synthetic scheme. We isolated I-66a as a byproduct (un-methylated) from the synthesis of I-58a.
Example 66
Synthesis of (S)—N-(3-(2-(4-(1-(2-methoxyethyl)pyrrolidin-3-ylamino)phenylamino)-9H-purin-6-yloxy)phenyl)acrylamide (I-67a)
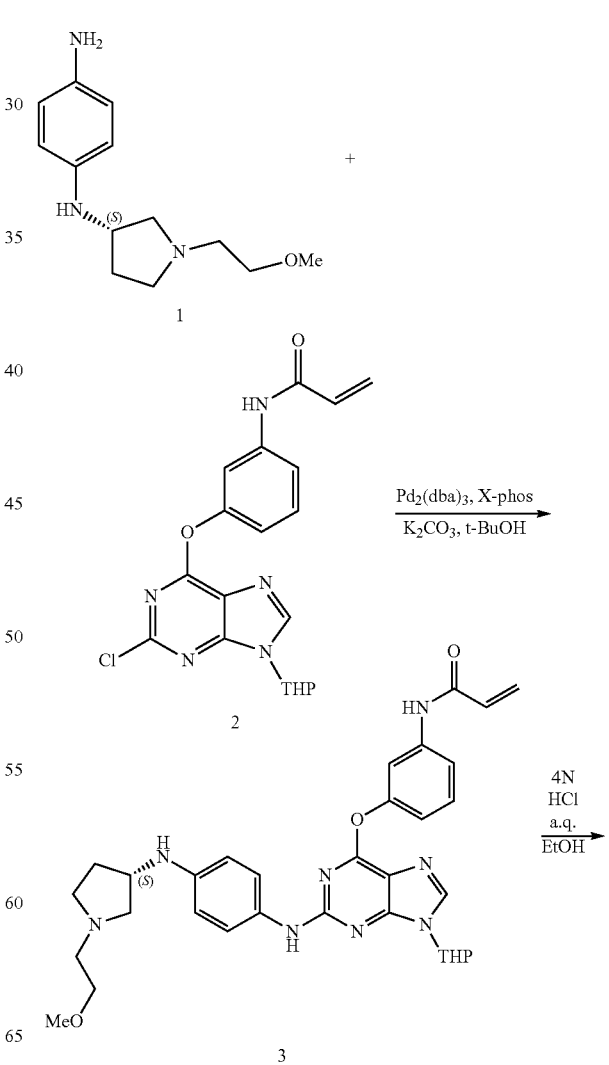

181
-continued

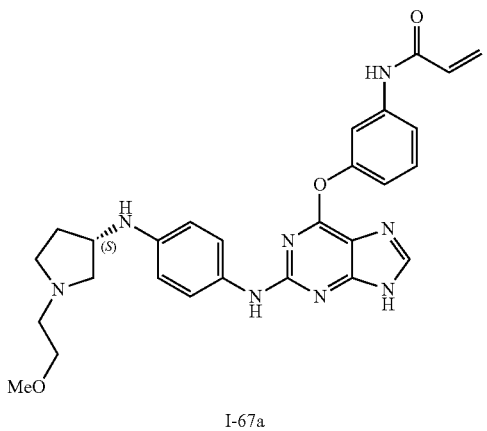

I-67a

Synthesis of N-(3-(2-(4-((S)-1-(2-methoxyethyl) pyrrolidin-3-ylamino)phenylamino)-9-(tetrahydro-2H-pyran-2-yl)-9H-purin-6-yloxy)phenyl)acrylamide (3)

Compound 1 (0.99 g), compound 2 (1.53 g), K$_2$CO$_3$ (1.90 g), tris(dibenzylideneacetone)dipalladium (0.21 g), dicyclohexyl (2',4',6'-triisopropylbiphenyl-2-yl) phosphine (0.23 g) and t-BuOH (25 mL) were sequentially added to the flask. The reaction mixture was stirred at refluxing under N$_2$ flow. After 20 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography (EtOAc/EtOH=10:1 as mobile phase) to afford compound 3 (1.0 g, 43.7%) as a slight yellow solid.

Synthesis of (S)—N-(3-(2-(4-(1-(2-methoxyethyl) pyrrolidin-3-ylamino)phenylamino)-9H-purin-6-yloxy)phenyl)acrylamide (I-67a)

To a solution of compound 3 (1.0 g) in EtOH (10 mL) was HCl aq. (3 mL, 4N). The mixture was stirred at room temperature overnight. The reaction was quenched and basified with NaHCO$_3$ aqueous solution. The mixture was extracted with ethyl acetate. The organic layer was separated, dried over anhydrous sodium sulfate and concentrated under reduced pressure. The crude was purified by column chromatography (EtOAc/EtOH=10/1 as mobile phase) to give compound I-67a (0.41 g, 47.7%, M+H$^+$=515.6).

182
Example 67

Synthesis of N-(3-(2-(4-(4-acetylpiperazin-1-yl) phenylamino)-9H-purin-6-yloxy)phenyl)acrylamide (I-68a)

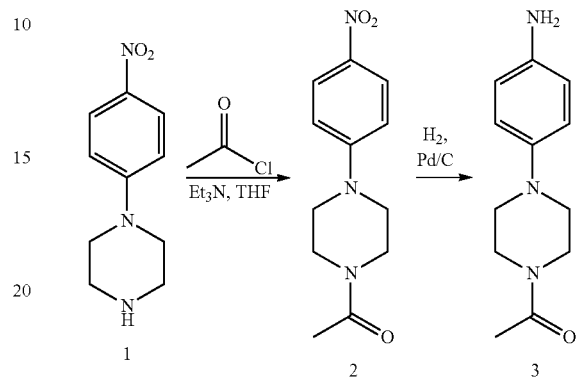

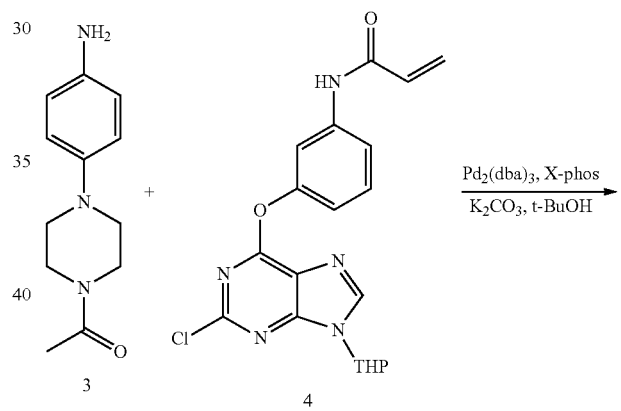

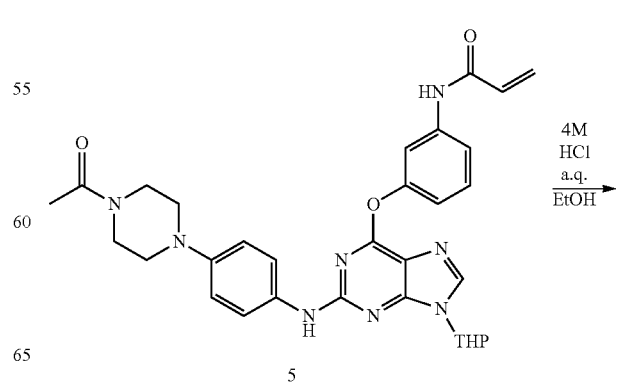

183
-continued

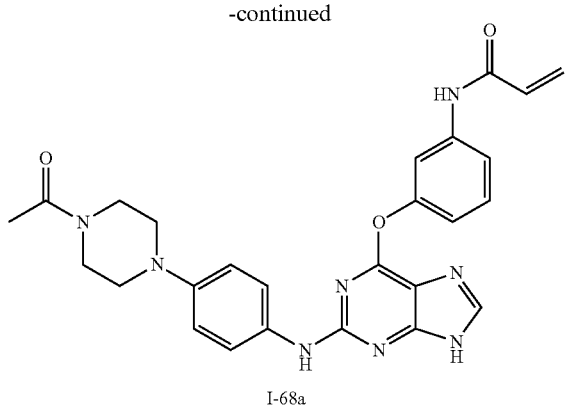

I-68a

Synthesis of 1-(4-(4-nitrophenyl)piperazin-1-yl)ethanone (2)

A solution of compound 1 (10 g), TEA (5.891 g) in THF (50 mL) at 0° C. was slowly added acetyl chloride (4.605 g). The mixture was stirred at this temperature for 1.5 h. Solvent was removed. The resulting residue was diluted with water (30 mL), basified with $K_2CO_3$ aqueous solution (saturated, 20 mL) and then extracted with ethyl acetate. The organic layers were combined, dried and concentrated under reduced pressure to afford crude compound 2 (10.2 g), which was used for next step without further purification.

Synthesis of 1-(4-(4-aminophenyl)piperazin-1-yl)ethanone (3)

A solution of 2 (9.0 g) and Pd/C (0.700 g, 10% activated on carbon) in THE (30 mL) and 1, 4-dioxane (30 mL) was hydrogenated with hydrogen balloon at room temperature overnight, Once TLC indicated the reaction was to be complete, the reaction mixture was filtered through Celite®. The filtrate was concentrated under reduced pressure to afford compound 3 (9.7 g), which was used for next step without further purification,

N-(3-(2-(4-(4-acetylpiperazin-1-yl)phenylamino)-9-(tetrahydro-2H-pyran-2-yl)-9H-purin-6-yloxy)phenyl)acrylamide (5)

Compound 3 (0.798 g), compound 4 (1.605 g), $K_2CO_3$ (1.32 g), tris(dibenzylideneacetone)dipalladium (0.167 g), dicyclohexyl (2',4',6'-triisopropylbiphenyl-2-yl) phosphine (0.172 g) and t-BuOH (30 mL) were sequentially added to the flask. The reaction mixture was stirred at refluxing under $N_2$ flow. After 5.5 h, TLC (DCM:Methanol=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography (EtOAc/EtOH=25:1 as mobile phase) to afford compound 5 (1.4 g, 66.0%) as a brown solid.

Synthesis of N-(3-(2-(4-(4-acetylpiperazin-1-yl)phenylamino)-9H-purin-6-yloxy)phenyl)acrylamide (I-68a)

To a solution of compound 5 (1.4 g) in EtOH (10 mL), HCl aq. (4.6 mL, 4N) was added. The mixture was stirred at room temperature for 5 h. Additional HCl aq. (1 mL, 12 M) was added and the reaction was stirred for another 18 h. TLC indicated the reaction to be complete. The reaction was quenched and basified with $K_2CO_3$ aq. The mixture was extracted with ethyl acetate. The organic layer was separated, dried over anhydrous sodium sulfate and concentrated under reduced pressure. The resulting crude was further purified by column chromatography (EtOAc/EtOH=15/1 as mobile phase) to give compound I-68a (0.254 g, 21.2%, M+H+=499.6).

Example 68

Synthesis of N-(3-(2-(4-(4-(2-(methylsulfonyl)ethyl)piperazin-1-yl)phenylamino)-9H-purin-6-yloxy)phenyl)acrylamide (I-69a)

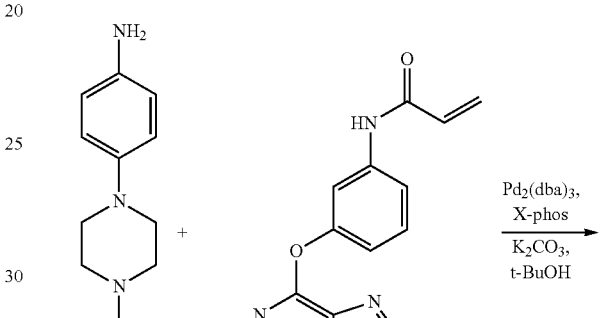

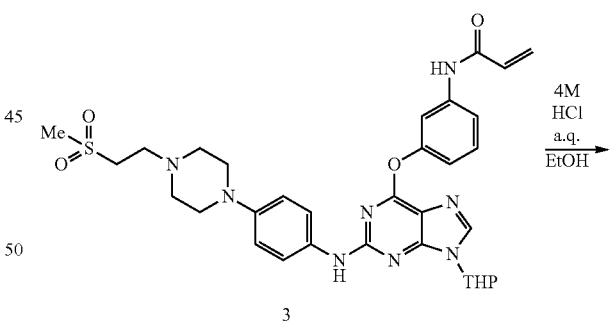

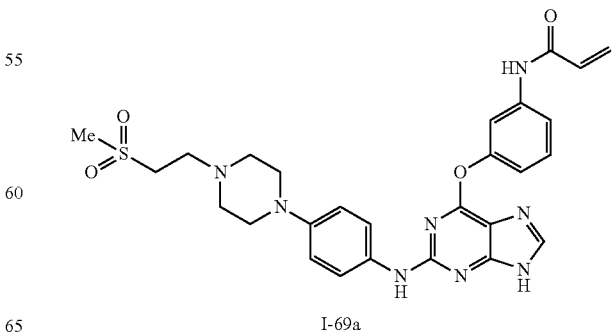

I-69a

Synthesis of N-(3-(2-(4-(4-(2-(methylsulfonyl)ethyl) piperazin-1-yl)phenylamino)-9-(tetrahydro-2H-pyran-2-yl)-9H-purin-6-yloxy)phenyl)acrylamide (3)

Compound 1 (1.033 g), compound 2 (1.616 g), K₂CO₃ (0.97 g), tris(dibenzylideneacetone)dipalladium (0.170 g), dicyclohexyl (2',4',6'-triisopropylbiphenyl-2-yl) phosphine (0.185 g) and t-BuOH (30 mL) were sequentially added to the flask. The reaction mixture was stirred at refluxing under N₂ flow. After 6 h, TLC (EtOAc:EtOH=5:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography (EtOAc/EtOH=15:1 as mobile phase) to afford compound 5 (1.4 g, 59.3%, M+H⁺= 647) as a slight yellow solid.

Synthesis of N-(3-(2-(4-(4-(2-(methylsulfonyl)ethyl) piperazin-1-yl)phenylamino)-9H-purin-6-yloxy)phenyl)acrylamide (I-69a)

To a solution of compound 3 (1.4 g) in EtOH (50 mL) was HCl aq. (4.5 mL, 4N). The mixture was stirred at room temperature for 5 h. Additional HCl aq. (1 mL, ~12M) was added and the reaction was stirred for another 60 h. TLC indicated the reaction to be complete. The reaction was quenched and basified with K₂CO₃ aq. The reaction mixture was extracted with ethyl acetate. The organic layer was separated, dried over anhydrous sodium sulfate and concentrated under reduced pressure. The resulting crude was purified by column chromatography (EtOAc/EtOH=20/1 as mobile phase) to give compound I-69a (0.22 g, 18%, M+H⁺= 563.5).

Example 69

Synthesis of N-(3-((2-((2,2-dioxido-1,3-dihydrobenzo[c]isothiazol-5-yl)amino)-5-methoxypyrimidin-4-yl)oxy)phenyl)acrylamide (I-70a)

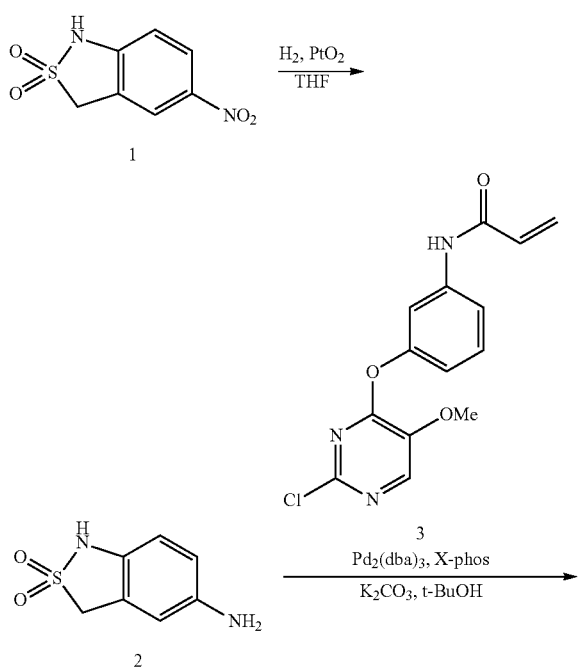

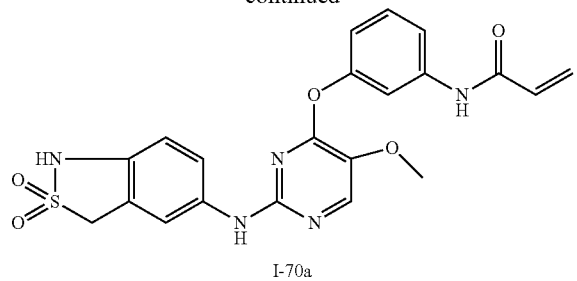

I-70a

Synthesis of 5-amino-1,3-dihydrobenzo[c]isothiazole 2,2-dioxide (2)

A mixture of 1 (180 mg, synthesized according to WO2005/12295) and PtO₂ (10 mg) in THF (4 mL) was hydrogenated with hydrogen balloon at room temperature overnight. TLC indicated the reaction to be complete. The reaction mixture was filtered through Celite®. The filtrate was concentrated under reduced pressure to afford 2 (0.11 g), which was used for the next step without further purification.

Synthesis of N-(3-((2-((2,2-dioxido-1,3-dihydrobenzo[c]isothiazol-5-yl)amino)-5-methoxypyrimidin-4-yl)oxy)phenyl)acrylamide (I-70a)

Compound 2 (0.11 g), compound 3 (0.219 g), K₂CO₃ (0.22 g), tris(dibenzylideneacetone)dipalladium (0.02 g), dicyclohexyl (2',4',6'-triisopropylbiphenyl-2-yl) phosphine (0.04 g) and t-BuOH (3 mL) were sequentially added to the flask. The reaction mixture was stirred at refluxing under N₂ flow. After 7.5 h, TLC (DCM:MeOH=10:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography (DCM/MeOH=50:1 as mobile phase) to afford compound I-70a (26 mg, 11.1%, M+H⁺=454.5) as a slight yellow solid.

Example 70

Synthesis of (S)—N-(3-(2-(4-(methyl(1-(methylsulfonyl)pyrrolidin-3-yl)amino)phenylamino)-9H-purin-6-yloxy)phenyl)acrylamide (I-71a)

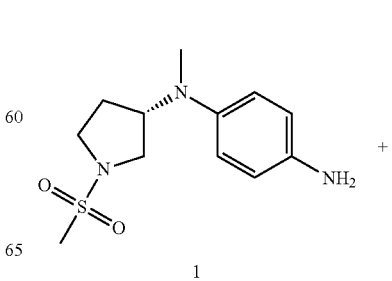

1

-continued

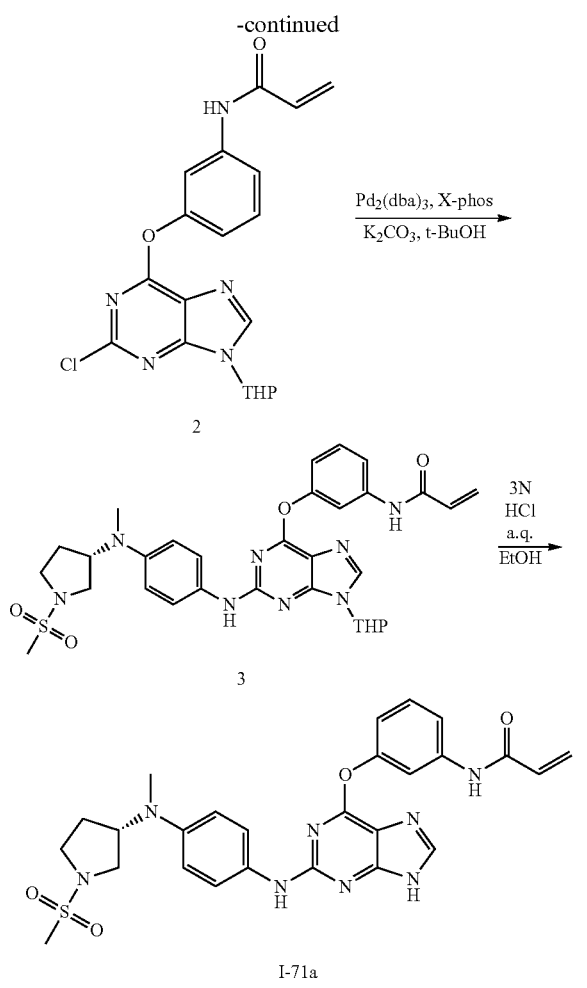

The organic layer was separated, dried over anhydrous sodium sulfate and concentrated under reduced pressure. The resulting crude was further purified by column chromatography (DCM/MeOH=20/1 as mobile phase) to give compound I-71a (0.31 g, 53.88%, M+H⁺=549.6).

Example 71

Synthesis of (R)—N-(3-(2-(4-((1-acetylpyrrolidin-3-yl)(methyl)amino)phenylamino)-5-methoxypyrimidin-4-yloxy)phenyl)acrylamide (I-72a)

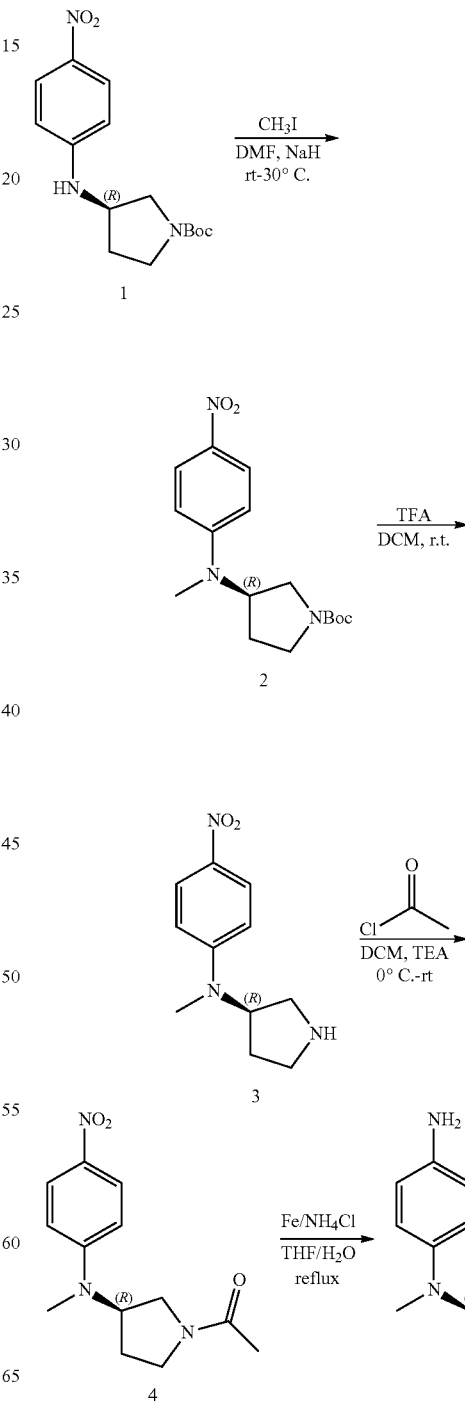

N-(3-(2-(4-(methyl((S)-1-(methylsulfonyl)pyrrolidin-3-yl)amino)phenylamino)-9-(tetrahydro-2H-pyran-2-yl)-9H-purin-6-yloxy)phenyl)acrylamide (3)

Compound 1 (0.35 g), compound 2 (0.532 g), K₂CO₃ (0.362 g), tris(dibenzylideneacetone)dipalladium (0.064 g), dicyclohexyl (2',4',6'-triisopropylbiphenyl-2-yl) phosphine (0.063 g) and t-BuOH (10 mL) were sequentially added to the flask. The reaction mixture was stirred at refluxing under N₂ flow. After 5 h, TLC (DCM:MeOH=25:1 as mobile phase) indicated the reaction to be complete. The reaction mixture was allowed to cool down to 40~50° C., and then filtered through Celite®. The celite layer was washed with ethyl acetate (50 mL). The combined filtrate was concentrated under reduced pressure to afford compound 3 (664 mg), which was used for next step without further purification.

Synthesis of (S)—N-(3-(2-(4-(methyl(1-(methylsulfonyl)pyrrolidin-3-yl)amino)phenylamino)-9H-purin-6-yloxy)phenyl)acrylamide (I-71a)

To a solution of compound 3 (1.4 g) in EtOH (20 mL) was HCl aq. (6 mL, 3N). The mixture was stirred at room temperature for 16 h. TLC indicated the reaction to be complete. The reaction was quenched and basified with K₂CO₃ aq. The mixture was extracted with ethyl acetate.

189
-continued

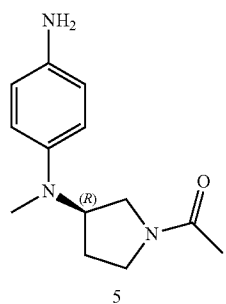

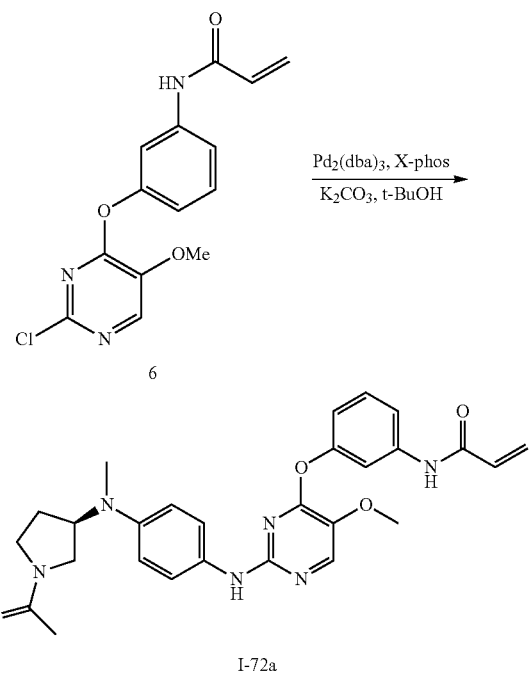

Synthesis of (R)-tert-butyl 3-(methyl(4-nitrophenyl)amino)pyrrolidine-1-carboxylate (2)

To a solution of (R)-tert-butyl 3-(4-nitrophenylamino)pyrrolidine-1-carboxylate (1, 5.1 g) in DMF (50 mL) at 0° C. was sequentially added NaH (0.6 g, 80% dispersion in mineral oil) and CH$_3$I (2.7 g). The resulting mixture was then stirred for 3 h. The reaction mixture was quenched with water and extracted with ethyl acetate. The combined organic layer was washed with water, dried over Na$_2$SO$_4$, and concentrated under reduced pressure. The resulting crude 2 (5.38 g) was used directly in next step without further purification.

Synthesis of (R)—N-methyl-N-(4-nitrophenyl)pyrrolidin-3-amine (3)

To the crude 2 (5.3 g) in DCM (15 mL) was added TFA (6.8 mL). The reaction mixture was stirred at room temperature until TLC (petroleum ether/ethyl acetate=1:3 as mobile phase) indicated the reaction to be complete. The reaction mixture was concentrated under reduced pressure to remove most of TEA. The resulting residue was basified with NaHCO$_3$ (aq, 30 mL) and extracted with EA (30 mL×4). The organic layers were combined, dried and concentrated to afford crude 3 (4.54 g), which was used for next step without further purification.

190

(R)-1-(3-(methyl(4-nitrophenyl)amino)pyrrolidin-1-yl)ethanone (4)

A solution of 3 (4.0 g), TEA (2.31 g) in MeOH (60 ml) at 0° C. was slowly added acetyl chloride (1.84 g). The mixture was warmed up and stirred at room temperature for 0.5 h. The reaction was quenched with water (30 mL) and extracted with DCM (25 mL×4). The organic layers were combined, dried and concentrated to afford crude 4 (3.72 g), which was used for next step without further purification.

Synthesis of (R)-1-(3-((4-aminophenyl)(methyl)amino)pyrrolidin-1-yl)ethanone (5)

A mixture of 4 (3.56 g) and Pd/C (310 mg, 10% activated on carbon) in THF (60 nit) was hydrogenated with hydrogen balloon at room temperature overnight. After the reaction was complete indicated by TLC, the reaction mixture was filtered through Celite®. The filtrate was concentrated under reduced pressure to afford 5 (3.21 g), which was used for next step without further purification.

Synthesis of (R)—N-(3-(2-(4-((1-acetylpyrrolidin-3-yl)(methyl)amino)phenylamino)-5-methoxypyrimidin-4-yloxy)phenyl)acrylamide (I-72a)

Compound 5 (3.21 g), compound 6 (4.26 g), K$_2$CO$_3$ (2.87 g), tris(dibenzylideneacetone)dipalladium (0.64 g), dicyclohexyl (2',4',6'-triisopropylbiphenyl-2-yl) phosphine (0.65 g) and t-BuOH (80 mL) were sequentially added to the flask. The reaction mixture was stirred at refluxing under N$_2$ flow. After 17 h, TLC indicated the reaction to be complete. The reaction mixture was allowed to cool down to 40~50° C., and then filtered through Celite®. The celite layer was washed with ethyl acetate (50 mL). The combined filtrate was concentrated under reduced pressure. The resulting crude was further purified by column chromatography (ethyl acetate/EtOH=20:1 as mobile phase) to afford compound I-72a (1.5 g, 22%, M+H$^+$=503.6).

Example 72

Btk Tyr223 Phosphorylation Inhibition Assays

Material and Methods
Cell Culture and Reagents

Ramos cell line was obtained from the American Type Culture Collection and was maintained at 37° C. with 5% CO2, in media supplemented with 10% fetal bovine serum, penicillin (100 units/mL) and streptomycin (100 μg/mL), Goat F(ab')2 Anti-Human IgM-UNLB was obtained from SouthernBiotech.

Western Blotting Assay

Ramos cells were treated with compounds at indicated doses for 45 min at room temperature, followed by stimulation of 12 μg/mL of IgM for 30 min, and then lysed. Western blots were performed on the cell lysate using Phospho-Btk (Tyr223), Phospho-Btk (Tyr551), Btk, Phospho-PLCγ2 (Tyr1217), PLCγ2, Phospho-p44/42 MAPK (Erk1/2) (Thr202/Tyr204) and p44/42 MAPK (Erk1/2) antibodies (Cell Signaling Technology). The density of blotting band was acquired using ImageJ software, and the IC$_{50}$ of Btk (Tyr223) phosphorylation was fitted using a non-linear regression model by GraphPad Prism version 4.0.

Pulse Chase Western Blotting Assay for Irreversibility Assessment of Compound

Ramos cells were treated with Compound I-1 at 100 nM for 45 min. Cells were then re-suspended in compound free media and stimulated with 6 µg/ml IgM at 0, 4, 6 or 8 hours after compound removal. Cells were then lysed after 30 mm IgM stimulation. West blotting analysis were then performed.

Btk Target Site Occupancy ELISA Assay

Ramos cells were treated with Compound I-1 at indicated concentrations for 1 h, followed by stimulation with 6 µg/mL of IgM for 30 mm, and then lysed. Lysates were incubated with Compound I-21 (biotin labeled) at a final concentration of 1 µM in a PBS, 0.05% Tween-20, 1% BSA solution while shaking for 1 h at room temperature. Samples were transferred to a streptavidin-coated 96-well ELISA plate and mixed while shaking for 1 h at room temperature. The Btk antibody (BD 611116, 1:1000 dilution in PBS+0.05% Tween-20+0.5% BSA) was then applied and incubated for 1 h at room temperature. After wash, goat anti-mouse-HRP (Pierce 31432, 1:1000 dilution in PBS+0.05% Tween-20+0.5% BSA) was added and incubated for 1 h at room temperature. The ELISA was developed with addition of tetramethyl benzidine (TMB) followed by Stop Solution and read at OD 450 nM.

Results

Compounds Significantly Reduced the Btk Tyr223 Phosphorylation in Ramos Cells

The results from this assay were shown in Table 1 below. Compounds having an activity designated as "A" provided an $IC_{50} \leq 10$ nM; compounds having an activity designated as "B" provided an $IC_{50}$ 10-100 nM; compounds having an activity designated as "C" provided an $IC_{50} > 100$ nM.

TABLE 1

| Compound # | BTK Inhibition |
| --- | --- |
| I-1 | A |
| I-2 | A |
| I-3 | A |
| I-4 | A |
| I-5 | A |
| I-6 | A |
| I-7 | B |
| I-8 | A |
| I-9 | A |
| I-10 | A |
| I-11 | B |
| I-12 | B |
| I-13 | A |
| I-14 | B |
| I-15 | A |
| I-16 | A |
| I-17 | A |
| I-18 | A |

Ramos cells were treated with compounds at indicated concentrations for 45 mins, and the phosphorylations of BTK and potential downstream effectors PLCγ2 and Erk were monitored. Most compounds dose-dependently inhibited the phosphorylation of BTK protein, Compound I-1 achieving the inhibition $IC_{50}$ at 1.1 nM and Compound I-2 achieving the inhibition $IC_{50}$ at 5.0 nM.

Compounds I-1 and I-2 Irreversibly Inhibited the BTK Phosphorylation in Ramos Cells Ramos cells were treated Compound 14 and Compound I-2 at 100 nM for 45 mins, and inhibition of BTK phosphorylation was monitored 4, 6 and 8 his post Compound I-1 and Compound I-2 removal. BTK remains inhibited up to 8 his after treatment with the covalent bonded Compound I-1 and Compound I-2, indicating that Compound I-1 and Compound I-2 are strong irreversible inhibitors of BTK protein.

Figure 3:
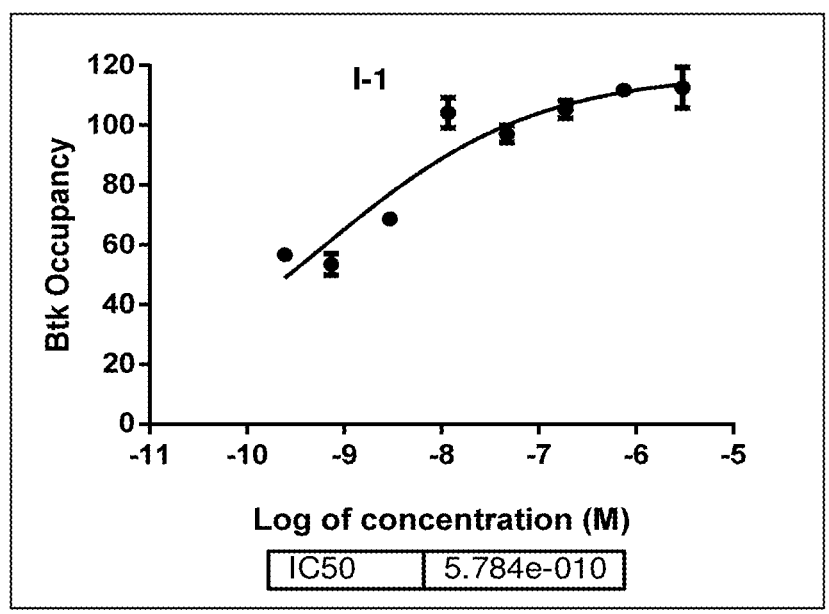
FIG. 3 shows dose-dependent inhibition of the BTK phosphorylation in Ramos cells by compound I-1.
Figure 4A:
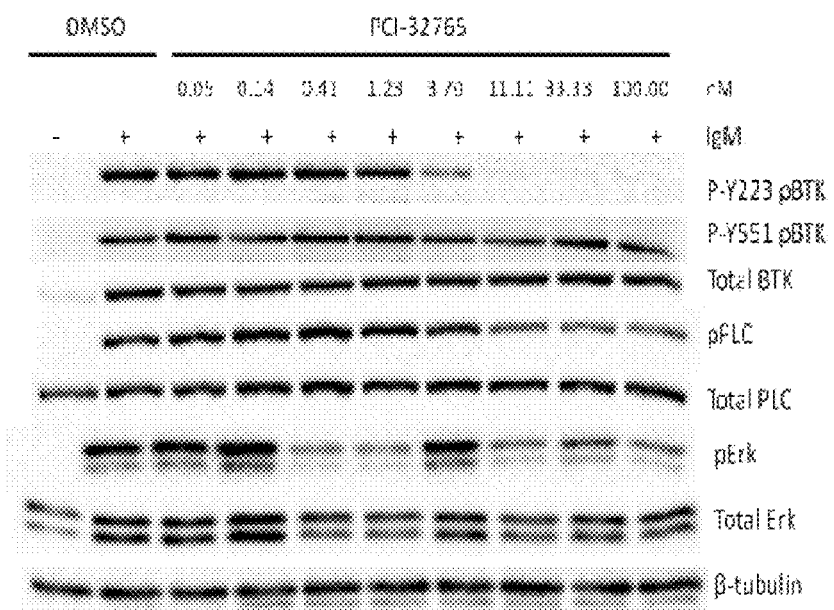
FIGS. 4A-4N show exemplary western blotting image $IC_{50}$ curves from several compounds, while PCI-32765 served as positive Btk inhibitor.
Figure 4B:
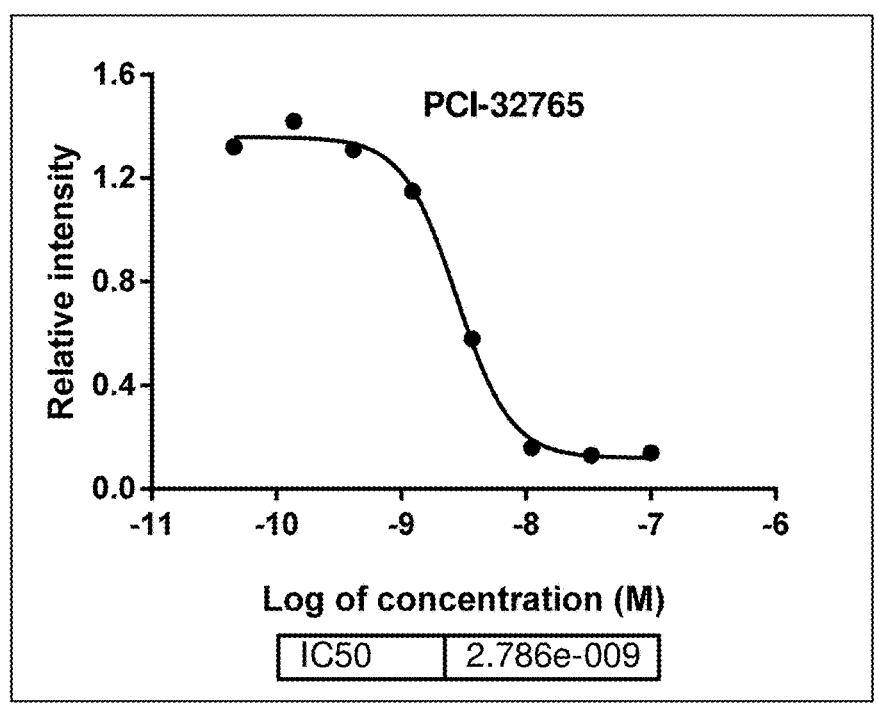
Figure 4C:
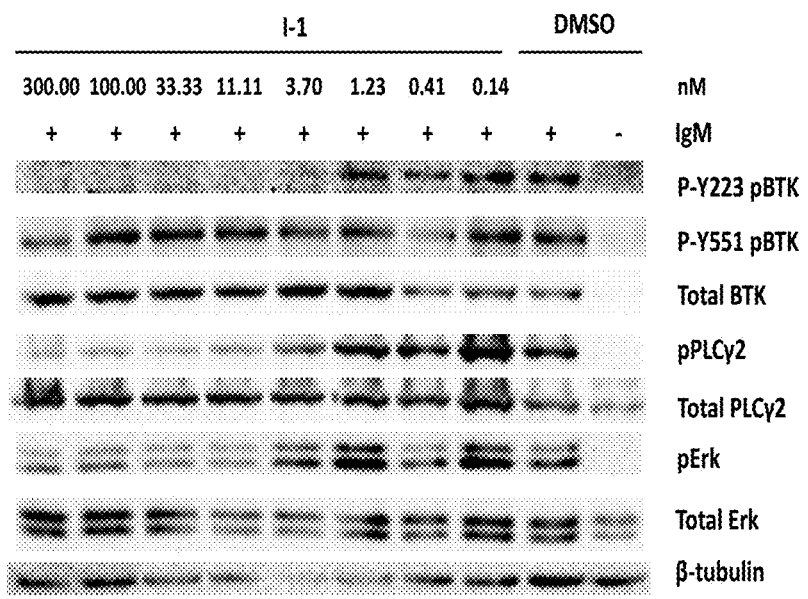
Figure 4D:
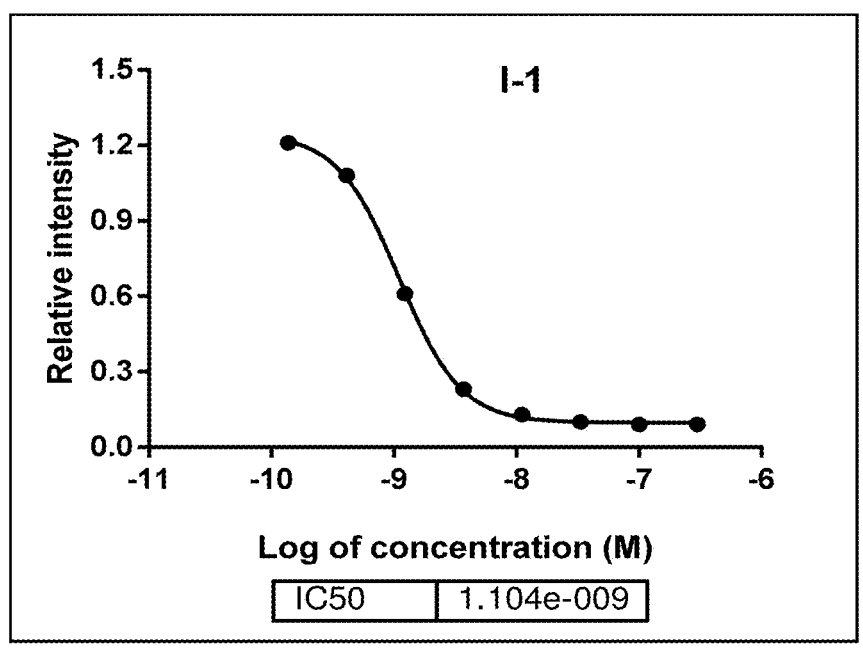
Figure 4E:
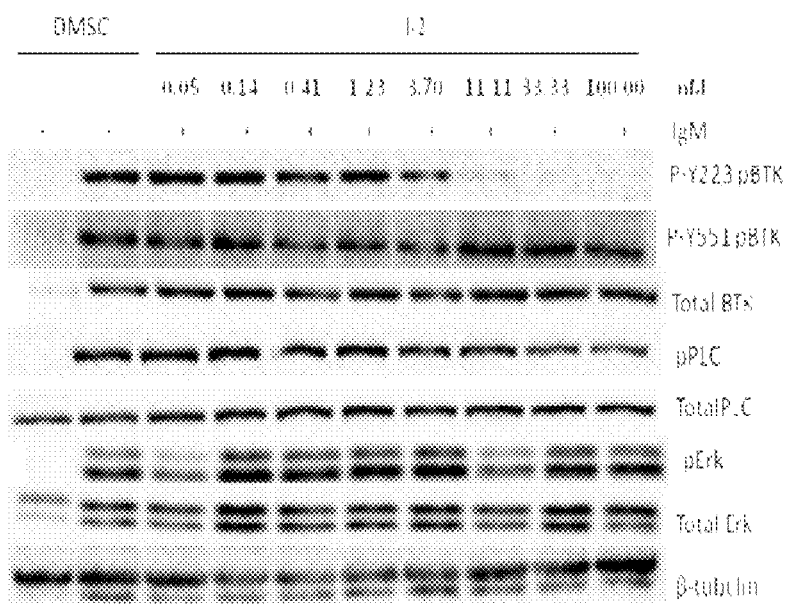
Figure 4F:
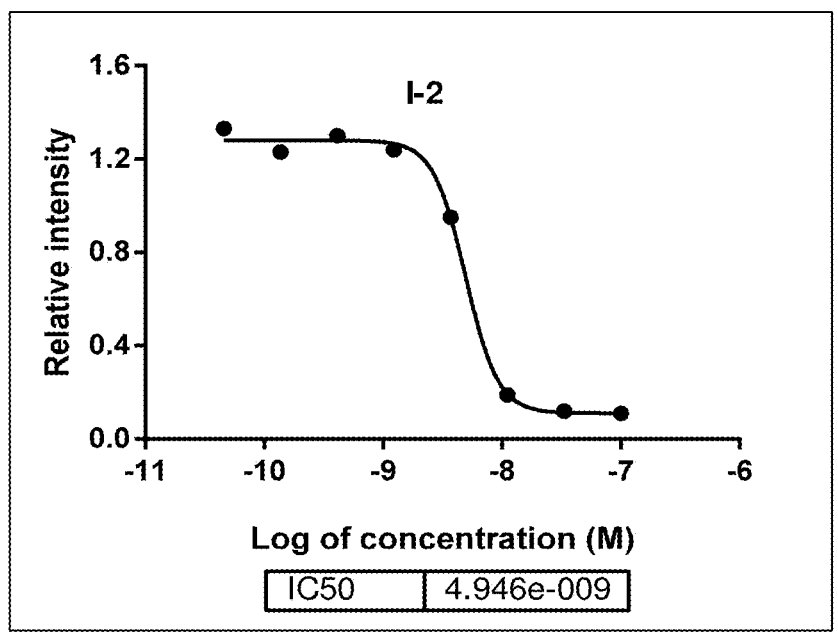
Figure 4G:
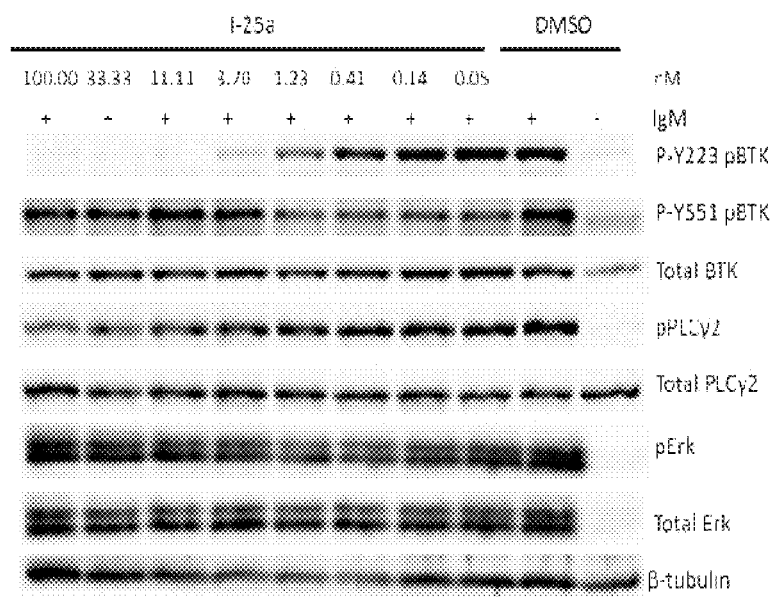
Figure 4H:
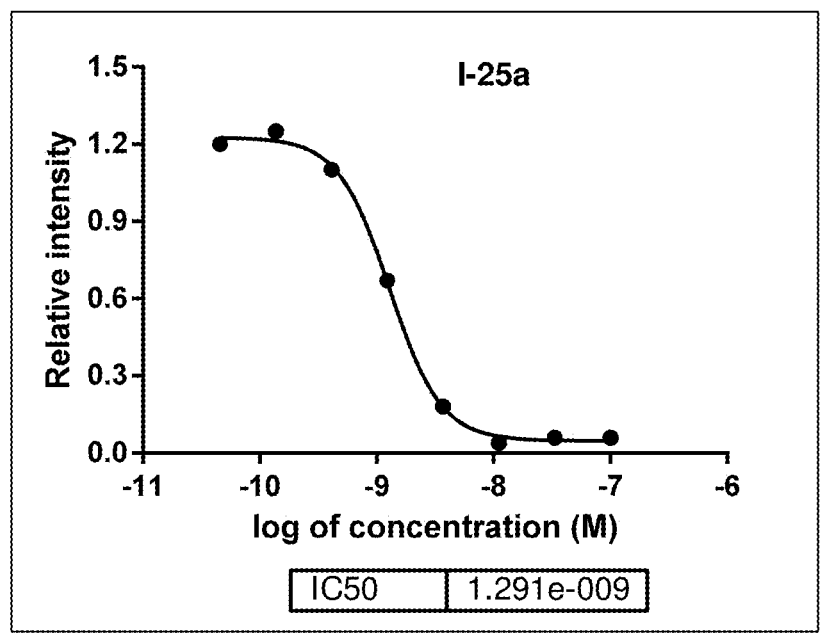
Figure 4I:
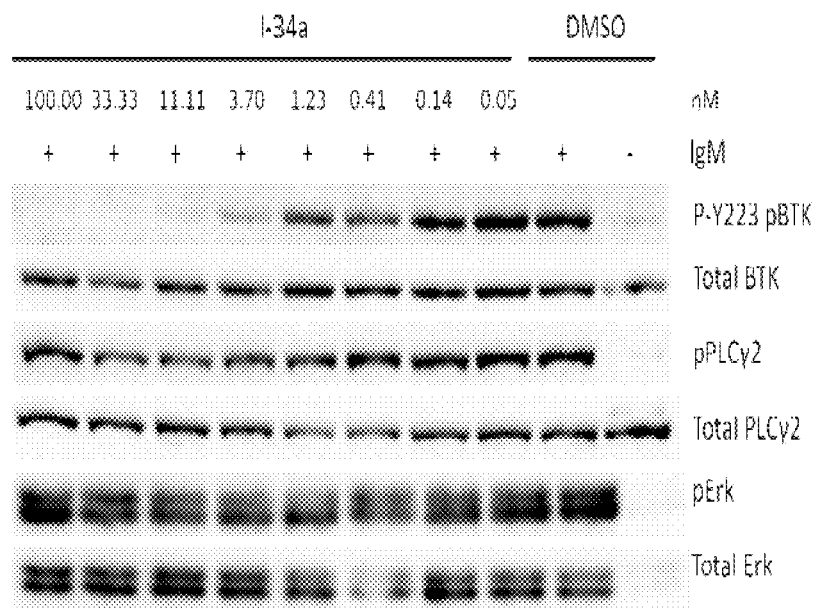
Figure 4J:
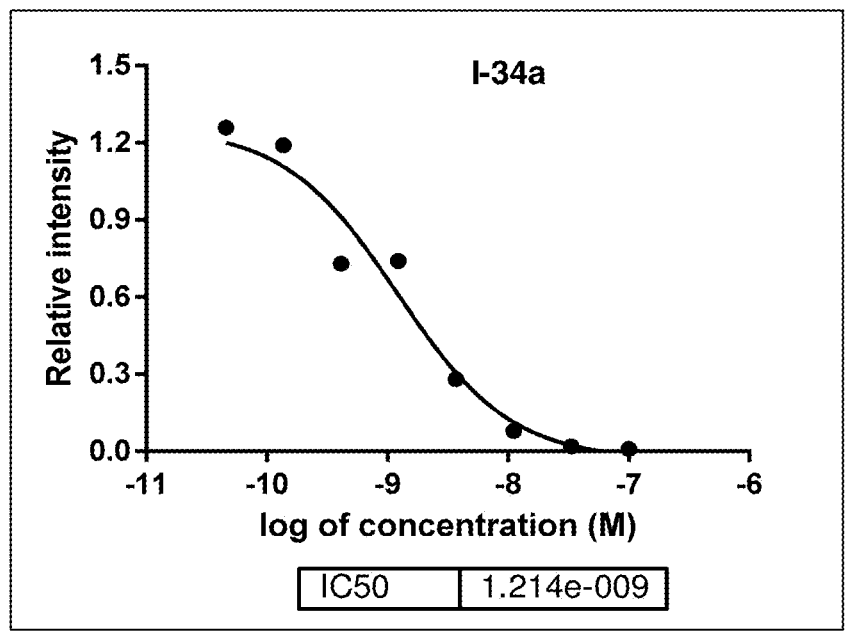
Figure 4K:
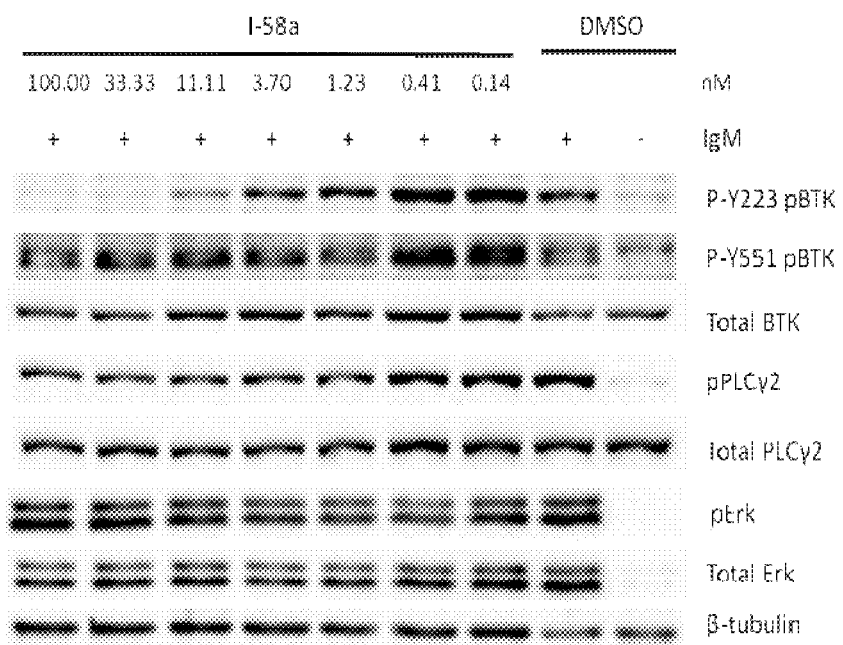
Figure 4L:
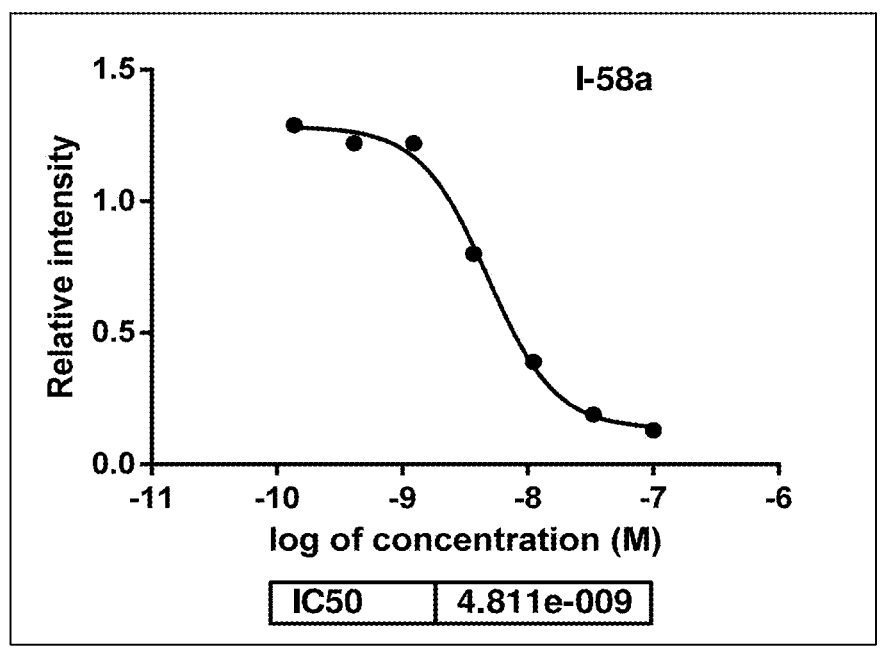
Figure 4M:
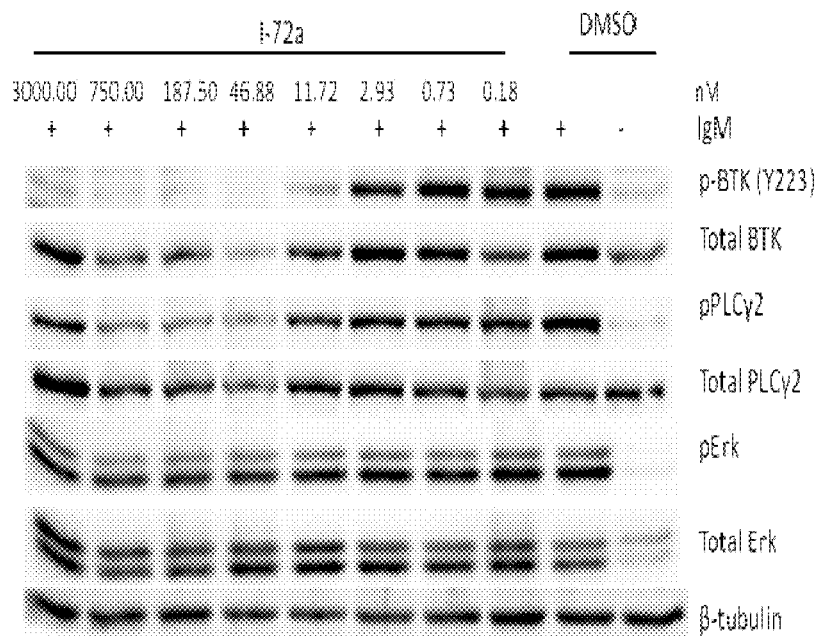
Figure 4N:
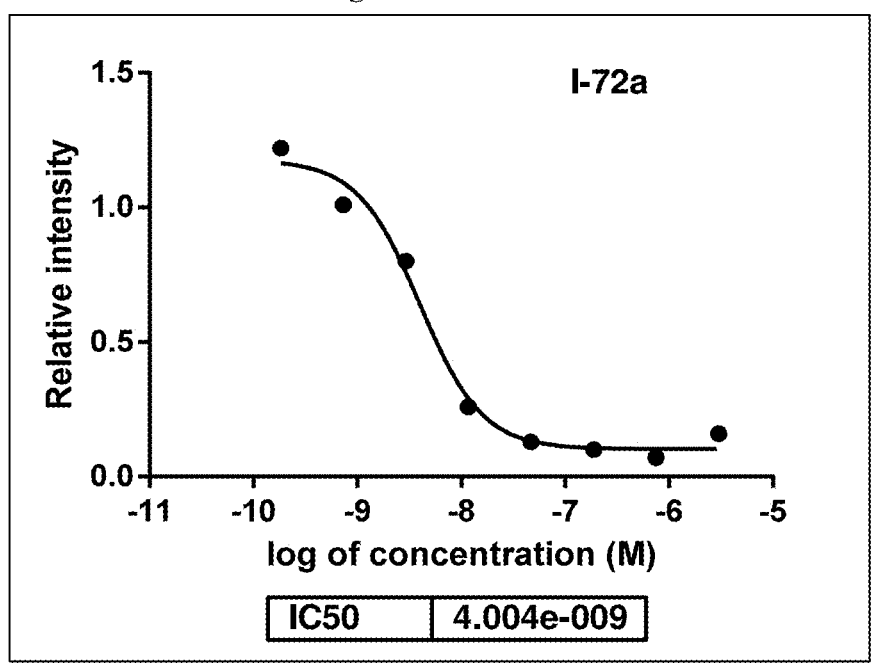

Compounds I-1 and I-2 Irreversibly Inhibited the Phosphorylation of the BTK in Ramos Cells The BTK target site occupancy ELISA was used to detect free BTK protein from Romas cells treated with increasing concentrations of Compounds I-1. As shown in Table 2 and FIG. 3, compound I-1 dose-dependent occupancy of the BTK proteins correlates with its inhibitory activity of BTK kinase, achieving $IC_{50}$ at 0.5 nM.

TABLE 2

| Compound I-1 (nM) | OD 450 (average) | free Btk (pg) |
| --- | --- | --- |
| 3000 | −0.0487 | −689 |
| 750 | −0.0456 | −646 |
| 188 | −0.0207 | −290 |
| 47 | 0.0114 | 168 |
| 12 | −0.0161 | −224 |
| 3 | 0.1219 | 1747 |
| 0.7 | 0.1811 | 2592 |
| 0.2 | 0.1686 | 2414 |
| 0 | 0.3888 | 5560 |

Example 73

Material and Methods

Cell Culture and Reagents

All cell lines were obtained from the American Type Culture Collection and were maintained at 37° C. with 5% CO2. Ramos cell line was maintained in media supplemented with 10% fetal bovine serum, penicillin (100 units/mL) and streptomycin (100 µg/mL). NK-92 cell line was maintained in media supplemented with 10% fetal bovine serum and 10% horse serum, penicillin (100 units/mL) and streptomycin (100 µg/mL), IL-2 10 ng/mL. Goat F(ab')2 Anti-Human IgM-UNLB was obtained from SouthernBiotech. IL-2 was obtained from Peprotech.

Western Blotting Assay for Btk

Ramos cells were treated with compounds at indicated doses for 45 min at room temperature, followed by stimulation of 6 µg/mL of anti-IgM for 30 min, and then lysed. Western blots were performed on the cell lysate using Phospho-Btk (Tyr223), Phospho-Btk (Tyr551), Btk, Phospho-PLCγ2 (Tyr1217), PLCγ2, Phospho-p44/42 MAPK (Erk1/2) (Thr202/Tyr204) and p44/42 MAPK (Erk1/2) antibodies (Cell Signaling Technology). The density of blotting band was acquired using ImageJ software, and the $IC_{50}$ of Btk (Tyr223) phosphorylation was fitted using a non-linear regression model by GraphPad Prism.

Western Blotting Assay for Jak3 and Stat5

NK-92 cells were treated with compounds at the dosed indicated for 1 hour in incubator, followed by the IL-2 stimulation for 15 minutes. Cells were then collected and lysed to prepare the cellular extraction. Western blots were performed on cell lysate using Phospho-Jak3, Jak3, Phospho-Stat5, Stat5 antibodies (Cell Signaling Technology). The intensity of blotting band was acquired using Image Lab (Bio-Rad) software, and the $IC_{50}$ of target was generated with GraphPad Prism.

Pulse Chase Western Blotting Assay to Assess the Binding Property of Compound

Ramos cells were treated with Compounds at 100 nM for 45 min. Cells were then re-suspended in compound free media and stimulated with 6 µg/ml anti-IgM at 0, 4, 6 or 8 hours after compound removal. Cells were then lysed after 30 mm anti-IgM stimulation. Western blotting analysis was then performed.

Btk Target Site Occupancy ELISA Assay

Ramos cells were treated with Compounds at indicated concentrations for 1 h, followed by stimulation with 6 µg/mL of anti-IgM for 30 mm, and then lysed. Lysates were incubated with Compound I-21 (biotin labeled) at a final concentration of 1 µM in a PBS, 0.05% Tween-20, 1% BSA solution while shaking for 1 h at room temperature. Samples were transferred to a streptavidin-coated 96-well ELISA plate and mixed while shaking for 1 h at room temperature. The Btk antibody (BD 611116, 1:1000 diluted in PBS+0.05% Tween-20+0.5% BSA) was then applied and incubated for 1 h at room temperature. After wash, goat anti-mouse-HRP (Pierce 31432, 1:1000 diluted in PBS+0.05% Tween-20+0.5% BSA) was added and incubated for 1 h at room temperature. The ELISA was developed with addition of tetramethylbenzidine (TMB) followed by Stop Solution and read at OD 450 nM.

Results

1. Compounds Significantly Reduced the Btk Tyr223 Phosphorylation in Ramos Cells The results from western blotting assay for Btk were shown in Table 3 below. Compounds having an activity designated as "A" provided an $IC_{50} \leq 10$ nM; compounds having an activity designated as "B" provided an $IC_{50}$ 10-100 nM; compounds having an activity designated as "C" provided an $IC_{50} \geq 100$ nM. "N/A" means the compound has not been tested. PCI-327265 was used as the positive control.

TABLE 3

| Compound # | Btk Inhibition<br>A: ≤10 nM<br>B: 10~100 nM<br>C: ≥100 nM |
| --- | --- |
| I-1 | A |
| I-2 | A |
| I-3 | A |
| I-4 | A |
| I-5 | A |
| I-6 | A |
| I-7 | B |
| I-8 | N/A |
| I-9 | A |
| I-10 | A |
| I-11 | B |
| I-12 | B |
| I-13 | A |
| I-14 | B |
| I-15 | A |
| I-16 | A |
| I-17 | A |
| I-18 | A |
| I-19 | A |
| I-20 | A |
| I-21 | N/A |
| I-22 | C |
| I-23a | B |
| I-24a | B |
| I-25a | A |
| I-26a | B |
| I-27a | A |
| I-28a | B |
| I-29a | C |
| I-30a | A |
| I-31a | A |
| I-32a | A |
| I-33a | B |
| I-34a | A |

TABLE 3-continued

| Compound # | Btk Inhibition<br>A: ≤10 nM<br>B: 10~100 nM<br>C: ≥100 nM |
| --- | --- |
| I-35a | A |
| I-36a | B |
| I-37a | B |
| I-38a | B |
| I-39a | B |
| I-40a | A |
| I-41a | B |
| I-42a | A |
| I-43a | A |
| I-44a | A |
| I-45a | B |
| I-46a | B |
| I-47a | A |
| I-48a | A |
| I-49a | A |
| I-50a | B |
| I-51a | A |
| I-52a | A |
| I-53a | A |
| I-54a | A |
| I-55a | C |
| I-56a | A |
| I-57a | A |
| I-58a | A |
| I-59a | A |
| I-60a | A |
| I-61a | A |
| I-62a | A |
| I-63a | A |
| I-64a | A |
| I-65a | A |
| I-66a | A |
| I-67a | B |
| I-68a | B |
| I-69a | B |
| I-70a | B |
| I-71a | A |
| I-72a | A |

Exemplary western blotting image from several of the above compounds are listed below left panel in FIG. 4, while PCI-32765 served as positive Btk inhibitor. $IC_{50}$ curves are displayed in the right panel in FIG. 4.

2. Compounds Reduced the Jak3 Phosphorylation in NK-92 Cells

The results from western blotting assay for Jak3 were shown in Table 4 below. Compounds having an activity designated as "A" provided an $IC_{50} \leq 200$ nM; compounds having an activity designated as "B" provided an $IC_{50}$ 200~400 nM; compounds having an activity designated as "C" provided an $IC_{50} \geq 400$ nM.

TABLE 4

| Compound # | Jak3 inhibition<br>A: ≤200 nM<br>B: 200~400 nM<br>C: ≥400 nM |
| --- | --- |
| I-1 | A |
| I-2 | B |
| I-25a | C |

3. Compounds Reduced the Stat5 Phosphorylation in NK-92 Cells

The results from western blotting assay for Stat5 were shown in Table 5 below. Compounds having an activity designated as "A" provided an $IC_{50} \leq 200$ nM; compounds having an activity designated as "B" provided an $IC_{50}$ 200~400 nM; compounds having an activity designated as "C" provided an IC$_{50}$≥400 nM.

TABLE 5

| Compound # | Stat5 inhibition<br>A: ≤200 nM<br>B: 200~400 nM<br>C: ≥400 nM |
|---|---|
| I-1 | C |
| I-2 | B |
| I-3 | B |
| I-4 | B |
| I-5 | B |
| I-6 | B |
| I-7 | C |
| I-9 | B |
| I-10 | B |
| I-11 | C |
| I-12 | B |
| I-13 | C |
| I-14 | C |
| I-15 | C |
| I-16 | C |
| I-17 | C |
| I-18 | B |
| I-23a | C |
| I-25a | C |
| I-30a | A |
| I-31a | C |
| I-32a | C |
| I-33a | C |
| I-34a | C |
| I-35a | B |
| I-36a | B |
| I-37a | C |
| I-38a | C |
| I-39a | C |
| I-40a | C |
| I-41a | B |
| I-42a | C |
| I-43a | B |
| I-44a | B |
| I-45a | B |
| I-46a | C |
| I-47a | B |
| I-48a | B |
| I-49a | C |
| I-50a | C |
| I-51a | C |
| I-52a | C |
| I-53a | C |
| I-54a | C |
| I-56a | B |
| I-57a | B |
| I-58a | C |

Figure 5A:
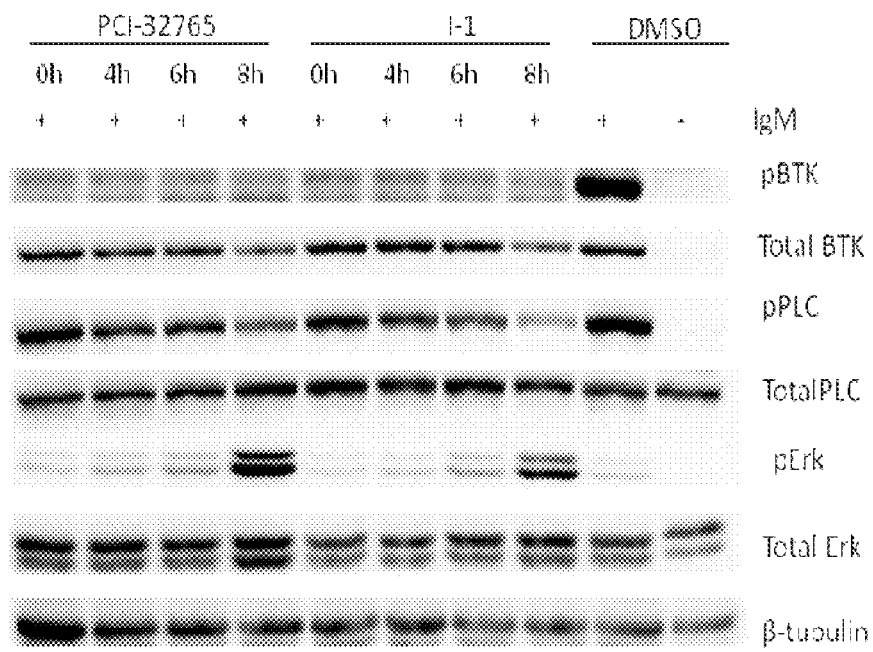
FIGS. 5A and 5B show that compounds I-1 and I-2 inhibited the Btk phosphorylation in Ramos cells after 8 hours of removal.
Figure 5B:
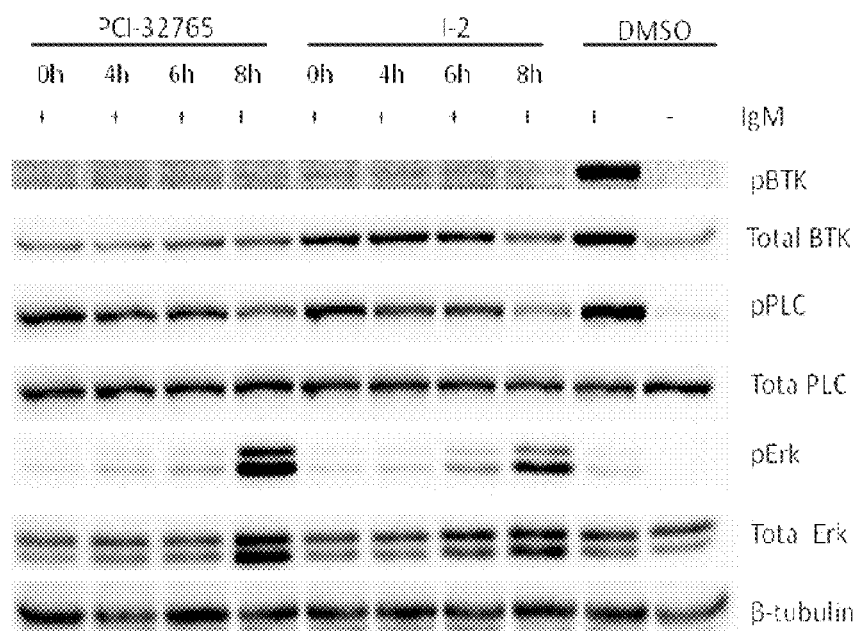
Figure 6A:
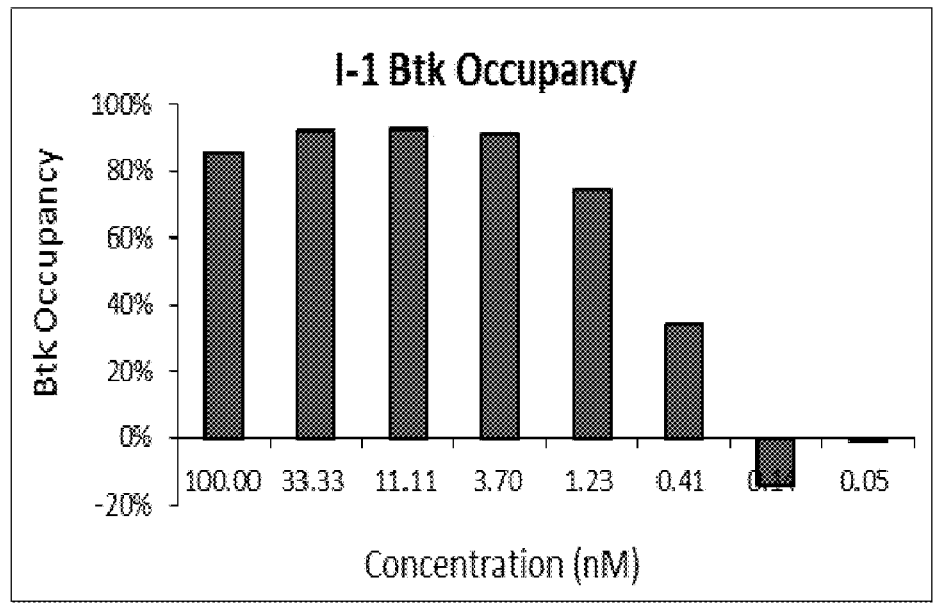
FIGS. 6A-6L show exemplary Btk Target Site Occupancy ELISA assay results from several compounds.
Figure 6B:
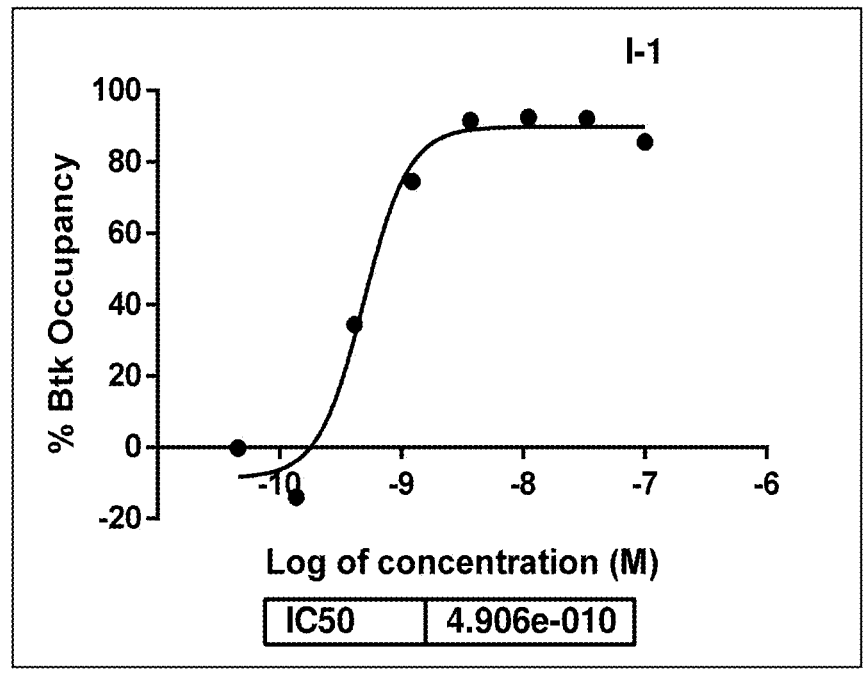
Figure 6C:
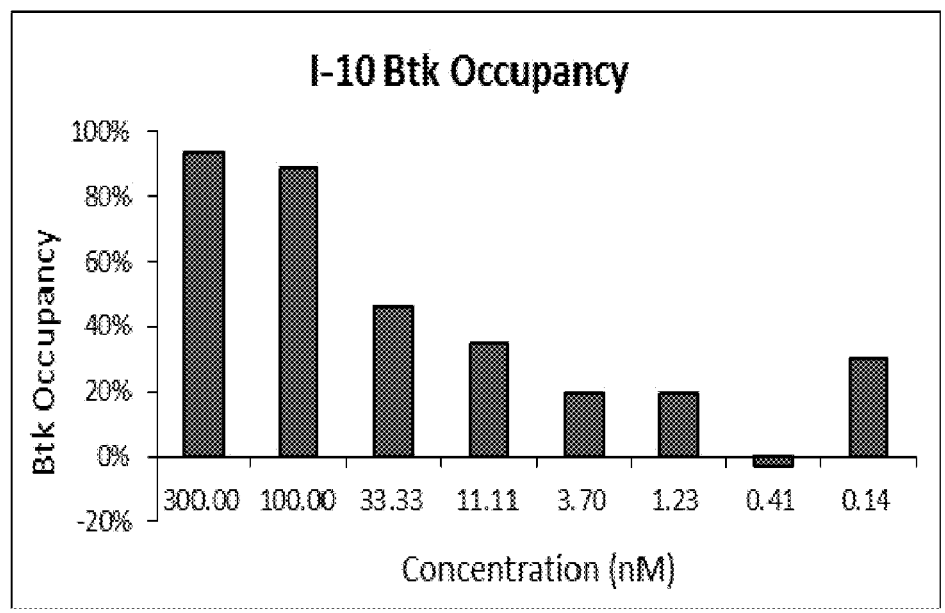
Figure 6D:
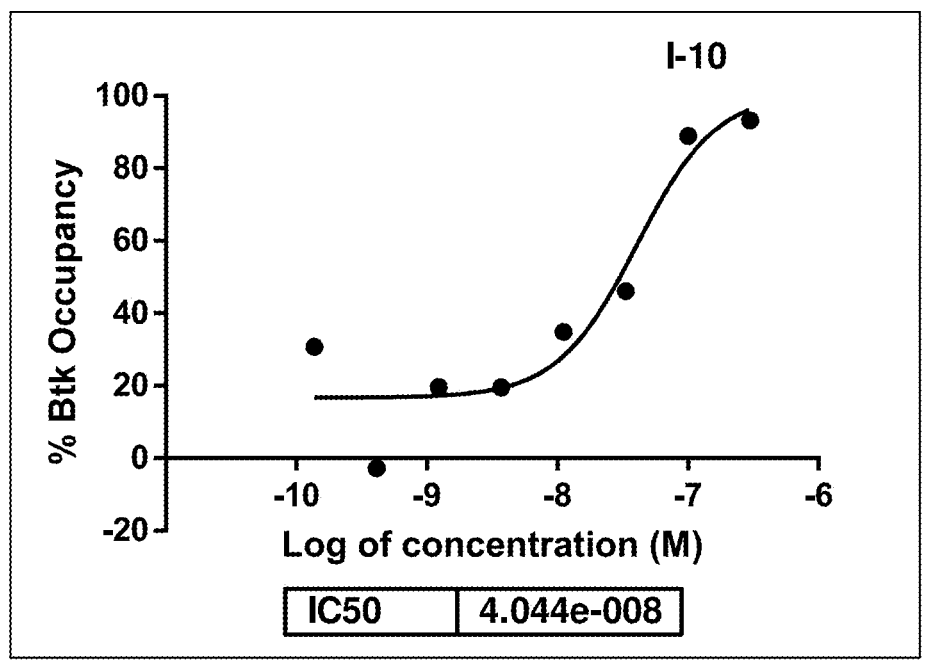
Figure 6E:
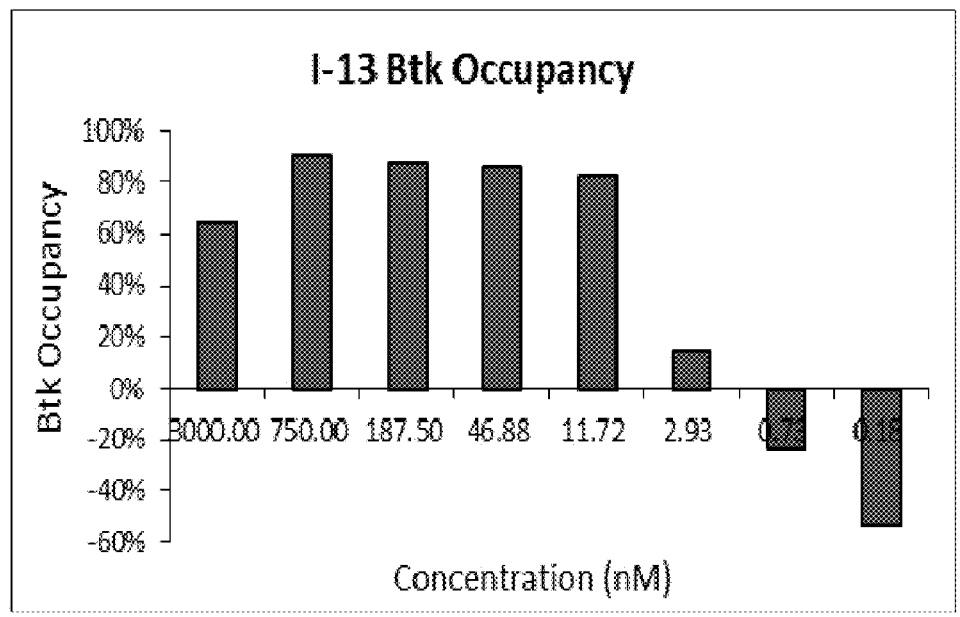
Figure 6F:
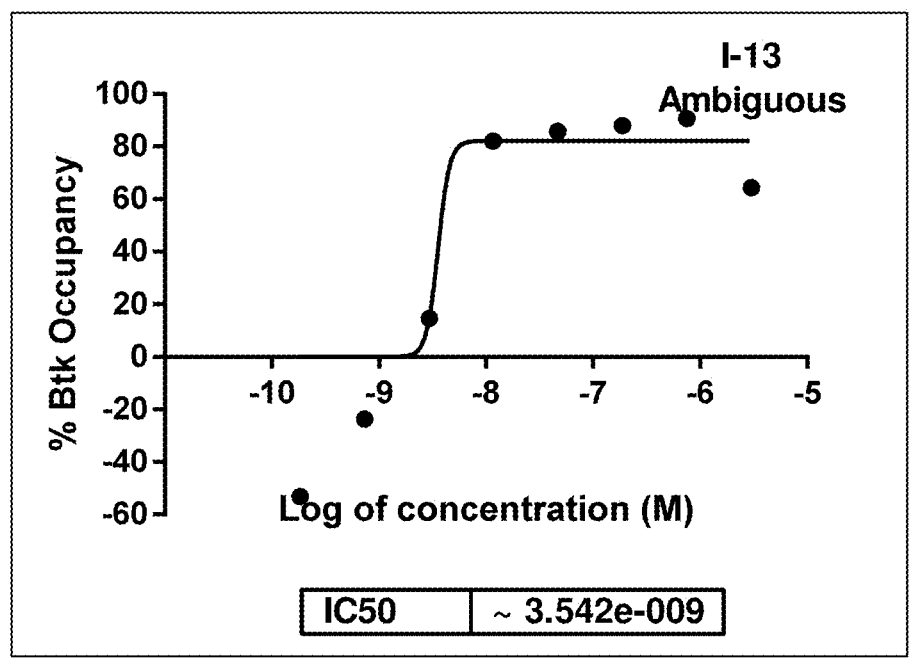
Figure 6G:
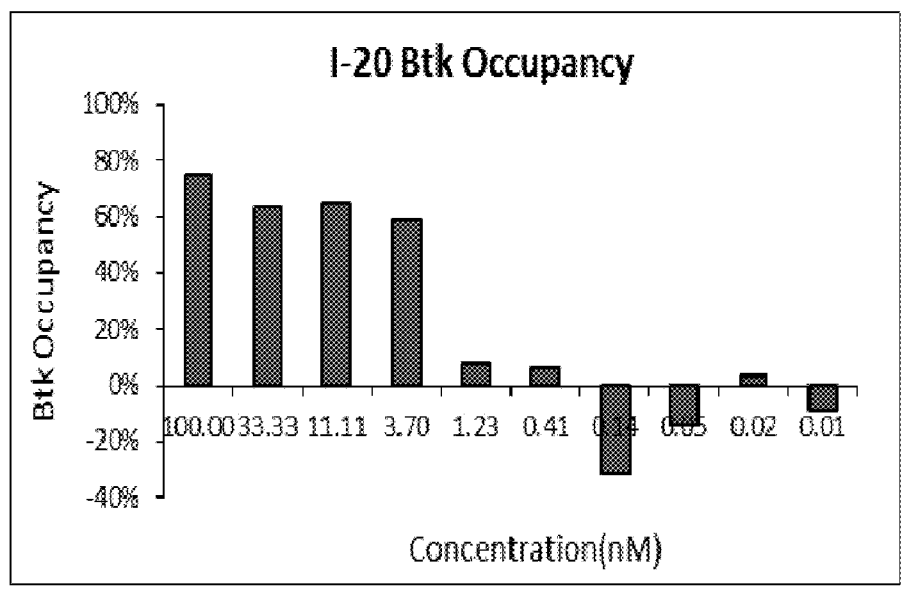
Figure 6H:
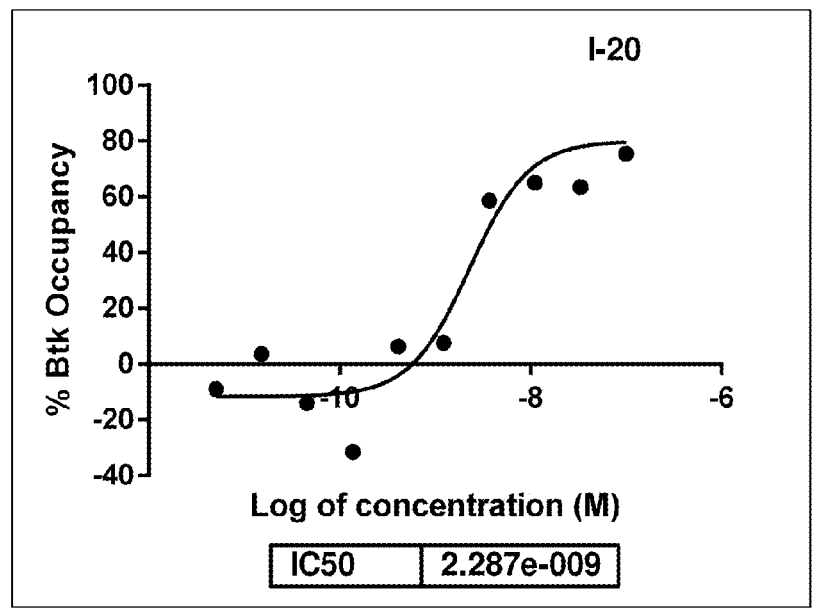
Figure 6I:
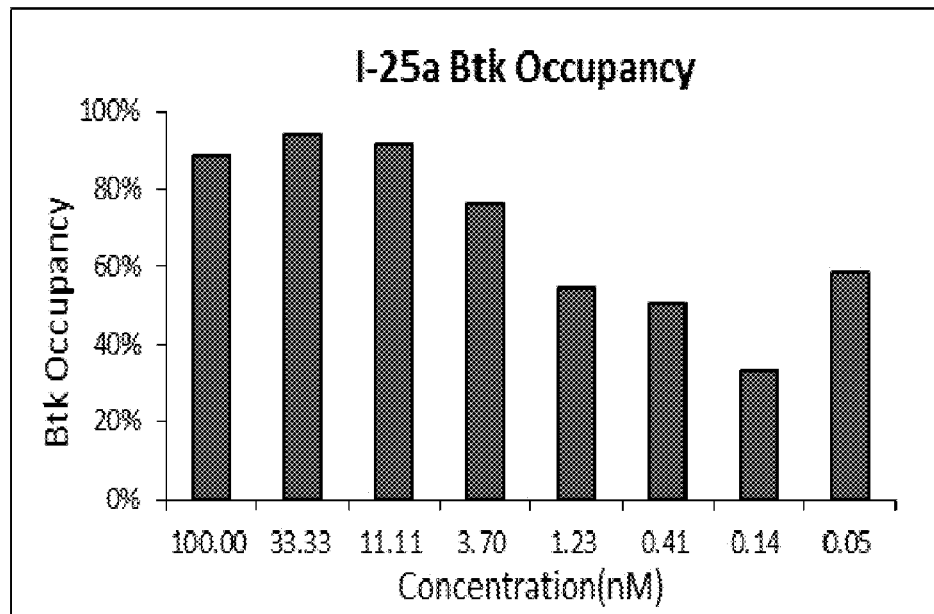
Figure 6J:
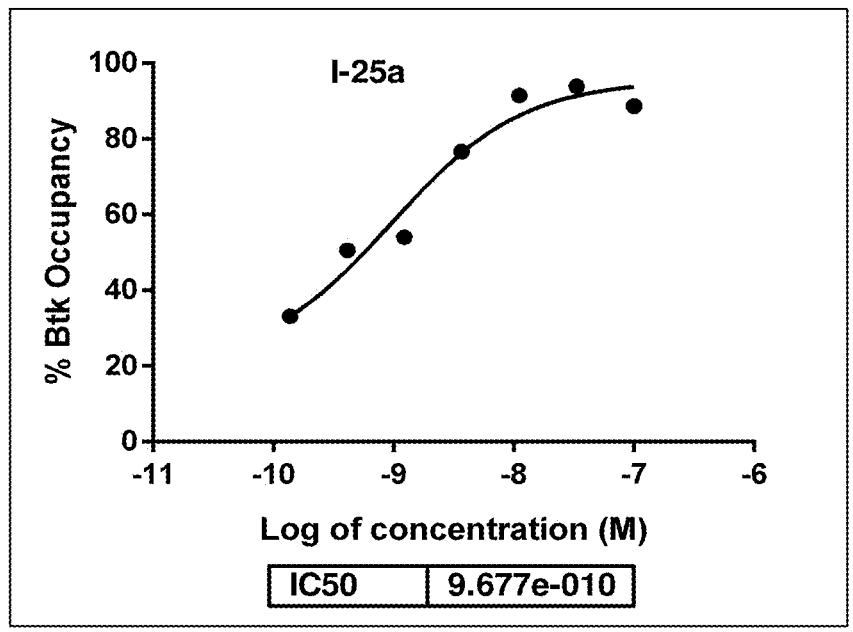
Figure 6K:
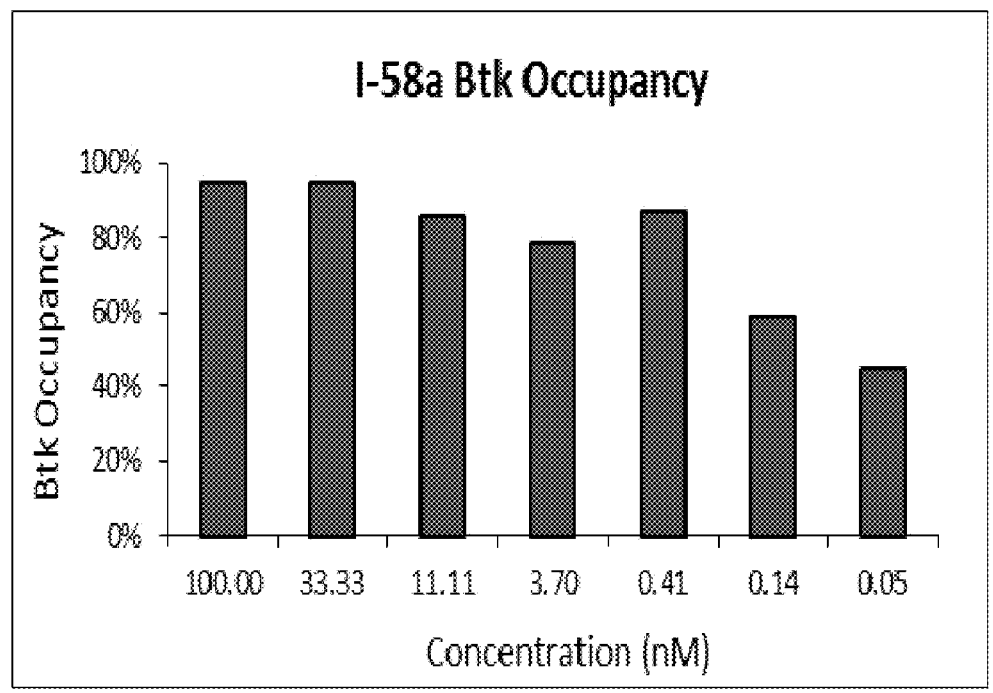
Figure 6L:
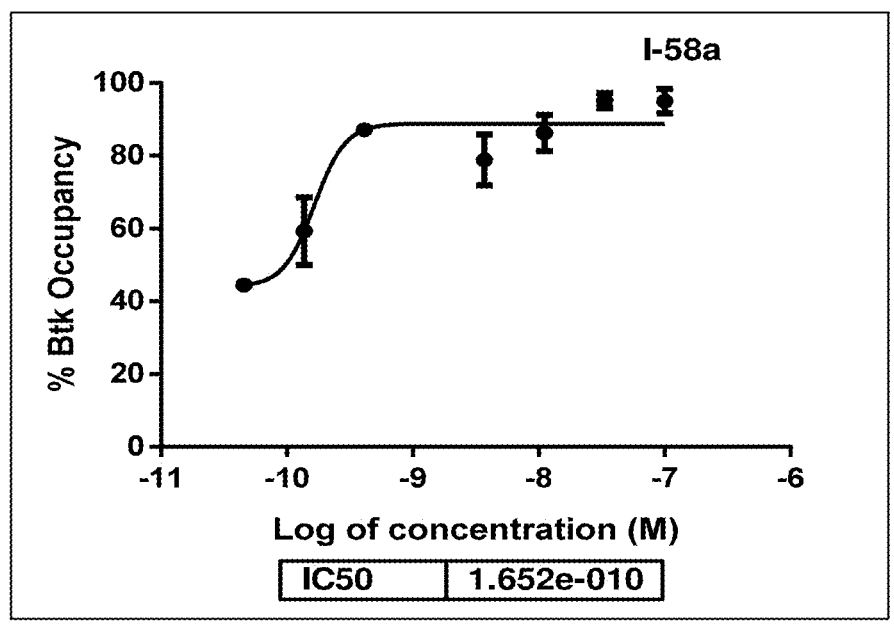

4. Pulse Chase Western Blotting Assay to Assess the Binding Property of Compounds As shown in FIGS. 5A and 5B, the result after compound I-1 and I-2 treated and removal, long term effect of the inhibition was observed after compounds removal up to 8 hours. This strong binding of the compound to the target enzyme indicates the strong binding of the compound I-1 and I-2, which was chemically designed to covalently bind Btk protein at the specific position.

As shown in FIGS. 5A and 5B, compounds I-1 and I-2 inhibited the Btk phosphorylation in Ramos cells after 8 hours of removal. Ramos cells were treated with Compound I-1 and Compound I-2 at 100 nM for 45 mins, and inhibition of Btk phosphorylation was monitored 4, 6 and 8 hrs post Compound I-1 and Compound I-2 removal. Btk remains inhibited up to 8 hrs after treatment with the covalent-bonded Compound I-1 and Compound I-2, indicating that Compound I-1 and Compound I-2 are strong irreversible inhibitors of Btk protein.

5. Btk Target Site Occupancy ELISA Assay

The Btk target site occupancy ELISA was used to detect free Btk protein from Romas cells treated with increasing concentrations of several compounds. Compounds dose-dependent occupancy of the Btk proteins correlates with their inhibitory activity of Btk kinase as shown in Table 6 below and in FIGS. 6A-6L.

TABLE 6

| Compound # | Btk Occupancy Assay (IC$_{50}$)<br>A: ≤10 nM<br>B: 10~100 nM<br>C: ≥100 nM |
|---|---|
| I-1 | A |
| I-10 | B |
| I-13 | A |
| I-20 | A |
| I-25a | A |
| I-58a | A |

The present invention is further illustrated by the following exemplary embodiments:

1. A compound of Formula (I):

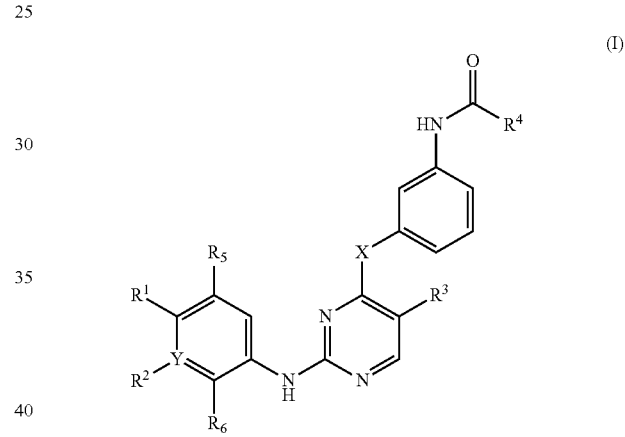

wherein
R$^1$ is H, or
NR$^c$R$^d$ wherein R$^c$ is H, C$_{1-4}$ alkyl or 3-7 member cyclic ring, and R$^d$ is H, C$_{1-4}$ alkyl, optionally substituted with OZ, wherein Z is H or C$_{1-4}$ alkyl; or
3-7 member cyclic ring substituted with R$^a$ wherein R$^a$ is C$_{1-8}$ alkyl optionally substituted with halo;
R$^2$ is H, halo, C$_{1-4}$ alkyl, or C$_{1-4}$ alkoxy;
R$^3$ is H, halo, C$_{1-4}$ alkyl, or C$_{1-4}$ alkoxy;
R$^5$ is H, halo, C$_{1-4}$ alkyl, or C$_{1-4}$ alkoxy;
R$^6$ is H, halo, C$_{1-4}$ alkyl, or C$_{1-4}$ alkoxy; or
R$^1$ and R$^5$ are part of 3-7 member cyclic ring, optionally substituted with C$_{1-4}$ alkyl substituted with OZ, wherein Z is H or C$_{1-4}$ alkyl; or
R$^1$ and R$^2$ are part of 3-7 member cyclic ring, optionally substituted with C$_{1-4}$ alkyl substituted with OZ, wherein Z is H or C$_{1-4}$ alkyl; or
R$^2$ and R$^6$ are part of 3-7 member cyclic ring, optionally substituted with C$_{1-4}$ alkyl substituted with OZ, wherein Z is H or C$_{1-4}$ alkyl; or
R$^4$ is C$_2$ alkenyl optionally substituted with C$_{1-4}$ alkyl, —CH$_2$OCH$_3$, or —CH$_2$N(CH$_3$)$_2$; and
X is O, C$_{1-4}$ alkyl optionally substituted with halo, or NR$^b$, wherein R$^b$ is H, or C$_{1-8}$ alkyl optionally substituted with halo, Y is CH optionally substituted with halo, or N,
wherein at least one of $R^2$, $R^3$, $R^5$ and $R^6$ is not H;
or a pharmaceutically acceptable salt thereof.

2. The compound of embodiment 1, wherein $R^1$ is H, and $R^2$ and $R^6$ are part of 3-7 member cyclic ring, optionally substituted with OZ, wherein Z is H or $C_{1-4}$ alkyl.

3. The compound of embodiment 1, wherein $R^1$ is $NR^cR^d$ and $R^c$ is methyl.

4. The compound of embodiment 1, wherein $R^1$ is $NR^cR^d$ and $R^c$ is 3-7 member cyclic ring.

5. The compound of embodiment 4, wherein the 3-7 member cyclic ring is $C_3$ cyclic ring.

6. The compound of any of embodiments 3-5, wherein $R^d$ is $C_2$ alkyl substituted with OZ, and Z is methyl.

7. The compound of embodiment 1, wherein $R^1$ is 3-7 member cyclic ring substituted with $R^a$.

8. The compound of embodiment 7, wherein $R^1$ is

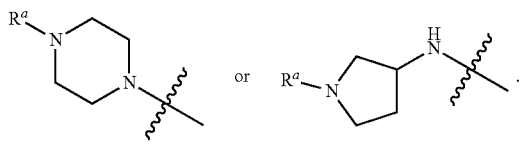

9. The compound of embodiment 8, wherein $R^1$ is

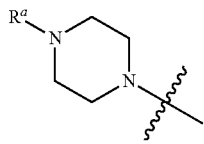

10. The compound of embodiment 9, wherein $R^a$ is $C_{1-4}$ alkyl optionally substituted with halo or $C_{1-4}$alkoxy.

11. The compound of embodiment 9 or 10, wherein $R^a$ is $C_{1-4}$ alkyl substituted with fluoro or $C_{1-8}$ alkyl substituted with fluoro.

12. The compound of embodiment 8, wherein $R^1$ is

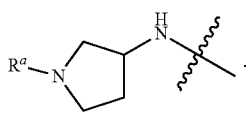

13. The compound of embodiment 12, wherein $R^a$ is $C_{1-4}$ alkyl optionally substituted with halo or $C_{1-4}$ alkoxy.

14. The compound of embodiment 12 or 13, wherein $R^a$ is $C_{1-4}$ alkyl substituted with fluoro or $C_{1-8}$ alkyl substituted with fluoro.

15. The compound of any of embodiments 1-14, wherein $R^2$ is H.

16. The compound of any of embodiments 1-14, wherein $R^2$ is halo.

17. The compound of any of embodiments 1-14, wherein $R^2$ is $C_{1-4}$ alkyl or $C_{1-4}$ alkoxy.

18. The compound of any of embodiments 1-14, wherein $R^5$ is H.

19. The compound of any of embodiments 1-14, wherein $R^5$ is halo.

20. The compound of any of claims 1-14, wherein $R^5$ is $C_{1-4}$ alkyl or $C_{1-4}$ alkoxy.

21. The compound of any of embodiments 1-14, wherein $R^6$ is H.

22. The compound of any of embodiments 1-14, wherein $R^6$ is halo.

23. The compound of any of embodiments 1-14, wherein $R^6$ is $C_{1-4}$ alkyl or $C_{1-4}$ alkoxy.

24. The compound of embodiment 1, wherein $R^1$ and $R^5$ are part of 3-7 member cyclic ring, optionally substituted with $C_{1-4}$ alkyl substituted with OZ, wherein Z is H or $C_{1-4}$ alkyl.

25. The compound of embodiment 1, wherein $R^1$ and $R^2$ are part of 3-7 member cyclic ring, optionally substituted with $C_{1-4}$ alkyl substituted with OZ, wherein Z is H or $C_{1-4}$ alkyl.

26. The compound of embodiment 1, wherein $R^2$ and $R^6$ are part of 3-7 member cyclic ring, optionally substituted with $C_{1-4}$ alkyl substituted with OZ, wherein Z is H or $C_{1-4}$ alkyl.

27. The compound of any of embodiments 24-26, wherein the 3-7 member cyclic ring is a 5 member cyclic ring.

28. The compound of embodiment 27, wherein the 5 member cyclic ring is heterocyclic ring.

29. The compound of embodiment 28, wherein the 5 member heterocyclic ring comprises a N atom.

30. The compound of any of embodiments 24-29, wherein the $C_{1-4}$ alkyl is $C_2$ alkyl.

31. The compound of embodiment 30, wherein Z is methyl.

32. The compound of any of embodiments 1-31, wherein $R^3$ is H.

33. The compound of any of embodiments 1-31, wherein $R^3$ is halo.

34. The compound of any of embodiments 1-31, wherein $R^3$ is $C_{1-4}$ alkyl or $C_{1-4}$ alkoxy.

35. The compound of any of embodiments 1-34, wherein $R^2$, $R^5$, or $R^6$ is H or halo and $R^3$ is halo, $C_{1-4}$ alkyl or $C_{1-4}$alkoxy.

36. The compound of any of embodiments 1-35, wherein $R^4$ is unsubstituted $C_2$ alkenyl.

37. The compound of any of embodiments 1-35, wherein $R^4$ is $C_2$ alkenyl substituted with $C_{1-4}$ alkyl, —$CH_2OCH_3$, or —$CH_2N(CH_3)_2$.

38. The compound of any of embodiments 1-37, wherein X is O.

39. The compound of any of embodiments 1-37, wherein X is $C_{1-4}$ alkyl optionally substituted with halo.

40. The compound of embodiment 39, wherein X is unsubstituted $C_{1-4}$ alkyl.

41. The compound of embodiment 40, wherein X is $CH_2$.

42. The compound of embodiment 39, wherein X is $C_{1-4}$ alkyl substituted with halo.

43. The compound of embodiment 42, wherein X is $CF_2$.

44. The compound of any of embodiments 1-37, wherein X is $NR^b$, and $R^b$ is H, or $C_{1-8}$ alkyl optionally substituted with halo.

45. The compound of embodiment 44, wherein $R^b$ is H.

46. The compound of embodiment 44, wherein $R^b$ is $C_{1-8}$ alkyl.

47. The compound of embodiment 46, wherein $R^b$ is $C_{1-4}$ alkyl.

48. The compound of embodiment 46 or 47, wherein $C_{1-4}$ alkyl or $C_{1-8}$ alkyl is substituted with halo.

49. The compound of any of embodiments 1-48, wherein Y is CH.

50. The compound of any of embodiments 1-48, wherein Y is CF or N.

51. The compound of embodiment 1, which is selected from the group consisting of compound I-1, I-2, I-3, I-4, I-5, I-6, I-7, I-8, I-9, I-12, I-13, I-14, I-15, I-16, I-17, I-18, I-19, I-20, I-21, I-22, I-23, I-24, I-25 and I-41.

52. A compound of Formula (II):

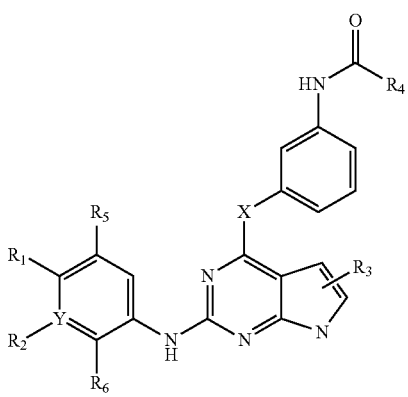

wherein
$R^1$ is H, or
$NR^cR^d$ wherein $R^c$ is H, $C_{1-4}$ alkyl or 3-7 member cyclic ring, and $R^d$ is H, $C_{1-4}$ alkyl, optionally substituted with OZ, wherein Z is H or $C_{1-4}$ alkyl; or
$NR^eR^f$ wherein $R^e$ is $C_{1-4}$ alkyl, and $R^f$ is 3-7 member cyclic ring optionally substituted with $C_{1-4}$ alkyl optionally substituted with halo; or
$OR^g$ wherein $R^g$ is $C_{1-4}$ alkyl substituted with $CH_3O—$, $CH_3CH_2O—$, $CH_3(O)_2S—$, $CF_3O—$,

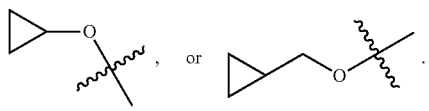 [SMILES: *OC1CC1 ; *OCC1CC1]

$R^2$ is H, halo, $C_{1-4}$ alkyl, or $C_{1-4}$ alkoxy;
$R^3$ is H, halo, $C_{1-4}$ alkyl, or $C_{1-4}$ alkoxy;
$R^5$ is H, halo, $C_{1-4}$ alkyl, or $C_{1-4}$ alkoxy;
$R^6$ is H, halo, $C_{1-4}$ alkyl, or $C_{1-4}$ alkoxy; or
$R^1$ and $R^5$ are part of 3-7 member cyclic ring, optionally substituted with $C_{1-4}$ alkyl substituted with OZ, wherein Z is H or $C_{1-4}$ alkyl; or
$R^1$ and $R^2$ are part of 3-7 member cyclic ring, optionally substituted with $C_{1-4}$ alkyl substituted with OZ, wherein Z is H or $C_{1-4}$ alkyl; or
$R^2$ and $R^6$ are part of 3-7 member cyclic ring, optionally substituted with $C_{1-4}$ alkyl substituted with OZ, wherein Z is H or $C_{1-4}$ alkyl; or
$R^4$ is $C_2$ alkenyl optionally substituted with $C_{1-4}$ alkyl, $—CH_2OCH_3$, or $—CH_2N(CH_3)_2$; and
X is O, $C_{1-4}$ alkyl optionally substituted with halo, or $NR^b$, wherein $R^b$ is H, or $C_{1-8}$ alkyl optionally substituted with halo,
Y is CH optionally substituted with halo, or N,
or a pharmaceutically acceptable salt thereof.
53. The compound of embodiment 52, wherein $R^1$ is H, and $R^2$ and $R^6$ are part of 3-7 member cyclic ring, optionally substituted with $C_{1-4}$ alkyl substituted with OZ, wherein Z is H or methyl.
54. The compound of embodiment 52, wherein $R^1$ is $NR^cR^d$ and $R^c$ is methyl.
55. The compound of embodiment 52, wherein $R^1$ is $NR^cR^d$ and $R^c$ is 3-7 member cyclic ring.
56. The compound of embodiment 55, wherein the 3-7 member cyclic ring is $C_3$ cyclic ring.
57. The compound of any of embodiments 54-56, wherein $R^d$ is $C_2$ alkyl substituted with OZ, and Z is methyl.
58. The compound of embodiment 52, wherein $R^1$ is $NR^eR^f$, $R^e$ is $C_{1-4}$ alkyl, and $R^f$ is 3-7 member cyclic ring optionally substituted with $C_{1-4}$ alkyl optionally substituted with halo.
59. The compound of embodiment 58, wherein the 3-7 member cyclic ring is 5 member cyclic ring.
60. The compound of embodiment 59, wherein the 5 member cyclic ring is heterocyclic ring.
61. The compound of embodiment 60, wherein the 5 member heterocyclic ring comprises a N atom.
62. The compound of any of embodiments 58-61, wherein the 3-7 member cyclic ring is substituted with $FCH_2CH_2—$.
63. The compound of embodiment 52, wherein $R^1$ is $OR^g$ and $R^g$ is $C_{1-4}$ alkyl substituted with $CH_3O—$, $CH_3CH_2O—$, $CH_3(O)_2S—$, $CF_3O—$,

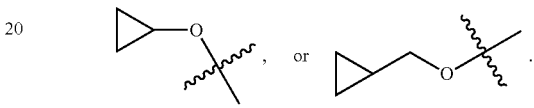

64. The compound of embodiment 63, wherein the $C_{1-4}$ alkyl is $C_2$ alkyl.
65. The compound of any of embodiments 52-64, wherein $R^2$ is H.
66. The compound of any of embodiments 52-64, wherein $R^2$ is halo.
67. The compound of any of embodiments 52-64, wherein $R^2$ is $C_{1-4}$ alkyl or $C_{1-4}$ alkoxy.
68. The compound of any of embodiments 52-64, wherein $R^5$ is H.
69. The compound of any of embodiments 52-64, wherein $R^5$ is halo.
70. The compound of any of embodiments 52-64, wherein $R^5$ is $C_{1-4}$ alkyl or $C_{1-4}$ alkoxy.
71. The compound of any of embodiments 52-64, wherein $R^6$ is H.
72. The compound of any of embodiments 52-64, wherein $R^6$ is halo.
73. The compound of any of embodiments 52-64, wherein $R^6$ is $C_{1-4}$ alkyl or $C_{1-4}$ alkoxy.
74. The compound of embodiment 52, wherein $R^1$ and $R^5$ are part of 3-7 member cyclic ring, optionally substituted with $C_{1-4}$ alkyl substituted with OZ, wherein Z is H or $C_{1-4}$ alkyl.
75. The compound of embodiment 52, wherein $R^1$ and $R^2$ are part of 3-7 member cyclic ring, optionally substituted with $C_{1-4}$ alkyl substituted with OZ, wherein Z is H or $C_{1-4}$ alkyl.
76. The compound of embodiment 52, wherein $R^2$ and $R^6$ are part of 3-7 member cyclic ring, optionally substituted with $C_{1-4}$ alkyl substituted with OZ, wherein Z is H or $C_{1-4}$ alkyl.
77. The compound of any of embodiments 74-76, wherein the 3-7 member cyclic ring is a 5 member cyclic ring.
78. The compound of embodiment 77, wherein the 5 member cyclic ring is heterocyclic ring.
79. The compound of embodiment 78, wherein the 5 member heterocyclic ring comprises a N atom.
80. The compound of any of embodiments 74-79, wherein the $C_{1-4}$ alkyl is $C_2$ alkyl.
81. The compound of embodiment 80, wherein Z is methyl.
82. The compound of any of embodiments 52-81, wherein $R^3$ is H.
83. The compound of any of embodiments 52-81, wherein $R^3$ is halo.

84. The compound of any of embodiments 52-81, wherein $R^3$ is $C_{1-4}$ alkyl or $C_{1-4}$ alkoxy.
85. The compound of any of embodiments 52-84, wherein $R^2$, $R^5$, or $R^6$ is H or halo and $R^3$ is halo, $C_{1-4}$ alkyl or $C_{1-4}$ alkoxy.
86. The compound of any of embodiments 52-85, wherein $R^4$ is unsubstituted $C_2$ alkenyl.
87. The compound of any of embodiments 52-85, wherein $R^4$ is $C_2$ alkenyl substituted with $C_{1-4}$ alkyl, —$CH_2OCH_3$, or —$CH_2N(CH_3)_2$.
88. The compound of any of embodiments 52-87, wherein X is O.
89. The compound of any of embodiments 52-87, wherein X is $C_{1-4}$ alkyl optionally substituted with halo.
90. The compound of embodiment 89, wherein X is unsubstituted $C_{1-4}$ alkyl.
91. The compound of embodiment 90, wherein X is $CH_2$.
92. The compound of embodiment 89, wherein X is $C_{1-4}$ alkyl substituted with halo.
93. The compound of embodiment 92, wherein X is $CF_2$.
94. The compound of any of embodiments 52-87, wherein X is $NR^b$, and $R^b$ is H, or $C_{1-8}$ alkyl optionally substituted with halo.
95. The compound of embodiment 94, wherein $R^b$ is H.
96. The compound of embodiment 94, wherein $R^b$ is $C_{1-8}$ alkyl.
97. The compound of embodiment 96, wherein $R^b$ is $C_{1-4}$ alkyl.
98. The compound of embodiment 96 or 97, wherein $C_{1-4}$ alkyl or $C_{1-8}$ alkyl is substituted with halo.
99. The compound of any of embodiments 52-98, wherein Y is CH.
100. The compound of any of embodiments 52-98, wherein Y is CF.
101. The compound of any of embodiments 52-98, wherein Y is N.
102. The compound of embodiment 52, wherein $R^1$ is $OR^g$ wherein $R^g$ is $C_{1-4}$ alkyl substituted with $CH_3O$—, $CH_3CH_2O$—, $CH_3(O)_2S$—, $CF_3O$—,

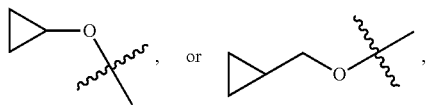 [SMILES: *OC1CC1 ; *OCC1CC1]

and $R^2$, $R^3$, $R^5$ and $R^6$ are H.
103. The compound of embodiment 102, wherein $R^g$ is $C_2$ alkyl substituted with $CH_3O$—.
104. The compound of any of embodiments 52-103, wherein at least one of $R^1$, $R^2$, $R^3$, $R^5$ and $R^6$ is not H.
105. The compound of embodiment 52, which is selected from the group consisting of compound I-10, I-11, I-26, I-27, I-28, I-29, I-30, I-31, I-32, I-33, I-34, I-35, I-36, I-37, I-38, I-39, and I-40.
106. A pharmaceutical composition comprising a compound of any of embodiments 1-105 admixed with at least one pharmaceutically acceptable carrier or excipient.
107. A compound according to any of embodiments 1-105 for use in therapy.
108. A method for treating and/or preventing a proliferation disorder, a cancer, a tumor, an inflammatory disease, an autoimmune disease, psoriasis, dry eye or an immunologically related disease, which comprises administering to a subject in need thereof an effective amount of a compound of any of embodiments 1-105 or a pharmaceutical composition of embodiment 106.
109. Use of a compound according to any of embodiments 1-105 for the manufacture of a medicament.
110. A combination for treating and/or preventing a proliferation disorder, a cancer, a tumor, an inflammatory disease, an autoimmune disease, psoriasis, dry eye or an immunologically related disease in a subject, which combination comprises an effective amount of a compound of any of embodiments 1-105, or a pharmaceutically acceptable salt thereof, and an effective amount of a second prophylactic or therapeutic agent for treating and/or preventing a proliferation disorder, a cancer, a tumor, an inflammatory disease, an autoimmune disease, psoriasis, dry eye or an immunologically related disease in a subject.
111. A method for treating and/or preventing a proliferation disorder, a cancer, a tumor, an inflammatory disease, an autoimmune disease, psoriasis, dry eye or an immunologically related disease in a subject, which methods comprises administering to a subject in need thereof an effective amount of the combination of embodiment 110.
112. A method for inhibiting an activity of a Bruton's tyrosine kinase (Btk or BTK) or a Janus kinase (JAK) in a cell or subject, which methods comprises administering to a cell or subject in need thereof an effective amount of a compound of any of embodiments 1-105, or a pharmaceutical composition of claim 106, or a combination of embodiment 110.
113. The method of embodiment 112, wherein the JAK is JAK1, JAK2 or JAK3.
114. The method of embodiment 112 or 113, which is used for treating and/or preventing a proliferation disorder, a cancer, a tumor, an inflammatory disease, an autoimmune disease, psoriasis, dry eye or an immunologically related disease in the subject.
115. The method of embodiment 114, wherein the proliferation disorder is selected from the group consisting of sarcoma, epidermoid cancer, fibrosarcoma, cervical cancer, gastric carcinoma, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancers, and pancreatic cancer.
116. The method of any of embodiments 112-115, wherein the compound is selected from the group consisting of compound I-1, I-2, I-3, I-4, I-5, I-6, I-7, I-8, I-9, I-10, I-11, I-12, I-13, I-14, I-15, I-16, I-17, I-18, I-19, I-20, I-21, I-22, I-23, I-24, I-25, I-26, I-27, I-28, I-29, I-30, I-31, I-32, I-33, I-34, I-35, I-36, I-37, I-38, I-39, I-40, and I-41.
117. A compound of Formula (III):

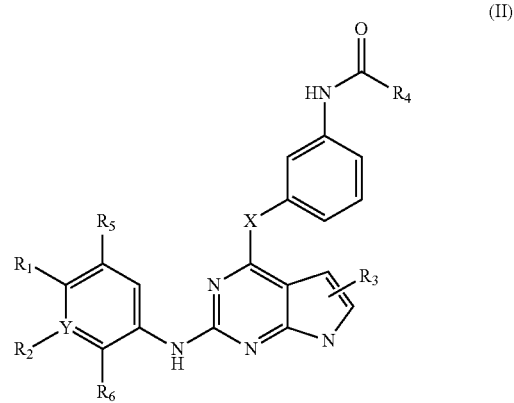

wherein
R¹ is

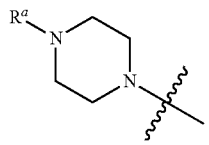

wherein $R^a$ is CO—$C_{1-4}$ alkyl-CONH—($C_{1-4}$ alkyl-O)$_m$—$C_{1-4}$ alkyl-NH-(Detectable Label), m being an integer 1-4;
$R^2$ is H, halo, $C_{1-4}$ alkyl, or $C_{1-4}$ alkoxy;
$R^3$ is H, halo, $C_{1-4}$ alkyl, or $C_{1-4}$ alkoxy;
$R^5$ is H, halo, $C_{1-4}$ alkyl, or $C_{1-4}$alkoxy;
$R^6$ is H, halo, $C_{1-4}$ alkyl, or $C_{1-4}$alkoxy; or
$R^1$ and $R^5$ are part of 3-7 member cyclic ring, optionally substituted with $C_{1-4}$ alkyl substituted with OZ, wherein Z is H or $C_{1-4}$alkyl; or
$R^1$ and $R^2$ are part of 3-7 member cyclic ring, optionally substituted with $C_{1-4}$ alkyl substituted with OZ, wherein Z is H or $C_{1-4}$alkyl; or
$R^2$ and $R^6$ are part of 3-7 member cyclic ring, optionally substituted with $C_{1-4}$ alkyl substituted with OZ, wherein Z is H or $C_{1-4}$alkyl; or
$R^4$ is $C_2$ alkenyl optionally substituted with $C_{1-4}$ alkyl, —$CH_2OCH_3$, or —$CH_2N(CH_3)_2$; and
X is O, $C_{1-4}$ alkyl optionally substituted with halo, or $NR^b$, wherein $R^b$ is H, or $C_{1-8}$ alkyl optionally substituted with halo,
Y is CH optionally substituted with halo, or N,
or a pharmaceutically acceptable salt thereof.
118. The compound of embodiment 117, wherein in $R^a$ $C_{1-4}$ alkyl is $C_2$ alkyl.
119. The compound of embodiment 117 or 118, wherein m is 3.
120. The compound of any of embodiments 117-119, wherein the Detectable Label is biotin.
121. The compound of embodiment 117, which is compound I-42.
122. A compound according to any of embodiments 117-121 for use in testing.

The present invention is further illustrated by the following exemplary embodiments:
1a. A compound of Formula (Ia):

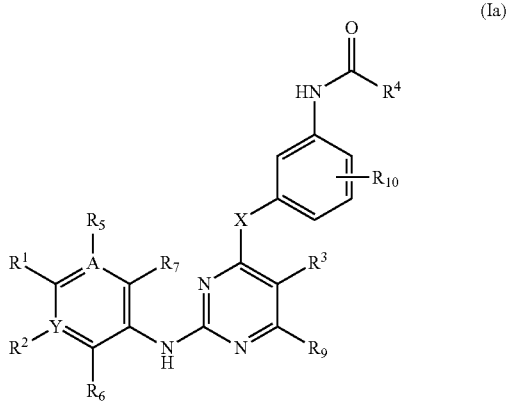

wherein
$R^1$ is H, or
$NR^cR^d$ wherein
$R^c$ is H, $C_{1-4}$ alkyl, $C_{1-4}$alkenyl, or 3-7 member cyclic ring, said $C_{1-4}$ alkyl, $C_{1-4}$alkenyl, or 3-7 member cyclic ring being optionally substituted with OZ or $NR_{11}R_{12}$, wherein Z, $R_{11}$, $R_{12}$ are independently H or $C_{1-4}$ alkyl, or said 3-7 member cyclic ring being optionally substituted with $C_{1-4}$ alkyl that is further optionally substituted with OZ or $NR_{11}R_{12}$, wherein Z, $R_{11}$, $R_{12}$ are independently H or $C_{1-4}$ alkyl, or said 3-7 member cyclic ring being optionally substituted with $SO_2(CH_2)_q$ H, wherein q is 1-4, or said 3-7 member cyclic ring being optionally substituted with $C_{1-4}$ alkyl that is further optionally substituted with $SO_2(CH_2)_q$H, wherein q is 1-4, or said 3-7 member cyclic ring being optionally substituted with $R_8CO$, wherein $R_8$ is $C_{1-4}$ alkyl, and
$R^d$ is H, $C_{1-4}$ alkyl, $C_{1-4}$alkenyl, or 3-7 member cyclic ring, said $C_{1-4}$ alkyl, $C_{1-4}$alkenyl or 3-7 member cyclic ring being optionally substituted with OZ or $NR_{11}R_{12}$, wherein Z, $R_{11}$, $R_{12}$ are independently H or $C_{1-4}$ alkyl; or
3-7 member cyclic ring substituted with $R^a$ wherein $R^a$ is $C_{1-8}$ alkyl optionally substituted with halo, $C_{1-4}$ alkoxy or $SO_2(CH_2)_q$H, wherein q is 1-4; or
$O(CH_2)_mSO_2$ $(CH_2)_n$H, wherein m is 1-4 and n is 1-4;
$R^2$ is absent, H, halo, $C_{1-4}$ alkyl, $C_{1-4}$alkoxy, or alkylamine ($NR_{11}R_{12}$), wherein $R_{11}$ and $R_{12}$ are independently H or $C_{1-4}$ alkyl;
$R^3$ is H, hydroxyl, halo, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl;
$R^5$ is absent, H, halo, $C_{1-4}$ alkyl, $C_{1-4}$alkoxy, or alkylamine ($NR_{11}R_{12}$), wherein $R_{11}$ and $R_{12}$ are independently H or $C_{1-4}$ alkyl;
$R^6$ is H, halo, $C_{1-4}$ alkyl, $C_{1-4}$ alkoxy; or alkylamine ($NR_{11}R_{12}$), wherein $R_{11}$ and $R_{12}$ are independently H or $C_{1-4}$ alkyl;
$R^7$ is H, halo, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl;
$R^9$ is H, hydroxyl, halo, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl;
$R^{10}$ is H, hydroxyl, halo, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl; or
$R^1$ and $R^5$ are part of 3-7 member cyclic ring, said 3-7 member cyclic being optionally substituted with $C_{1-4}$ alkyl optionally substituted with OZ or $NR_{11}R_{12}$ wherein Z, $R_{11}$ and $R_{12}$ are independently H or $C_{1-4}$ alkyl, or said 3-7 member cyclic being optionally substituted with $R_8CO$, wherein $R_8$ is $C_{1-4}$ alkyl, or said 3-7 member cyclic being optionally substituted with $SO_2(CH_2)_q$H, wherein q is 1-4; or
$R^1$ and $R^2$ are part of 3-7 member cyclic ring, optionally substituted with $C_{1-4}$ alkyl, said $C_{1-4}$ alkyl further optionally substituted with halo, OZ, or $NR_{11}R_{12}$ wherein Z, $R_{11}$ and $R_{12}$ are independently H or $C_{1-4}$ alkyl, or one or more members of said 3-7 member cyclic ring is optionally part of a carbonyl group or a sulfonyl group; or
$R^2$ and $R^6$ are part of 3-7 member cyclic ring, optionally substituted with $C_{1-4}$ alkyl optionally substituted with OZ or $NR_{11}R_{12}$ wherein Z, $R_{11}$ and $R_{12}$ are independently H or $C_{1-4}$ alkyl;

$R^4$ is $C_2$ alkenyl optionally substituted with $C_{1-4}$ alkyl, —$CH_2OCH_3$, or —$CH_2N(CH_3)_2$;

X is O, $C_{1-4}$ alkyl optionally substituted with halo, or $NR^b$, wherein $R^b$ is H, or $C_{1-8}$ alkyl optionally substituted with halo;

Y is C, CH optionally substituted with halo, or N;

A is C, CH optionally substituted with halo or N; and wherein at least one of $R^2$, $R^3$, $R^5$ and $R^6$ is not H;

or a pharmaceutically acceptable salt thereof.

2a. The compound of embodiment 1 a, wherein R is H, and $R^2$ and $R^6$ are part of 3-7 member cyclic ring, optionally substituted with $C_{1-4}$ alkyl substituted with OZ or $NR_{11}R_{12}$ wherein Z, $R_{11}$ and $R_{12}$ are independently H or $C_{1-4}$ alkyl.

3a. The compound of embodiment 1 a, wherein $R^1$ is $NR^cR^d$ and $R^c$ is H.

4a. The compound of embodiment 1 a, wherein $R^1$ is $NR^cR^d$ and $R^c$ is $C_{1-4}$ alkyl, e.g., methyl, optionally substituted with OZ or $NR_{11}R_{12}$, wherein Z, $R_{11}$, $R_{12}$ are independently H or $C_{1-4}$ alkyl.

5 a. The compound of embodiment 1 a, wherein $R^1$ is $NR^cR^d$ and $R^c$ is $C_{1-4}$alkenyl, optionally substituted with OZ or $NR_{11}R_{12}$, wherein Z, $R_{11}$, $R_{12}$ are independently H or $C_{1-4}$ alkyl.

6 a. The compound of embodiment 1 a, wherein $R^1$ is $NR^cR^d$ and $R^c$ is 3-7 member cyclic ring, optionally substituted with OZ or $NR_{11}R_{12}$, wherein Z, $R_{11}$, $R_{12}$ are independently H or $C_{1-4}$ alkyl.

7 a. The compound of embodiment 1 a, wherein $R^1$ is $NR^cR^d$ and $R^c$ is 3-7 member cyclic ring being optionally substituted with $C_{1-4}$ alkyl that is further optionally substituted with OZ or $NR_{11}R_{12}$, wherein Z, $R_{11}$, $R_{12}$ are independently H or $C_{1-4}$ alkyl.

8 a. The compound of embodiment 1 a, wherein $R^1$ is $NR^cR^d$ and $R^c$ is 3-7 member cyclic ring being optionally substituted with $SO_2(CH_2)_qH$, wherein q is 1-4.

9 a. The compound of embodiment 8 a, wherein the 3-7 member cyclic ring is a 5 member cyclic ring that comprises a N atom, the H linked to the N atom is substituted with $SO_2(CH_2)_qH$, wherein q is 1-4.

10 a. The compound of embodiment 9 a, wherein q is 1.

11 a. The compound of embodiment 1 a, wherein $R^1$ is $NR^cR^d$ and $R^c$ is 3-7 member cyclic ring being optionally substituted with $C_{1-4}$ alkyl that is further optionally substituted with $SO_2(CH_2)_qH$, wherein q is 1-4.

12 a. The compound of embodiment 11 a, wherein the 3-7 member cyclic ring is a 5 member cyclic ring that comprises a N atom, the H linked to the N atom is substituted with $C_{1-4}$ alkyl that is further substituted with $SO_2(CH_2)_qH$, wherein q is 1-4.

13 a. The compound of embodiment 12 a, wherein the H linked to the N atom is substituted with $C_2$ alkyl that is further substituted with $SO_2CH_3$.

14 a. The compound of embodiment 1 a, wherein $R^1$ is $NR^cR^d$ and $R^c$ is 3-7 member cyclic ring being optionally substituted with $R_8CO$, wherein $R_8$ is $C_{1-4}$ alkyl.

15 a. The compound of embodiment 14 a, wherein $R^1$ is $NR^cR^d$ and $R^c$ is a 5 member cyclic ring that comprises a N atom, the H linked to the N atom is substituted with $R_8CO$, wherein $R_8$ is $C_{1-4}$ alkyl.

16 a. The compound of embodiment 15 a, wherein the H linked to the N atom is substituted with $CH_3CO$.

17 a. The compound of any of embodiments 3-16 a, wherein $R^d$ is H.

18 a. The compound of any of embodiments 3-16 a, wherein $R^d$ is $C_{1-4}$ alkyl, optionally substituted with OZ or $NR_{11}R_{12}$, wherein Z, $R_{11}$, $R_{12}$ are independently H or $C_{1-4}$ alkyl.

19 a. The compound of any of embodiments 3-16 a, wherein $R^d$ is $C_{1-4}$ alkenyl, optionally substituted with OZ or $NR_{11}R_{12}$, wherein Z, $R_{11}$, $R_{12}$ are independently H or $C_{1-4}$ alkyl.

20 a. The compound of any of embodiments 3-16 a, wherein $R^d$ is 3-7 member cyclic ring, optionally substituted with OZ or $NR_{11}R_{12}$, wherein Z, $R_{11}$, $R_{12}$ are independently H or $C_{1-4}$ alkyl.

21 a. The compound of embodiment 20 a, wherein $R^c$ is a 5 member cyclic ring that comprises a N atom, the H linked to the N atom is substituted with $C_{1-4}$ alkyl that is further substituted with OZ, wherein Z is independently $C_{1-4}$ alkyl, and $R^d$ is 3-7 member cyclic ring, e.g., $C_3$ cyclic ring.

22 a. The compound of embodiment 1 a, wherein $R^1$ is 3-7 member cyclic ring substituted with $R^a$ wherein $R^a$ is $C_{1-8}$ alkyl optionally substituted with halo, $C_{1-4}$alkoxy or $SO_2(CH_2)_qH$, wherein q is 1-4.

23 a. The compound of embodiment 22 a, wherein the 3-7 member cyclic ring comprises a N atom.

24 a. The compound of embodiment 23 a, wherein the H linked to the N atom is substituted with halo, $C_{1-4}$ alkoxy or $SO_2(CH_2)_qH$, wherein q is 1-4.

25 a. The compound of any of embodiments 22-24 a, wherein $R^1$ is selected from the group consisting of

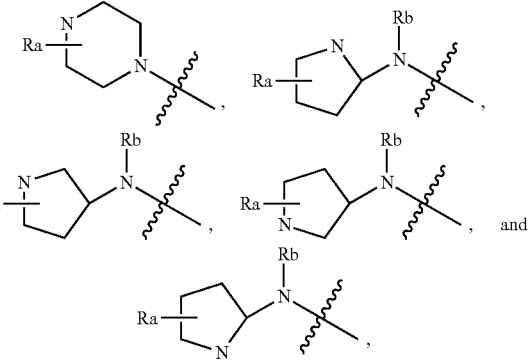

$R^a$ is $C_{1-8}$ alkyl optionally substituted with halo, $C_{1-4}$ alkoxy or $SO_2(CH_2)_qH$, wherein q is 1-4, and $R^b$ is H or $C_{1-8}$ alkyl optionally substituted with halo, $C_{1-4}$ alkoxy or $SO_2(CH_2)_qH$, wherein q is 1-4.

26 a. The compound of embodiment 25 a, wherein $R^1$ is selected from the group consisting of

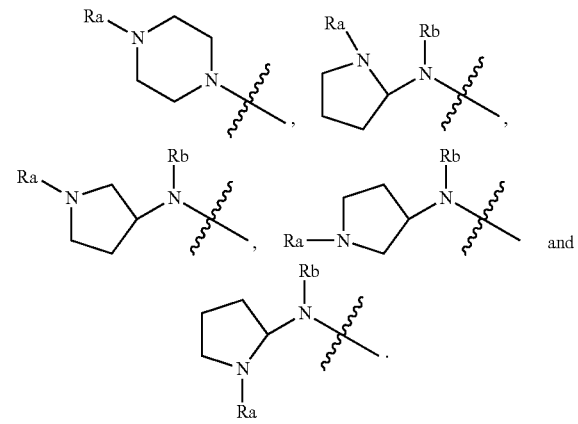

27 a. The compound of embodiment 26 a, wherein $R^1$ is

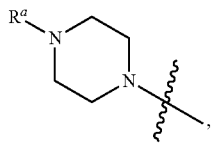

and $R^a$ is $C_2$ alkyl further substituted with methoxy.

28 a. The compound of embodiment 26 a, wherein $R^1$ is

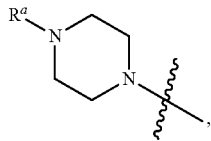

and $R^a$ is $C_2$ alkyl further substituted with $SO_2CH_3$.

29 a. The compound of embodiment 1 a, wherein $R^1$ is $O(CH_2)_mSO_2(CH_2)_nH$, wherein m is 1-4 and n is 1-4.

30 a. The compound of embodiment 29 a, wherein $R^1$ is $O(CH_2)_2SO_2CH_3$.

31 a. The compound of any of embodiments 1 a and 3-30 a, wherein $R^2$ is H or halo.

32 a. The compound of any of embodiments 1 a and 3-30 a, wherein $R^2$ is $C_{1-4}$ alkyl or $C_{1-4}$ alkoxy.

33 a. The compound of any of embodiments 1 a and 3-30 a, wherein $R^2$ is alkylamine ($NR_{11}R_{12}$), and $R_{11}$ and $R_{12}$ are independently H or $C_{1-4}$ alkyl.

34 a. The compound of any of embodiments 1-33 a, wherein $R^3$ is H.

35 a. The compound of any of embodiments 1-33 a, wherein $R^3$ is hydroxyl.

36 a. The compound of embodiment 35 a, wherein $R^1$ is

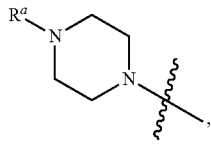

and $R^a$ is $C_{1-8}$ alkyl optionally substituted with halo, $C_{1-4}$alkoxy or $SO_2(CH_2)_qH$, wherein q is 1-4.

37 a. The compound of any of embodiments 1-33 a, wherein $R^3$ is halo.

38 a. The compound of any of embodiments 1-33 a, wherein $R^3$ is $C_{1-4}$ alkyl.

39 a. The compound of any of embodiments 1-33 a, wherein $R^3$ is $C_{1-4}$alkoxy.

40 a. The compound of any of embodiments 1-33 a, wherein $R^3$ is alkylamine ($NR_{11}R_{12}$), wherein $R_{11}$ and $R_{12}$ are independently H or $C_{1-4}$ alkyl.

41 a. The compound of any of embodiments 1-40 a, wherein $R^5$ is H.

42 a. The compound of any of embodiments 1-40 a, wherein $R^5$ is halo.

43 a. The compound of any of embodiments 1-40 a, wherein $R^5$ is $C_{1-4}$ alkyl.

44 a. The compound of any of embodiments 1-40 a, wherein $R^5$ is $C_{1-4}$alkoxy.

45 a. The compound of any of embodiments 1-40 a, wherein $R^5$ is alkylamine ($NR_{11}R_{12}$), wherein $R_{11}$ and $R_{12}$ are independently H or $C_{1-4}$ alkyl.

46 a. The compound of any of embodiments 1 a and 3-45 a, wherein $R^6$ is H.

47 a. The compound of any of embodiments 1 a and 3-45 a, wherein $R^6$ is halo.

48 a. The compound of any of embodiments 1 a and 3-45 a, wherein $R^6$ is $C_{1-4}$ alkyl.

49 a. The compound of any of embodiments 1 a and 3-45 a, wherein $R^6$ is $C_{1-4}$ alkoxy.

50 a. The compound of any of embodiments 1 a and 3-45 a, wherein $R^6$ is alkylamine ($NR_{11}R_{12}$), wherein $R_{11}$ and $R_{12}$ are independently H or $C_{1-4}$ alkyl.

51 a. The compound of any of embodiments 1-50 a, wherein $R^7$ is H.

52 a. The compound of any of embodiments 1-50 a, wherein $R^7$ is halo.

53 a. The compound of any of embodiments 1-50 a, wherein $R^7$ is $C_{1-4}$ alkyl.

54 a. The compound of any of embodiments 1-50 a, wherein $R^7$ is $C_{1-4}$alkoxy.

55 a. The compound of embodiment 54 a, wherein $R^7$ is methoxy.

56 a. The compound of any of embodiments 1-50 a, wherein $R^7$ is alkylamine ($NR_{11}R_{12}$), wherein $R_{11}$ and $R_{12}$ are independently H or $C_{1-4}$ alkyl.

57 a. The compound of any of embodiments 1-56 a, wherein $R^9$ is H.

58 a. The compound of any of embodiments 1-56 a, wherein $R^9$ is hydroxyl.

59 a. The compound of any of embodiments 1-56 a, wherein $R^9$ is halo.

60 a. The compound of any of embodiments 1-56 a, wherein $R^9$ is $C_{1-4}$ alkyl.

61 a. The compound of any of embodiments 1-56 a, wherein $R^9$ is $C_{1-4}$alkoxy.

62 a. The compound of any of embodiments 1-56 a, wherein $R^9$ is $C_{1-4}$alkylamine ($NR_{11}R_{12}$), wherein $R_{11}$ and $R_{12}$ are independently H or $C_{1-4}$ alkyl.

63 a. The compound of any of embodiments 1-62 a, wherein $R^{10}$ is H.

64 a. The compound of any of embodiments 1-62 a, wherein $R^{10}$ is hydroxyl.

65 a. The compound of any of embodiments 1-62, a wherein $R^{10}$ is halo.

66 a. The compound of any of embodiments 1-62 a, wherein $R^{10}$ is $C_{1-4}$ alkyl.

67. The compound of any of embodiments 1-62 a, wherein $R^{10}$ is $C_{1-4}$ alkoxy.

68 a. The compound of any of embodiments 1-62 a, wherein $R^{10}$ is alkylamine ($NR_{11}R_{12}$), wherein $R_{11}$ and $R_{12}$ are independently H or $C_{1-4}$ alkyl.

69 a. The compound of embodiment 1 a, wherein $R^1$ and $R^5$ are part of 3-7 member cyclic ring, said 3-7 member cyclic being optionally substituted with $C_{1-4}$ alkyl optionally substituted with OZ or $NR_{11}R_{12}$ wherein Z, $R_{11}$ and $R_{12}$ are independently H or $C_{1-4}$ alkyl.

70 a. The compound of embodiment 1 a, wherein $R^1$ and $R^5$ are part of 3-7 member cyclic ring, said 3-7 member cyclic being optionally substituted with $R_8CO$, wherein $R_8$ is $C_{1-4}$ alkyl.

71 a. The compound of embodiment 70 a, wherein the 3-7 member cyclic ring is substituted with $CH_3CO$.

72 a. The compound of embodiment 1 a, wherein $R^1$ and $R^5$ are part of 3-7 member cyclic ring, said 3-7 member cyclic being optionally substituted with $SO_2(CH_2)_qH$, wherein q is 1-4.

73 a. The compound of embodiment 72 a, wherein the 3-7 member cyclic is substituted with $SO_2CH_3$.

74 a. The compound of embodiment 1 a, wherein $R^1$ and $R^2$ are part of 3-7 member cyclic ring, optionally substituted with $C_{1-4}$ alkyl, said $C_{1-4}$ alkyl further optionally substituted with halo, OZ, or $NR_{11}R_{12}$ wherein Z, $R_{11}$ and $R_{12}$ are independently H or $C_{1-4}$ alkyl.

75 a. The compound of embodiment 1 a, wherein $R^1$ and $R^2$ are part of 3-7 member cyclic ring, and one or more members of said 3-7 member cyclic ring is optionally part of a carbonyl group or a sulfonyl group.

76 a. The compound of embodiment 75 a, wherein the carbonyl group is an amide or an ester group.

77 a. The compound of embodiment 1 a, wherein $R^2$ and $R^6$ are part of 3-7 member cyclic ring, optionally substituted with $C_{1-4}$ alkyl substituted optionally with OZ or $NR_{11}R_{12}$ wherein Z, $R_{11}$ and $R_{12}$ are independently H or $C_{1-4}$ alkyl.

78 a. The compound of any of embodiments 1-77 a, wherein $R^4$ is unsubstituted $C_2$ alkenyl.

79 a. The compound of any of embodiments 1-77 a, wherein $R^4$ is $C_2$ alkenyl substituted with $C_{1-4}$ alkyl.

80 a. The compound of any of embodiments 1-77 a, wherein $R^4$ is $C_2$ alkenyl substituted with —$CH_2OCH_3$.

81 a. The compound of any of embodiments 1-77 a, wherein $R^4$ is $C_2$ alkenyl substituted with —$CH_2N(CH_3)_2$.

82 a. The compound of any of embodiments 1-81 a, wherein X is O.

83 a. The compound of any of embodiments 1-81 a, wherein X is unsubstituted $C_{1-4}$ alkyl, e.g., $CH_2$, or $C_{1-4}$ alkyl substituted with halo, e.g., $CF_2$.

84 a. The compound of any of embodiments 1-81 a, wherein X is $NR^b$, and $R^b$ is H, or $C_{1-8}$ alkyl optionally substituted with halo.

85 a. The compound of any of embodiments 1-84 a, wherein Y is C.

86 a. The compound of embodiment 85 a, wherein Y is CH or CH substituted with halo, e.g., $CF_2$.

87 a. The compound of embodiment 85 a, wherein Y is N.

88 a. The compound of any of embodiments 1-87 a, wherein A is C.

89 a. The compound of any of embodiments 1-87 a, wherein A is N.

90 a. The compound of any of embodiments 1-89 a, wherein the 3-7 member cyclic ring is a 3 member cyclic ring.

91 a. The compound of any of embodiments 1-89 a, wherein the 3-7 member cyclic ring is a 4 member cyclic ring.

92 a. The compound of any of embodiments 1-89 a, wherein the 3-7 member cyclic ring is a 5 member cyclic ring.

93 a. The compound of any of embodiments 1-89 a, wherein the 3-7 member cyclic ring is a 6 member cyclic ring.

94 a. The compound of any of embodiments 1-89 a, wherein the 3-7 member cyclic ring is a 7 member cyclic ring.

95 a. The compound of any of embodiments 1-94 a, wherein the 3-7 member cyclic ring is a heterocyclic ring.

96 a. The compound of embodiment 95 a, wherein the heterocyclic ring comprises a N atom.

97 a. The compound of embodiment 1 a, which is selected from the group consisting of compound I-1, I-2, I-3, I-4, I-5, I-6, I-7, I-8, I-9, I-12, I-13, I-14, I-15, I-16, I-17, I-18, I-19, I-20, I-21, I-22, I-23, I-24, I-25, I-41, I-23a, I-25a, I-28a, I-29a, I-30a, I-31a, I-32a, I-33a, I-34a, I-35a, I-38a, I-39a, I-42a, I-43a, I-44a, I-45a, I-50a, I-51a, I-52a, I-53a, I-54a, I-55a, I-56a, I-57a, I-58a, I-59a, I-60a, I-66a, I-70a, and I-72a.

98 a. A compound of Formula (IIa):

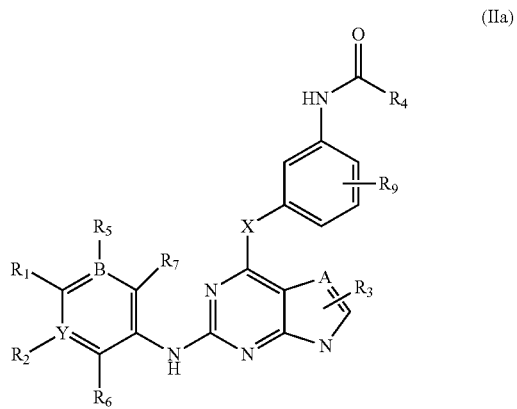

wherein
$R^1$ is H, or
$NR^cR^d$ wherein $R^c$ is H, $C_{1-4}$ alkyl or 3-7 member cyclic ring, said 3-7 member cyclic ring optionally substituted with $C_{1-4}$ alkyl optionally substituted with OZ or $NR_{10}R_{11}$ wherein Z, $R_{10}$ and $R_{11}$ are independently H or $C_{1-4}$ alkyl, or said 3-7 member cyclic ring being optionally substituted with $R_8CO$, wherein $R_8$ is $C_{1-4}$ alkyl, or said 3-7 member cyclic ring being optionally substituted with $SO_2(CH_2)_qH$, wherein q is 1-4, and $R^d$ is H, $C_{1-4}$ alkyl, optionally substituted with OZ or $NR_{10}R_{11}$ wherein Z, $R_{10}$ and $R_{11}$ are H or $C_{1-4}$ alkyl; or $NR^eR^f$ wherein $R^e$ is $C_{1-4}$ alkyl, and $R^f$ is 3-7 member cyclic ring optionally substituted with $C_{1-4}$ alkyl optionally substituted with halo; or $OR^g$ wherein $R^g$ is $C_{1-4}$ alkyl substituted with $CH_3O$—, $CH_3CH_2O$—, $CH_3(O)_2S$—, $CF_3O$—,

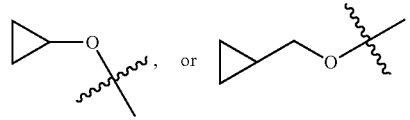 [SMILES: *OC1CC1 ; *OCC1CC1]

or
3-7 member cyclic ring substituted with $R^a$ wherein $R^a$ is $C_{1-8}$ alkyl optionally substituted with halo, $C_{1-4}$ alkoxy or $SO_2(CH_2)_qH$, wherein q is 1-4, or said 3-7 member cyclic ring being optionally substituted with $R_8CO$, wherein $R_8$ is $C_{1-4}$ alkyl;

$R^2$ is absent, H, halo, $C_{1-4}$ alkyl, $C_{1-4}$alkoxy, or alkylamine $(NR_{10}R_{11})$, wherein $R_{10}$ and $R_{11}$ are independently H or $C_{1-4}$ alkyl;

$R^3$ is absent, H, halo, $C_{1-4}$ alkyl, or $C_{1-4}$alkoxy, or alkylamine $(NR_{10}R_{11})$, wherein $R_{10}$ and $R_{11}$ are independently H or $C_{1-4}$ alkyl;

$R^5$ is absent, H, halo, $C_{1-4}$ alkyl, or $C_{1-4}$alkoxy, or alkylamine $(NR_{10}R_{11})$, wherein $R_{10}$ and $R_{11}$ are independently H or $C_{1-4}$ alkyl;

$R^6$ is H, halo, $C_{1-4}$ alkyl, or $C_{1-4}$alkoxy, alkylamine $(NR_{10}R_{11})$, wherein $R_{10}$ and $R_{11}$ are independently H or $C_{1-4}$ alkyl;

$R^7$ is H, halo, $C_{1-4}$ alkyl, $C_{1-4}$ alkoxy, or alkylamine ($NR_{10}R_{11}$), wherein $R_{10}$ and $R_{11}$ are independently H or $C_{1-4}$ alkyl;

$R^9$ is H, halo, $C_{1-4}$ alkyl, or $C_{1-4}$ alkoxy, or alkylamine ($NR_{10}R_{11}$), wherein $R_{10}$ and $R_{11}$ are independently H or $C_{1-4}$ alkyl; or $R^1$ and $R^5$ are part of 3-7 member cyclic ring, optionally substituted with $C_{1-4}$ alkyl optionally substituted with OZ or $NR_{10}R_{11}$ wherein Z, $R_{10}$ and $R_{11}$ are independently H or $C_{1-4}$ alkyl; or $R^1$ and $R^2$ are part of 3-7 member cyclic ring, optionally substituted with $C_{1-4}$ alkyl optionally substituted with OZ or $R_{10}$ and $R_{11}$ wherein Z, $R_{10}$ and $R_{11}$ are independently are H or $C_{1-4}$ alkyl; or $R^2$ and $R^6$ are part of 3-7 member cyclic ring, optionally substituted with $C_{1-4}$ alkyl optionally substituted with OZ or $R_{10}$ and $R_{11}$ wherein Z, $R_{10}$ and $R_{11}$ are independently H or $C_{1-4}$ alkyl;

$R^4$ is $C_2$ alkenyl optionally substituted with $C_{1-4}$ alkyl, —$CH_2OCH_3$, or —$CH_2N(CH_3)_2$;

X is O, $C_{1-4}$ alkyl optionally substituted with halo, or $NR^b$, wherein $R^b$ is H, or $C_{1-8}$ alkyl optionally substituted with halo;

Y is C, CH optionally substituted with halo, or N;
A is C, CH optionally substituted with halo, or N; and
B is C, CH optionally substituted with halo, or N,
or a pharmaceutically acceptable salt thereof.

99 a. The compound of embodiment 98 a, wherein $R^1$ is H, and $R^2$ and $R^6$ are part of 3-7 member cyclic ring, optionally substituted with $C_{1-4}$ alkyl optionally substituted with OZ or $R_{10}$ and $R_{11}$ wherein Z, $R_{10}$ and $R_{11}$ are independently H or $C_{1-4}$ alkyl.

100 a. The compound of embodiment 98 a, wherein $R^1$ is $NR^cR^d$ and $R^c$ is H.

101 a. The compound of embodiment 98 a, wherein $R^1$ is $NR^cR^d$ and $R^c$ is $C_{1-4}$ alkyl.

102 a. The compound of embodiment 98 a, wherein $R^1$ is $NR^cR^d$ and $R^c$ is 3-7 member cyclic ring, said 3-7 member cyclic ring optionally substituted with $C_{1-4}$ alkyl optionally substituted with OZ or $NR_{10}R_{11}$ wherein Z, $R_{10}$ and $R_{11}$ are independently H or $C_{1-4}$ alkyl.

103 a. The compound of embodiment 102 a, wherein said 3-7 member cyclic ring is substituted with $C_2$ alkyl substituted with methoxy.

104 a. The compound of embodiment 98 a, wherein $R^1$ is $NR^cR^d$ and $R^c$ is 3-7 member cyclic ring, said 3-7 member cyclic ring being optionally substituted with $R_8CO$, wherein $R_8$ is $C_{1-4}$ alkyl.

105 a. The compound of embodiment 104 a, wherein said 3-7 member cyclic ring is substituted with $CH_3CO$.

106 a. The compound of embodiment 98 a, wherein $R^1$ is $NR^cR^d$ and $R^c$ is 3-7 member cyclic ring, said 3-7 member cyclic ring being optionally substituted with $SO_2(CH_2)_qH$, wherein q is 1-4.

107 a. The compound of embodiment 106 a, wherein said 3-7 member cyclic ring is substituted with $CH_3SO_2$.

108 a. The compound of any of embodiments 1-107 a, wherein $R^d$ is H.

109 a. The compound of any of embodiments 1-107 a, wherein $R^d$ is $C_{1-4}$ alkyl, optionally substituted with OZ or $NR_{10}R_{11}$ wherein Z, $R_{10}$ and $R_{11}$ are H or $C_{1-4}$ alkyl.

110 a. The compound of embodiment 98 a, wherein $R^1$ is $NR^eR^f$ and $R^e$ is $C_{1-4}$ alkyl.

111 a. The compound of embodiment 98 a, wherein $R^1$ is $NR^eR^f$ and $R^f$ is 3-7 member cyclic ring optionally substituted with $C_{1-4}$ alkyl optionally substituted with halo.

112 a. The compound of embodiment 98 a, wherein $R^1$ is $OR^g$ wherein $R^g$ is $C_{1-4}$ alkyl substituted with $CH_3O$—, $CH_3CH_2O$—, $CH_3(O)_2S$—, $CF_3O$—,

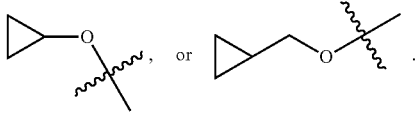 [SMILES: *OC1CC1 ; *OCC1CC1]

113 a. The compound of embodiment 98 a, wherein $R^1$ is 3-7 member cyclic ring substituted with $R^a$ wherein $R^a$ is $C_{1-8}$ alkyl optionally substituted with halo, $C_{1-4}$alkoxy or $SO_2(CH_2)_qH$, wherein q is 1-4.

114 a. The compound of embodiment 113 a, wherein $R^a$ is $C_2$ alkyl substituted with methoxy.

115 a. The compound of embodiment 113 a, wherein $R^a$ is $CH_3SO_2CH_2CH_2$.

116 a. The compound of embodiment 98 a, wherein $R^1$ is 3-7 member cyclic ring, said 3-7 member cyclic ring being optionally substituted with $R_8CO$, wherein $R_8$ is $C_{1-4}$ alkyl.

117 a. The compound of embodiment 116 a, wherein said 3-7 member cyclic ring is substituted with $CH_3CO$.

118 a. The compound of any of embodiments 113-117 a, wherein $R^1$ is selected from the group consisting of

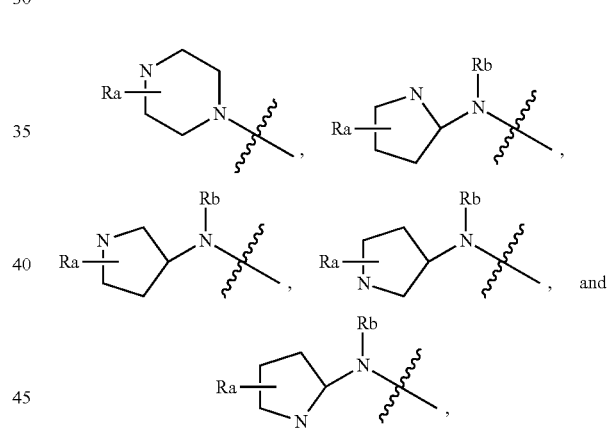

$R^a$ is $C_{1-8}$ alkyl optionally substituted with halo, $C_{1-4}$alkoxy or $SO_2(CH_2)_qH$, wherein q is 1-4, and $R^b$ is H or $C_{1-8}$ alkyl optionally substituted with halo, $C_{1-4}$alkoxy or $SO_2(CH_2)_qH$, wherein q is 1-4.

119 a. The compound of embodiment 118 a, wherein $R^1$ is selected from the group consisting of

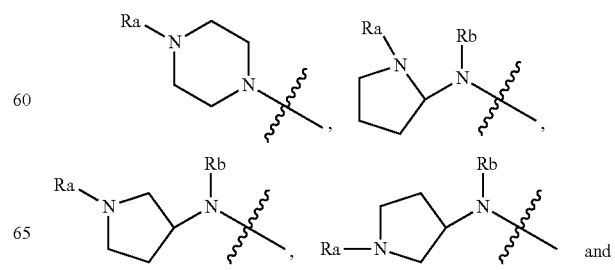

-continued

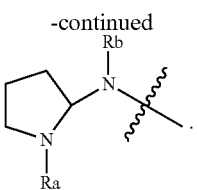

120 a. The compound of embodiment 119 a, wherein $R^1$ is

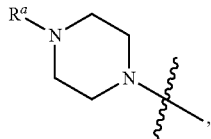

and $R^a$ is $C_2$ alkyl further substituted with methoxy.

121 a. The compound of embodiment 119 a, wherein $R^1$ is

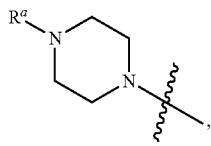

and $R^a$ is $C_2$ alkyl further substituted with $SO_2CH_3$.

122 a. The compound of any of embodiments 98 a and 100-121 a, wherein $R^2$ is absent or H.

123 a. The compound of any of embodiments 98 a and 100-121 a, wherein $R^2$ is halo.

124 a. The compound of any of embodiments 98 a and 100-121 a, wherein $R^2$ is $C_{1-4}$ alkyl or $C_{1-4}$ alkoxy.

125 a. The compound of any of embodiments 98 a and 100-121 a, wherein $R^2$ is alkylamine ($NR_{10}R_{11}$), wherein $R_{10}$ and $R_{11}$ are independently H or $C_{1-4}$ alkyl.

126 a. The compound of any of embodiments 98-125 a, wherein $R^3$ is absent.

127 a. The compound of any of embodiments 98-125 a, wherein $R^3$ is H.

128 a. The compound of any of embodiments 98-125 a, wherein $R^3$ is halo.

129 a. The compound of any of embodiments 98-125 a, wherein $R^3$ is $C_{1-4}$ alkyl.

130 a. The compound of any of embodiments 98-125 a, wherein $R^3$ is $C_{1-4}$alkoxy.

131 a. The compound of any of embodiments 98-125 a, wherein $R^3$ is alkylamine ($NR_{10}R_{11}$), wherein $R_{10}$ and $R_{11}$ are independently H or $C_{1-4}$ alkyl.

132 a. The compound of any of embodiments 98-125 a, wherein $R^5$ is absent.

133 a. The compound of any of embodiments 98-125 a, wherein $R^5$ is H.

134 a. The compound of any of embodiments 98-125, a wherein $R^5$ is halo.

135 a. The compound of any of embodiments 98-125 a, wherein $R^5$ is $C_{1-4}$ alkyl.

136 a. The compound of any of embodiments 98-125 a, wherein $R^5$ is $C_{1-4}$alkoxy.

137 a. The compound of any of embodiments 98-125 a, wherein $R^5$ is alkylamine ($NR_{10}R_{11}$), wherein $R_{10}$ and $R_{11}$ are independently H or $C_{1-4}$ alkyl.

138 a. The compound of any of embodiments 98 a and 100-137 a, wherein $R^6$ is H.

139 a. The compound of any of embodiments 98 a and 100-137 a, wherein $R^6$ is halo.

140 a. The compound of any of embodiments 98 a and 100-137 a, wherein $R^6$ is $C_{1-4}$ alkyl.

141 a. The compound of any of embodiments 98 a and 100-137 a, wherein $R^6$ is $C_{1-4}$alkoxy.

142 a. The compound of any of embodiments 98 a and 100-137 a, wherein $R^6$ is alkylamine ($NR_{10}R_{11}$), wherein $R_{10}$ and $R_{11}$ are independently H or $C_{1-4}$ alkyl.

143 a. The compound of any of embodiments 98-142 a, wherein $R^7$ is H.

144 a. The compound of any of embodiments 98-142 a, wherein $R^7$ is halo.

145 a. The compound of any of embodiments 98-142 a, wherein $R^7$ is $C_{1-4}$ alkyl.

146 a. The compound of any of claims 98-142 a, wherein $R^7$ is $C_{1-4}$alkoxy.

147 a. The compound of any of embodiments 98-142 a, wherein $R^7$ is alkylamine ($NR_{10}R_{11}$), wherein $R_{10}$ and $R_{11}$ are independently H or $C_{1-4}$ alkyl.

148 a. The compound of any of embodiments 98-147 a, wherein $R^9$ is H.

149 a. The compound of any of embodiments 98-147 a, wherein $R^9$ is halo.

150 a. The compound of any of embodiments 98-147 a, wherein $R^9$ is $C_{1-4}$ alkyl.

151 a. The compound of any of embodiments 98-147 a, wherein $R^9$ is $C_{1-4}$alkoxy.

152 a. The compound of any of embodiments 98-147 a, wherein $R^9$ is alkylamine ($NR_{10}R_{11}$), wherein $R_{10}$ and $R_{11}$ are independently H or $C_{1-4}$ alkyl.

153 a. The compound of embodiment 98 a, wherein $R^1$ and $R^5$ are part of 3-7 member cyclic ring, optionally substituted with $C_{1-4}$ alkyl optionally substituted with OZ or $NR_{10}R_{11}$ wherein Z, $R_{10}$ and $R_{11}$ are independently H or $C_{1-4}$ alkyl.

154 a. The compound of embodiment 98 a, wherein $R^1$ and $R^2$ are part of 3-7 member cyclic ring, optionally substituted with $C_{1-4}$ alkyl optionally substituted with OZ or $R_{10}$ and $R_{11}$ wherein Z, $R_{10}$ and $R_{11}$ are independently are H or $C_{1-4}$ alkyl.

155 a. The compound of embodiment 98 a, wherein $R^2$ and $R^6$ are part of 3-7 member cyclic ring, optionally substituted with $C_{1-4}$ alkyl optionally substituted with OZ or $R_{10}$ and $R_{11}$ wherein Z, $R_{10}$ and $R_{11}$ are independently H or $C_{1-4}$ alkyl.

156 a. The compound of any of embodiments 98-155 a, wherein X is O.

157 a. The compound of any of embodiments 98-155 a, wherein X is unsubstituted $C_{1-4}$ alkyl, e.g., $CH_2$, or $C_{1-4}$ alkyl substituted with halo, e.g., $CF_2$.

158 a. The compound of any of embodiments 98-155 a, wherein X is $NR^b$, and $R^b$ is H, or $C_{1-8}$ alkyl optionally substituted with halo.

159 a. The compound of any of embodiments 98-158 a, wherein Y is C.

160 a. The compound of any of embodiments 98-158 a, wherein Y is CH or CH substituted with halo, e.g., CF.

161 a. The compound of any of embodiments 98-158 a, wherein Y is N.

162 a. The compound of any of embodiments 98-161 a, wherein A is C.

163 a. The compound of any of embodiments 98-161 a, wherein A is CH or CH substituted with halo, e.g., CF.

164 a. The compound of any of embodiments 98-161 a, wherein A is N.

165 a. The compound of any of embodiments 98-164 a, wherein B is C.

166 a. The compound of any of embodiments 98-164 a, wherein B is CH or CH substituted with halo, e.g., CF.

167 a. The compound of any of embodiments 98-164 a, wherein B is N.

168 a. The compound of any of embodiments 98-167 a, wherein the 3-7 member cyclic ring is a 3 member cyclic ring.

169 a. The compound of any of embodiments 98-167 a, wherein the 3-7 member cyclic ring is a 4 member cyclic ring.

170 a. The compound of any of embodiments 98-167 a, wherein the 3-7 member cyclic ring is a 5 member cyclic ring.

171 a. The compound of any of embodiments 98-167 a, wherein the 3-7 member cyclic ring is a 6 member cyclic ring.

172 a. The compound of any of embodiments 98-167 a, wherein the 3-7 member cyclic ring is a 7 member cyclic ring.

173 a. The compound of any of embodiments 98-172 a, wherein the 3-7 member cyclic ring is a heterocyclic ring.

174 a. The compound of embodiment 173 a, wherein the heterocyclic ring comprises a N atom.

175 a. The compound of embodiment 98 a, which is selected from the group consisting of compound I-10, I-11, I-26, I-27, I-28, I-29, I-30, I-31, I-32, I-33, I-34, I-35, I-36, I-37, I-38, I-39, 1-40, I-24a, I-26a, I-27a, I-36a, I-37a, I-40a, I-41a, I-46a, I-47a, I-48a, I-49a, I-61a, I-62a, I-63a, I-64a, I-65a, I-67a, I-68a, I-69a, and I-71a.

176 a. A pharmaceutical composition comprising a compound of any of embodiments 1-175 a admixed with at least one pharmaceutically acceptable carrier or excipient.

177 a. A compound according to any of embodiments 1-175 a for use in therapy.

178 a. A method for treating and/or preventing a proliferation disorder, a cancer, a tumor, an inflammatory disease, an autoimmune disease, psoriasis, dry eye or an immunologically related disease, or lupus, which comprises administering to a subject in need thereof an effective amount of a compound of any of embodiments 1-175 a or a pharmaceutical composition of embodiment 176 a.

179 a. Use of a compound according to any of embodiments 1-175 a for the manufacture of a medicament.

180 a. A combination for treating and/or preventing a proliferation disorder, a cancer, a tumor, an inflammatory disease, an autoimmune disease, psoriasis, dry eye or an immunologically related disease or lupus in a subject, which combination comprises an effective amount of a compound of any of embodiments 1-175 a, or a pharmaceutically acceptable salt thereof, and an effective amount of a second prophylactic or therapeutic agent for treating and/or preventing a proliferation disorder, a cancer, a tumor, an inflammatory disease, an autoimmune disease, psoriasis, dry eye or an immunologically related disease or lupus in a subject.

181 a. A method for treating and/or preventing a proliferation disorder, a cancer, a tumor, an inflammatory disease, an autoimmune disease, psoriasis, dry eye or an immunologically related disease or lupus in a subject, which methods comprises administering to a subject in need thereof an effective amount of the combination of embodiment 180 a.

182 a. A method for inhibiting an activity of a Bruton's tyrosine kinase (Btk or BTK) or a Janus kinase (JAK), EGFR (including HER), Alk, PDGFR, BLK, BMX/ETK, FLT3(D835Y), ITK, TEC, TXK, and the respective pathways, in a cell or subject, which methods comprises administering to a cell or subject in need thereof an effective amount of a compound of any of embodiments 1-175 a, or a pharmaceutical composition of embodiment 176 a, or a combination of embodiment 180 a.

183 a. The method of embodiment 182 a, wherein the JAK is JAK1, JAK2 or JAK3.

184 a. The method of embodiment 182 a or 183 a, which is used for treating and/or preventing a proliferation disorder, a cancer, a tumor, an inflammatory disease, an autoimmune disease, psoriasis, dry eye or an immunologically related disease or lupus in the subject.

185 a. The method of embodiment 184 a, wherein the proliferation disorder is selected from the group consisting of sarcoma, epidermoid cancer, fibrosarcoma, cervical cancer, gastric carcinoma, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancers, and pancreatic cancer.

186 a. The method of any of embodiments 178 a and 181-185 a, wherein the compound is selected from the group consisting of compound I-1, I-2, I-3, I-4, I-5, I-6, I-7, I-8, I-9, I-12, I-13, 1-14, I-15, I-16, I-17, I-18, I-19, I-20, I-21, I-22, I-23, I-24, I-25, I-41, I-23a, I-25a, I-28a, I-29a, I-30a, I-31a, I-32a, I-33a, I-34a, I-35a, I-38a, I-39a, I-42a, I-43a, I-44a, I-45a, I-50a, I-51a, I-52a, I-53a, I-54a, I-55a, I-56a, I-57a, I-58a, I-59a, I-60a, I-66a, I-70a, I-72a, I-10, I-11, I-26, I-27, I-28, I-29, I-30, I-31, I-32, I-33, I-34, I-35, I-36, I-37, I-38, I-39, I-40, I-24a, I-26a, I-27a, I-36a, I-37a, I-40a, I-41a, I-46a, I-47a, I-48a, I-49a, I-61a, I-62a, I-63a, I-64a, I-65a, I-67a, I-68a, I-69a, and I-71a.

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

The invention claimed is:

1. A method for treating and/or preventing a proliferation disorder, a cancer, a tumor, an inflammatory disease, an autoimmune disease, psoriasis, dry eye or an immunologically related disease, or lupus, which comprises administering to a subject in need thereof an effective amount of a compound of Formula (Ia)

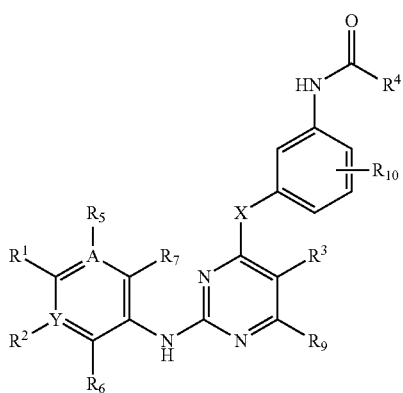

(Ia)

wherein
$R^1$ is
 $NR^cR^d$ wherein
  $R^c$ is H, $C_{1-4}$ alkyl, $C_{1-4}$ alkenyl, or 3-7 member cyclic ring, said $C_{1-4}$ alkyl, $C_{1-4}$ alkenyl, or 3-7 member cyclic ring being optionally substituted with OZ or $NR_{11}R_{12}$, wherein Z, $R_{11}$, $R_{12}$ are independently H or $C_{1-4}$ alkyl, or said 3-7 member cyclic ring being optionally substituted with $C_{1-4}$ alkyl that is further optionally substituted with OZ or $NR_{11}R_{12}$, wherein Z, $R_{11}$, $R_{12}$ are independently H or $C_{1-4}$ alkyl, or said 3-7 member cyclic ring being optionally substituted with $SO_2(CH_2)_qH$, wherein q is 1-4, or said 3-7 member cyclic ring being optionally substituted with $C_{1-4}$ alkyl that is further optionally substituted with $SO_2(CH_2)_qH$, wherein q is 1-4, or said 3-7 member cyclic ring being optionally substituted with $R_8CO$, wherein $R_8$ is $C_{1-4}$ alkyl, and
  $R^d$ is H, $C_{1-4}$ alkyl, $C_{1-4}$ alkenyl, or 3-7 member cyclic ring, said $C_{1-4}$ alkyl, $C_{1-4}$ alkenyl or 3-7 member cyclic ring being optionally substituted with OZ or $NR_{11}R_{12}$, wherein Z, $R_{11}$, $R_{12}$ are independently H or $C_{1-4}$ alkyl; or
 3-7 member cyclic ring substituted with $R^a$ wherein $R^a$ is $C_{2-8}$ alkyl optionally substituted with halo, $C_{1-4}$ alkoxy or $SO_2(CH_2)_qH$, wherein q is 1-4; or $O(CH_2)_mSO_2(CH_2)_nH$, wherein m is 1-4 and n is 1-4;
$R^2$ is absent, H, halo, $C_{1-4}$ alkyl, $C_{2-4}$ alkoxy, or alkylamine ($NR_{11}R_{12}$), wherein $R_{11}$ and $R_{12}$ are independently H or $C_{1-4}$ alkyl;
$R^3$ is hydroxyl, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl;
$R^5$ is absent, H, halo, $C_{1-4}$ alkyl, $C_{2-4}$ alkoxy, or alkylamine ($NR_{11}R_{12}$), wherein $R_{11}$ and $R_{12}$ are independently H or $C_{1-4}$ alkyl;
$R^6$ is H, halo, $C_{1-4}$ alkyl, $C_{2-4}$ alkoxy, or alkylamine ($NR_{11}R_{12}$), wherein $R_{11}$ and $R_{12}$ are independently H or $C_{1-4}$ alkyl;
$R^7$ is H, halo, $C_{1-4}$ alkyl, $C_{2-4}$ alkoxy, or alkylamine ($NR_{11}R_{12}$), wherein $R_{11}$ and $R_{12}$ are independently H or $C_{1-4}$ alkyl;
$R^9$ is H, hydroxyl, halo, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl;
$R^{10}$ is H, hydroxyl, halo, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl; or $R^1$ and $R^5$ are part of 3-7 member cyclic ring, said 3-7 member cyclic being optionally substituted with $C_{1-4}$ alkyl optionally substituted with OZ or $NR_{11}R_{12}$ wherein Z, $R_{11}$ and $R_{12}$ are independently H or $C_{1-4}$ alkyl, or said 3-7 member cyclic being optionally substituted with $R_8CO$, wherein $R_8$ is $C_{1-4}$ alkyl, or said 3-7 member cyclic being optionally substituted with $SO_2(CH_2)_qH$, wherein q is 1-4; or $R^1$ and $R^2$ are part of 3-7 member cyclic ring, optionally substituted with $C_{1-4}$ alkyl, said $C_{1-4}$ alkyl further optionally substituted with halo, OZ, or $NR_{11}R_{12}$ wherein Z, $R_{11}$ and $R_{12}$ are independently H or $C_{1-4}$ alkyl, or one or more members of said 3-7 member cyclic ring is optionally part of a carbonyl group or a sulfonyl group; or $R^2$ and $R^6$ are part of 3-7 member cyclic ring, optionally substituted with $C_{1-4}$ alkyl optionally substituted with OZ or $NR_{11}R_{12}$ wherein Z, $R_{11}$ and $R_{12}$ are independently H or $C_{1-4}$ alkyl;

$R^4$ is $C_2$ alkenyl optionally substituted with $C_{1-4}$ alkyl, $-CH_2OCH_3$, or $-CH_2N(CH_3)_2$;

X is O, $C_{1-4}$ alkyl optionally substituted with halo, or $NR^b$, wherein $R^b$ is H, or $C_{1-8}$ alkyl optionally substituted with halo;

Y is C, CH optionally substituted with halo, or N;

A is C, CH optionally substituted with halo or N; and wherein at least one of $R^2$, $R^3$, $R^5$ and $R^6$ is not H;

or a pharmaceutically acceptable salt thereof.

2. A combination for treating and/or preventing a proliferation disorder, a cancer, a tumor, an inflammatory disease, an autoimmune disease, psoriasis, dry eye or an immunologically related disease or lupus in a subject, which combination comprises an effective amount of a compound of Formula (Ia), or a pharmaceutically acceptable salt thereof, and an effective amount of a second prophylactic or therapeutic agent for treating and/or preventing a proliferation disorder, a cancer, a tumor, an inflammatory disease, an autoimmune disease, psoriasis, dry eye or an immunologically related disease or lupus in a subject; wherein the compound of Formula (Ia) is:

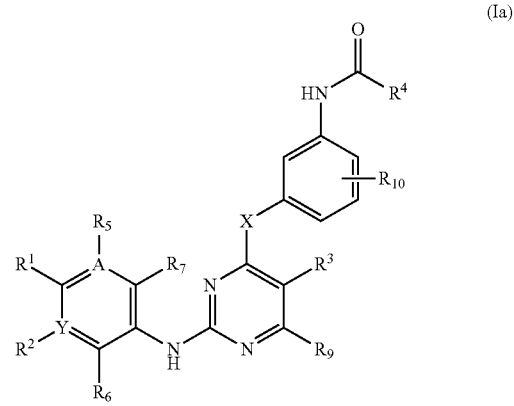

(Ia)

wherein
$R^1$ is
 $NR^cR^d$ wherein
  $R^c$ is H, $C_{1-4}$ alkyl, $C_{1-4}$ alkenyl, or 3-7 member cyclic ring, said $C_{1-4}$ alkyl, $C_{1-4}$ alkenyl, or 3-7 member cyclic ring being optionally substituted with OZ or $NR_{11}R_{12}$, wherein Z, $R_{11}$, $R_{12}$ are independently H or $C_{1-4}$ alkyl, or said 3-7 member cyclic ring being optionally substituted with $C_{1-4}$ alkyl that is further optionally substituted with OZ or $NR_{11}R_{12}$, wherein Z, $R_{11}$, $R_{12}$ are independently H or $C_{1-4}$ alkyl, or said 3-7 member cyclic ring being optionally substituted with $SO_2(CH_2)_q$H, wherein q is 1-4, or said 3-7 member cyclic ring being optionally substituted with $C_{1-4}$ alkyl that is further optionally substituted with $SO_2(CH_2)_q$H, wherein q is 1-4, or said 3-7 member cyclic ring being optionally substituted with $R_8$CO, wherein $R_8$ is $C_{1-4}$ alkyl, and $R^d$ is H, $C_{1-4}$ alkyl, $C_{1-4}$ alkenyl, or 3-7 member cyclic ring, said $C_{1-4}$ alkyl, $C_{1-4}$ alkenyl or 3-7 member cyclic ring being optionally substituted with OZ or $NR_{11}R_{12}$, wherein Z, $R_{11}$, $R_{12}$ are independently H or $C_{1-4}$ alkyl; or 3-7 member cyclic ring substituted with $R^a$ wherein $R^a$ is $C_{2-8}$ alkyl optionally substituted with halo, $C_{1-4}$ alkoxy or $SO_2(CH_2)_q$H, wherein q is 1-4; or $O(CH_2)_mSO_2(CH_2)_n$H, wherein m is 1-4 and n is 1-4;

$R^2$ is absent, H, halo, $C_{1-4}$ alkyl, $C_{2-4}$ alkoxy, or alkylamine ($NR_{11}R_{12}$), wherein $R_{11}$ and $R_{12}$ are independently H or $C_{1-4}$ alkyl;

$R^3$ is hydroxyl, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl;

$R^5$ is absent, H, halo, $C_{1-4}$ alkyl, $C_{2-4}$ alkoxy, or alkylamine ($NR_{11}R_{12}$), wherein $R_{11}$ and $R_{12}$ are independently H or $C_{1-4}$ alkyl;

$R^6$ is H, halo, $C_{1-4}$ alkyl, $C_{2-4}$ alkoxy, or alkylamine ($NR_{11}R_{12}$), wherein $R_{11}$ and $R_{12}$ are independently H or $C_{1-4}$ alkyl;

$R^7$ is H, halo, $C_{1-4}$ alkyl, $C_{2-4}$ alkoxy, or alkylamine ($NR_{11}R_{12}$), wherein $R_{11}$ and $R_{12}$ are independently H or $C_{1-4}$ alkyl;

$R^9$ is H, hydroxyl, halo, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl;

$R^{10}$ is H, hydroxyl, halo, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl; or $R^1$ and $R^5$ are part of 3-7 member cyclic ring, said 3-7 member cyclic ring being optionally substituted with $C_{1-4}$ alkyl optionally substituted with OZ or $NR_{11}R_{12}$ wherein Z, $R_{11}$ and $R_{12}$ are independently H or $C_{1-4}$ alkyl, or said 3-7 member cyclic being optionally substituted with $R_8$CO, wherein $R_8$ is $C_{1-4}$ alkyl, or said 3-7 member cyclic being optionally substituted with $SO_2(CH_2)_q$H, wherein q is 1-4; or $R^1$ and $R^2$ are part of 3-7 member cyclic ring, optionally substituted with $C_{1-4}$ alkyl, said $C_{1-4}$ alkyl further optionally substituted with halo, OZ, or $NR_{11}R_{12}$ wherein Z, $R_{11}$ and $R_{12}$ are independently H or $C_{1-4}$ alkyl, or one or more members of said 3-7 member cyclic ring is optionally part of a carbonyl group or a sulfonyl group; or $R^2$ and $R^6$ are part of 3-7 member cyclic ring, optionally substituted with $C_{1-4}$ alkyl optionally substituted with OZ or $NR_{11}R_{12}$ wherein Z, $R_{11}$ and $R_{12}$ are independently H or $C_{1-4}$ alkyl;

$R^4$ is $C_2$ alkenyl optionally substituted with $C_{1-4}$ alkyl, —$CH_2OCH_3$, or —$CH_2N(CH_3)_2$;

X is O, $C_{1-4}$ alkyl optionally substituted with halo, or $NR^b$, wherein $R^b$ is H, or $C_{1-8}$ alkyl optionally substituted with halo;

Y is C, CH optionally substituted with halo, or N;

A is C, CH optionally substituted with halo or N; and wherein at least one of $R^2$, $R^3$, $R^5$ and $R^6$ is not H;

or a pharmaceutically acceptable salt thereof.

3. A method for treating and/or preventing a proliferation disorder, a cancer, a tumor, an inflammatory disease, an autoimmune disease, psoriasis, dry eye or an immunologically related disease or lupus in a subject, which methods comprises administering to a subject in need thereof an effective amount of the combination of claim 2.

4. A method for inhibiting an activity of a Bruton's tyrosine kinase (Btk or BTK) or a Janus kinase (JAK), EGFR (including HER), Alk, PDGFR, BLK, BMX/ETK, FLT3(D835Y), ITK, TEC, TXK, and the respective pathways, in a cell or subject, which methods comprises administering to a cell or subject in need thereof an effective amount of a compound of Formula (Ia)

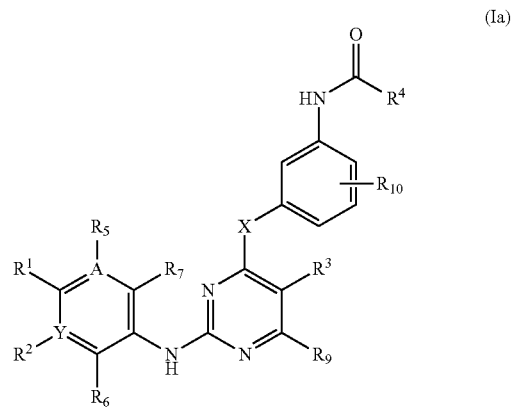

(Ia)

wherein
$R^1$ is
$NR^cR^d$ wherein
$R^c$ is H, $C_{1-4}$ alkyl, $C_{1-4}$ alkenyl, or 3-7 member cyclic ring, said $C_{1-4}$ alkyl, $C_{1-4}$ alkenyl, or 3-7 member cyclic ring being optionally substituted with OZ or $NR_{11}R_{12}$, wherein Z, $R_{11}$, $R_{12}$ are independently H or $C_{1-4}$ alkyl, or said 3-7 member cyclic ring being optionally substituted with $C_{1-4}$ alkyl that is further optionally substituted with OZ or $NR_{11}R_{12}$, wherein Z, $R_{11}$, $R_{12}$ are independently H or $C_{1-4}$ alkyl, or said 3-7 member cyclic ring being optionally substituted with $SO_2(CH_2)_q$H, wherein q is 1-4, or said 3-7 member cyclic ring being optionally substituted with $C_{1-4}$ alkyl that is further optionally substituted with $SO_2(CH_2)_q$H, wherein q is 1-4, or said 3-7 member cyclic ring being optionally substituted with $R_8$CO, wherein $R_8$ is $C_{1-4}$ alkyl, and $R^d$ is H, $C_{1-4}$ alkyl, $C_{1-4}$ alkenyl, or 3-7 member cyclic ring, said $C_{1-4}$ alkyl, $C_{1-4}$ alkenyl or 3-7 member cyclic ring being optionally substituted with OZ or $NR_{11}R_{12}$, wherein Z, $R_{11}$, $R_{12}$ are independently H or $C_{1-4}$ alkyl; or 3-7 member cyclic ring substituted with $R^a$ wherein $R^a$ is $C_{2-8}$ alkyl optionally substituted with halo, $C_{1-4}$ alkoxy or $SO_2(CH_2)_q$H, wherein q is 1-4; or $O(CH_2)_mSO_2(CH_2)_n$H, wherein m is 1-4 and n is 1-4;

$R^2$ is absent, H, halo, $C_{1-4}$ alkyl, $C_{2-4}$ alkoxy, or alkylamine ($NR_{11}R_{12}$), wherein $R_{11}$ and $R_{12}$ are independently H or $C_{1-4}$ alkyl;

$R^3$ is hydroxyl, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl;

$R^5$ is absent, H, halo, $C_{1-4}$ alkyl, $C_{2-4}$ alkoxy, or alkylamine ($NR_{11}R_{12}$), wherein $R_{11}$ and $R_{12}$ are independently H or $C_{1-4}$ alkyl;

$R^6$ is H, halo, $C_{1-4}$ alkyl, $C_{2-4}$ alkoxy, or alkylamine ($NR_{11}R_{12}$), wherein $R_{11}$ and $R_{12}$ are independently H or $C_{1-4}$ alkyl;

$R^7$ is H, halo, $C_{1-4}$ alkyl, $C_{2-4}$ alkoxy, or alkylamine ($NR_{11}R_{12}$), wherein $R_{11}$ and $R_{12}$ are independently H or $C_{1-4}$ alkyl;

$R^9$ is H, hydroxyl, halo, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl;

$R^{10}$ is H, hydroxyl, halo, $C_{1-4}$ alkyl, $C_{1-4}$ alkoxy, or alkylamine ($NR_{11}R_{12}$), wherein $R_{11}$ and $R_{12}$ are independently H or $C_{1-4}$ alkyl; or $R^1$ and $R^5$ are part of 3-7 member cyclic ring, said 3-7 member cyclic being optionally substituted with $C_{1-4}$ alkyl optionally substituted with OZ or $NR_{11}R_{12}$ wherein Z, $R_{11}$ and $R_{12}$ are independently H or $C_{1-4}$ alkyl, or said 3-7 member cyclic being optionally substituted with $R_8CO$, wherein $R_8$ is $C_{1-4}$ alkyl, or said 3-7 member cyclic being optionally substituted with $SO_2(CH_2)_qH$, wherein q is 1-4; or $R^1$ and $R^2$ are part of 3-7 member cyclic ring, optionally substituted with $C_{1-4}$ alkyl, said $C_{1-4}$ alkyl further optionally substituted with halo, OZ, or $NR_{11}R_{12}$ wherein Z, $R_{11}$ and $R_{12}$ are independently H or $C_{1-4}$ alkyl, or one or more members of said 3-7 member cyclic ring is optionally part of a carbonyl group or a sulfonyl group; or $R^2$ and $R^6$ are part of 3-7 member cyclic ring, optionally substituted with $C_{1-4}$ alkyl optionally substituted with OZ or $NR_{11}R_{12}$ wherein Z, $R_{11}$ and $R_{12}$ are independently H or $C_{1-4}$ alkyl;

$R^4$ is $C_2$ alkenyl optionally substituted with $C_{1-4}$ alkyl, $-CH_2OCH_3$, or $-CH_2N(CH_3)_2$;

X is O, $C_{1-4}$ alkyl optionally substituted with halo, or $NR^b$, wherein $R^b$ is $C_{1-8}$ alkyl optionally substituted with halo;

Y is C, CH optionally substituted with halo, or N;

A is C, CH optionally substituted with halo or N; and wherein at least one of $R^2$, $R^3$, $R^5$ and $R^6$ is not H; or a pharmaceutically acceptable salt thereof.

5. The method of claim 4, which is used for treating and/or preventing a proliferation disorder, a cancer, a tumor, an inflammatory disease, an autoimmune disease, psoriasis, dry eye or an immunologically related disease or lupus in the subject.

6. The method of claim 5, wherein the proliferation disorder is selected from the group consisting of sarcoma, epidermoid cancer, fibrosarcoma, cervical cancer, gastric carcinoma, skin cancer, leukemia, lymphoma, lung cancer, non-small cell lung cancer, colon cancer, CNS cancer, melanoma, ovarian cancer, renal cancer, prostate cancer, breast cancer, liver cancer, head and neck cancers, and pancreatic cancer.

7. The method of claim 1, wherein the compound is selected from the group consisting of compounds I-3, I-5, I-7, I-9, I-13, I-14, I-16, I-17, I-25a, I-28a, I-29a, I-30a, I-31a, I-32a, I-33a, I-34a, I-35a, I-38a, I-39a, I-42a, I-43a, I-44a, I-45a, I-50a, I-51a, I-52a, I-53a, I-54a, I-55a, I-56a, I-57a, I-58a, I-59a, I-60a, I-66a, I-70a, and I-72a.

8. The method of claim 1, wherein $R_4$ is $C_2$ alkenyl.

9. The method of claim 8, wherein $R_9$ is H.

10. The method of claim 9, wherein $R_{10}$ is H.

11. The method of claim 10, wherein A and Y are each independently C or CH.

12. The method of claim 11, wherein $R_2$ and $R_5$ are each independently absent or H.

13. The method of claim 12, wherein $R_6$ and $R_7$ are each H.

14. The method of claim 13, wherein $R^1$ is $NR^cR^d$ and $R^c$ is 3-7 member cyclic ring.

15. The method of claim 14, wherein the 3-7 member cyclic ring is optionally substituted with $R_8CO$, wherein $R_8$ is $C_{1-4}$ alkyl.

16. The method of claim 15, wherein $R^d$ is $C_{1-4}$ alkyl, optionally substituted with OZ or $NR_{11}R_{12}$, wherein Z, $R_{11}$, $R_{12}$ are independently H or $C_{1-4}$ alkyl.

17. The method of claim 16, wherein $R^1$ is $NR^cR^d$ and $R^c$ is a 5 member cyclic ring that comprises a N atom, and the H linked to the N atom is substituted with $R_8CO$, wherein $R_8$ is $C_{1-4}$ alkyl.

18. The method of claim 17, wherein the H linked to the N atom is substituted with $CH_3CO$.

19. The method of claim 18, wherein $R^d$ is methyl.

20. The method of claim 19, wherein $R_3$ is methoxy.

21. The method of claim 20, wherein X is O.

* * * * *